(12) United States Patent
Ganz et al.

(10) Patent No.: US 11,464,660 B2
(45) Date of Patent: Oct. 11, 2022

(54) OBESITY TREATMENT DEVICES, SYSTEMS, AND METHODS

(71) Applicant: Ganz Brake, LLC, Salt Lake City, UT (US)

(72) Inventors: Alexander S. Ganz, Minnetonka, MN (US); Robert A. Ganz, Minnetonka, MN (US); Travis Sessions, Cedar Hills, UT (US); Steven Berhow, St. Michael, MN (US); Michael W. Augustine, St. Michael, MN (US)

(73) Assignee: Ganz Brake, LLC, Salt Lake City, UT (US)

( * ) Notice: Subject to any disclaimer, the term of this patent is extended or adjusted under 35 U.S.C. 154(b) by 105 days.

(21) Appl. No.: 16/455,696

(22) Filed: Jun. 27, 2019

(65) Prior Publication Data
US 2019/0314181 A1 Oct. 17, 2019

Related U.S. Application Data

(63) Continuation of application No. 15/853,793, filed on Dec. 23, 2017, now Pat. No. 10,596,021.
(Continued)

(51) Int. Cl.
*A61F 5/00* (2006.01)
*A61B 90/00* (2016.01)
(Continued)

(52) U.S. Cl.
CPC ...... *A61F 5/0073* (2013.01); *A61B 17/00234* (2013.01); *A61B 90/02* (2016.02);
(Continued)

(58) Field of Classification Search
CPC .. A61F 5/0036; A61F 2/04; A61F 5/00; A61F 5/0003; A61F 2002/045; A61F 5/0076; A61M 29/00
See application file for complete search history.

(56) References Cited

U.S. PATENT DOCUMENTS

| 5,143,085 A | 1/1992 | Wilson |
| 6,149,581 A | 11/2000 | Klingenstein |

(Continued)

FOREIGN PATENT DOCUMENTS

| CN | 2699854 Y | 5/2005 |
| CN | 2894655 Y | 5/2007 |

(Continued)

OTHER PUBLICATIONS

Boccia, Gabriella, et al., Dyspeptic Symptoms in Children: The Result of a Constipation-Induced Cologastric Brake?, Clinical Gaslioenterology and Hepatology, 2008, pp. 556-560, vol. 6, No. 5.

(Continued)

*Primary Examiner* — George J Ulsh
(74) *Attorney, Agent, or Firm* — Med Venture Management, LLC; Daniel C. Higgs

(57) ABSTRACT

Various devices, systems, and methods that can be used in the treatment of obesity and related illnesses are disclosed. In some instances, the cecum of an obese patient is distended to a pathophysiological size for a therapeutically effective period. The distention may be achieved by introduction of an object that is of foreign origin relative to the body of the patient into the cecum of the patient. In some instances, the distention is achieved by a medical device that transitions from an undeployed state, in which the medical device is introduced into the cecum of the patient, to an expanded state in which the medical device distends the cecum by an amount sufficient to trigger a colo-gastric brake in the patient.

44 Claims, 65 Drawing Sheets

Related U.S. Application Data

(60) Provisional application No. 62/849,169, filed on May 17, 2019, provisional application No. 62/690,878, filed on Jun. 27, 2018, provisional application No. 62/526,007, filed on Jun. 28, 2017, provisional application No. 62/438,569, filed on Dec. 23, 2016.

(51) Int. Cl.
*A61B 17/00* (2006.01)
*A61F 2/958* (2013.01)
*A61F 2/04* (2013.01)

(52) U.S. Cl.
CPC .............. *A61F 2/04* (2013.01); *A61F 2/958* (2013.01); *A61F 5/0089* (2013.01); *A61B 2017/0034* (2013.01); *A61F 2002/045* (2013.01); *A61F 2210/0014* (2013.01); *A61F 2250/0059* (2013.01)

(56) References Cited

U.S. PATENT DOCUMENTS

| | | | |
|---|---|---|---|
| 6,675,809 B2 | 1/2004 | Stack et al. | |
| 7,462,192 B2 | 12/2008 | Norton et al. | |
| 7,476,256 B2 | 1/2009 | Meade et al. | |
| 7,931,693 B2 | 4/2011 | Binmoeller | |
| 8,075,582 B2 | 12/2011 | Lointier et al. | |
| 8,100,932 B2 | 1/2012 | Nihalani | |
| 8,147,561 B2 | 4/2012 | Binmoeller | |
| 8,211,186 B2 | 7/2012 | Belhe et al. | |
| 8,585,771 B2 | 11/2013 | Binmoeller et al. | |
| 8,602,974 B2 | 12/2013 | Goldwasser et al. | |
| 8,603,023 B2 | 12/2013 | Albrecht et al. | |
| 8,628,554 B2 | 1/2014 | Sharma | |
| 8,876,761 B2 | 11/2014 | Albrecht et al. | |
| 9,456,916 B2 | 10/2016 | Connor | |
| 9,526,648 B2 | 12/2016 | Sharma | |
| 9,649,185 B2 | 5/2017 | Bangera et al. | |
| 9,750,660 B2 | 9/2017 | Felder et al. | |
| 9,895,103 B2 | 2/2018 | Hyde et al. | |
| 10,183,154 B2 | 1/2019 | Hyde et al. | |
| 10,299,857 B2 * | 5/2019 | Rajagopalan | A61B 18/1492 |
| 10,596,021 B2 | 3/2020 | Ganz et al. | |
| 2002/0183853 A1 | 12/2002 | Mitchell et al. | |
| 2003/0014127 A1 | 1/2003 | Talja et al. | |
| 2005/0038415 A1 | 2/2005 | Rohr et al. | |
| 2006/0058829 A1 | 3/2006 | Sampson et al. | |
| 2006/0161139 A1 | 7/2006 | Levine et al. | |
| 2006/0178557 A1 | 8/2006 | Mintchev et al. | |
| 2007/0100367 A1 | 5/2007 | Quijano et al. | |
| 2008/0065136 A1 | 3/2008 | Young | |
| 2008/0161645 A1 | 7/2008 | Goldwasser et al. | |
| 2008/0275445 A1 | 11/2008 | Kelly et al. | |
| 2008/0312678 A1 | 12/2008 | Pasricha | |
| 2009/0012469 A1 | 1/2009 | Nita | |
| 2009/0105735 A1 | 4/2009 | Stam et al. | |
| 2009/0187206 A1 | 7/2009 | Binmoeller et al. | |
| 2009/0192588 A1 | 7/2009 | Shin et al. | |
| 2010/0105983 A1 | 4/2010 | Oneda et al. | |
| 2010/0145301 A1 | 6/2010 | Magal | |
| 2010/0249825 A1 | 9/2010 | Nihalani | |
| 2010/0324362 A1 | 12/2010 | Forsell | |
| 2011/0040231 A1 | 2/2011 | Gregory | |
| 2011/0160558 A1 | 6/2011 | Rassatt et al. | |
| 2011/0196411 A1 | 8/2011 | Forsell | |
| 2011/0295178 A1 | 12/2011 | Albrecht et al. | |
| 2011/0295299 A1 | 12/2011 | Braithwaite et al. | |
| 2013/0041424 A1 | 2/2013 | Neisz | |
| 2013/0109912 A1 | 5/2013 | Binmoeller et al. | |
| 2014/0114228 A1 | 4/2014 | Binmoeller et al. | |
| 2014/0180188 A1 | 6/2014 | Chin et al. | |
| 2014/0364959 A1 | 12/2014 | Attar et al. | |
| 2015/0011919 A1 | 1/2015 | Felder et al. | |
| 2016/0058593 A1 | 3/2016 | Bangera et al. | |
| 2016/0338865 A1 | 11/2016 | Campbell et al. | |
| 2017/0056226 A1 | 3/2017 | Sharma | |
| 2017/0172778 A1 | 6/2017 | Brister et al. | |
| 2018/0092732 A1 | 4/2018 | Kringle et al. | |
| 2018/0177623 A1 | 6/2018 | Ganz et al. | |
| 2020/0170818 A1 | 6/2020 | Ganz et al. | |

FOREIGN PATENT DOCUMENTS

| | | |
|---|---|---|
| DE | 10 2005 027 809 A1 | 12/2006 |
| EP | 3558162 | 10/2019 |
| EP | 3813729 | 5/2021 |
| WO | 2012099610 A1 | 7/2012 |
| WO | 2015085010 A1 | 6/2015 |
| WO | 2018119477 A1 | 6/2018 |
| WO | 2020006279 A1 | 1/2020 |
| WO | 2020264526 | 12/2020 |

OTHER PUBLICATIONS

Jackson, Daniel, Bowel Management Algorithm, 2007, 3 pages, available at https://pdfs.semanticscholar.org/dc36/59288d52bfce2babd268f804f009eb620983.pdf.

Jaffe, Tracy, et al., Large-Bowel Obstruction in the Adult: Classic Radiographic and CT Findings, Etiology, and Mimics, Radiology, Jun. 2015, pp. 651-663, vol. 275, No. 3.

Lee, Thomas, Leptos Biomedical to call it quits, MedCity News, Feb. 9, 2010, 2 pages, available at https://medcitynews.com/2010/02/leptos-biomedical-to-call-it-quits/.

Moon, Taegyun, et al., New Approach to Radial Expansive Force Measurement of Self Expandable Esophageal Metal Stents, ASAIO Journal, 2001, pp. 646-650.

Musial, F., et al., Effect of prolonged, continuous rectal distention on mouth-to-cecum and colonic transit time in pigs, Physiology and Behavior, 1992, p. 1021 (Absliact), vol. 52, No. 5.

Tjeerdsma, Hilda C., et al., Voluntary Suppression of Defecation Delays Gastric Emptying, Digestive Diseases and Sciences, May 1993, pp. 832-833, vol. 38, No. 5.

International Searching Agency, Search Report and Written Opinion of the ISA, International Application No. PCT/US2017/068378, dated Mar. 12, 2018, 19 pages.

European Patent Office, Extended European Search Report in European Patent Application No. 17884899.0, dated Jul. 7, 2020, 6 pages.

United States Patent and Trademark Office, Office Action in U.S. Appl. No. 15/853,793, dated Jul. 19, 2019, 27 pages.

United States Patent and Trademark Office, Applicant-Initiated Interview Summary in U.S. Appl. No. 15/853,793, dated Dec. 19, 2019, 3 pages.

Response to Office Action in U.S. Appl. No. 15/853,793, dated Jan. 20, 2020, 35 pages.

United States Patent and Trademark Office, Notice of Allowance in U.S. Appl. No. 15/853,793, dated Jan. 30, 2020, 32 pages.

Amendment Pursuant to 37 C.F.R. 1.312 in U.S. Appl. No. 15/853,793, dated Feb. 7, 2020, 35 pages.

United States Patent and Trademark Office, Response to Rule 312 Communication in U.S. Appl. No. 15/853,793, dated Feb. 14, 2020, 7 pages.

International Searching Agency, Search Report and Written Opinion of the ISA, International Application No. PCT/US2019/039575, dated Jun. 27, 2019, 10 pages.

International Searching Agency, Search Report and Written Opinion of the ISA, International Application No. PCT/US2020/040190, dated Dec. 3, 2020, 16 pages.

U.S. Appl. No. 17/562,219, filed Dec. 27, 2021, 192 pages.

European Patent Office, Extended European Search Report issued with respect to European Patent Application No. 19825234.8, dated Mar. 9, 2022, 8 pages.

* cited by examiner

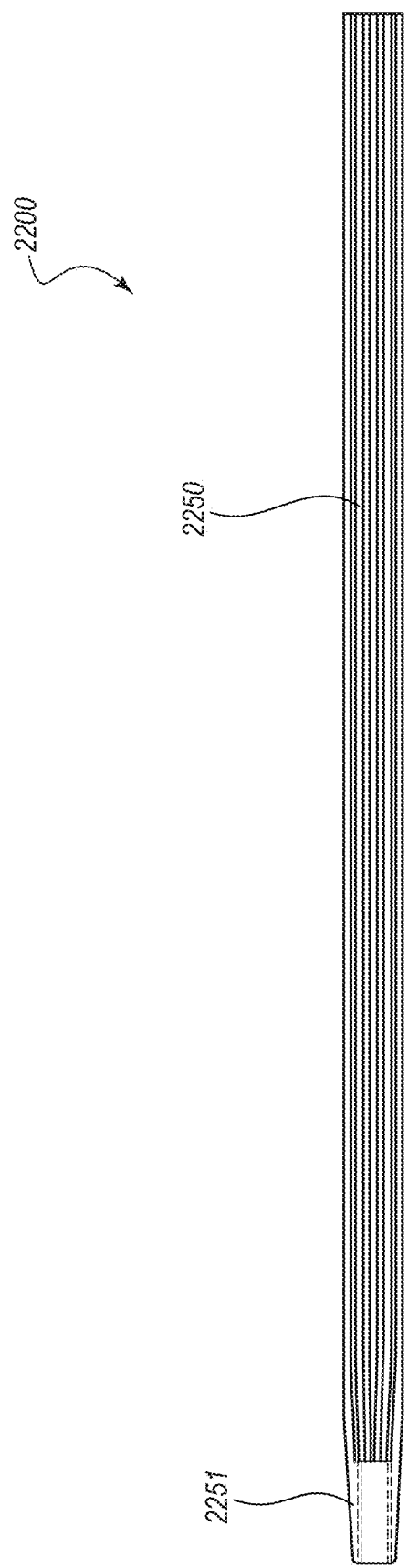

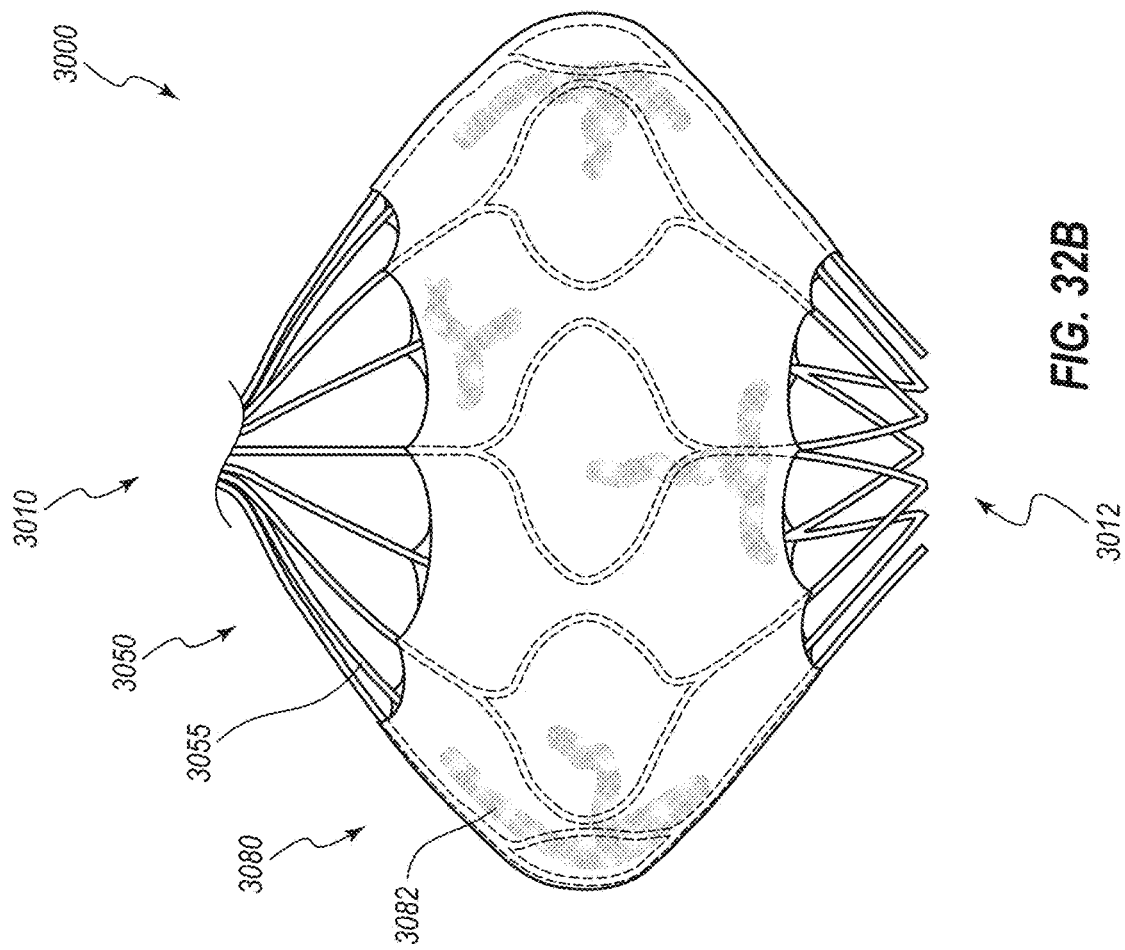
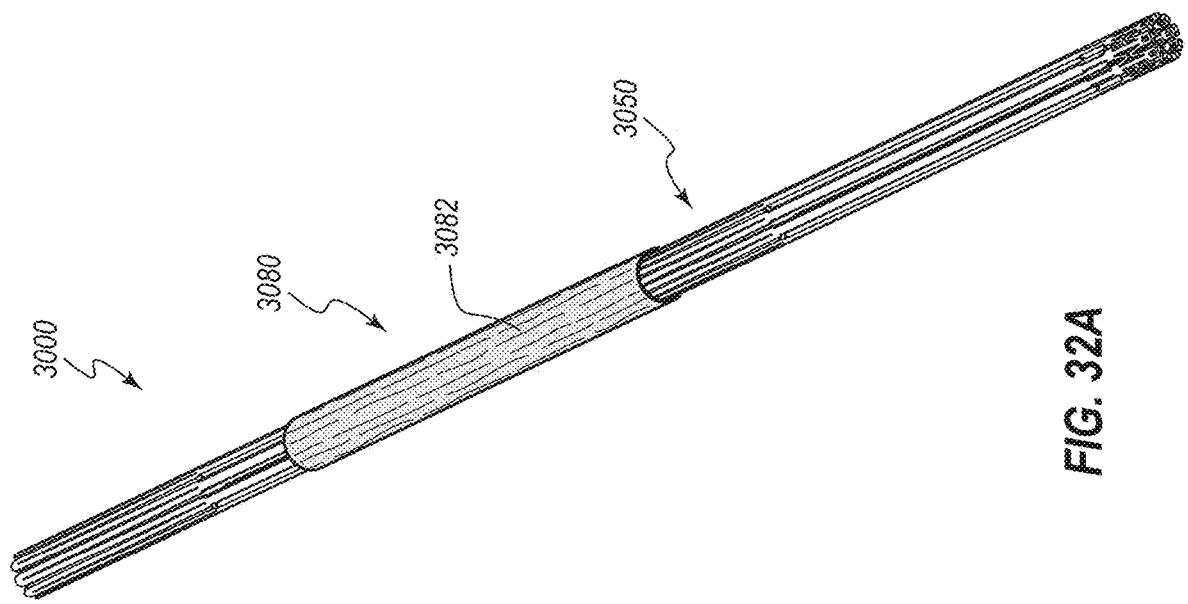
FIG. 32B
FIG. 32A

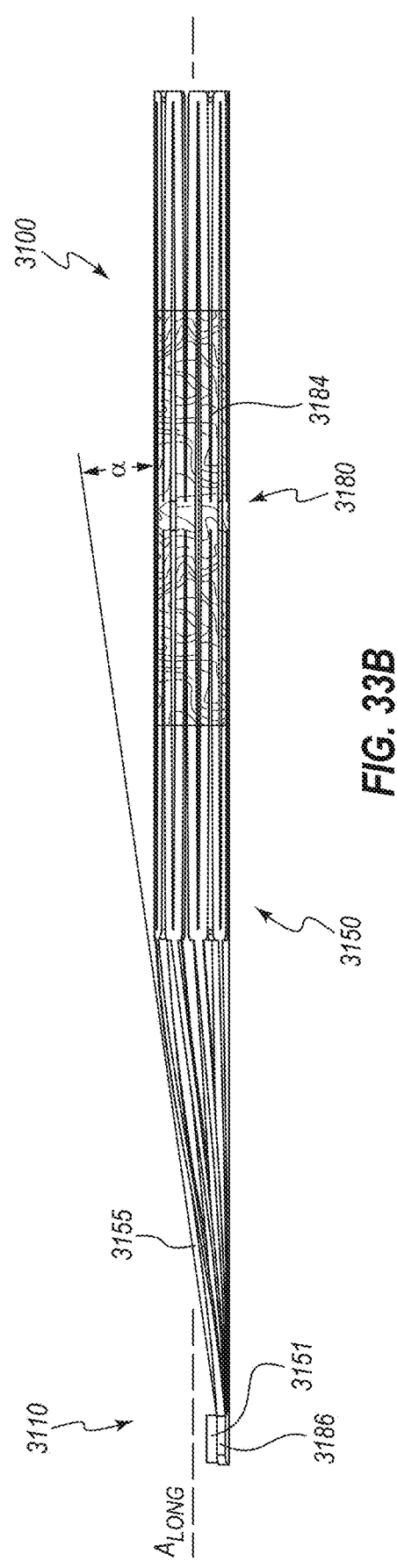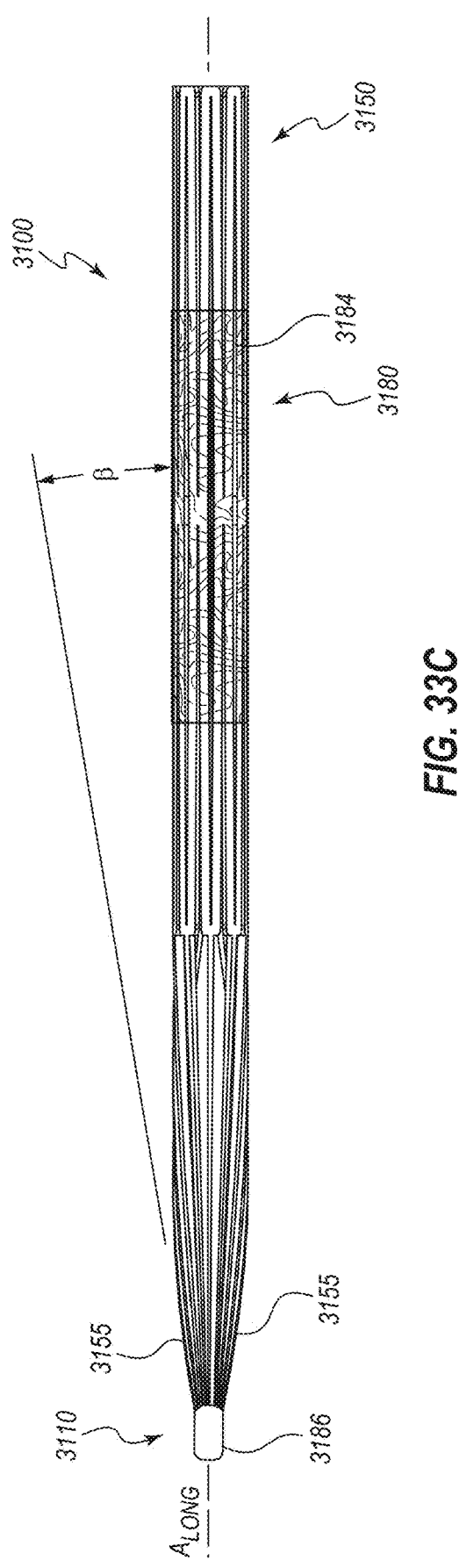
FIG. 33B
FIG. 33C

OBESITY TREATMENT DEVICES, SYSTEMS, AND METHODS

CROSS-REFERENCE TO RELATED APPLICATIONS

Pursuant to 35 U.S.C. § 120, this application is a continuation-in-part of prior U.S. patent application Ser. No. 15/853,793, filed on Dec. 23, 2017, titled OBESITY TREATMENT DEVICES, SYSTEMS, AND METHODS, which claims the benefit of U.S. Provisional Patent Application No. 62/438,569, filed on Dec. 23, 2016, titled Treatment of Obesity and Diabetes, and also claims the benefit of U.S. Provisional Patent Application No. 62/526,007, filed on Jun. 28, 2017, titled Treatment of Obesity and Diabetes; further, this application claims the benefit under 35 U.S.C. § 119(e) of U.S. Provisional Patent Application No. 62/690,878, titled OBESITY TREATMENT DEVICES, SYSTEMS, AND METHODS, filed on Jun. 27, 2018, and of U.S. Provisional Patent Application No. 62/849,169, titled OBESITY TREATMENT DEVICES, SYSTEMS, AND METHODS, filed on May 17, 2019; the entire contents of each of the foregoing applications are hereby incorporated by reference herein.

BACKGROUND

Obesity is a common and important issue in the U.S. and worldwide that involves over 500 million obese people total. This number includes approximately 35-40% of adults in the U.S. with an associated cost of approximately $315 billion dollars for obesity-related diseases. At present, the global economic impact of obesity and related diseases approaches $2 trillion, much of that due to shortened lifespans, obesity-associated comorbidities, and lost productivity. Among other diseases, obesity is directly related to heart disease and diabetes. Diabetes affects 382 million people worldwide, and up to 30 million adults in the U.S., with a U.S. cost of about $245 billion and an approximate worldwide cost of $600 billion per annum. Effective treatment of obesity in many cases can reverse diabetes and ameliorate heart disease, so effective treatment of obesity is an urgent medical need.

There are many medical, surgical, and device approaches to treating obesity, but none is ideal. There are at least 30 drugs on the market for obesity, but these have limited effects. There are at least five surgical procedures for weight loss, including, among others, Roux-en-Y gastric bypass, vertical sleeve gastrectomy, bilio-pancreatic diversion, gastric banding, and vagal nerve pacing. Surgery is effective, and multiple randomized, controlled trials have demonstrated profound weight loss (up to 60% at 5-year follow-ups), reduced mortality, and resolution of diabetes for the various surgical techniques. Surgery, however, is highly invasive, with associated mortality and morbidity, important pathophysiologic side-effects, and substantial cost. Major complications are common (up to 10%), including leaks, need for reoperation and revision, and malabsorption with multiple associated nutrient deficiencies are routinely seen. Most insurance companies do not routinely cover bariatric surgery, and most patients cannot afford the cost, so these procedures are underutilized.

There are also numerous endoscopic, and non-endoscopic, approaches to treating obesity, including endoscopic suturing devices (endoscopic sleeve gastrectomies), barrier/liner devices (e.g., those of GI dynamics, of Boston, Mass., or ValenTx, of Maple Grove, Minn.), and devices that ablate duodenal mucosa (e.g., those of Fractyl, of Lexington, Mass.). These approaches are safer and less invasive than surgery, but are not as efficacious as they yield more limited weight loss and are of only limited durability. Intragastric balloons (e.g., Orbera®, of Apollo Endosurgery, or ReShape™, of ReShape Medical Inc.) for treating obesity also exist. These are solid balloons that are placed and inflated in the stomach to cause gastric distention and create a sense of fullness and satiety.

Embodiments disclosed herein address, resolve, ameliorate, and/or eliminate one or more of the disadvantages of known approaches for treating obesity and illnesses related thereto. For example, various methods, systems, and devices for treatment of obesity are achieved in less invasive manners, are more economical, are safer, are more effective, and/or are advantageous in other or further ways than one or more of the previously known approaches.

SUMMARY

Embodiments of devices, systems, and methods that can be used in the treatment of obesity and related illnesses are disclosed. In some embodiments, the cecum of an obese patient is enlarged to a pathophysiological size for a therapeutically effective period. The distention may be achieved by introduction of an object that is of foreign origin relative to the body of the patient into the cecum of the patient. In some embodiments, the distention is achieved by a medical device that transitions from an undeployed state, in which the medical device is introduced into the cecum of the patient, to an expanded state in which the medical device distends the cecum to the pathophysiological size. In various embodiments, the expanded device can trigger a colo-gastric brake in the patient, can yield acute inflammation, chronic inflammation, fibrosis and/or wall thickening, and/or can alter the microbiome of the cecum. One or more of these phenomena can individually and/or collectively contribute to weight loss in a patient. Other embodiments are also disclosed.

DESCRIPTION OF FIGURES

The written disclosure herein describes illustrative embodiments that are non-limiting and non-exhaustive. Reference is made to certain of such illustrative embodiments that are depicted in the drawings, which are not necessarily to scale. The dimensions of various features may be arbitrarily expanded or reduced, or may be altered for clarity or to facilitate the corresponding discussion. In the accompanying drawings:

FIG. 22A is a side elevation view of another embodiment of an expandable medical device that is configured for placement in the cecum of a patient to treat obesity, the medical device being depicted in a contracted or undeployed state;

FIG. 30B being a plan view thereof, with the distal end (from the perspective of the gastrointestinal tract) being in the foreground and the proximal end being in the background;

FIG. 30C being an enlarged end-on, substantially plan view of the proximal end thereof;

FIG. 30D being an enlarged perspective view of the proximal end thereof;

FIG. 30E being an enlarged substantially end-on, perspective view of certain strut portions thereof;

FIG. 30F being an enlarged elevation view of certain of the strut portions; and

FIG. 30G being an elevation view of a front half thereof, this view including tracings of two force-application lines or regions that each extend about a full periphery of the device;

FIG. 32A is a perspective view of another embodiment of an expansion medical device that includes a covering—specifically, a cover attached to a frame—and is configured for deployment in the cecum of a patient, the medical device being depicted in a low-profile, collapsed, or undeployed configuration;

FIG. 32B is an elevation view of the expansion medical device of FIG. 32A depicted in an expanded or deployed configuration;

FIG. 33B is an elevation view of the undeployed medical device of FIG. 33A;

FIG. 33C is a plan view of the undeployed medical device of FIG. 33A;

DETAILED DESCRIPTION

Figure 1:
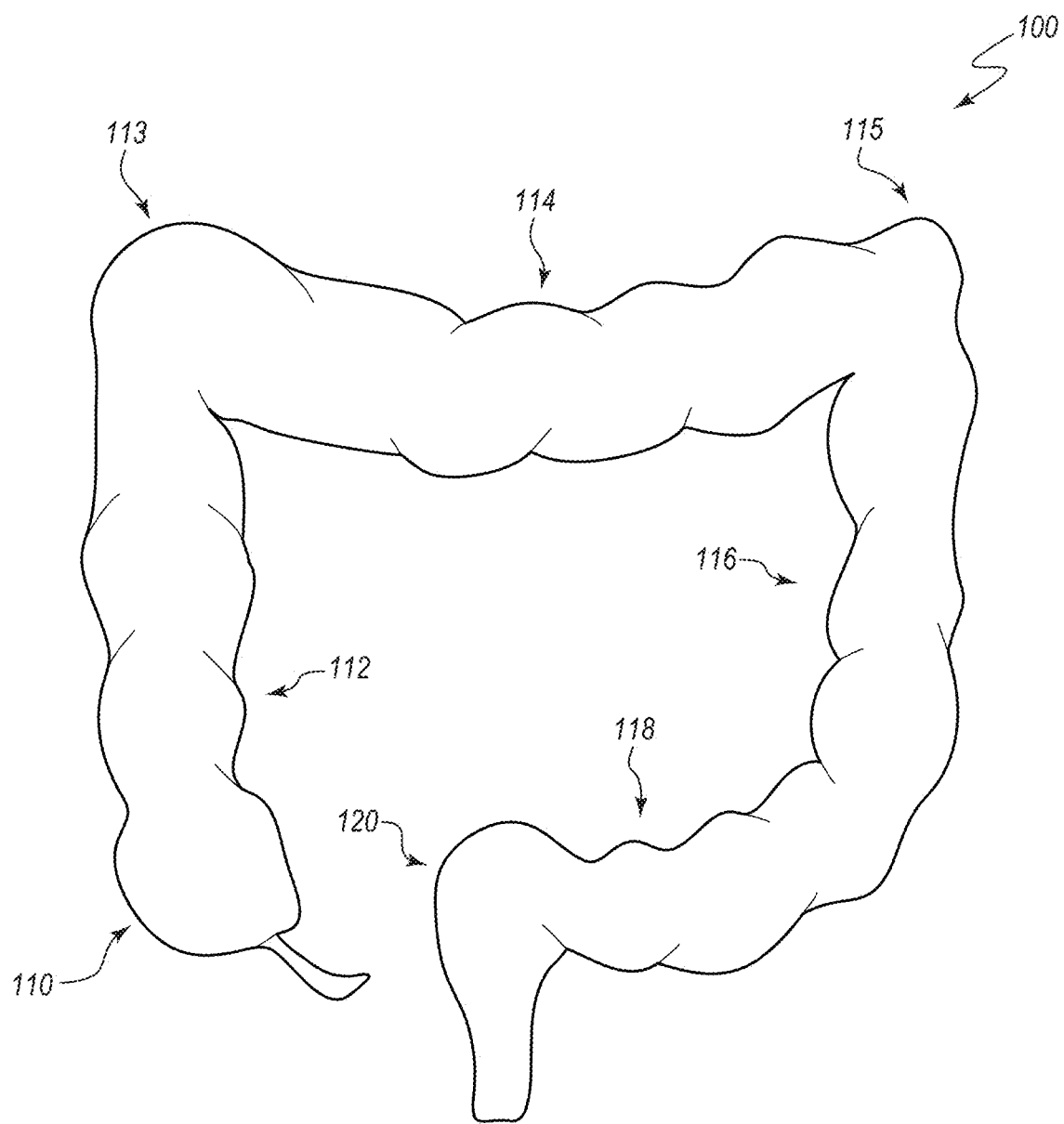
FIG. 1 is an elevation view of a colon in a natural or non-distended state.

Certain embodiments disclosed herein make advantageous use of a natural physiological response to distention of the cecum to treat obesity and illnesses related thereto. In particular, certain embodiments mimic the effects of bowel obstruction and bowel distention and/or reproduce the normal physiological "colo-gastric brake," which is described further below. For example, certain embodiments artificially distend the cecum without causing an actual obstruction (or complete obstruction) of the bowel. Stated otherwise, various embodiments involve distention of the cecum to trigger a colo-gastric brake and/or a loss or reduction of appetite associated therewith, while permitting normal flow of material through the cecum while the cecum is thus distended. Triggering of the colo-gastric brake and/or a loss or reduction of appetite may be attributable to one or more other or further phenomena as a result of the presence of an inserted or implanted distention device.

Bowel obstructions of the colon or small intestine, that are either partial or complete, are poorly tolerated by humans (and other animals) and can cause loss of appetite (anorexia), nausea, and/or vomiting. This occurs because, with obstruction of any portion of the bowel (including obstruction of the bile ducts or pancreatic ducts), there can be both local distention of said organs and/or distention of the entire proximal bowel or portions of the more proximal bowel. Bowel distention in any part of the tubular gastrointestinal tract (small intestine, colon, etc.) drives chemical, hormonal, and neurological signaling that is the direct cause of the loss of appetite, nausea and vomiting, that occurs when any portion of the bowel is obstructed. Various gradations of symptoms can occur depending on exactly where the distention occurs, how distended the bowel becomes, and how rapidly the distention occurs.

Sometimes physiologic, non-obstructing distention of portions of the bowel that can occur as part of normal life can have effects similar to a bowel obstruction. As an example, when the colon in general, or, for example, the cecum (the most proximal portion of the colon) specifically, is distended during or following a meal as part of normal physiologic processes, appetite can be suppressed. Also, if a person has constipation, which can yield colon distention with stool, appetite can be suppressed. Or even during passage of stool following a large meal, such as with rectal distention, there can be suppression of appetite, and in rare cases, nausea or vomiting.

These effects are the normal physiologic response to colon, cecal, or rectal distention, which signals satiety to a person to prevent overeating. In part, this satiety signaling occurs because of the known "colo-gastric brake." The colo-gastric brake is a normal physiologic mechanism that slows or delays gastric emptying as the colon, cecum, or rectum distends. When this occurs, signals are sent to the brain and other parts of the gastrointestinal tract to both suppress appetite and decrease food intake, and also to delay gastric emptying which also suppresses appetite. As the cecum and/or more distal colon and rectum empty, the "brake" mechanism resolves, and stomach emptying and appetite return to normal. Similar braking can occur with cecal or rectal distention alone and/or distention of other portions of the colon or even small bowel. These braking effects may be referred to generally herein as "intestinal-gastric braking," or as an "intestinal-gastric brake." The term intestinal-gastric brake includes the colo-gastric brake mechanism just described. In further instances, it can be particularly desirable to trigger an intestinal-gastric brake without—or without significantly, completely, or otherwise disadvantageously—obstructing the bowel. Certain embodiments disclosed herein thus achieve the advantages of intestinal-gastric (e.g., colo-gastric) braking for obesity treatment—such as, for example, appetite suppression—without triggering one or more of the disadvantageous effects of bowel obstruction. The intestinal-gastric or colo-gastric braking can result specifically from distention of the cecum, and may thus be referred to herein as cecal-gastric braking. Stated otherwise, certain embodiments can give rise to a colo-gastric brake due to alterations to the cecum, which may alternatively be referred to herein as triggering a cecal-gastric brake or as cecal-gastric braking.

Various embodiments disclosed herein differ significantly from intragastric balloons (from manufacturers like Orbera, Reshape Medical, etc.) that are used to treat obesity. Intragastric balloons are solid balloons, meaning that they do not define any openings or channels through which materials can pass, that are placed and inflated in the stomach to cause gastric distention and create a sense of fullness and satiety. It should be noted that use of such solid balloons is limited to placement in the stomach only. The stomach is a distensible, and uniquely J-shaped gastrointestinal organ that can accommodate a solid balloon or other structure with limited fear of obstruction.

Placement of a solid balloon in more tubular shaped parts of the gastrointestinal tract, such as the small bowel or colon, of a sufficient size to distend the bowel may have a high likelihood of causing an emergency bowel obstruction outside of the stomach. It should also be noted that intragastric solid balloons are also not particularly efficacious for weight loss, since the great distensibility of the stomach allows patients to eat significant portions despite the presence of a balloon. Solid gastric balloons also have limited durability. They cannot be spontaneously passed into the more distal tubular bowel for fear of causing an emergency bowel obstruction, hence they need to be removed endoscopically.

One proposal for treating obesity and its comorbidities involves placement of one or more devices in the rectum and/or the small intestine to provide outward pressure to these specific regions of the gastrointestinal tract, but without marked distention thereto (i.e., with only minimal distention thereof that is insufficient to distort the normal architecture of these regions and, allegedly, insufficient to cause the patient discomfort), to evoke therapeutically useful responses. The focus of the proposal is to pressurize the small intestine or rectum, with only minimal distention, due to these portions of the gut being less compliant than either the stomach or compliant storage regions of the large intestine (i.e., the cecum). In particular, this proposal is based on an observation that the small bowel especially appears to exhibit autoregulation of its diameter, in that distention of local parts is opposed via a localized contractile response.

According to the proposal, a device is used to impart an expansile or other outward physical/mechanical force upon the rectum or the small intestine. Importantly, the proposal indicates that it is the outward pressure exerted by the device itself that evokes clinically meaningful responses, but stipulates that the outward pressure of the device should not be so great as to distort the normal architecture of the section of the small intestine (e.g., the duodenum), in which the device may be deployed. This is because expansion of non-compliant regions of the small or large intestine will signal a bowel obstruction and cause intolerable side effects, such as, for example, nausea or vomiting.

If the proposed devices were used to not only pressurize but actually significantly distend sections of the inelastic small bowel or most areas of the colon which, unlike the cecal portion of the colon, are typically non-distensible, it would almost certainly cause a patient great discomfort. With respect to the proposed small-intestinal devices, the consistent pressure imparted to the small intestine would almost certainly lead to nausea and/or other physiological ailments. With respect to the proposed rectal devices, the consistent pressure imparted thereby would yield the undesired side-effects of a consistent urge to defecate and tenesmus, which is rectal discomfort associated with urgency. In contrast, cecal distention as disclosed herein does not typically yield urgency to defecate or tenesmus. The foregoing and/or other drawbacks associated with certain proposed small-intestine and rectal devices are overcome by embodiments of devices, systems, and methods disclosed herein that are specially configured for use in the cecum.

As will be apparent from the present disclosure, certain embodiments herein vary significantly from the proposed small-intestinal- or rectum-based devices and methods and, further, overcome complications associated therewith. For example, whereas the small-intestinal- and rectum-based devices would operate on significant pressurization, rather than distention, of bowel segments, certain embodiments of the present disclosure are directed to an opposite approach—specifically, marked distention of a specific, highly elastic or expansible segment of the bowel (i.e., the cecum) that, because it is physiologically distensible, may be achieved without significant pressurization.

Stated otherwise, according to LaPlace's law, the wall tension of a vessel (e.g., cylindrical or spherical) is directly proportional to the product of the pressure within the vessel and the radius of the vessel. Vessels that are resistant to radial expansion, such as the small intestine, thus can be pressurized without significant changes in size. A far different approach, however, is to instead increase the tension in the wall of an expandable vessel (e.g., the cecum) to increase the radius of the vessel, but without significantly altering the internal pressure on the vessel wall. That is, certain embodiments herein can increase cecal wall tension by increasing cecal radius without significantly increasing pressure on the cecal wall (e.g., applying relatively low pressure to the cecal wall) which may maintain intraluminal pressure within a normal range or elevate intraluminal pressure only slightly. Such an approach is far different from purposefully increasing the intraluminal pressure of the small intestine or rectum, while maintaining the radius thereof substantially constant, to thereby increase wall tension.

As a further example, certain embodiments disclosed herein expand the cecum by large amounts, including to a pathophysiological size. Some embodiments (e.g., other or further embodiments) can permit the cecum to naturally expand to an even larger size, beyond the pathophysiological size, and because the cecum is naturally distensible, the devices may partially or completely discontinue tensioning the cecum during these periods of natural enlargement. Other and further embodiments are also disclosed.

In general, certain configurations and methods described herein can provide for safer and more efficacious non-surgical means to treat obesity that are minimally invasive and readily and/or relatively cheaply be applied to the majority of obese subjects. These and/or other advantages of one or more embodiments will be apparent from the discussion herein. In some examples, the cecum is distended to a pathophysiologic diameter to exaggerate the effects of normal, physiologic post-prandial cecum distention without actually causing bowel obstruction or causing the symptoms of obstruction (e.g., pain or nausea).

In certain embodiments, an object or structure is placed within the cecum of a patient so as to distend the cecum. Such distension can trigger a colo-gastric brake (e.g., a cecal-gastric brake) in the patient. The object or structure may include or define one or more passageways through which material can pass. In particular, the passageway(s) can be sufficiently large to permit passage therethrough of material (e.g., air, semiliquid, liquid, semisolid, or solid materials) that would otherwise pass through the cecum in the absence of the object or structure. The passageway(s) may permit such passage substantially without obstructing the natural passage of the material, and thus may cause distention of the cecum without obstructing the bowel. In some embodiments, the one or more passageways are sized and/or oriented so as to ensure that material that passes through the ileocecal valve can readily pass into the cecum. For example, in some embodiments, the structure or object includes a sidewall that at least intermittently contacts the cecum to enlarge the cecum. The structure or object may bear against, abut, apply outward force to, press on, push on, provide an expansion bias to, increase tension in, or otherwise influence the cecal wall to expand the cecum. The sidewall can define a primary passageway that may be aligned with a longitudinal axis of the cecum, and the sidewall can include large secondary passageways (e.g., openings) and/or or narrow struts or other supports or structural features that are configured not to block, or to only minimally block, passage of material into the cecum through the ileocecal valve.

In certain embodiments, the object or structure includes an expandable structure that is introduced into the cecum in an unexpanded state. The structure is expanded within the cecum to distend the cecum. When in the expanded state, the structure can define one or more passageways, which can be pathways through the device and/or between portions of the device that may include, or be in fluid communication with, one or more openings, perforations, channels, paths, etc. through which material can enter, pass through or by, and/or exit the structure. In some embodiments, the passageway is not entirely enclosed by the structure. Stated otherwise, the structure may define only a portion of the passageway, and may cooperate with the wall of the cecum to define a fully encircled or encompassed pathway through which material passes. The passageway(s) at least partially defined by the structure when in the expanded or deployed state allow gas, semiliquid, liquid, semisolid and/or solid material to pass through, thus avoiding actual obstruction of the bowel. In various embodiments, the structure may be secured to the cecum wall. For example, the structure may be placed in tension against the wall, may be anchored to the wall, may be adhered to the wall, may be integrated with or into the wall over time (e.g., via tissue ingrowth), and/or may otherwise be secured to the wall. In other embodiments, the structure may be free floating within the cecum. The structure can be sized or otherwise configured to not migrate to more distal regions of the large intestine. Stated otherwise, the structure can be applied to or reside in the cecum.

In some examples, the object or structure includes multiple components that are assembled within the cecum. For example, the structure may be formed of multiple filler components and/or one or more adhesives. The structure may be assembled within the cecum, such as by adhering filler components to the cecum lining and/or to each other. As more and more filler and/or adhesive is applied, the cecum wall can be distended to a variable degree. In some instances, an adhesive can include a mucosal adhesive that can adhere, or partially adhere, to the inner lining of the bowel and/or may additionally adhere filler components to each other. In other or further instances, an adhesive may be used to adhere the filler components to each other. For example, in some instances, the components are adhered only to each other without adhering to the cecum. Accordingly, the structure may comprise a conglomerate of the filler components, and the conglomerate can be adhered directly to the lining of the bowel or, in other instances, the conglomerate can be freely mobile in the lumen of the cecum. For example, rather than being adhered directly to the cecum, the conglomerate can be free floating within the cecum. The conglomerate can be sized or otherwise configured to not migrate to more distal regions of the large intestine.

FIG. 1 depicts a large intestine or colon 100 in a natural state. The colon 100 includes multiple sections. The most proximal section of the colon 100 is the cecum 110, which receives material from the small intestine (specifically, the ileum). Distal to the cecum 110 is the right or ascending colon 112, the hepatic flexure 113, the transverse colon 114, the splenic flexure 115, the left or descending colon 116, the sigmoid colon 118, and the rectum 120. Stool material or chyme that passes through the colon 100 is substantially in liquid or semiliquid form within the cecum 110 and the ascending colon 112, and progressively solidifies along more distal tracts of the colon 100.

Figure 2:
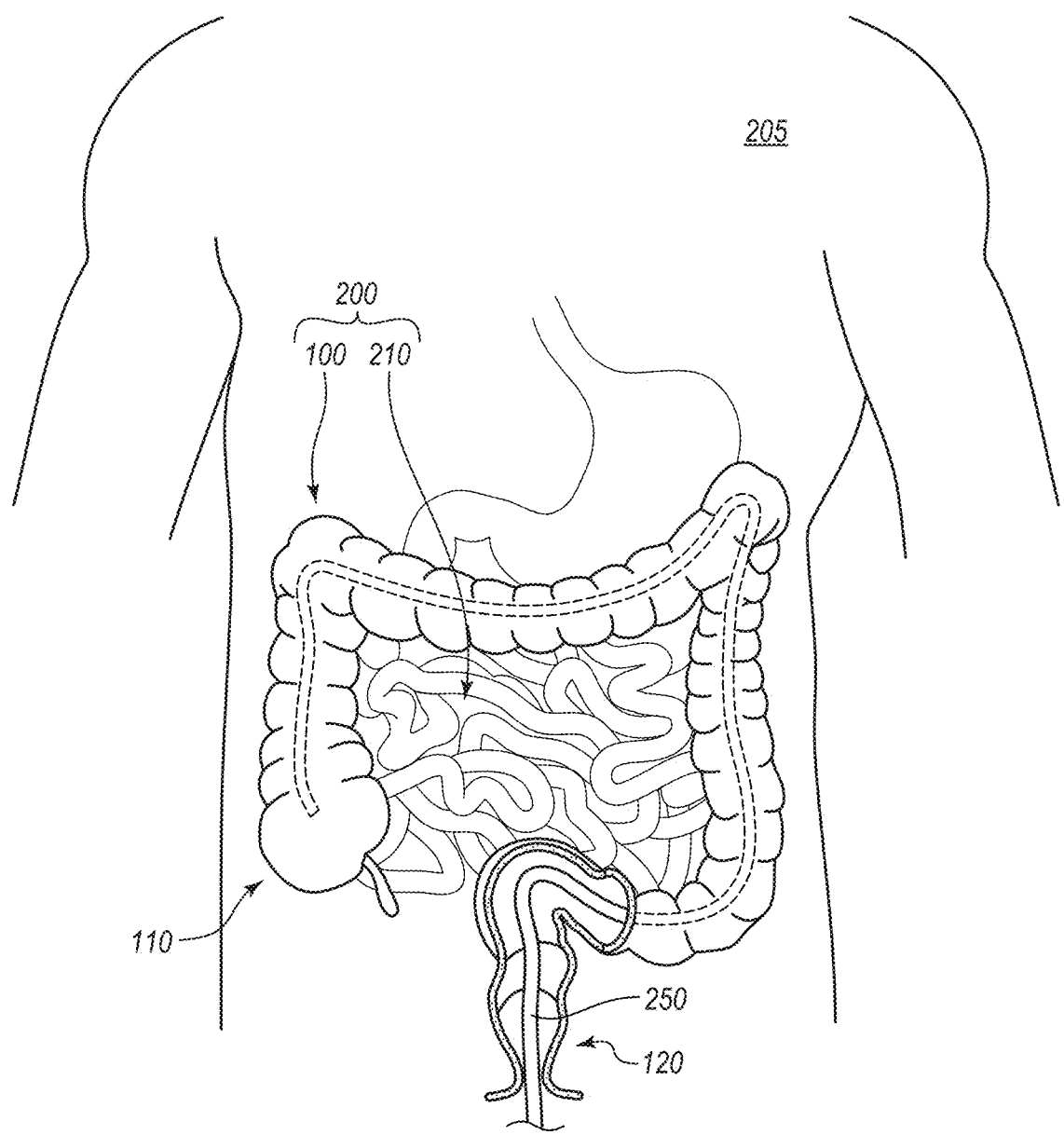
FIG. 2 is a cutaway elevation view of a patient showing the bowel of the patient, wherein a stage of an illustrative method for treating obesity of the patient in which an endoscope has been advanced to the cecum of the patient is depicted.

FIG. 2 depicts the bowel 200 of a patient 205. The bowel 200 includes the small intestine 210 and the colon 100.

Figure 3:
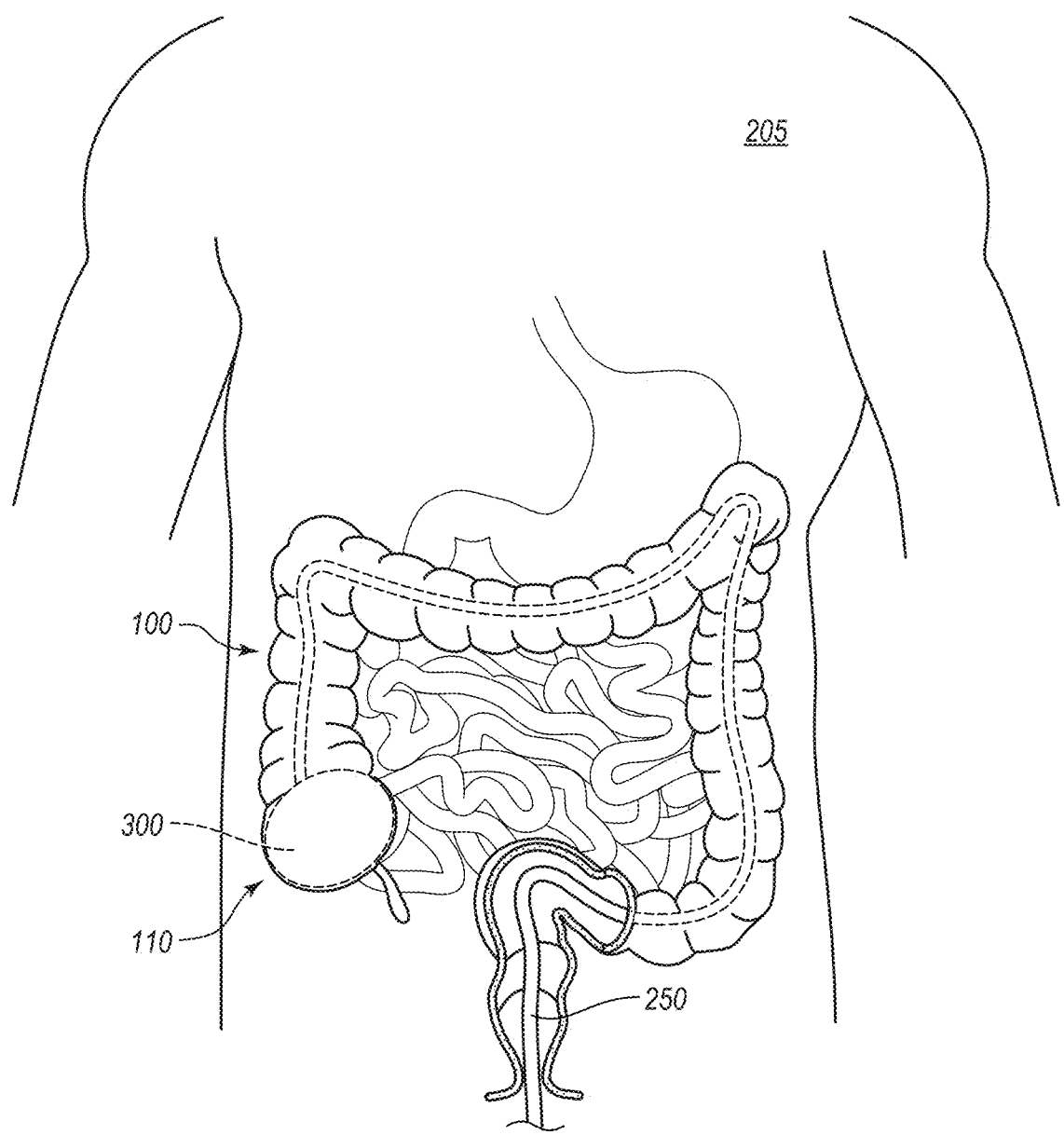
FIG. 3 is another cutaway elevation view of the patient such as that of FIG. 2 showing another stage of the method in which a structure has been implanted in the cecum of the patient.

FIGS. 2 and 3 depict separate stages of a method for treating obesity of the patient 205. The patient 205 may be suffering not only from obesity, but potentially from other diseases or illnesses caused by, tied to, or otherwise related to obesity (e.g., comorbidities of obesity). For example, amelioration or resolution of the underlying obesity condition could ameliorate or resolve one or more other conditions of the patient 205. Accordingly, although the method may be termed as a method for treating the obesity of the patient 205, the method may simultaneously also be a method for treating one or more of the other conditions of the patient 205, such as, for example, diabetes mellitus, nonalcoholic fatty liver disease, nonalcoholic steatohepatitis, etc. For example, a method of treating obesity of the patient 205 may likewise, further, alternatively, or independently be termed as a method of treating diabetes mellitus, a method of treating steatohepatitis, and/or a method of treating some other condition that is treatable by reducing the weight (e.g., the excess weight) of the patient. Thus, any mention herein of devices, systems, or methods related to the treatment of obesity can additionally or alternatively apply to the treatment of such other conditions.

As shown in FIG. 3, the illustrated method includes the placement of a medical device 300, which may also or alternatively be referred to herein as a structure or object 300, which is of foreign origin relative to the patient 205, within the bowel 200. The term "of foreign origin relative to the patient" is used herein to describe items, whether naturally occurring or synthetic, that originate externally from the patient. Thus, the objects or structures may themselves be naturally occurring items (for example, nutrients; bacteria; natural filler materials, such as natural fibers; etc.) or artificial items (for example, non-naturally occurring or synthetic materials, such as synthetic fibers; stent-like structures, balloons, or cages formed of synthetic materials; etc.), but the items originate external to the patient 205. For example, stool that might distend a portion of the bowel is not an object of foreign origin relative to the patient 205, due to the generation or creation thereof within the patient, whereas a medical device that is introduced into the bowel 200 for distention in any suitable manner is an object of foreign origin relative to the patient. Stated otherwise, chyme or stool are not objects of foreign origin relative to the body—instead, these materials or compositions are developed within the body as food is digested by the body—whereas the food as originally ingested is an object of foreign origin relative to the body.

The object 300 can be introduced into a specified region of the patient 205 by non-natural mechanisms. In such instances, the mechanisms are separate from physiological processes that are naturally conducted by the body (e.g., material transport through the digestive tract), and may be achieved or controlled by a medical practitioner. For example, placement of the object 300 within the bowel 200 may be achieved via an endoscope, catheter, guidewire, and/or other device that has been advanced into the bowel by a medical practitioner. Other placement methods or mechanisms are also possible.

With reference again to FIG. 2, in the illustrated method, an endoscope 250 is introduced through the rectum 120 of the patient 205 and advanced through the bowel 200 into the cecum 110. The advancement may be termed "proximal" advancement, relative to the patient, as the endoscope 250 is being advanced to regions that are more proximal within the bowel. Alternatively, the advancement may be termed "distal" advancement relative to the practitioner who is performing the procedure, as the distal tip of the endoscope 250 is being advanced away from the practitioner. The terms "proximal" and "distal" are thus used herein in manners that should be clear from the context in which they arise.

The term "patient" is used herein broadly to mean any subject within whom or within which any of the medical devices described herein are positioned and/or on whom or on which any of the methods described herein are performed. A patient may be an animal subject, such as a mammal (human, canine, etc.).

The endoscope 250 may, specifically, be a colonoscope, and may be advanced to the cecum 110 in manners typically employed in colonoscopy procedures. The endoscope 250 may include an internal lumen or instrument channel (see FIG. 5A, lumen 262), which may also be referred to as a working channel, biopsy channel, or tool channel, via which the object 300 can be introduced into the cecum 110.

With reference again to FIG. 3, the structure 300 is shown within the cecum 110 after having been advanced through the instrument channel of the endoscope 250 and assembled, expanded, and/or otherwise oriented within the cecum 110 so as to distend the cecum 110. The structure 300 distends the cecum 110 sufficiently to trigger a colo-gastric brake (e.g., a cecal-gastric brake) in the patient 205. Moreover, the structure 300 may permit passage of material through the cecum 110, such as in manners discussed below. For example, the structure 300 may define one or more passageways through which material passes. Specifically, the one or more passageways permit passage therethrough of material that would otherwise pass through the cecum, in the absence of the structure 300. Accordingly, the structure 300 can distend the cecum 110 without obstructing the natural flow or passage of material through the cecum 110. The structure 300 thus may trigger physiological responses to distention, without triggering one or more physiological responses that might otherwise accompany such distention due to an obstruction of the bowel lumen.

After placement, or implantation, the structure 300 is then left in the cecum 110 while distending the cecum 110. In some instances, the distention may be partial. For example, in some instance, the structure 300 may contact, abut, bear on or against, push, press, urge, force outwardly, or otherwise provide an expansion bias to, and thus expand, only a portion of a periphery of the cecum 110. In other instances, the distention may be complete. For example, the structure 300 may contact and provide an expansion bias to an entire periphery of the cecum 110 (e.g., may contact and expand an entire inner circumference of the cecum 110).

In some instances, the distention may be continuous. For example, the structure 300 may distend the cecum 110 by a constant amount, which amount may be sufficient to retain the cecum 110 in the expanded orientation independent of conditions that would otherwise cause natural fluctuations in the size of the cecum 110 over time. By way of illustration, in some embodiments, the structure 300 is or includes an expandable stent-like device which, when expanded, is placed in tension against an inner wall of the bowel 200. In other embodiments, the structure 300 is or includes an expandable cage, ball, balloon, or other similar mechanism, such as described below. Once expanded, the device can maintain a substantially constant size and configuration, and may maintain the cecum 110 in a substantially constant distended state. The device may distend the cecum 110 by a sufficient amount such that if the cecum 110 encounters natural conditions that would cause the cecum 110 to expand, in the absence of the device, the cecum 110 nevertheless does not expand due to the already enlarged configuration imparted to it by the device.

The term "stent" may be used herein to describe medical devices that resemble stents in one or more aspects, such as one or more of like materials, similar overall appearance, analogous methods of deployment and/or retraction, etc. Stents, however, are generally used to restore an abnormally constricted, damaged, or otherwise narrowed passageway to a natural size thereof. Stent-like devices disclosed herein, however, are configured to enlarge the cecum relative to a natural or relaxed state. Indeed, certain embodiments are specifically configured to transition the cecum from a natural, normal, or relaxed state to an enlarged or expanded state, and indeed, in various embodiments, to a pathophysiological size (as this term is defined below). Accordingly, the term "stent" may be used herein for convenience, but should be interpreted in a manner consistent with the present disclosure.

In other or further instances, the structure 300 may intermittently distend the cecum 110, such as by permitting fluctuations in the size (e.g., a diameter) of the cecum 110. For example, the structure 300 may distend the cecum 110 to a minimum distended state (i.e., an enlarged state that becomes the new minimum size of the cecum 110), but may permit the cecum 110 to fluctuate naturally to larger distended states when particularly distending conditions arise in the cecum 110. In certain of such instances, the structure 300 is secured to the wall of the cecum 110 so as to fluctuate in size in tandem with the cecum 110. For example, in certain embodiments, the structure 300 comprises a stent (e.g., a stent-like device, as previously discussed) that is configured to define a minimum expanded size (e.g., minimum diameter), but can expand beyond the minimum size to larger sizes. The stent may, for example, be a self-expanding and/or or resilient (e.g., elastically resilient) stent that generally contacts and provides an expansion bias to the cecum 110 to achieve a state of equilibrium, at which the cecum 110 is distended. When the cecum 110 expands beyond this distended state due to natural conditions within the cecum 110, such as increased pressure therein, the stent may likewise increase in size due to its resilient outward bias and/or the reduced inward force on the stent from the cecum 110 due to the natural conditions that tend to enlarge the cecum 110. In some embodiments, the stent may be delimited to fluctuate to no greater than a maximum size (e.g., a maximum diameter beyond which the stent may extend no further). Accordingly, if the cecum 110 expands beyond this maximum size of the stent, and the stent is not secured to the cecum wall, the stent may temporarily no longer contact or press outwardly against the cecum 110.

In other instances, the maximum size of the stent may be such that even under such natural conditions that tend to enlarge the cecum 110, the stent can maintain contact with and bear against the cecum 110. In various embodiments, contact is maintained between the stent and the cecum 110 due to one or more of a resilient outward bias of the device; tissue ingrowth into the device; clips (e.g., hemoclips), sutures and/or any other suitable attachment features that connect the stent to the device; etc. In instances where the stent-like device continues to bear outwardly against the cecum 110 throughout such periods of natural distention, the device may be said to provide continuous distention of the cecum 110.

In other instances, in which the structure 300 intermittently distends the cecum 110, the structure 300 may not secured to the wall or lining of the cecum 110 in a manner that would cause the structure 300 to fluctuate in size in tandem with the cecum. For example, the structure 300 may define a substantially constant size as it distends the cecum 110 in the minimum distended state, and may not be capable of expanding beyond (or significantly beyond) this size. Accordingly, as the cecum 110 expands naturally to a more enlarged state, the structure 300 may become free floating within the cecum 110. The structure 300 may, for example, rotate about a longitudinal axis and/or one or more lateral axes and/or may translate longitudinally within the cecum 110.

By way of illustration, in some embodiments, the structure 300 comprises a stent (e.g., stent-like structure), ball, cage, balloon, or other structure that is expandable to a fixed size. After the structure 300 has been expanded in the cecum 110 to this fixed size to distend the cecum 110 to an initial distention state (which may also be referred to as a minimum distention state, a treatment distention state, etc.), the structure 300 may remain substantially fixed relative to the cecum 110 under normal conditions, such as due to frictional interference between an outer surface of the structure 300 and the lining of the cecum 110. However, when particularly distending conditions arise in the cecum 110, the cecum 110 may naturally distend to a size greater than that caused by the expanded structure 300. As the structure 300 is not fixedly secured to the cecum 110, the structure 300 may be free to float within the cecum 110 and make intermittent contact therewith. The structure 300 thus may axially and/or laterally rotate, longitudinally and/or laterally translate, "bounce around," and/or otherwise move within the cecum 110. The structure 300 may be desirably sized and/or otherwise configured (e.g., provided with a tapered end or tapered ends, be sized significantly larger than more distal portions of the large intestine, etc.) that can prevent the structure 300 from migrating from the cecum 110 to more distal portions of the colon 100 under such circumstances. In some instances, at least some portion of the structure 300 substantially always remains in contact with the cecum 110, even during such periods of further enlargement of the cecum 110.

In view of the foregoing, the structure 300 may continuously and/or intermittently trigger the colo-gastric brake. In many instances, the periods of excessive enlargement of the cecum 110 may be relatively infrequent, such that the structure 300 acts to expand the cecum 100 during the majority of the time that it has been implanted or deployed (e.g., greater than 50, 60, 70, 80, 90, or 95 percent of the time it has been implanted or deployed). Distention of the cecum 110 in this manner, which is substantially constant (although sometimes the distension is due only to the outward force provided by the structure 300 and other times may be due at least in part to intermittent or temporary natural distention events within the cecum 110, as just discussed), can reduce an appetite of the patient 205 and/or otherwise reduce a food intake of the patient 205. Over time, the reduced food intake of the patient 205 can result in weight loss for the patient. The structure 300 can remain within the bowel 200 of the patient 205 for a therapeutically effective period.

In some instances, the structure 300 can remain within the bowel 200 for at least a therapeutically effective period. Or stated otherwise, the structure 300 may remain within the patient 205 beyond a therapeutically effective period. For example, in some instances the patient 205 may lose an amount of weight that is effective in treatment of obesity and/or some other related disease, yet the structure 300 may nevertheless remain within the patient. The structure 300 may, in such instances, contribute to further therapeutic weight loss. It may be said that the structure 300 remains in place for an extended therapeutically effective period and/or for an additional therapeutically effective period. In some instances, the structure 300 may substantially ameliorate or even cure a condition, such as obesity (i.e., the patient's BMI may drop below 30.0), and the structure 300 may nevertheless remain in place thereafter. In some instances, the structure 300 may be implanted or otherwise positioned within the cecum of the patient 205 indefinitely, with no planned removal.

As used herein the term "therapeutically effective period" denotes a period of time over which a therapeutically or clinically significant, or otherwise desired or targeted, amount of weight loss is achieved for the patient 205. Thus, the period may be therapeutically effective in the treatment of obesity, generally defined as a body mass index (BMI) of 30.0 or higher, and/or one or more related diseases of the patient due to weight reduction of the patient 205 achieved during its duration. In various instances, the therapeutically effective period is an amount of time sufficient to achieve a total weight loss of the patient 205 of no less than 5, 10, 15, 20, 25, 30, 35, 40, 45, or 50 percent. In other or further instances, the therapeutically effective period is an amount of time sufficient to achieve an excess weight loss of no less than 10, 15, 20, 25, 30, 35, 40, 50, 60, 70, 80, or 90 percent. As used herein, the term "excess weight loss" refers to a reduction of excess weight, the excess weight being calculated as a difference between the patient's actual body weight at the time the structure 300 is first introduced into the patient 205 and a target healthy weight of the patient. The target healthy weight of the patient can be determined in any suitable manner. For example, the target healthy weight can be calculated to be the weight necessary to achieve a BMI of 24.9 (i.e., the maximum BMI to be within the normal weight range). In other or further instances, the therapeutically effective period is no less than 2, 3, or 4 weeks; no less than 1, 2, 3, 4, 5, 6, 7, 8, 9, 10, or 11 months; or no less than 1, 2, or 3 years.

Moreover, as previously mentioned, in some instances, a structure 300 can be positioned within a patient indefinitely. The structure 300 can achieve a desired amount of weight loss, and may, in some instances, act prophylactically to inhibit or prevent a patient from thereafter regaining some or all of the weight that was lost.

As previously noted, the structure 300 can be configured to distend the cecum 110 by an amount sufficient to trigger the colo-gastric brake. In some instances, the structure 300 is configured to trigger the colo-gastric brake by expanding the cecum to a pathophysiological size. Due to variations in cecum size from one patient anatomy to another, natural expansibility of the cecum under both natural and unnatural circumstances, and other properties of the cecum, a discussion of what is intended herein by the term "pathophysiological size" is in order.

The cecum 110 is a pouch-like structure that undergoes frequent fluctuations in size. By way of analogy, the cecum 110 may at times behave like a sock or other flexible tube through which different media may pass. Whereas the various regions of the small intestine are generally resistant to expansion and tend to each maintain a generally constant tubular shape and diameter, the cecum is a far more malleable structure that can fluctuate in size depending on the contents therein and/or the pressure of those contents at any given time.

In adult patients, the cecum is typically approximately 6 centimeters in length-due to anatomical variation, however, the cecum is generally no shorter than about 1.5 centimeters and no longer than about 8 centimeters. The cecum generally resides in a collapsed state, but is naturally expansible to a generally open, patent, or non-collapsed state. When in this generally open state, the cecum is typically 4 to 6.5 centimeters in diameter—due to anatomical variation, however, the cecum is generally no smaller than about 1.5 centimeters and no larger than about 9 centimeters when in this non-collapsed state. Accordingly, there can be a significant variation in cecum size from one patient anatomy to another.

The cecum is capable of expanding to larger diameters than those just recited without perforating. In some instances, although rare, the cecum can expand to these larger sizes under natural conditions (e.g., in the absence of a pathological even or condition). For example, the cecum may naturally expand to 5, 6, 7, 8, 9, or 10 centimeters at various times during digestion (e.g., due to passage therethrough of gases, chyme, stool, and/or other materials) without perforating, although typically such expansion rarely exceeds 6 centimeters. Although these larger sizes may, in rare instances, be achieved naturally, it is not natural for the cecum to remain at such enlarged sizes for extended periods. Rather, the cecum returns to a smaller state after the passage of the material that caused the expansion, which passage may take place within a period that is on the order of seconds, minutes, or possibly hours.

More typically, when the cecum expands to such enlarged sizes, it is indicative of an underlying pathological event or condition. In some cases, this can particularly be true if the larger sizes are maintained for relatively long periods. For example, an expanded cecum can result from or otherwise be associated with or indicative of large bowel obstruction. According to Tracy Jaffe et al., "[b]ecause the cecum is the largest diameter of the colon, it requires the least amount of pressure to distend." Large-Bowel Obstruction in the Adult: Classic Radiographic and CT Findings, Etiology, and Mimics, Radiology, Volume 275, Number 3, pp. 651-63, 652 (June 2015). Excessive cecal distension can lead to increased wall tension and, without intervention, could progress to ischemia and necrosis. See id. The size at which the cecum is at risk for perforation from large bowel obstruction ranges in the literature from 9 centimeters to 15 centimeters. See id "In intermittent or chronic obstruction, however, the cecal wall may become hypertrophied and the colon may greatly exceed 10 cm in diameter without perforation. It is important to note that [with respect to perforation,] the exact size of the cecum is less important than the duration and rapidity of cecal distension." Id. As a further example, in certain disease states (e.g., Ogilvie's Syndrome), the cecum may be capable of expanding up to 15 or even 20 centimeters in diameter without perforating.

Accordingly, there can be some overlap of distended cecal sizes that can occur naturally, albeit rarely, and those associated with a pathological event or condition. When the enlarged sizes are reached naturally, however, it is abnormal or unnatural for these sizes to be sustained for significant periods. If and when these enlarged sizes are achieved naturally, they are only intermittent or short-lived. Moreover, certain enlarged sizes, regardless of whether achieved naturally or due to a pathological event, may be associated with perforation risks, although such perforation risks may be lower when there is an underlying pathology, such as a hypertrophied cecal wall due to intermittent or chronic obstruction. Further, certain cecal sizes are clearly abnormally large or unnatural, and if reached, are indicative of an underlying pathological event or condition.

In view of the foregoing, as used herein, the term "patho-physiological size," as applied to the cecum, is meant to denote a relatively enlarged size that (1) is itself irregular, abnormal, or unnatural for the anatomy of a particular patient and/or is generally indicative of an underlying pathological event or condition; (2) can potentially be achieved naturally on an intermittent basis (e.g., on the order of seconds, minutes or hours), but not for a sustained period (e.g., for and/or for at least three days); and/or (3) poses a risk of perforation or other serious medical complication. In general, for a cecum, a pathophysiological size is a size that is indicative of and/or can result in one or more pathological events or conditions if that size is sustained for long periods—i.e., for a significant or abnormally long temporal increment such as, e.g., for up to, for, and/or for at least: 3, 4, 5, or 6 days; 1, 2, 3, or 4 weeks; 1, 2, 3, 4, 5, 6, 7, 8, 9, 10, or 11 months; and/or 1, 2, or 3 years), with each of the foregoing temporal increments being considered individually or in any suitable combination (for example, for 3 days; for at least 3 days; for at least 3 days and for up to or for at least 1, 2, or 3 years; etc.). Stated another way, for a cecum, a pathophysiological size is a size that, if achieved within a patient due to biological processes, would be indicative of and/or could result in one or more pathological events or conditions, if that size were to be sustained for long periods.

Embodiments disclosed herein may expand the cecum to a pathophysiological size, and may maintain the cecum at such an expanded size for a sustained period (e.g., for up to, for, and/or for at least: 3, 4, 5, or 6 days; 1, 2, 3, or 4 weeks; 1, 2, 3, 4, 5, 6, 7, 8, 9, 10, or 11 months; and/or 1, 2, or 3 years), with each of the foregoing temporal increments being considered individually or in any suitable combination. For example, various embodiments can expand the cecum to an expanded size for a therapeutically effective period or treatment period that exceeds, e.g., three, four, five, or six days; one, two, three, or four weeks; one, two, three, four, five, six, or nine months; or one, two, or three years. As previously discussed, some embodiments can be configured to remain within the patient indefinitely beyond such periods, with no planned removal.

In some embodiments, when the cecum is expanded to a pathophysiological size, the cecum can define a maximum diameter of, for example, no less than about 5, 6, 7, 8, 9, 10, or 11 centimeters, or within a range of from about 5 centimeters to about 6, 7, 8, 9, 10, or 11 centimeters, about 6 centimeters to about 7, 8, 9, 10, or 11 centimeters, about 7 centimeters to about 8, 9, 10, or 11 centimeters, about 8 centimeters to about 9, 10, or 11 centimeters, about 9 centimeters to about 10 or 11 centimeters, or about 10 to about 11 centimeters. In other or further embodiments, when the cecum is expanded to a pathophysiological size, an internal volume defined by the cecal wall can be no less than, for example, 0.25, 0.33, or 0.4 liters. Larger sizes are also contemplated, such as for larger anatomies, and smaller sizes are also contemplated, such as for smaller adults, adolescents, or children. In still other or further embodiments, when the cecum is expanded to a pathophysiological size, a maximum diameter of the cecum increases by no less than 20, 30, 40, 50, 60, 75, or 100 percent.

In some instances, a general shape or configuration of the cecum may be altered as the cecum is transitioned to a pathophysiological size. For example, the cecum may be transitioned from a substantially tubular or substantially cylindrical configuration to an enlarged substantially bulbous configuration, which can include a central or intermediate position at which the cecum defines the maximum diameter. And as previously discussed, when the cecum is in such a bulbous state, this maximum diameter can be much larger than the maximum diameter when the cecum is in the substantially tubular or substantially cylindrical configuration.

Distention of the cecum 110 can be achieved relative to a healthy state of the cecum 110. Stated otherwise, the structure 300 can be sized or otherwise configured to distend the cecum 110 relative to a normal size of the cecum 110. The purpose of the structure 300 may not, in various instances, be to expand the cecum 110 so as to return it from an abnormally small condition (e.g., due to cancer or other disease) to normal dimensions, but rather, to distend the cecum 110 from a natural size to an enlarged size to trigger the colo-gastric brake and/or otherwise trigger phenomena associated with loss of appetite and/or weight loss. Thus, certain structures 300 can be very different from stents or the like whose purpose is to expressly to open or enlarge a vessel or lumen of a patient from a pathologically constricted state to a substantially normal (but not expanded) state, such as merely to maintain patency of the tubular structure.

The structure 300 can be eliminated from the cecum 110 and/or, more generally, from the body of the patient 205 in a variety of manners. In some embodiments, as further discussed below, the structure 300 can be configured to break down within the body of the patient 205 over time. For example, the structure 300 can include a bioresorbable material that degrades over time. The structure 300 may degrade sufficiently such that it no longer distends the cecum 110, and may pass spontaneously or naturally through the remaining portion of the colon 100 and out of the patient 205. It may be desirable for degradation, to the point of discontinued distention and/or natural expulsion of the structure 300 from the patient 205, to occur at some point in time after completion of the therapeutically effective period discussed above. In other or further instances, after completion of the therapeutically effective period, the structure 300 may be actively retrieved from the patient 205. For example, a colonoscopy procedure may be performed to retrieve the structure 300 from the patient 205. In certain instances, standard retrieval techniques may be used, such as by the use of a snare or other device deployed from the colonoscope.

Implanting one or more structures 300 in the cecum 110 can be particularly advantageous. In this region of the bowel 200, material that naturally passes through the intestinal tract (e.g., stool or chyme) is substantially liquid or semi-liquid. Accordingly, passageways defined by the one or more structures 300 can readily pass the material therethrough. Moreover, distention of the bowel in this region generally will not give rise to an urge in the patient 205 to defecate, as might occur in more distal portions of the colon (e.g., the rectum, which would rapidly yield an urge to defecate with pressurization and limited distention). Furthermore, in some instances, positioning device or devices within the cecum 110 can reduce any likelihood of an unintended bowel obstruction, such as in situations where the devices degrade over time and are permitted to pass naturally through the bowel. The cecum 110 is distal to the ileocecal valve, at which such degraded devices, or pieces of such degraded devices, could get caught and give rise to an obstruction. Stated otherwise, certain devices positioned in the small intestine can risk getting caught up in the ileocecal valve, thus giving rise to a small bowel obstruction.

A wide variety of configurations are contemplated for the structure 300, which is schematically depicted in FIG. 3 and discussed in more detail with respect thereto. Illustrative examples of such structures are depicted in FIGS. 4 through 39 and are further discussed in the written descriptions associated with these drawings. Accordingly, the foregoing general discussion with respect to structures 300 are equally and specifically applicable, as appropriate, to the various embodiments depicted in, and discussed with respect to, the drawings.

Figure 4:
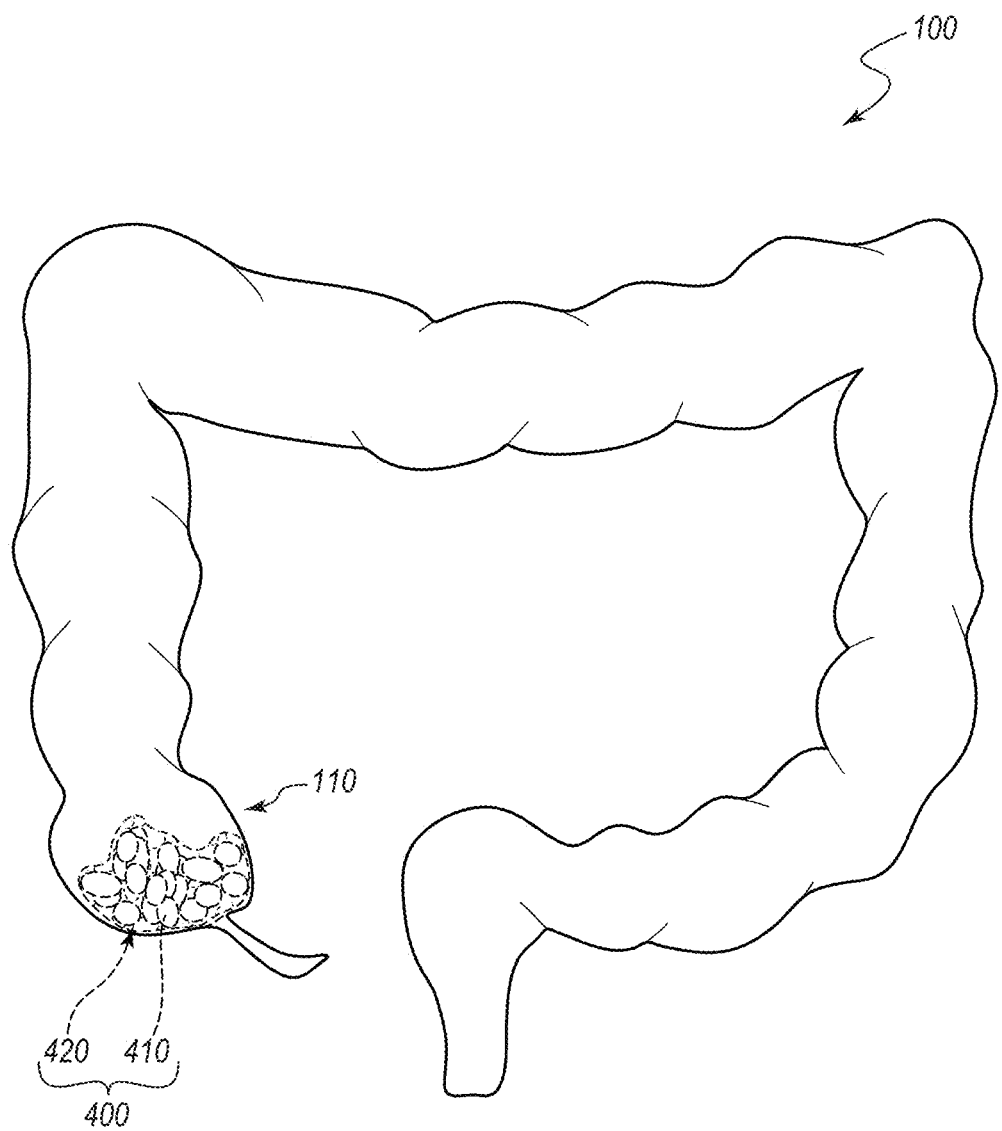
FIG. 4 is another elevation view of the colon similar to that of FIG. 1, but depicting a stage of another illustrative method in which a structure that has been introduced into the cecum of a patient to distend the cecum.

FIG. 4 depicts a stage in another method of treating obesity of the patient 205, in which a medical device, object, or structure 400, has been implanted in the cecum 110 of the patient 205. In particular, the structure 400 is formed of a plurality of individual components or particles 410 that have been introduced into the cecum 110. The particles 410 can be assembled within the cecum 110 to form a conglomerate structure, which can partially fill the cecum 110. The particles 410 can be adhered—e.g., via one or more adhesives 420—to the lining of the cecum 110 and/or each other, and in various embodiments, the resultant conglomerate structure 400 can be adhered to the lining, can otherwise be secured to the lining (e.g., may be tensioned against the lining upon formation of a structure with sufficient rigidity to press against the bowel wall), or can be unattached relative to the lining and free floating within the cecum 110.

In certain embodiments where the structure 400 is freely movable within the colon 100, a first amount of adhesive 420 can be applied to the lining, and then further adhesive 420 can be added thereto. The additional adhesive thus can adhere to adhesive material already initially applied in the lumen of the bowel, creating, in essence, a large ball or mass of glue or slime which sticks to itself, but not to the wall of the bowel. The initial adhesive application can cure quickly, preventing attachment to the wall, and then additional adhesive can be applied to the initial adhesive amount. Curing can be of variable time periods. In some instances, the structure 400 may be formed entirely of one or more adhesives.

In some embodiments, the adhesive is further combined in various amounts with various amounts of one or more of fiber (e.g., soluble or insoluble fibers of any type), cellulose, hemicellulose, lignans, mucilages, beta-glucans, pectin, guar, polydextrose, starches, dextrins, inulins, psyllium, bran, and/or any other type of natural or artificial fiber or other filler, to create a ball or mass shape of any suitable size, thereby distending the lumen of the bowel to any suitable size or diameter. The relative amounts of adhesive versus filler material can vary. For example, in various embodiments, the structure 400 includes 100% adhesive, a majority of adhesive, a minority of adhesive, 100% filler material, a majority of filler material, a minority of filler material, or relatively equal amounts of adhesive and filler material. As previously noted, the final conglomerate structure 400, which may assume a ball shape or other suitable shape, can be adherent to the wall or non-adherent to the wall of the bowel.

The conglomerate structure 400 can also be degradable over variable periods of time. The adhesive can degrade over a variable period of time, slowly dissolving or degrading, and either be absorbable or pass out of the bowel, naturally like stool. As the adhesive degrades, variable amounts of filler material are released and pass out of the bowel, similar to stool, thus gradually decreasing the size of the conglomerate structure and gradually reducing the distention effect.

Thus, the effects of bowel distention achieved by the conglomerate structure 400 can be reversible over a variable period of time, depending on the degradation characteristics of the adhesive and/or filler material. This can be the case whether the conglomerate structure 400 is adherent or nonadherent to the wall.

The conglomerate structure 400 can be positioned in place via adhesion to a variety of different portions of the bowel and, further, at a variety of different locations on the wall of the bowel. The conglomerate structure 400 can be attached and/or formed in a variety of different configurations. For example, the structure 400 can be formed as a series of layers, may be substantially spherical (e.g., ball-shaped), can define an annulus (e.g., circumferentially applied to the wall to ultimately distend the wall about a full periphery thereof), can define a portion of an annulus (e.g., hemi-circumferentially applied), and/or may define other fully or partially obstructing configurations. In some instances, a non-adherent and freely movable structure 400 may stay in place due to virtue of its size. For example, the structure 400 may define a ball shape of a diameter that is larger than the diameter of the bowel lumen, and may define one or more passages through which material can pass through the bowel. In further instances, due to naturally occurring constricted regions (e.g., regions of reduced diameter) along the bowel tract, the large diameter of the structure 400 prevents the structure 400 from migrating distally through the bowel. Accordingly, the structure 400 may not be permitted to pass through the distal regions of the bowel and out of the patient 205 until the structure 400 has degraded by a sufficient amount. In some instances, the substantially ball-shaped structure 400 may be formed with one or more passageways therethrough to permit passage of material therethrough prior to such degradation and spontaneous passage (e.g., defecation) of the structure 400, or portions thereof.

Specific adhesives that can be applied to the wall of the bowel include various materials known in the field of tissue adhesives, such as polyethylene glycols, polyethylene glycol copolymers, triglycerides, diglycerides, esters, fatty alcohol esters, polyacids, polyamines, gelatins, chitosans, polyactive esters, isocyonates, anhydrides, cyanoacrylates, methylmethacrolyates, cross-linking adhesives, other tissue adhesives. In other or further instances, the adhesives can include materials such as those that bind dentures to teeth, mollusk glues, etc. The adhesives may be used in any suitable combination, cured in any of a variety of manners (e.g., as are known in the art), used with or without added enzymes or preservatives, used with or without added salts, and/or be partially or completely degradable, etc. The adhesives may be used in any suitable amount and may yield any desired orientation and/or configuration.

In some embodiments, the conglomerate structure 400 can contain one or more varieties of antibiotics and/or anti-microbial material (such as copper or silver) that can have delayed release, which can favorably impact the surrounding microbiome. In some embodiments, the conglomerate structure 400 includes one or more of any of a variety of drugs that can affect the microbiome and/or that can directly treat obesity and/or diabetes.

In some embodiments, the conglomerate structure 400 is attached to native bowel wall mucosa. In other embodiments, the mucosa of the bowel wall is purposely damaged or ablated with radio-frequency energy, heat, cryotherapy, or other forms of electromagnetic radiation in order to damage, remove and/or fibrose the mucosa. In some instances, the structure 400 can better attach to the bowel wall where such ablation has been performed, either by adhering to new fibrotic tissue, or by adhering to deeper layers of the bowel wall, such as the submucosa or deeper muscle layers, or both. In some instances, such an ablation technique can also be used to sterilize the bowel wall underneath the adhesive.

With continued reference to FIG. 4, in the illustrated method, a colonoscope (e.g., such as the endoscope 250 depicted in FIGS. 2 and 3) is advanced into the cecum 110. Thereafter, adhesive 420 and/or filler material 410 is injected through an injectable catheter placed through the biopsy port (i.e., the tool channel) in the endoscope, or may be injected directly through the endoscope. In other instances, rather than injecting the adhesive 420 and/or the filler material 410, some other form of application is employed (brushing, spraying, etc.). In other instances, the adhesive and/or the filler material is instead advanced into the cecum 110 alongside the endoscope, such as via a channel through a removable or disposable covering over the endoscope. In some methods, one or more adhesives are first applied to the wall of the cecum 110. Thereafter, one or more particles 410 are applied to the adhesive 410. In still other embodiments, the one or more particles 410 and the adhesive 420 may be combined (e.g., prior to advancement through the endoscope or within the endoscope) and then applied to the wall of the cecum 110, or otherwise introduced into the cecum 110, via the endoscope. The processes may be repeated until a conglomerate structure 400 of a desired configuration is achieved. The conglomerate structure 400 can distend at least a portion of the cecum 410 in an amount sufficient to trigger a colo-gastric brake.

As previously discussed, in various embodiments, the conglomerate structure 400 can adhere to the mucosa (inner lining) or deeper layers of the cecum 410, such as the submucosal or muscle layers, or fill between the spaces of the bowel wall layers, and fill the bowel wall and/or lumen thus distending said portion to a diameter of a desired size. As more adhesive and/or filler material is applied, the new material could adhere to the previous material and pile up in a mass or ball of material of various size and shape, but all to the effect of distending the lumen or wall of said bowel.

In various embodiments, the conglomerate structure 400 can specifically be positioned within the cecum. In some embodiments, the conglomerate structure 400 is sufficiently large to expand the cecum to a pathophysiological size. The conglomerate structure 400 can be spaced away from the ileocecal valve so as to avoid blocking passage of material therethrough and into the cecum.

In other embodiments, an implantable object for distending the cecum can be an expandable structure that is delivered directly to an interior of the cecum. The structure can be delivered in an undeployed (e.g., reduced profile, unexpanded, partially expanded) state and can be deployed within the cecum to an expanded state. Any of a variety of such structures are contemplated. For example, in various embodiments, an expandable medical device can comprise a stent-like device, a cage, a ball, a balloon, or other similar mechanism. In various embodiments, the structure can define one or more passageways (e.g., openings, perforations, channels, pathways, or the like) that allow materials (e.g., gasses, semiliquids, liquids, semisolids, and/or solids) to pass through the structure. In some embodiments, the structure can be freely movable (e.g., free floating) in the lumen of the bowel, but may be sized and/or otherwise include features that prevent migration (e.g., distal migration) out of the cecum and through the bowel. In other embodiments, the structure is at least temporarily or intermittently secured to the cecum wall or inner lining of the cecum. In further embodiments, the structure can be continuously and/or fixedly secured to the cecum wall or inner lining of the cecum. In various embodiments, the structure can fill, or partially fill, the cecum pouch, and may distend the cecum by a designated, predetermined, or desired amount. The expandable medical device can be configured to expand the cecum to a pathophysiological size. In some instances, the device ensures that the cecum is never collapsed or contracted to a size smaller than the pathophysiological size during treatment via the device. In further instances, the device can permit the cecum to naturally expand to a larger size that exceeds the pathophysiological size, and in various examples of such instances, the device can be free floating within the cecum, can remain in contact with only a portion of the cecum, or can expand so as to contact and/or remain in contact with, e.g., a full periphery of the cecum during the natural enlargement of the cecum. A variety of configurations are contemplated, of which a few illustrative examples are discussed hereafter.

FIGS. 5A-5D depict various stages of an illustrative method of implanting or deploying a medical device 500 (FIGS. 5C and 5D) in the colon 100 of the patient 205. The medical device 500 may also or alternatively be referred to herein as a distention device, distention object, expandable structure, implant, etc. In the illustrated embodiment, the device 500 is an expandable stent-like device, and in particular, is a balloon-expandable stent-like device. Accordingly, the device 500 may alternatively be referred to herein as a stent (subject to the prior discussion of this terminology), as a stent-like device, or as an expansion device 500.

Figure 5A:
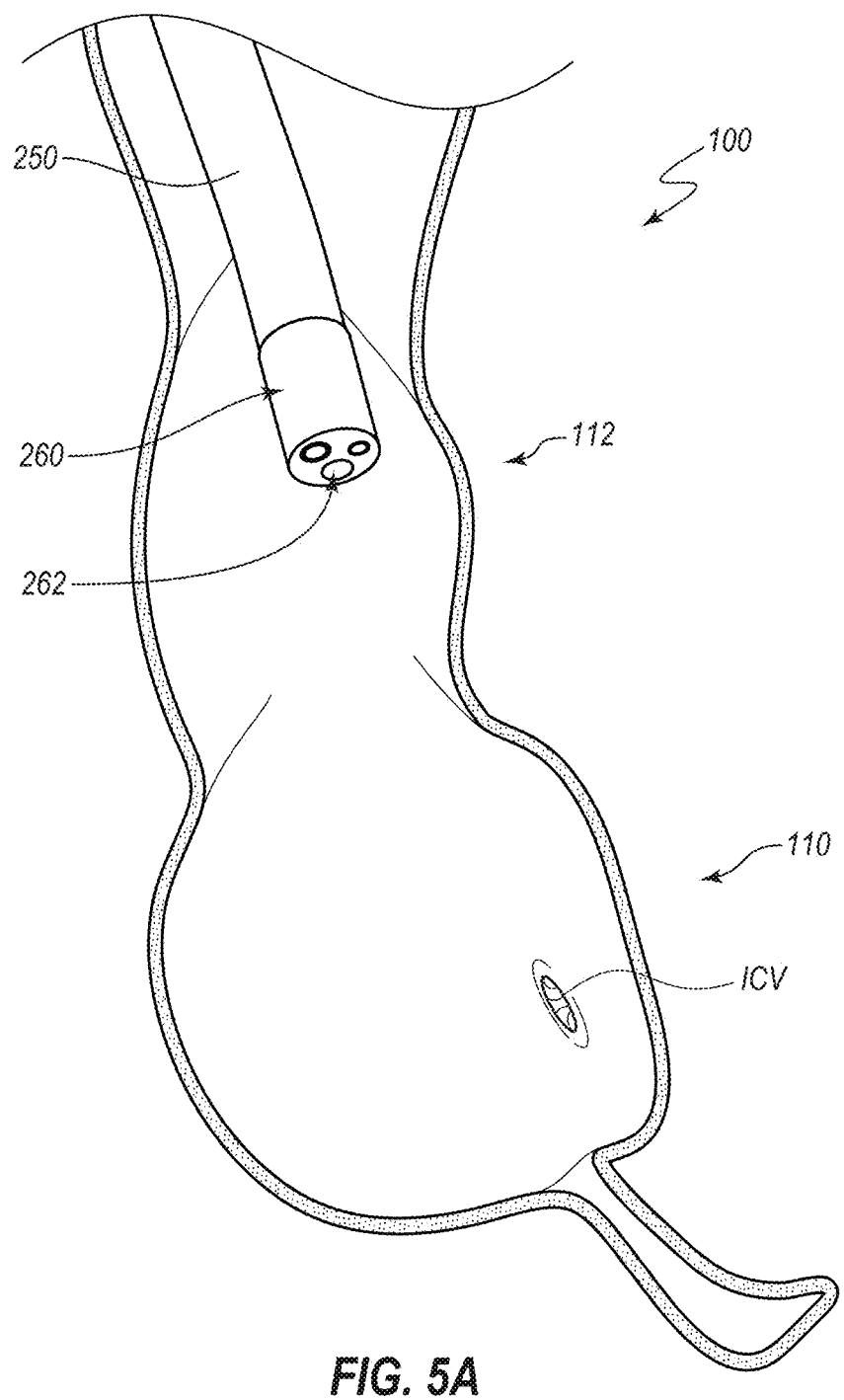
FIG. 5A is a cross-sectional view of a portion of the colon of a patient during another illustrative method in which an endoscope, shown in perspective, is being advanced toward the cecum of the patient.

With reference to FIG. 5A, in an early stage of the method, an endoscope 250 is inserted into the colon 100 in the same manner as depicted in FIG. 2. In particular, as shown in FIG. 2, the endoscope 250 is introduced through the rectum 120 of the patient 205 and is advanced proximally through the lumen of the colon 100. A longitudinal axis of the endoscope 250 can be aligned with, parallel to, or may otherwise track or follow a longitudinal axis of the lumen of the colon. FIG. 5A depicts a tip 260 of the endoscope 250 at a proximal end of the ascending colon 112 and nearing the cecum 110. Unless otherwise specified hereafter (or as may otherwise be clear from context, such as from the perspective of a practitioner who is delivering a device into a patient, rather than from the perspective of the patient), the terms "proximal" and "distal" refer to the direction of passage of material through the gastrointestinal tract of the patient 205. Thus, the patient's mouth is at the proximal end of the gastrointestinal tract and the rectum is at the distal end of the gastrointestinal tract. The endoscope 250 includes a lumen 262, which may be referred to as a tool channel, an instrument channel, or simply as a channel.

Figure 5B:
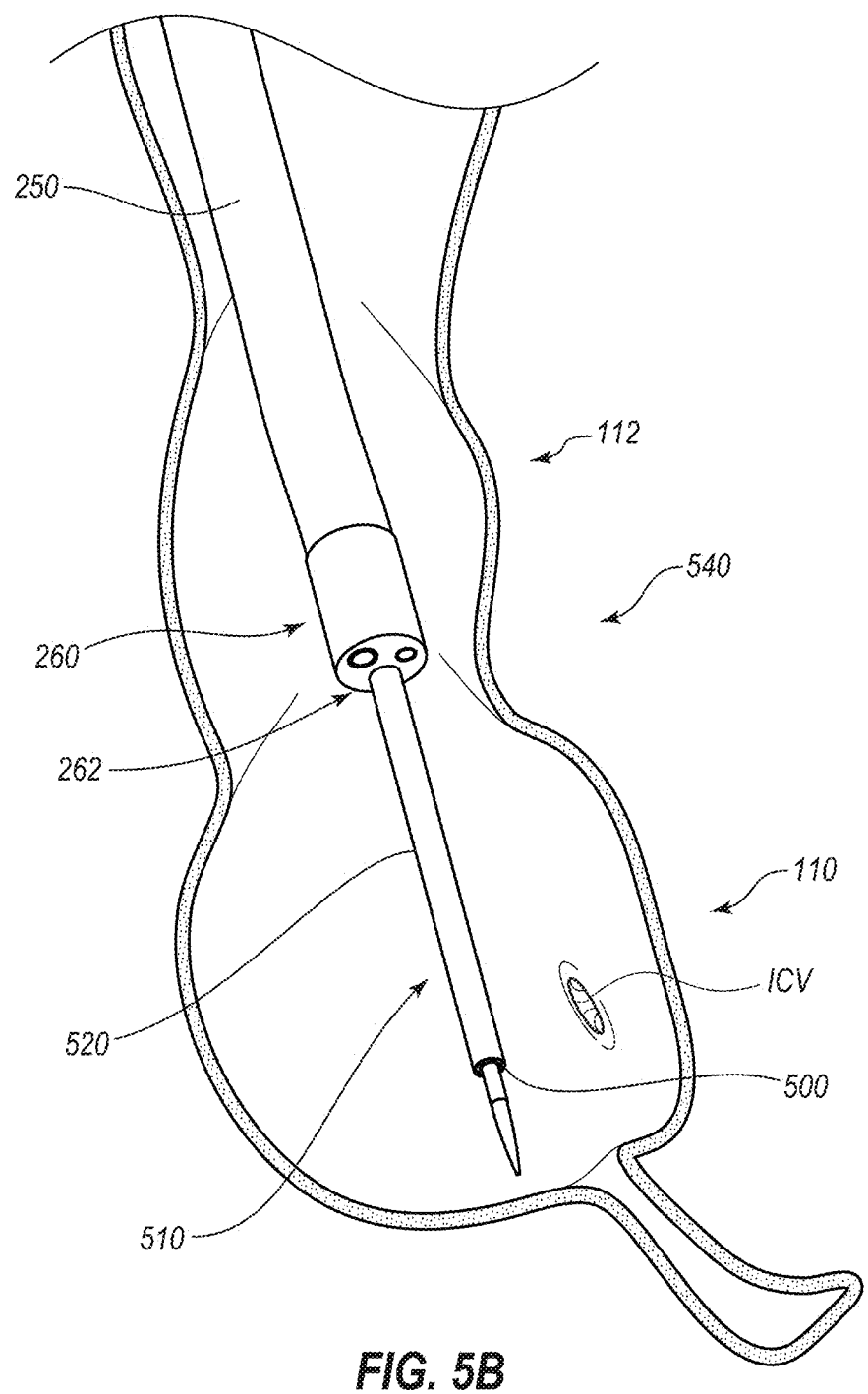
FIG. 5B depicts another stage of the method in which a catheter is advanced out of a distal end of the endoscope into the cecum.

FIG. 5B depicts a later stage of the method at which the endoscope 250 has been advanced slightly further toward the cecum 110 and held in place. A catheter 510 to which the expansion device 500 is coupled is then inserted proximally through the lumen 262 of the endoscope 250 so as to position the expansion device 500 within the cecum 110. In the illustrated embodiment, the expansion device 500 is covered with a protective sleeve 520, which may also be referred to as a retention sleeve. In some methods, the sleeve 520 is removed from the expansion device 500 and retracted through the endoscope 250 prior to deployment of the expansion device 500. For example, the sleeve 520 may retracted via a wire to which it is attached or via any other suitable mechanism. In some embodiments, the expansion device 500 is self-expandable, such that removal of the sleeve 520 permits the expansion device 500 to expand outwardly into contact with the walls of the cecum 110 and distend the cecum 110 to an expanded diameter. In other embodiments, such as that presently illustrated, the expansion device 500 is not self-expanding. In other or further embodiments, a sleeve 520 is not used.

The endoscope 250, the catheter 510, and the expansion device 500 may be referred to as a system 540 for treating obesity (or associated illnesses). The system 540, or some or all of the components thereof, may also or alternatively be referred to as a medical device deployment system for distending the cecum.

Figure 5C:
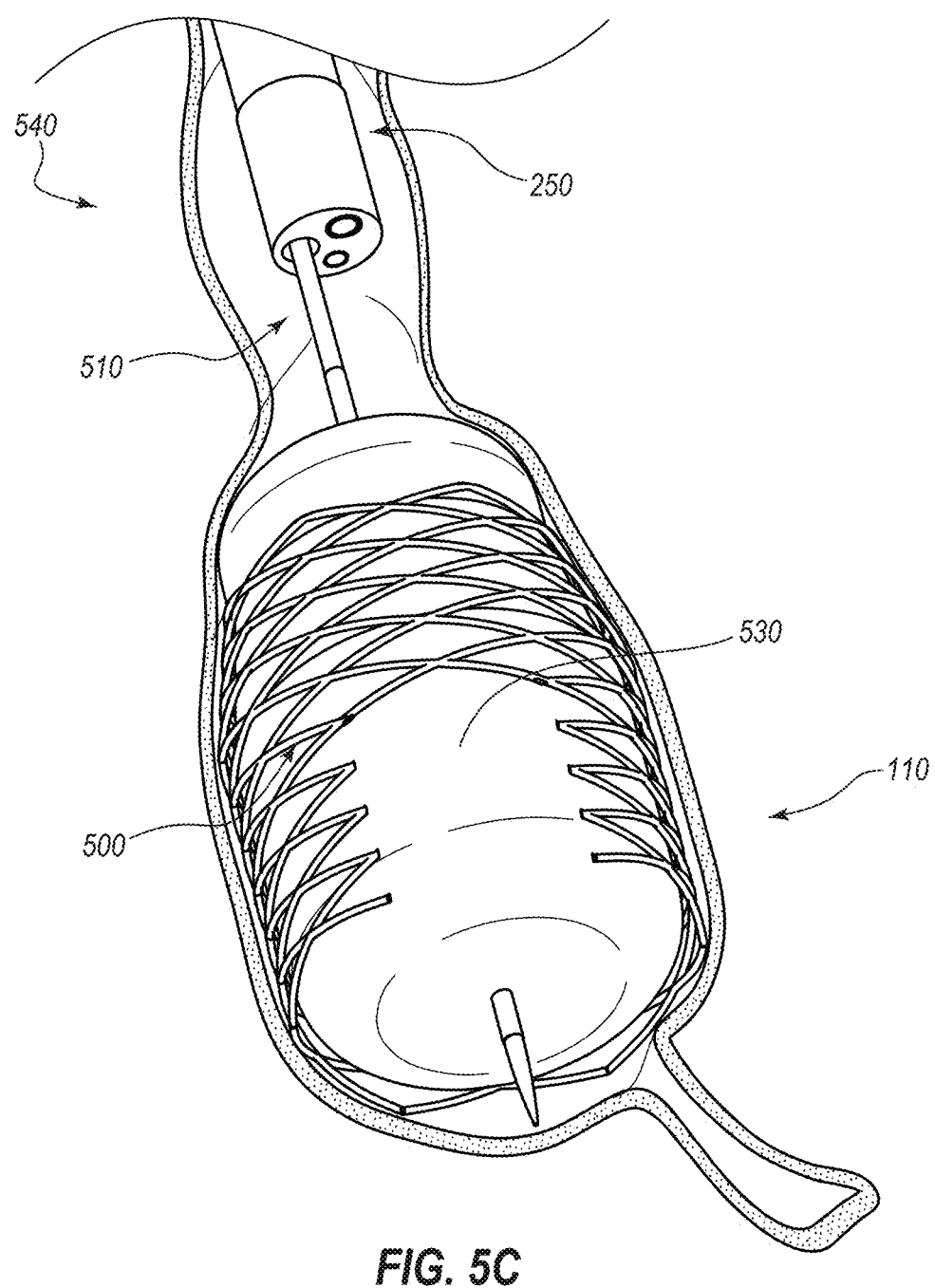
FIG. 5C depicts another stage of the method in which an expandable medical device is being deployed into contact with the cecum via the catheter.

FIG. 5C depicts a later stage of the illustrative method after which the sleeve 520 has been removed. At the moment depicted in this drawing, a balloon 530 that is coupled to the catheter 510, and over which expansion device 500 has been positioned, is being inflated via the catheter 510. For example, a proximal end of the catheter (i.e., the end that remains external to the patient 205) may be coupled with an inflation syringe (not shown) or other suitable inflation device, and fluid may be delivered from the inflation syringe, through a lumen of the catheter 510, and into the balloon 530 to expand the balloon 530 and thereby expand the expansion device 500. As used herein, the term "fluid" is used in its ordinary sense and includes materials that have no fixed shape, yield easily to external pressure, or are flowable, such as gases (e.g., air, nitrogen, etc.) and liquids (e.g., saline, deionized water, etc.).

Figure 5D:
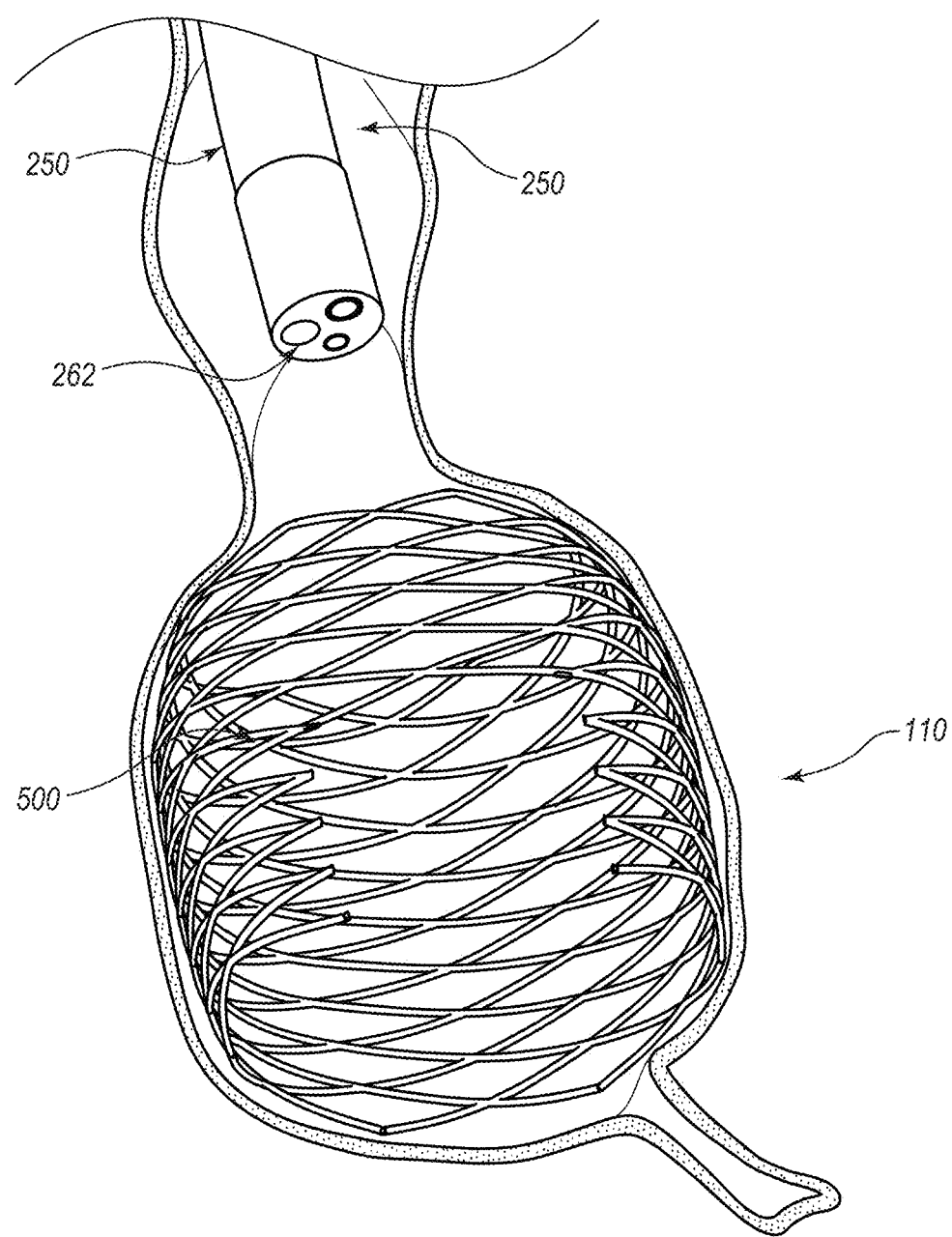
FIG. 5D depicts another stage of the method in which the expandable medical device has been deployed to expand the cecum to a pathophysiological size and the catheter has been retracted relative to the endoscope.

FIG. 5D depicts yet a later stage of the illustrative method after which the expansion device 500 has been fully deployed into its final expanded configuration via the balloon 530, the balloon 530 has then been deflated (e.g., via retraction of the inflation fluid), and the catheter 510 has been at least partially withdrawn through the lumen 262 of the endoscope 250. After complete or partial withdrawal of the catheter 510, the endoscope 250 (and, in some instances, the catheter 510 if still positioned within the lumen 262) is withdrawn from the patient 205.

With continued reference to FIG. 5D, in some instances the cecum 110 can be substantially tubular prior to expansion. For example, the cecum 110 can generally define a cylindrical shape, and the length of the cylinder may be roughly the same as or on about the same order as the diameter thereof. In some embodiments, the expansion device 500, when fully deployed, can reorient the cecum 110 into a more bulbous configuration. Stated otherwise, in various embodiments, the expansion device 500 can be bulbous, ovoid, spherical, orb-like, pill-shaped, ball-like, etc. The illustrated expansion device 500 is somewhat bulbous, and includes a tapered end corresponding to the distal end of the cecum 110. In other embodiments, the expansion device 500 may expand to a more bulbous state. In some embodiments, a maximum diameter defined by the expansion device 500 can exceed a longitudinal length of the device 500 (see, e.g., FIGS. 23G, 23H, 30A). As previously discussed, the expansion device 500 can enlarge the cecum 110 to a pathophysiological size. For example, in some embodiments, the cecum 110 may be expanded by an amount greater than what is shown in FIG. 5D (e.g., the amount of distension of the cecum 110 may be significantly greater than what is depicted in FIG. 5D). As previously discussed, prior disclosures regarding amounts by which the cecum 110 can be expanded (e.g., the discussion regarding pathophysiological expansion) are applicable to the present and other embodiments disclosed herein.

Figure 5E:
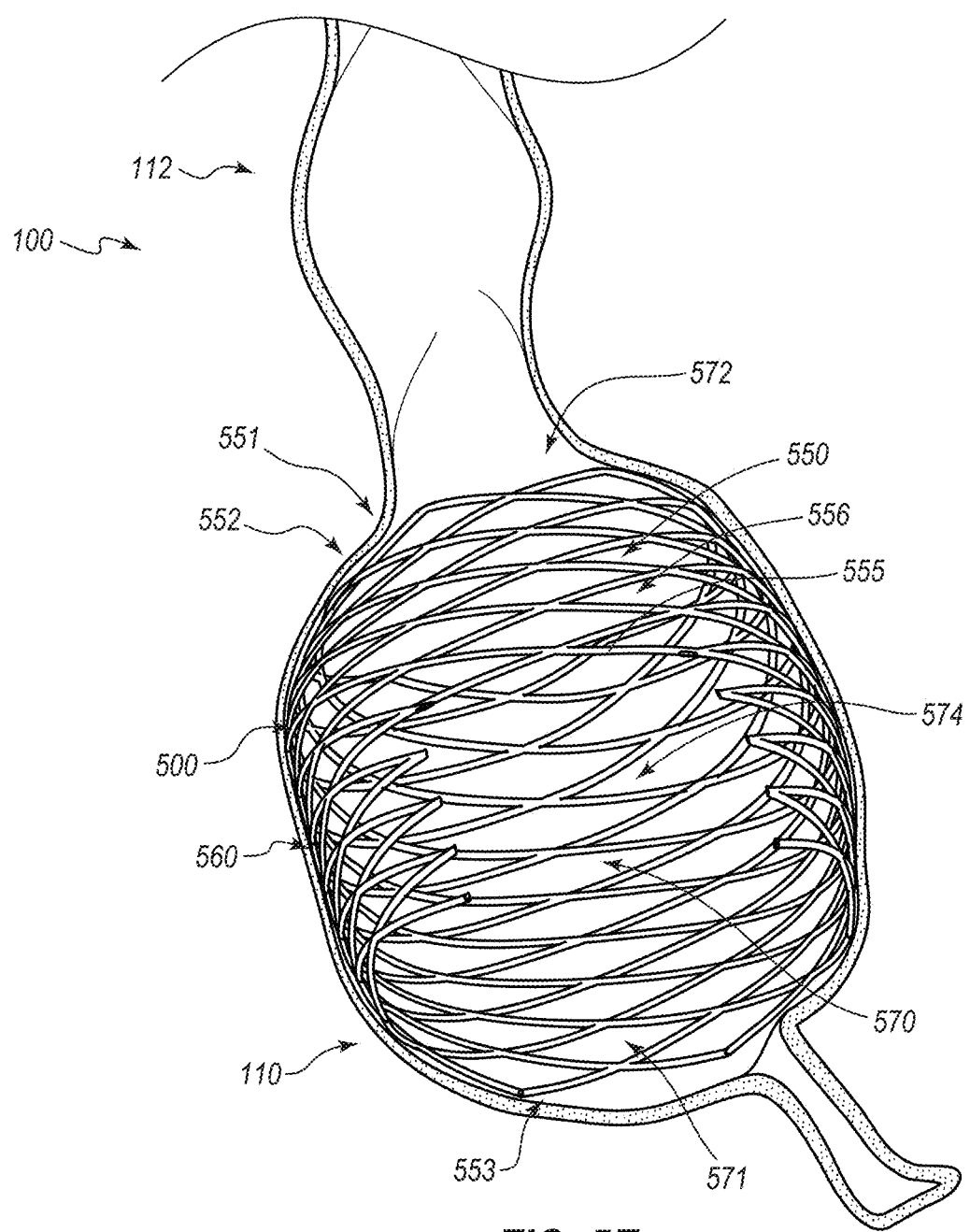
FIG. 5E depicts another stage of the method in which the expandable medical device is implanted in the cecum and the endoscope has been retracted from the patient.

FIG. 5E depicts a later stage of the illustrative method after the endoscope 250 has been withdrawn from the patient 205. The expansion device 500 remains in its expanded configuration and continues to distend the wall of the cecum 110. As previously discussed, the expansion device 500 can continuously or intermittently distend the cecum 110 by an amount sufficient to trigger a colo-gastric brake of the patient 205, which can suppress an appetite of the patient. The expansion device 500 can remain implanted in the patient 205 for a therapeutically effective period over which a weight of the patient is reduced by a desired amount.

In various embodiments, the expansion device 500 may include any of the dimensions or other features discussed above with respect to the device 300. For example, in various embodiments, an outer or maximum diameter of the expansion device 500 is within a range of from about 6 centimeters to about 10 centimeters, or that is no less than about 6, about 7, about 8, about 9, or about 10 centimeters. Indeed, the expansion device 500 is an example of the device 300 described above, and thus may exhibit some or all of the properties described above with respect thereto. As a further example, the illustrated embodiment of the expansion device 500, once expanded to the deployed state, defines a substantially constant configuration, or stated otherwise, is not susceptible to fluctuations due to varying physiological conditions experienced within the cecum 110, as might be experienced by more resiliently flexible devices. Various embodiments of the expansion device 500 thus may achieve continuous distention of the cecum 110 or intermittent distention of the cecum 110, depending on a magnitude of the distention encountered by the cecum 110 (e.g., percentage increase in size) and/or the severity of the physiological conditions encountered within the cecum 110 over the course of implantation.

In the illustrated embodiment, the expansion device 500 is tensioned against the wall of the cecum 110 to achieve distention thereof. The expansion device 500 thus may be secured to the wall of the cecum 110, although, in other or further embodiments, the expansion device 500 may nevertheless, at times, be free floating within the cecum 110. The term "free floating" does not necessarily or solely connote a complete lack of contact with the wall of the cecum 110, although such may be the case on at least some occasions (such as if the cecum 110 expands beyond the distended configuration imparted thereto by the expansion device 500). Rather, this term also includes situations where the expansion device 500 contacts only a portion of a periphery of the wall and/or only a portion of a periphery of the expansion device 500 contacts the wall, such as may occur as the expansion device 500 moves around in the cecum 110. In some embodiments, the expansion device 500 may be attached to the wall more securely or more permanently, so as to be less susceptible to movement (e.g., rotation) within the cecum 110. For example, one or more anchoring protrusions (e.g., hooks or spikes—not shown) may extend outwardly from a frame or body 550 of the expansion device 500 and may embed in the wall of the cecum 110. In other or further instances, the body 550 may promote tissue ingrowth that can fix the expansion device 500 in place. For example, in the illustrated embodiment, tissue ingrowth may occur between and/or over or about individual struts 555 (FIG. 5E). In still other or further instances, the expansion device 500 may be attached to the wall of the cecum 110 during deployment in any suitable manner. For example, in some embodiments, the expansion device 500 is secured about at least a portion of its periphery to the cecal wall via any of the adhesives previously described herein, one or more sutures, one or more clips, one or more mechanical fasteners of any other suitable variety, and/or any other suitable fixation technique, device, or system.

Whether or not the expansion device 500 is anchored or otherwise securely fastened to the wall of the cecum 110, in various embodiments, the expansion device 500 can include features that inhibit or prevent migration (or premature migration, in the case of stents 500 that are configured to eventually pass through the bowel and out of the patient 205) to more distal regions of the colon 100. For example, in the illustrated embodiment, the expansion device 500 generally defines a bulbous shape that is similar to, and in some embodiments is enlarged relative to, a bulbous shape that the cecum 110 may naturally achieve. In the illustrated embodiment, a distal end 551 includes a taper 552 by which a diameter of the expansion device 500 is reduced in the distal direction. This taper 552 can assist in maintaining the expansion device 500 pointed in the distal direction. In particular, the narrowing of the expansion device 500 in the distal direction can assist in pointing the expansion device 500 in the same direction that the colon 100 narrows, which is likewise in the distal direction. Moreover, at least one of the maximum and minimum diameters of the expansion device 500 may be sufficiently large to prevent the expansion device 500 from migrating distally, given that the cecum 110 defines a larger diameter than does at least an immediately adjacent portion of the ascending colon 112. Further, in some embodiments, the taper 552 of the distal end, which may serve to center or embed the distal end 551 of the expansion device 500 at a distal end of the cecum 110, and/or a length of the expansion device 500, which may exceed a diameter of the expansion device 500 in some embodiments, can prevent or inhibit rotation of the expansion device 500 about axes perpendicular to a longitudinal axis of the expansion device 500 (which can be substantially aligned with a longitudinal axis of the cecum 110). In general, the terms "distal" and "proximal," as used relative to the expansion device 500, are from the perspective of the digestive tract, rather than from the perspective of the practitioner who may be placing the expansion device 500.

In other or further embodiments, the expansion device 500 may include a similar taper at a proximal end 553 thereof. Such a taper may allow the expansion device 500 to more closely conform to the natural, somewhat bulbous shape of the cecum 110.

The body 550 of the illustrated expansion device 500 includes a maximum diameter region 560 that extends along a small portion of its length, and is capped by a more conical, parabolic, or rounded shape defined by the taper 552, as previously discussed. The body 550 can be formed in any suitable manner. In the illustrated embodiment, the body 550 comprises a plurality of wires, struts, connectors, or support members 555, which in the illustrated embodiment cross each other at consistent angles and extend along regularly spaced paths or intervals. The widths of the support members 555 are relatively small, such that the support members 555 define a plurality of large openings 556.

The body 550 is substantially hollow, in that it defines a large primary channel or passageway 570. Each of the openings 556 defined by the support members 555 is in fluid communication with the passageway 570, and thus each opening 556 defines an entrance to or exit from the passageway 570. Moreover, the body 550 defines a proximal opening 571 at an entry to and a distal opening 572 at an exit of the passageway 570.

The passageway 570 may be sufficiently large to permit passage of material therethrough without substantially impeding the flow of the material. Stated otherwise, the body 550 of the expansion device 500 can effectively distend the wall of the cecum 110 while the passageway 570 defined by the body 550 can permit substantially unimpeded or unobstructed flow of the material through the body 550. Due to the thinness of the struts 555 and the expanded lumen size provided by the expansion device 500, in some embodiments, the presence of the expansion device 500 actually expand the flow capacity of the cecum 110. In various other embodiments, the expansion device 500 reduces the flow capacity of the cecum 110 by no greater than 5, 10, 15, 20, 25, 30, 40, or 50 percent. In other or further embodiments, the expansion device 500 obstructs no greater than 5 percent of material from passing through the cecum 110.

In the illustrated embodiment, a sidewall region defines a notch 574, which extends the proximal opening 571 longitudinally. In some embodiments, the notch 574 can be aligned with the ileocecal valve ICV (FIGS. 5A and 5B) upon implantation of the expansion device 500. Flow material from the ilium thus may pass through or by the notch 574 and into the expansion device 500. The expansion device 500 thus may provide even less impedance to material flow into the cecum 110. In other embodiments, the notch 574 may be absent, and in further embodiments, this absence may have little overall effect on flow of material into the passageway 570 due to the size and number of the openings 556.

In the arrangement illustrated in FIG. 5E, the notch 574 has not been aligned with the ileocecal valve during deployment. In order for alignment to have been achieved, the expansion device 500 would need to have been rotated about a longitudinal axis thereof by approximately 150 degrees in a clockwise direction (as viewed from the proximal or bottom end thereof, as in FIG. 5E).

In some instances, even if the notch 574 is properly aligned with the ileocecal valve at the time of deployment, the notch 574 may become misaligned from the ileocecal valve at later times. For example, in embodiments in which the expansion device 500 is not fixedly secured to the cecal wall (such as by fastening devices and/or tissue ingrowth), upon natural expansion of the cecum 110 to a size larger than the pathophysiological size achieved by the expansion device 500, the expansion device 500 may become free floating within the cecum 110 and may be subject to rotation about a longitudinal axis thereof. When the natural enlargement of the cecum 110 ends, such that the cecum 110 contracts again around the expansion device 500, the notch 574 may no longer be aligned with the ileocecal valve, such as depicted in FIG. 5E. In some embodiments, the expansion device 500 may be fixedly secured to a portion of the cecal wall to maintain a rotational alignment of the notch 574 with the ileocecal valve. Any suitable attachment technique is contemplated, such as those previously disclosed. For example, a longitudinal length of the expansion device 500 may be fixedly secured to the cecal wall at a position opposite the notch 574.

In various embodiments, the expansion device 500 may comprise braided filament, such as wire or other material, or may be laser cut from a material. Any suitable material is contemplated, including, for example, metals (e.g., stainless steel), metal alloys (e.g., cobalt-chrome, platinum-chrome), shape-memory alloys (e.g., Nitinol), polymers, bioresorbable material (e.g., magnesium, poly-L-lactide acid, tyrosine polycarbonate, salicylic acid polymers), etc. The expansion devices 500 can be made of any suitable shape and oriented as needed or desired to interface with the anatomy of the patient 205. Illustrative examples of other shapes are depicted, for example, in FIG. 22A through FIG. 30F. In some embodiments, the expansion device 500 can be self-expanding. For example, in some embodiments the expansion device 500 may be formed of a heat-setting or elastomeric material.

In some embodiments, the expansion device 500 can be drug- and/or nutrient-eluting. Stated otherwise, the expansion device 500 can comprise an eluting material that includes one or more drugs, nutrients, hormones, peptides, neurotransmitters, bacteria, and/or other substances that can be released over time. The substances may be appetite suppressants of any suitable variety and/or may otherwise be useful or therapeutic in the treatment of obesity and/or related illnesses. In some embodiments, the expansion device 500 may be formed with a metallic scaffold and an elutable substance (drug, nutrient, or otherwise) can be dispersed in a polymer matrix, which may conformally surround the scaffold. The polymers may be primarily biostable to bind the substance to the stent and modulate the elution of the substance into the bowel.

In various embodiments, substances that the expansion device 500 can elute over time can include peptides, such as cholecystokinin (CCK) for stents 500 configured for implantation in the upper or small intestine, or glucagon-like peptide-1 (GLP1) and/or oxyntomodulin for stents 500 configured for implantation in the lower intestine or colon.

In other or further embodiments, the expansion device 500, or portions thereof, may be formed of a biodegradable or bioresorbable material of any suitable variety. In some embodiments, as the material of which the expansion device 500 is formed biodegrades or is bioresorbed over time, the structural integrity of the material weakens. Accordingly, whereas the expansion device 500 may initially have sufficient structural rigidity to contact and provide an expansion bias to the wall of the cecum to distend the cecum, the expansion device 500 may eventually weaken or break apart to where it is no longer able to distend the cecum. Ultimately, the expansion device 500 may reduce in size to be spontaneously passed through the bowel and out of the patient 205. For example, in some instances, the expansion device 500 may weaken and/or may break down into multiple separate pieces that may each be sufficiently small to naturally or spontaneously pass through the bowel. In various embodiments, the expansion device 500 could last a predetermined amount of time in the applied position (e.g., days, weeks, months, or years). In some instances, the expansion device 500 is configured to ensure that bioresorption proceeds to the point of terminating distention only after a therapeutically effective period has passed from the time of implantation.

In some embodiments, the expansion device 500 is configured to be retrievable, such as via an additional colonoscopy procedure. For example, in various embodiments, the expansion device 500 can have features that permit a medical practitioner to grab it, collapse it, and retrieve it, such as, for example, via any suitable snaring device and/or a reduced diameter cover into which the snaring device may draw the expansion device 500.

Figure 6:
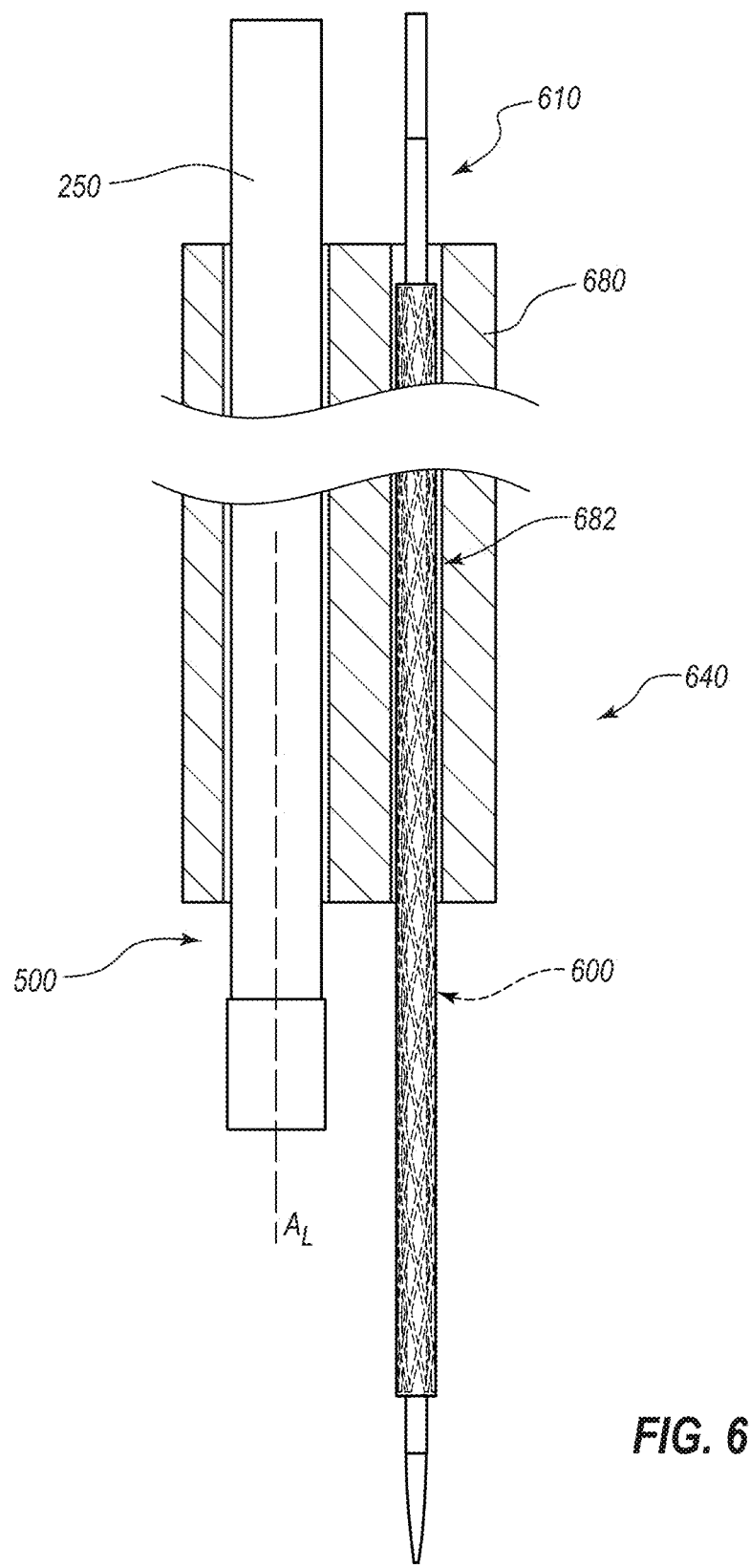
FIG. 6 is a cross sectional view of an embodiment of a system that can be used to implant an embodiment of an expandable medical device within the cecum of a patient.

FIG. 6 depicts another system 640 that can resemble the system 540 described above in certain respects. Accordingly, like features are designated with like reference numerals, with the leading digits incremented to "6." Relevant disclosure set forth above regarding similarly identified features thus may not be repeated hereafter. Moreover, specific features of the system 640 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 640. Any suitable combination of the features and variations of the same described with respect to the system 540 can be employed with the system 640, and vice versa. The same is also true of an expansion device 600 that is deployable via the system 640 and the expansion device 500 of the system 540. That is, disclosures regarding various medical devices can be appropriately applied to other, medical devices (e.g., similarly numbered medical devices) herein, in the interest of streamlining the present discussion. This pattern of disclosure applies equally to further embodiments depicted in subsequent figures and described hereafter, wherein the leading digits may be further incremented.

The system 640 can include the endoscope 250 discussed above (which can comprise any suitable endoscope, such as any suitable variety of colonoscope), and can further include a covering 680 or attachment for the endoscope, and a balloon catheter 610 to which an expansion device 600 is coupled. The system 640 can be used to implant the expansion device 600 in a patient 205 in manners such as those discussed above. However, rather than inserting a catheter 610 through a lumen of the endoscope 250, the catheter 610 is instead inserted through a lumen 682 defined by the attachment or covering 680. In various embodiments, the covering 680 may be selectively attachable to and/or detachable from the endoscope 250, and may be disposable. The lumen 682 may be substantially parallel to the instrument channel of the endoscope 250, and likewise may be substantially parallel to a longitudinal axis $A_L$. In various embodiments, a longitudinal axis of the instrument channel of the endoscope 250 may be colinear or aligned with the longitudinal axis $A_L$, or may run parallel thereto. Accordingly, in the illustrated embodiment, the expansion device 600 may be introduced into the patient 205 alongside (e.g., exterior to an outer surface of) the endoscope 250.

Figure 7A:
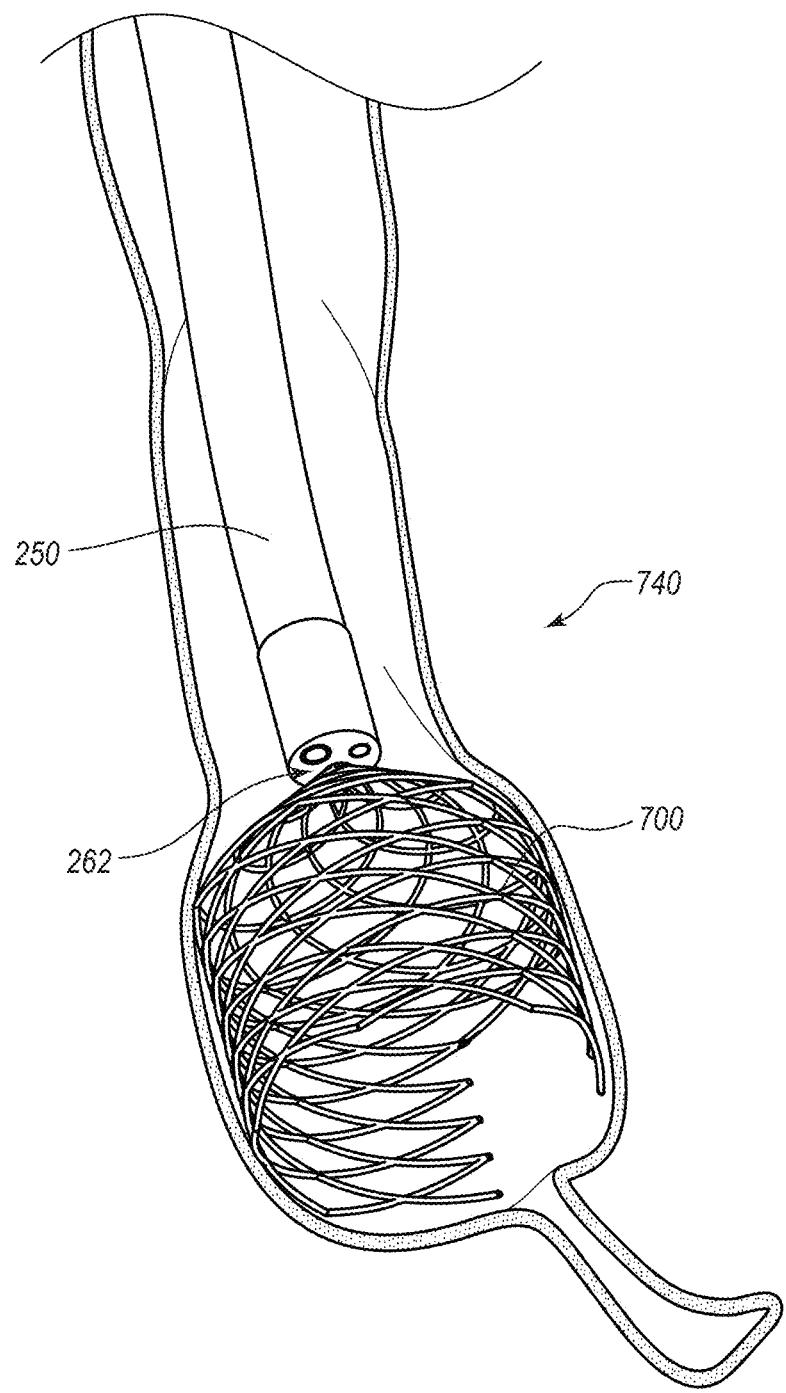
FIG. 7A is a cross-sectional view of a portion of the colon of a patient during another illustrative method in which an expandable medical device, shown in perspective, is being delivered to the cecum of the patient directly from an instrument channel of an endoscope, also shown in perspective.
Figure 7B:
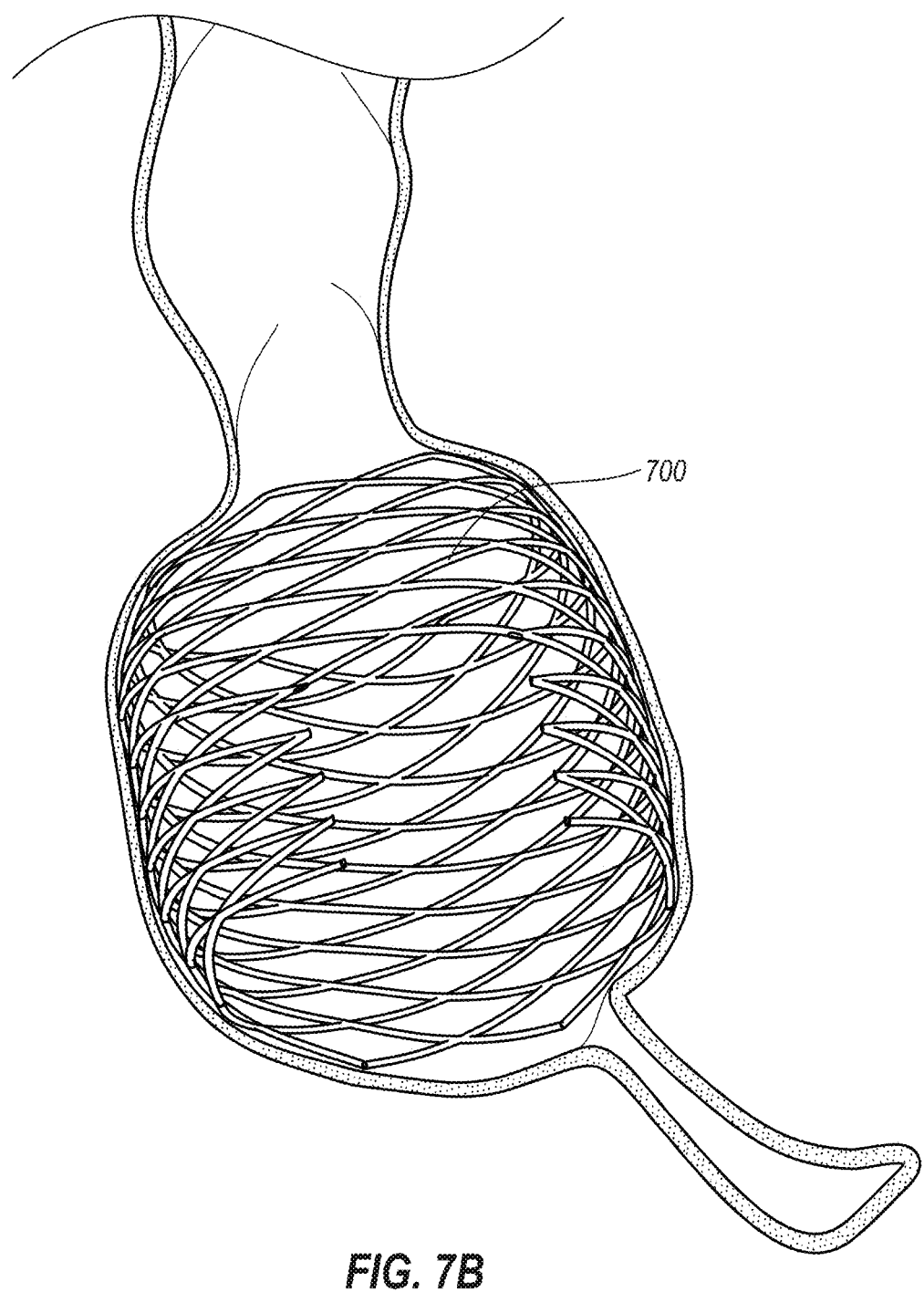
FIG. 7B depicts another stage of the method in which the expandable medical device has been deployed to expand the cecum to a pathophysiological size and the endoscope has been removed from the patient.

FIGS. 7A and 7B depict stages of an illustrative method for using a system 740 to introduce a medical device or expansion device 700 into the patient 205. The system 740 can include the endoscope 250, the expansion device 700, and a deployment mechanism (not shown) for advancing the expansion device 700 from the channel 262 of the endoscope 250. The method can be substantially the same as that discussed above with respect to FIGS. 5A-5E. However, rather than inserting a balloon catheter through the instrument channel 262 of the endoscope 250 to deploy the expansion device 700, in the instant method, the expansion device 700 is self-expanding and may itself be advanced through instrument channel 262 and can be deployed directly from the instrument channel 262. For example, in some embodiments, the expansion device 700 may be positioned at the tip of the endoscope 250 prior to insertion of the endoscope 250 into the patient 205. Once the tip of the endoscope 250 is in the desired position, the expansion device 700 can be pushed out of the channel 262 in any suitable manner (e.g., may be pushed by a push rod, wire, or other suitable deployment mechanism) and can expand automatically once no longer restrained within the channel 262. In other or further instances, a restriction sleeve may be positioned over or around the expansion device 700 to maintain the expansion device 700 in a collapsed, low-profile, or constricted state, and can be removed from the expansion device 700 prior to or during deployment to permit self-expansion of the expansion device 700. In still other or further instances, the expansion device 700 may be pushed through a larger portion of the channel 262 (e.g., an entirety thereof) after the tip of the endoscope 250 has been positioned as desired.

Figure 8A:
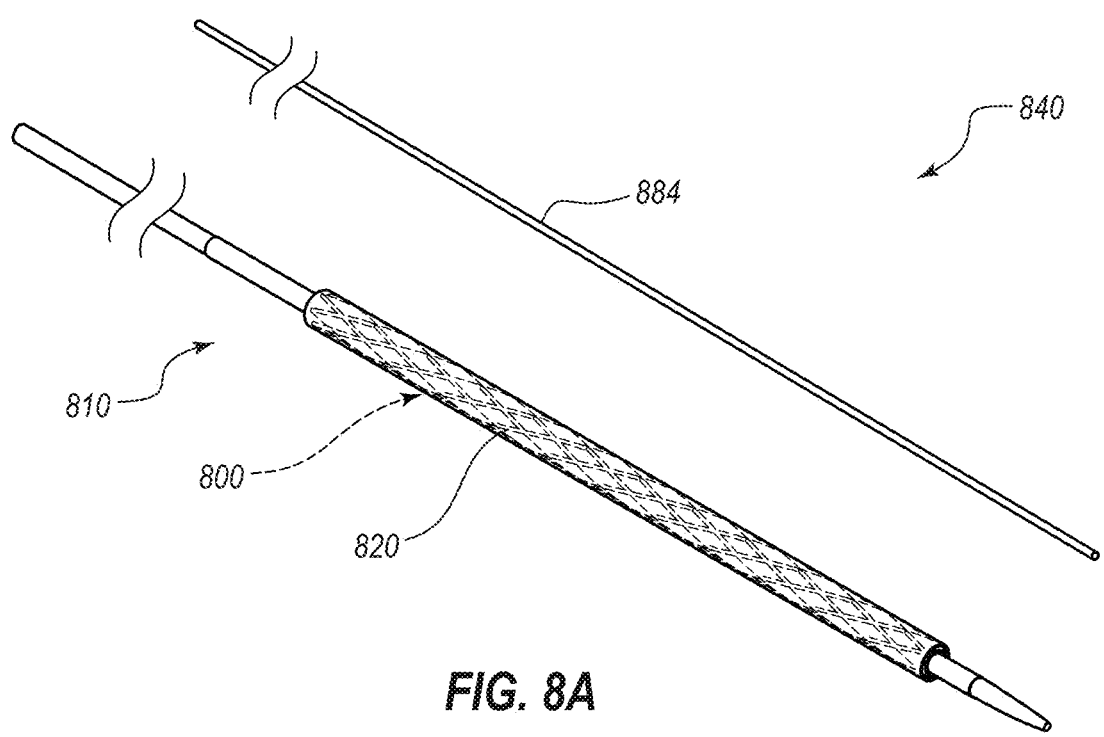
FIG. 8A is a perspective view of another embodiment of a system that can be used to implant an embodiment of an expandable medical device within the cecum of a patient.
Figure 8B:
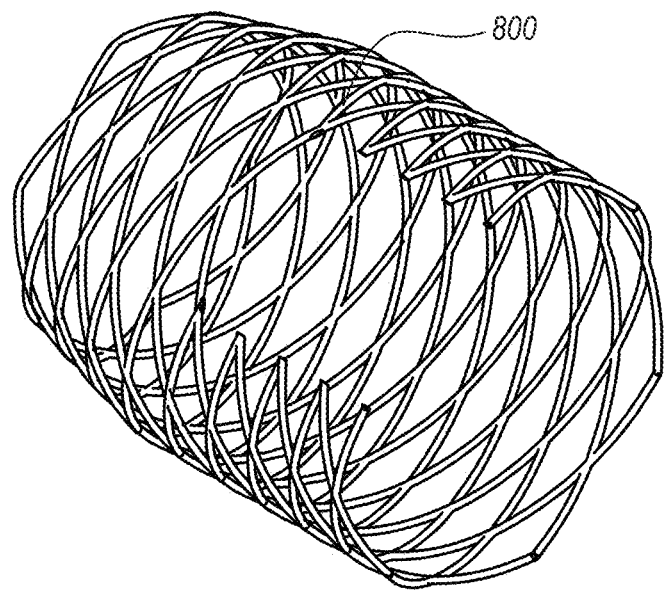
FIG. 8B is a perspective view of the expandable medical device in a deployed or expanded state.

FIGS. 8A and 8B depict an illustrative system 840 for implanting an embodiment of a self-expanding stent-like expansion device 800. The system 840 includes a catheter 810 to which the expansion device 800 is coupled. Unlike the catheter 510, in which the stent is positioned over an expandable balloon, the expansion device 800 is instead resiliently biased outward so as to naturally assume an expanded position upon removal of a retention sleeve 820 that is positioned about the expansion device 800. The method for introducing the expansion device 800 into the cecum 110 of the patient 205 can be substantially the same as that discussed above with respect to FIGS. 5A-5E. However, rather than passing the catheter through the instrument channel of the endoscope, the catheter 810 is advanced along the guidewire 884. For example, in some methods, the guidewire 884 may be advanced through the bowel of the patient 205 to the cecum 110 (e.g., via fluoroscopic or other imaging assistance). Once in place, the guidewire 884 may be positioned within an internal or external lumen defined by the catheter 810, and the lumen may be advanced over the guidewire 884 until the catheter is in the desired position. The restrictive sleeve 820 may then be removed, such as by retraction of a wire attached thereto, and the self-expanding expansion device 800 can naturally expand outwardly into contact with the cecum 110 to distend the cecum, as it assumes the deployed or expanded configuration depicted in FIG. 8B.

In the present example, the expansion device 800 can be placed without using an endoscope. In other instances, the guidewire 884 may be positioned in the patient in the manner just discussed, and then an endoscope can be advanced over the guidewire into position. For example, the guidewire may pass through the instrument channel of the endoscope. The guidewire may then be removed, and the catheter 810 may then be advanced through the instrument channel of the endoscope. In some instances, the endoscope is advanced into the patient, and the guidewire may be advanced through the endoscope and beyond the distal end thereof to facilitate advancement of the endoscope through the gastrointestinal tract. In various embodiments, the guidewire may remain within the endoscope and the expansion device passed thereover through the endoscope, or the guidewire may be removed before advancing the device through the endoscope. In various instances, visualization for placement of the expansion device 800 may be provided by the endoscope, fluoroscopy, and/or any other suitable imaging technique. Any other suitable techniques for using a guidewire and/or for positioning the expansion device in the patient are also contemplated.

Figure 9:
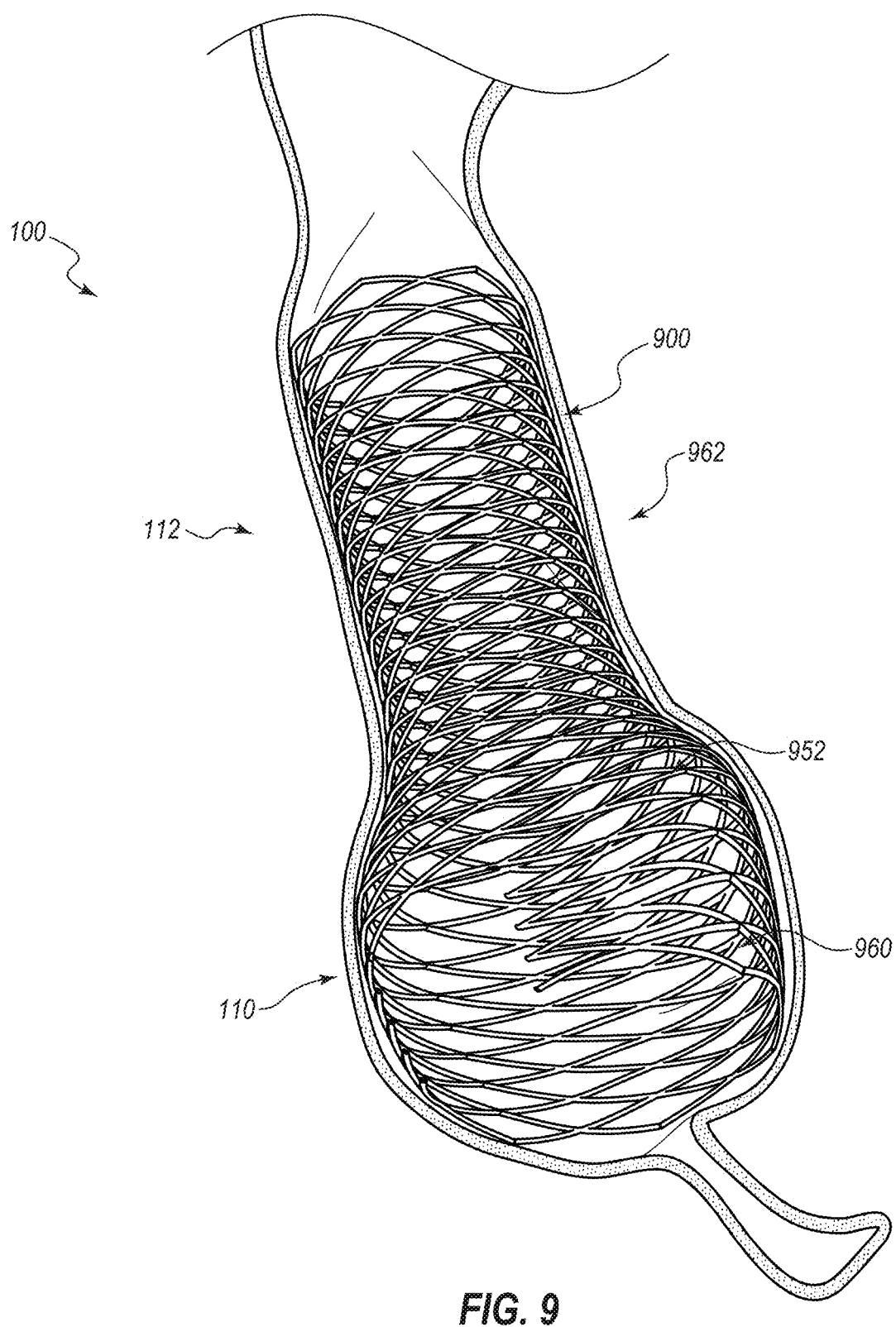
FIG. 9 is a cross-sectional view of a portion of the colon of a patient in which another embodiment of an expandable medical device, shown in perspective, has been delivered.

FIG. 9 depicts another embodiment of an expansion device 900 implanted in the colon 100 of the patient 205. Specifically, a bulbous portion at a proximal end of the expansion device 900 is positioned in the cecum 110, and an elongated distal extension 962 of the expansion device 900 extends into the proximal portion of the ascending colon 112. In the illustrated embodiment, a proximal portion of the expansion device 900 is substantially identical to the expansion device 500. The primary difference between the two expansion devices is the distally directed extension 962, which resides within the ascending colon 112. The expansion device 900 includes a taper 952 that can prevent migration in manners previously discussed. The expansion device 900 can be less prone to rotation about non-longitudinal axis than the expansion device 500. The expansion device 900 can be configured to distend one region of the bowel (i.e., the cecum 110) proportionally more than another portion. For example, in some embodiments, the distal extension 962 of the expansion device 900 primarily serves as anchoring leg for the expansion device 900, and may provide the ascending colon 112 with little or no distention, whereas the proximal end of the expansion device 900 may significantly distend the cecum 110, e.g., by a pathophysiological amount or to a pathophysiological size, to trigger a colo-gastric brake. In other embodiments, both ends of the expansion device 900 can distend the respective regions of the bowel 200, and may each contribute to the colo-gastric brake. In some embodiments, one end of the expansion device 900 expands the bowel by a percentage that is greater than a percentage by which the other end expands the bowel, or in other embodiments, both ends can yield similar distention percentages.

Figure 10A:
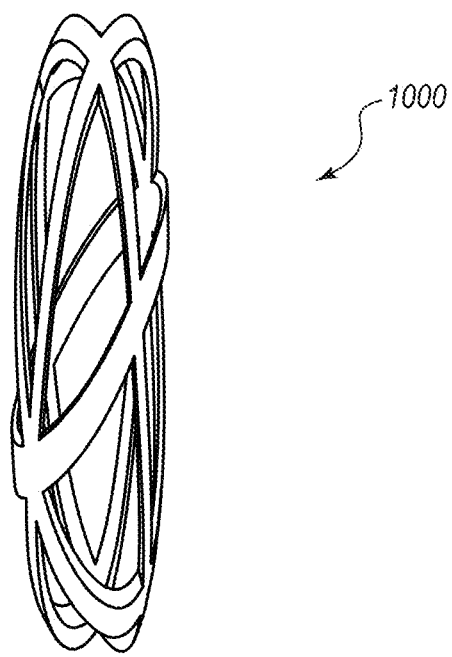
FIG. 10A is a perspective view of another embodiment of a medical device for the treatment of obesity, wherein the medical device is depicted in a contracted or undeployed state.
Figure 10B:
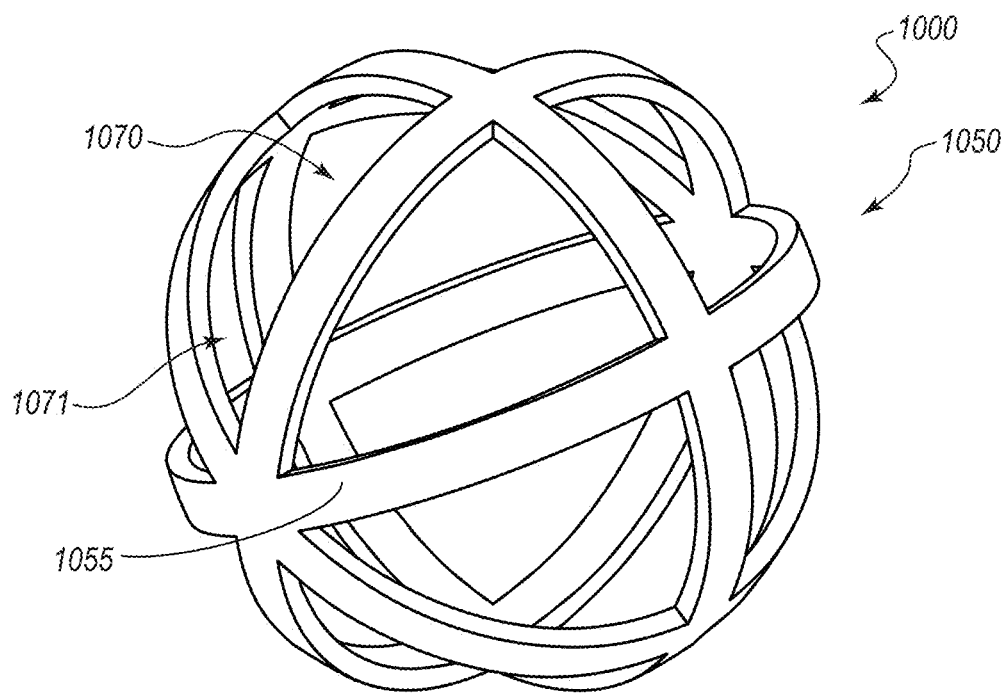
FIG. 10B is another perspective view of the medical device that depicts the device in an expanded or deployed state.

FIGS. 10A and 10B depict another embodiment of a medical device 1000, which may also be referred to herein as an expansion device, a stent ball, or a cage. The device 1000 is depicted in an undeployed, contracted, constricted, or unexpanded state in FIG. 10A, and is depicted in a deployed configuration in FIG. 10B. In some embodiments, the device 1000 can be expanded and can distend the cecum 110 in manners similar to the stent-like expansion devices previously discussed. For example, in some embodiments, the device 1000 may be deployed directly from an endoscope lumen or from a catheter lumen. In some embodiments, the device 1000 may be compacted to a smaller profile than what is illustrated in FIG. 10A, as compared to FIG. 10B. For example, in various embodiments, the struts may bend relative to one another more than is depicted, such that the unexpanded device 1000 is more elongated with a narrower profile than is shown in FIG. 10A.

The device 1000 may be formed of any suitable material, whether self-expanding or expandable with, e.g., balloon assistance. For example, in various embodiments, self-expanding versions may comprise Nitinol or other shape-memory material to expand from the generally tubular constricted configuration to the generally spherical expanded configuration once within the cecum.

The device 1000 can include a body 1050, which may be defined by a series of interconnected struts 1055, which have a substantially rectangular cross-sectional profile. The struts 1055 can define a plurality of openings 1071 of a passageway 1071 thorough the device 1000. The illustrated embodiment includes 12 total wedge-shaped openings 1071. The openings 1071 and passageway 1071 are relatively large, and thus are capable of permitting a large flow rate of material to pass through when the device 1000 is implanted.

Figure 11:
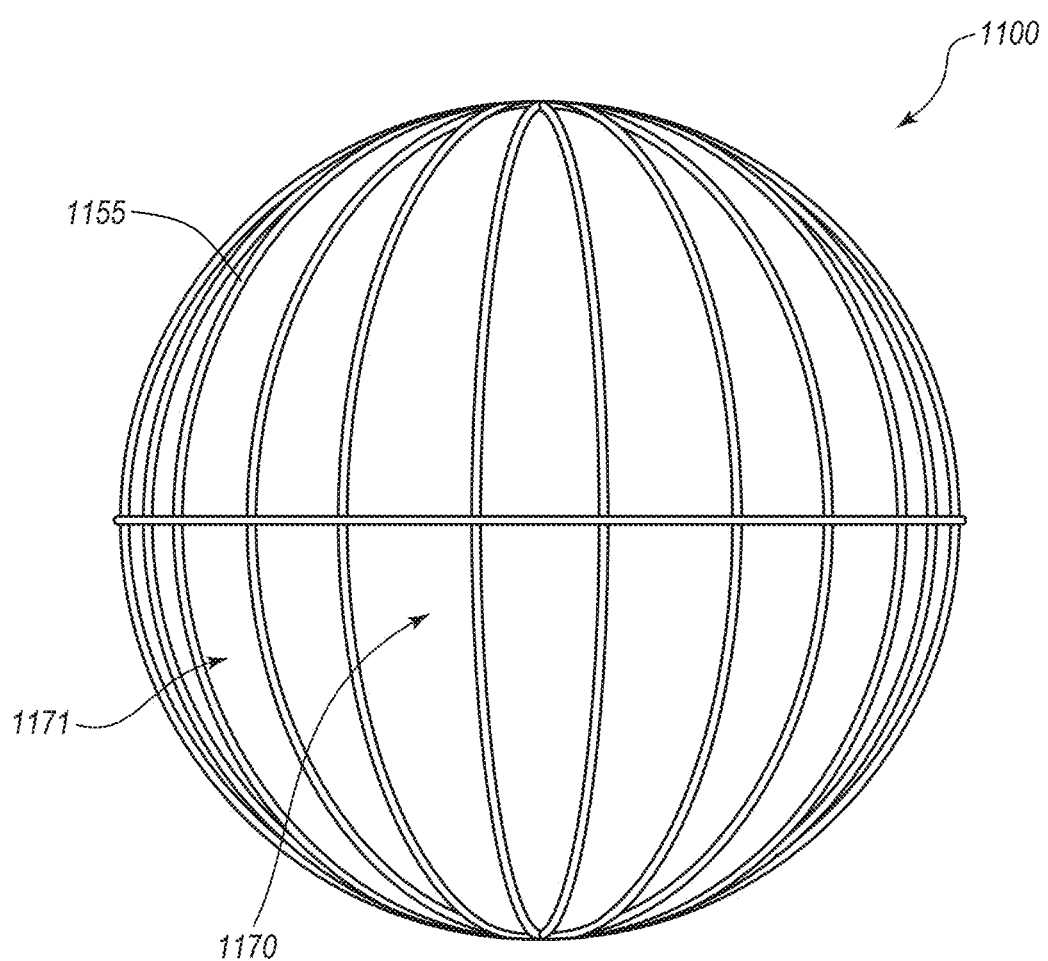
FIG. 11 is a perspective view of another embodiment of a medical device for the treatment of obesity.

FIG. 11 depicts another embodiment of a device 1100, which can resemble the device 1000 in many respects, and can be a mechanical self-expandable or otherwise expandable cage. The device 1100 may include a plurality of interconnected struts 1155 that may be formed and connected in any suitable manner. In the illustrated embodiment, the struts 1155 are formed as wires or rods with substantially circular cross-sectional profiles.

The struts 1155 define a plurality of openings 1171 of a passageway 1070. The illustrated embodiment includes 44 total wedge-shaped openings 1071. Other numbers and configurations of the openings 1071 are contemplated. The openings 1171 and passageway 1171 are relatively large, and thus are capable of permitting a large flow rate of material to pass through when the device 1100 is implanted.

As with other devices disclosed herein, in some embodiments, the device 1100 can be made of material that is biodegradable or bioresorbable over time, and thus may eventually naturally pass from the patient 205. In other or further instances, the device 1100 may be retrievable from its implantation site. For example, the device 1100 may be readily collapsible via mechanical manipulation.

Figure 12:
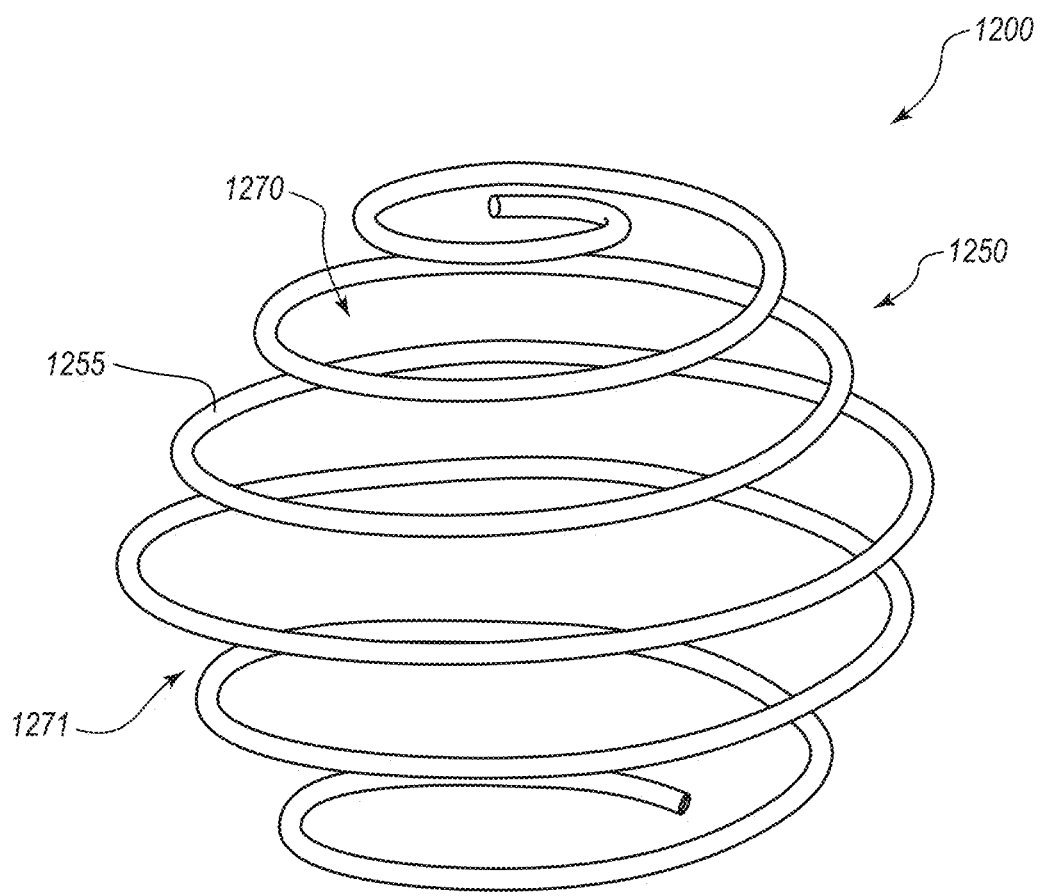
FIG. 12 is a perspective view of another embodiment of a medical device for the treatment of obesity.

FIG. 12 depicts another embodiment of a medical device 1200 that likewise resembles a cage. The device 1200 includes a frame or body 1250 that is formed from a single rod or wire 1255. The wire 1255 is wound or spiraled in a somewhat spherical shape, or may be termed as a spiral ball. The wire 1255 defines an extended opening 1271 of a passageway 1270 that passes through the ball. In particular, the opening 1270 is likewise spiral shaped.

As with other embodiments described herein, the device 1200 can comprise any suitable material, and may be self-expandable or may expand with assistance (e.g., via any suitable mechanical manipulation, such as balloon expansion). Illustrative examples include metals (e.g., stainless steel) and/or polymeric materials of any suitable variety, nanomaterials, etc. In some embodiments, the device 1200 comprises any suitable shape-memory material (e.g., Nitinol).

In some embodiments, the device 1200 may be introduced through the lumen of a catheter or endoscope. For example, in some instances, the device 1200 may be in a straightened configuration (e.g., have a substantially linear form) when in an undeployed or unexpanded configuration, and can be advanced through the lumen of the catheter or endoscope in this orientation. Once having exited the lumen and/or having been placed at a desired position within the bowel, the device 1200 may naturally (e.g., if formed of a resilient or shape-memory material) transition (e.g., return) to the space-filling, volume-defining, expanded ball shape depicted in FIG. 12 and distend the cecum.

In other embodiments, the device 1200 may be formed of a material that is configured to expand due to absorption of material (e.g., water) within the bowel. For example, in some embodiments, the device comprises a superabsorbent polymer. The polymer can function the same as or similar to expandable water toys, also known as grow-in-water toys. For example, the device may be sponge-like when in an undeployed state. The device 1200 could be inserted in substantially linear form through the working channel of an endoscope into the bowel in a "dry" (or low moisture content) condition, can assume the spiral shape upon exiting the endoscope, and then can expand when exposed to water or colonic effluent once introduced into the bowel. In some embodiments, the device 1200 can expand sufficiently to distend the cecum, such as to a pathophysiological size, as discussed elsewhere herein.

In other or further embodiments, a variety of coatings and/or compositions may be applied to the frame of the device 1200. In some embodiments, the coating may comprise an eluting material that can prevent or inhibit inflammation of the cecal wall and/or that can prevent or inhibit tissue ingrowth. For example, in some embodiments, the device 1200 includes a drug-eluting composition of any suitable variety. The eluted drugs may be, for example, immunosuppressive and/or antiproliferative. In various illustrative embodiments, the drug-eluting composition may comprise one or more of paclitaxel, sirolimus, or everolimus. In some embodiments, a polymer coating bound to the device frame includes the one or more drugs.

As with other devices disclosed herein, in other or further instances, the coatings and/or compositions applied to the device can elute beneficial substances, such as appetite suppressants. For example, in some embodiments, the device 1200 is coated with a polyethylene glycol resin that contains, e.g., a complex carbohydrate or other nutrient source for the patient 205 directly, or contains, e.g., cellulose or some other material that provides nutrients for bacteria that reside in the bowel. Bacteria may eat and derive nutrients from the material over time, and may be sufficient to independently achieve or to assist in achieving satiety for the patient. Items like cellulose may be advantageous, as they need not be preserved (e.g., refrigerated) prior to implantation. In some embodiments, the material that may be eluted can comprise nutrients for the patient 205, such as, for example, any suitable complex carbohydrate, simple carbohydrate, fat, or protein. In other or further embodiments, the material that may be eluted can comprise nutrients for bacteria, either including or in exclusively, some materials that are non-nutritive for the patient, such as, for example, cellulose or psyllium.

In some embodiments, a pouch or other container is positioned at interior of the device 1200. For example, the pouch may comprise a millipore netting or the like that is positioned within the frame or body 1250. The pouch can include nutrients that leach out or are otherwise consumed over time. Nutrients or other materials can be consumed over time and assist in satiating the patient. In other or further embodiments, the body 1250 is independently formed of a separate bioresorbable material that degrades over time and, eventually, spontaneously passes out through the bowel and out of the patient 205.

FIGS. 13A-13G depict additional embodiments of devices 1300, 1301, 1302, 1303, 1304, 1305, 1306 that can be implanted in the patient 205 to trigger a colo-gastric brake, such as by transitioning from an undeployed or unexpanded state to an expanded state in which the device distends the cecum. The devices 1300-1306 may also be referred to as cages, shells, balls, or balloons.

Each device 1300, 1301, 1302, 1303, 1304, 1305, 1306 can include a body 1350 that defines a plurality of openings 1371 that are in fluid communication with a cavity of the body 1350. The cavity is a passageway 1370 through which material can pass. The size, shape, number, pattern (or lack thereof), and/or orientation of the openings 1371 can be varied, depending on, for example, performance preferences. The devices 1300, 1301, 1302, 1303, 1304, 1305, 1306 are illustrative a wide variety of possible options for different sizes, shapes, numbers, patterns, and/or orientations of the openings. The openings 1370 can be any shape or size. The openings 1371 and the passageway 1370 of each device can permit passage of material through the body 1350.

In some embodiments, the body 1350 is a hollow shell of material. The shell may be relatively thin. In some embodiments, the material of which the body 1350 is formed is resiliently flexible or elastomeric. For example, in some embodiments, the body 1350 can be compressed or otherwise compacted to a smaller profile to transition the device to the undeployed state. Upon placement in the cecum, the body 1350 can be released from the compressed state and can naturally transition to the deployed or expanded configuration.

The body 1350 can define a variety of different shapes or configurations. In FIGS. 13A-13E, the bodies 1350 each define a substantially spherical outer surface that is perforated by the various openings 1371. In FIGS. 13F and 13G, the bodies 1350 are more oblong. In some instances, the oblong shapes may more readily conform the pouch-like configuration of the cecum and/or may be less susceptible to rotation (e.g., rotation about axes other than a longitudinal axis of the body) when retained in the bowel in a free-floating arrangement.

The set of openings 1371 and the passageways 1370 with which they communicate can be sufficiently large to permit material that would naturally pass through the portion of the bowel in the absence of the body 1350 to pass through the body 1350 substantially unimpeded. In some embodiments, the body 1350 is multi-chambered, and thus may define multiple passageways. All such passageways may desirably provide sufficient flow capacity to permit material that would naturally pass through the portion of the bowel in the absence of the body 1750 to pass through the body 1750 substantially unimpeded.

In various embodiments, the body 1750 is configured to obstruct no greater than 5, 10, 15, or 20 percent of material from passing through the portion of the bowel within which the body 1750 is positioned. In various embodiments, the body 1750 is configured to reduce a flow capacity through a lumen defined by the portion of the bowel by no greater than 10, 20, 30, 40, or 50 percent.

Figure 13A:
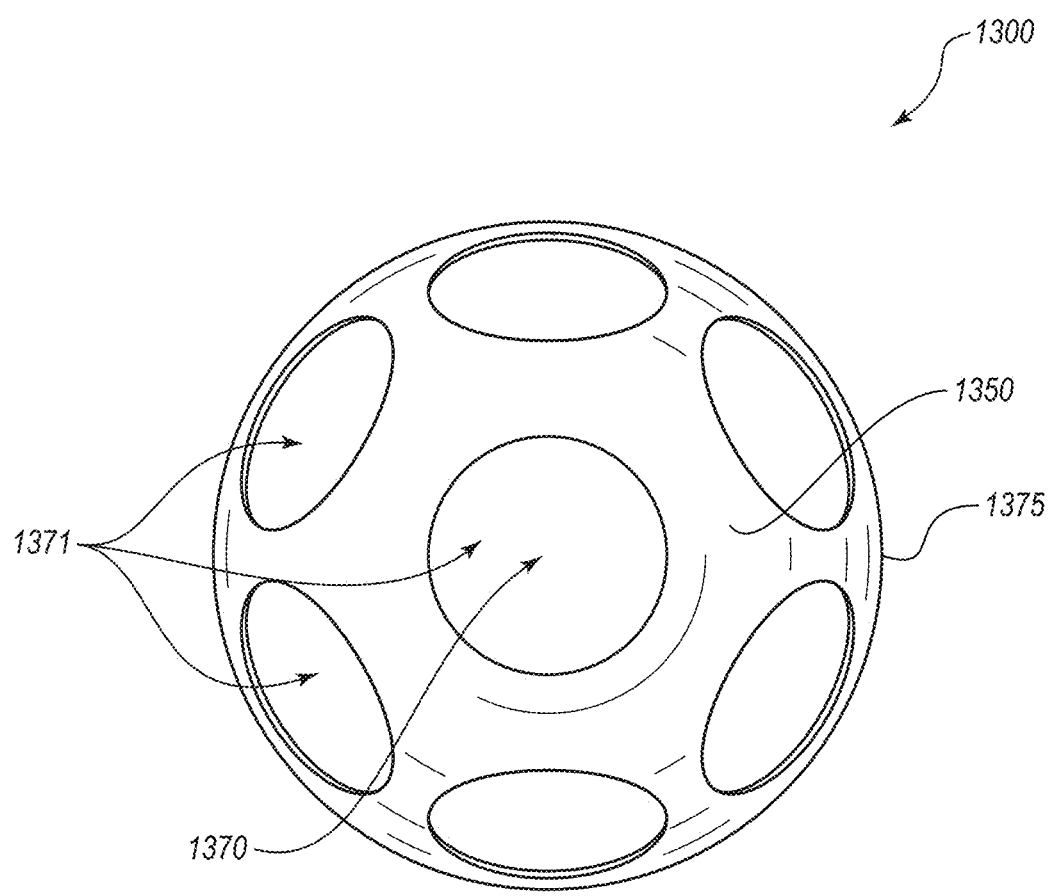
FIGS. 13A-13G are perspective view of additional embodiments of medical devices for the treatment of obesity.
Figure 13B:
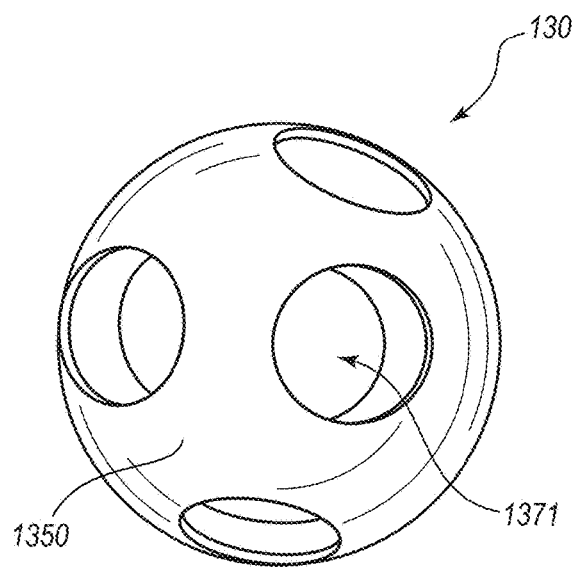
Figure 13C:
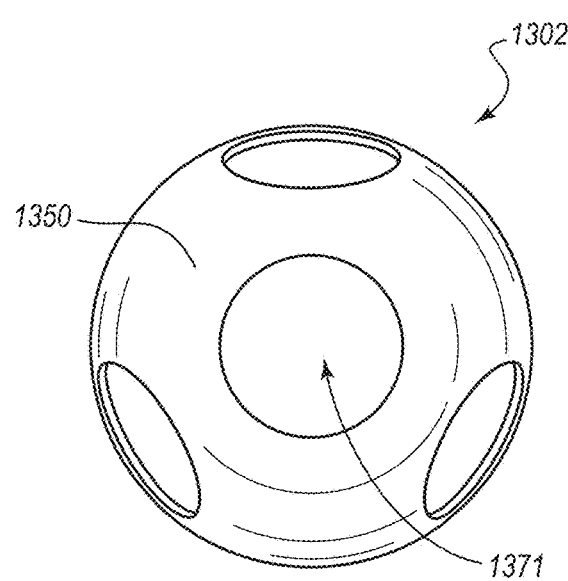
Figure 13D:
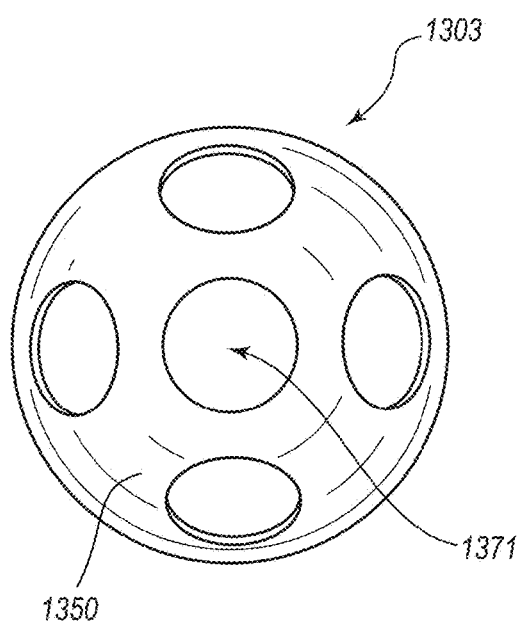
Figure 13E:
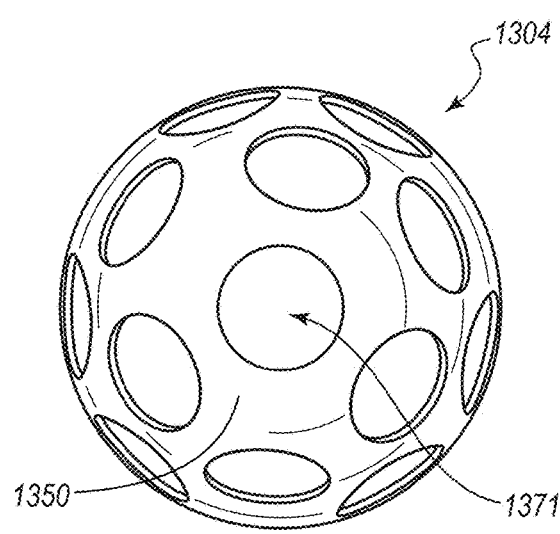
Figure 13F:
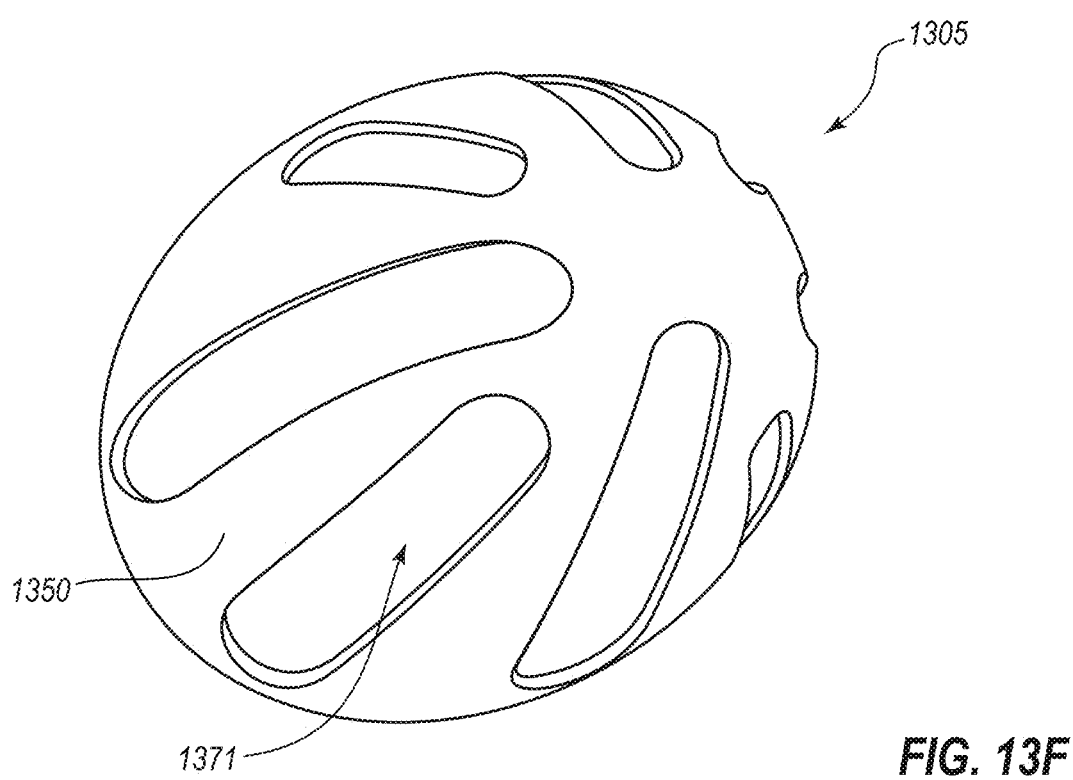
Figure 13G:
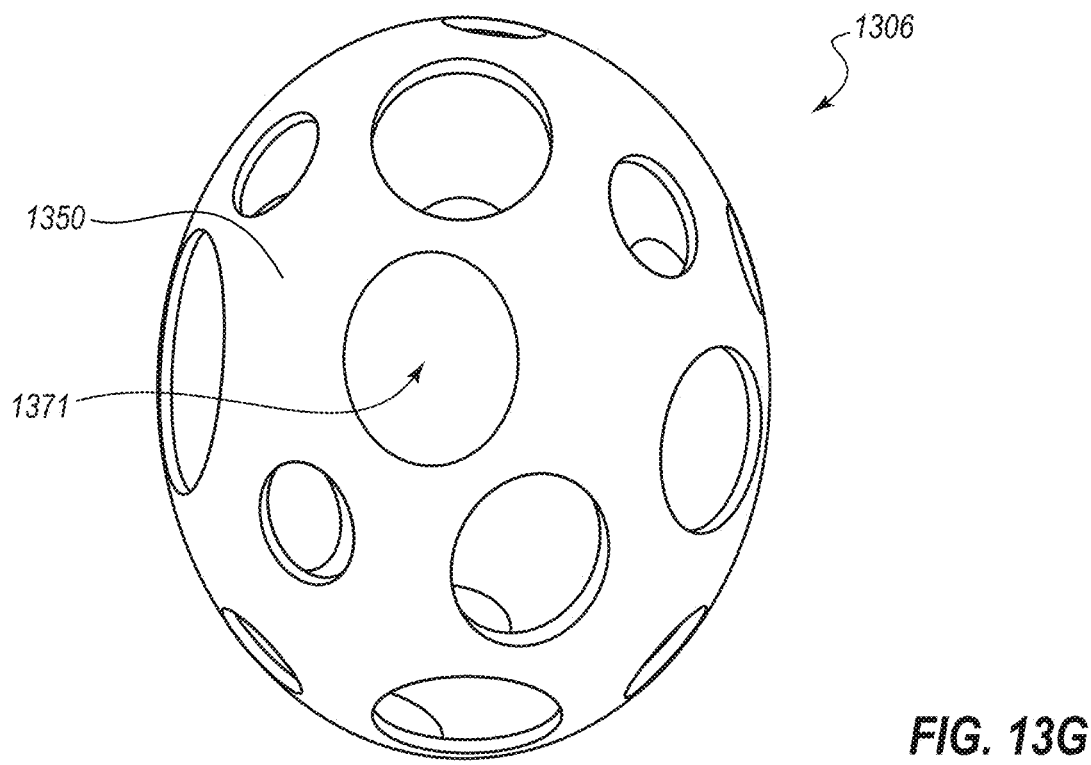

With reference to FIG. 13A, the body 1750 can define an outermost perimeter 1375. In some instances, the outermost perimeter 1375 contacts the cecum as the body 1750 distends the cecum. For example, in some instances, the perimeter 1375 of the body 1750 may be fully in contact with an inner surface of the cecum. Stated otherwise, the body 1750 may contact the cecum about the full perimeter 1375 (or periphery), and a full perimeter of an inner surface of the cecum may contact the perimeter 1375. For example, the device 1300 could be positioned within cecum such that a longitudinal axis of the cecum is substantially aligned with an axis that passes directly through the center of the device 1300 and is perpendicular to the plane of the page of FIG. 13A. In further instances, such as when the device 1300 is in full contact with the bowel and/or distends the portion of the bowel with which it is in contact, the bowel wall can be in contact with the full perimeter 1375. In certain of such instances, it may be said that the body 1370 define a longitudinal axis (e.g., longitudinal relative to its position in the lumen) that is substantially aligned with a direction of material flow through the passageway 1370.

In some embodiments, the perimeter 1375 of the body 1350 defines a maximum cross-sectional area along a plane that is transverse to the longitudinal axis of the body 1350. For example, in the illustrated embodiment, this plane is the plane of the page. It may also be said that the passageway 1370 defines a minimum cross-sectional area along a different plane transverse to the longitudinal axis. As an example, the passageway 1350 has a minimum area at the opening 1371, which is on a plane that is parallel to the plane of the page. In various embodiments, the minimum cross-sectional area defined by the passageway 1370 (e.g., the area of the opening 1371) is smaller than the maximum cross-sectional area defined by the body by no greater than 10, 20, 30, 40, 50, 60, 70, 80, or 90 percent. With respect to the stents depicted in the drawings, the lumen size can be substantially the same as the lumen size of the bowel. With respect to the device 1300 of FIG. 13A, however, the minimum size of the passageway 1370 is substantially smaller than the size of the perimeter 1375. In certain embodiments (e.g., a cylindrical tubular stent), the planes of maximum perimeter and minimum passageway size may be coplanar.

In some embodiments, a summation of the areas defined by the entrance openings 1371 of the passageways is smaller than the maximum cross-sectional area defined by the body 1350, along a plane transverse to the longitudinal axis (e.g., a transverse plane through the bowel lumen when the device is implanted therein) by no greater than 10, 20, 30, 40, or 50 percent. This ratio of areas can be a good indication of the amount of flow reduction that may be caused by the presence of the device 1300, in some instances.

Figure 14A:
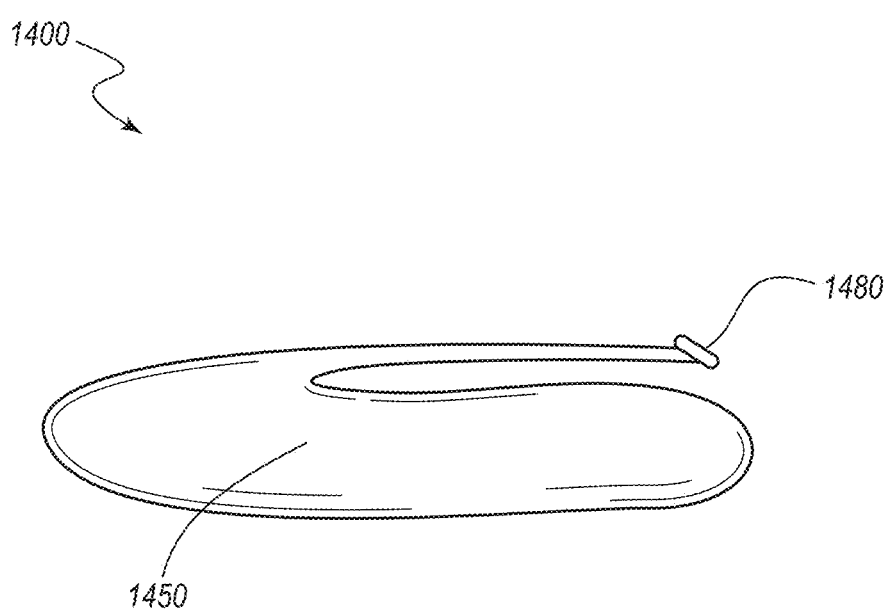
FIG. 14A is a perspective view of another embodiment of a medical device for the treatment of obesity, wherein the medical device is depicted in a contracted or undeployed state.
Figure 14B:
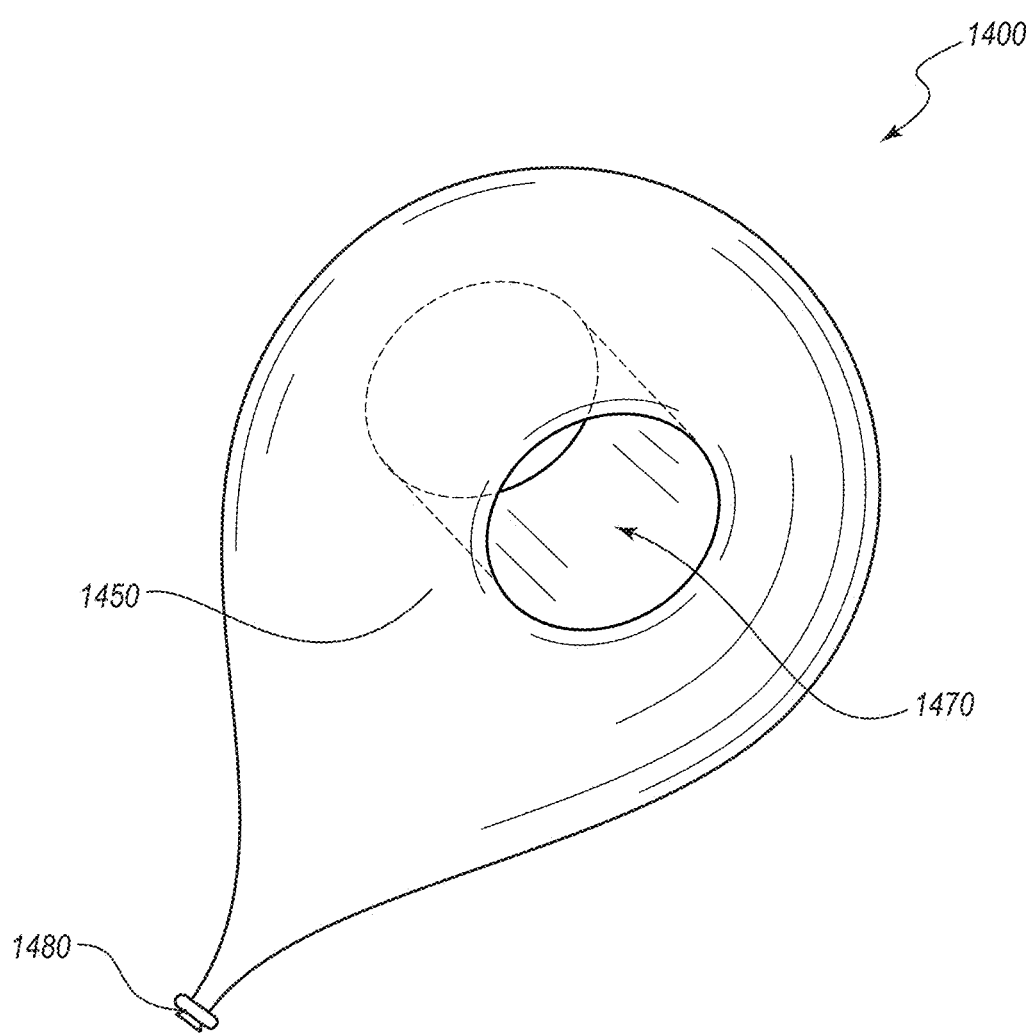
FIG. 14B is another perspective view of the medical device that depicts the device in an expanded or deployed state.

FIGS. 14A and 14B depict another embodiment of a medical device 1400 or structure that is formed as a balloon with an integrated channel. The device 1400 can be inflated at the desired location and/or inflated and delivered thereto.

The device 1400 includes a body 1450 that defines a channel 1470 when in the expanded state. The structure can be self-sealing, such as via any suitable closure 1480, such as a one-way valve. For example, in some embodiments, the closure 1480 includes a one-way valve through which fluid is introduced into the body 1450, and then subsequently maintained in the balloon. In various embodiments, the body 1450 can be advanced into the bowel in a deflated or partially deflated state. The body 1450 may, for example, be delivered to a desired site—e.g., the cecum—over a guidewire, over or through an endoscope, or in any other suitable manner. The structure can be applied in a specific segment of the bowel and take 3-dimensional shape when inflated in order to distend the lumen.

In various embodiments the body 1450 is formed of latex, nonlatex, rubber, derivatives of rubber, any rubber-like material or elastomeric material, or any other suitable material. The body 1450 can be expanded with one or more fluids (e.g., air or saline). Once inflated, the body 1450 may be either free floating in the lumen of the bowel or attached or otherwise secured to the wall of the bowel. For example, in some instances, the body 1450 may be attached to the wall by sutures or an adhesive. In other or further embodiments, the body 1450 may be tensioned in place by achieving a suitable pressure of the inflation fluid. The balloon can be expanded to a variety of sizes or shapes, causing a variety of distention amounts of the bowel.

In some embodiments, at least a portion of the balloon body 1450 comprises a material that is degradable over time (e.g., any suitable bioresorbable material). Degradation can yield leaks in the walls, leading to loss of fluid and size reduction. In other or further embodiments, at least a portion of the closure 1480 comprises a degradable (e.g., bioresorbable) material, which can yield a leak by which the device 1400 is deflated and may eventually spontaneously pass from the patient. Any suitable bioresorbable material is contemplated.

In some embodiments, in order to prevent bowel obstruction from the balloon, the balloon includes the channel 1470. It may be desirable to orient the balloon such that the channel 1470 is substantially aligned with a longitudinal axis of the bowel lumen. The bowel lumen thus can be simultaneously expanded by the balloon, yet the balloon passageway or channel 1470 can allow air, liquid, semiliquid, semi-solid or solid stool to pass therethrough.

Certain illustrative methods of implanting the device 1400 will now be described. In some instances, the device 1400 comes prepackaged with an inflation catheter. Stated otherwise, when removed from packaging, the device 1400 may already be attached to an inflation catheter. The device 1400 and catheter can be inserted through the working channel of an endoscope. In some instances, the device 1400 and catheter are advanced through the working channel of the endoscope to position the device 1400 at the distal end of the working channel prior to inserting the endoscope into the patient. The endoscope, catheter, and device 1400 are then advanced together through the bowel of the patient into the cecum. The catheter can be advanced distally relative to the endoscope to move the device 1400 out of the working channel and into the cecum. Any suitable inflation mechanism may be coupled to a proximal end of the catheter, and inflation fluid can thereby be delivered through the catheter into the device 1400 to inflate the device 1400. As the device 1400 is inflated, it can move into contact with and expand the cecal wall to a pathophysiological size. The catheter can then be decoupled from the device 1400, which can self-seal in manners such as previously disclosed (e.g., via the valve 1480). The catheter and endoscope can then be removed from the patient.

Figure 15:
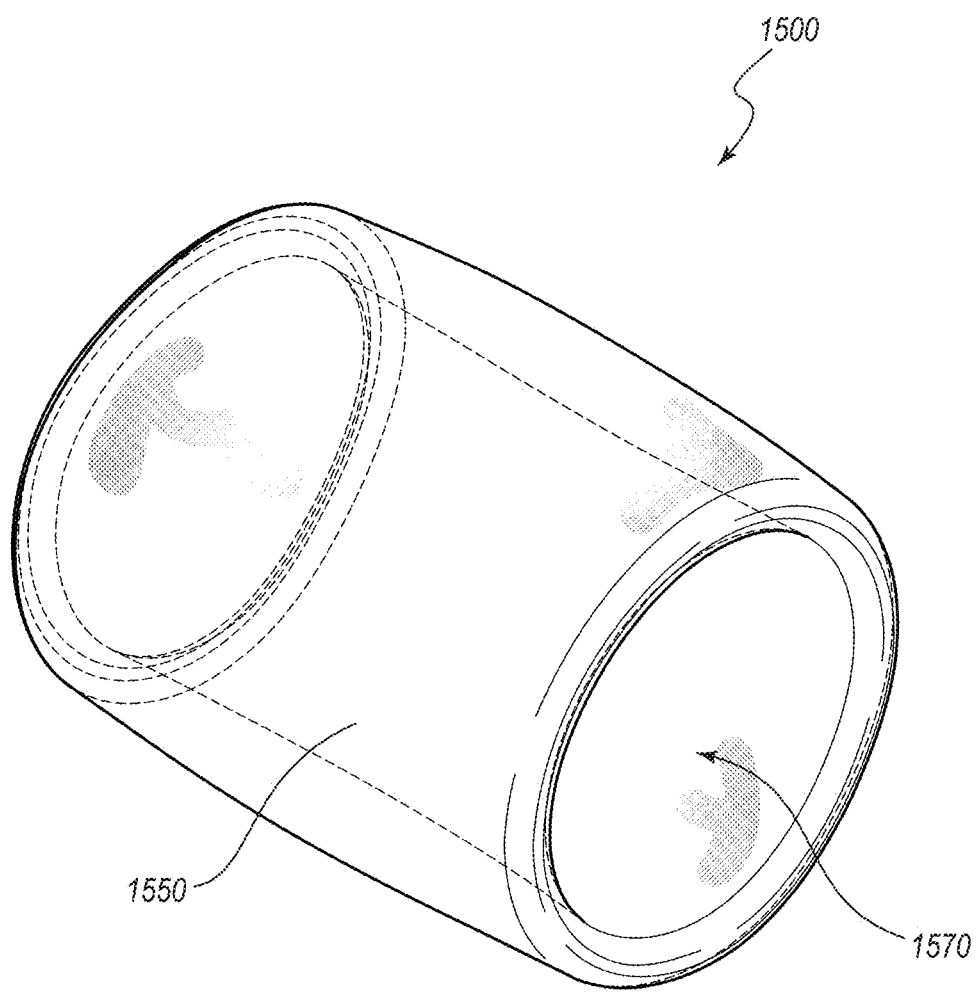
FIG. 15 is a perspective view of another embodiment of a medical device for the treatment of obesity, wherein the medical device is depicted in an expanded or deployed state.

FIG. 15 depicts another embodiment of a device 1500 that can include an inflatable balloon body 1550, which may also include a self-sealing closure (such as the valve 1480 previously described). The body 1550 defines a large central passageway 1570.

The shape of the body 1550 may assist in ensuring that passageway 1570 remains aligned with the lumen of the bowel. For example, the illustrated embodiment may fit well in the pouch-like cecum, and a length of the body 1550 is such that rotation of the device relative to the bowel in a manner that could close the passageway 1570 would be inhibited.

In some embodiments, an opening through a sidewall of the balloon structure into the primary passageway 1570 may be provided. The opening can be aligned with the ileocecal valve to ensure the device 1500 does not block the flow of material therefrom.

Figure 16:
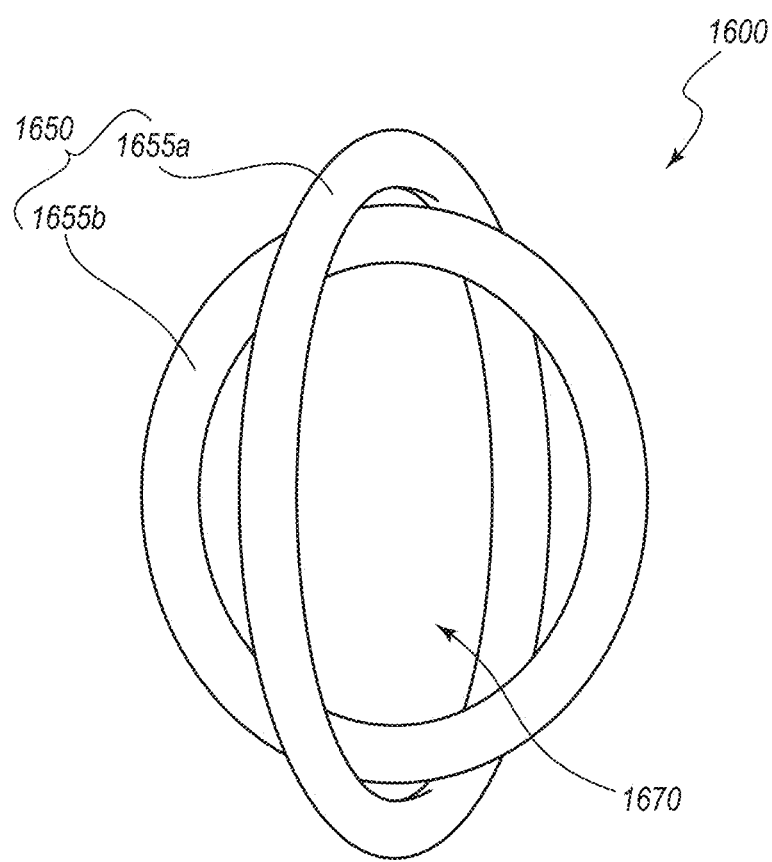
FIG. 16 is a perspective view of another embodiment of a medical device for the treatment of obesity.

As shown in FIG. 16, another example structure or medical device 1600 can include a plurality of inflatable structures 1655a, 1655b that define a body 1650 of the device. The body 1650 defines a passageway 1670 through which material can pass when the device 1600 is implanted. The structures 1655a, 1655b are each substantially tubular rings that are oriented perpendicularly to each other, such as to form an atom shape. In various embodiments, the device 1600 can include two attached or interlocking circular or hemi-circular balloons. Other arrangements are possible, such as discussed further below. The structures 1655a, 1655b can be oriented relative to each other in a manner to allow wide openings between the individual balloons.

In the illustrated embodiment, each structure 1655a, 1655b is self-contained. Or stated otherwise, each structure 1655a, 1655b defines a separate chamber. Thus, the body 1650 is a two-chamber system, with each chamber being separate from the other. In some embodiments, each structure 1655a, 1655b contains a self-sealing or auto-closing closure, and each structure 1655a, 1655b may be inflated separately. The structures 1655a, 1655b may be attached to each other in any suitable manner. In some embodiments, the structures 1655a, 1655b are secured to each other via a bioresorbable material, such as a bioresorbable adhesive.

Embodiments can thus include multiple circular or hemi-circular interlocking balloons in any manner or shape that would allow expansion of the balloons but also allow for spaces or openings between the balloons, such as the example structures shown in FIGS. 17-20.

In other embodiments, configurations other than circular or hemi-circular are used. Any suitable geometric shape in combination with any other shapes are contemplated. Thus, the balloon could be partially circular or circular or hemi-circular in combination with any other shape or shapes, so long as there are spaces or perforations between or in the balloon or balloons to allow air or fluid or liquid or semi-liquid or semi-solid stool to pass. The balloons or portions of the balloons could be as thin as ribbons or tubular or any thickness or size. Thus, the combination of balloons is essentially limitless as long as there are spaces incorporated within the design to allow passage of air, solid, or liquid.

In other embodiments, the structures 1655a, 1655b are connected so as to define a single chamber. Accordingly, the body 1650 can be inflated via a single port.

In certain embodiments, the material of which the body 1650 is formed can degrade which can lead fluid to escape and the body to deflate. In other or further embodiments, the structures 1655a, 1655b are held together by material that degrades or deflates. For example, a bioresorbable material can hold together the separate structures 1655a, 1655b prior to degradation, and degradation of the bioresorbable material releases the separate pieces from each other. One or more of the deflated and/or degraded structures 1655a, 1655b, or individual pieces thereof, can pass through the bowel and be eliminated spontaneously. In other or further embodiments, the body 1650 can be removed endoscopically.

More generally, with respect to various embodiments disclosed herein, connections between various facets of the structure, such as connections holding two or more balloons together, or two or more mechanical features together (such as certain of the struts 555 [see FIG. 5E], 1055 [see FIG. 10B], 1155 [see FIG. 11]), could degrade or deflate over time, allowing for separation of the structure and partial or complete elimination of the structure in stool over time.

Figure 17:
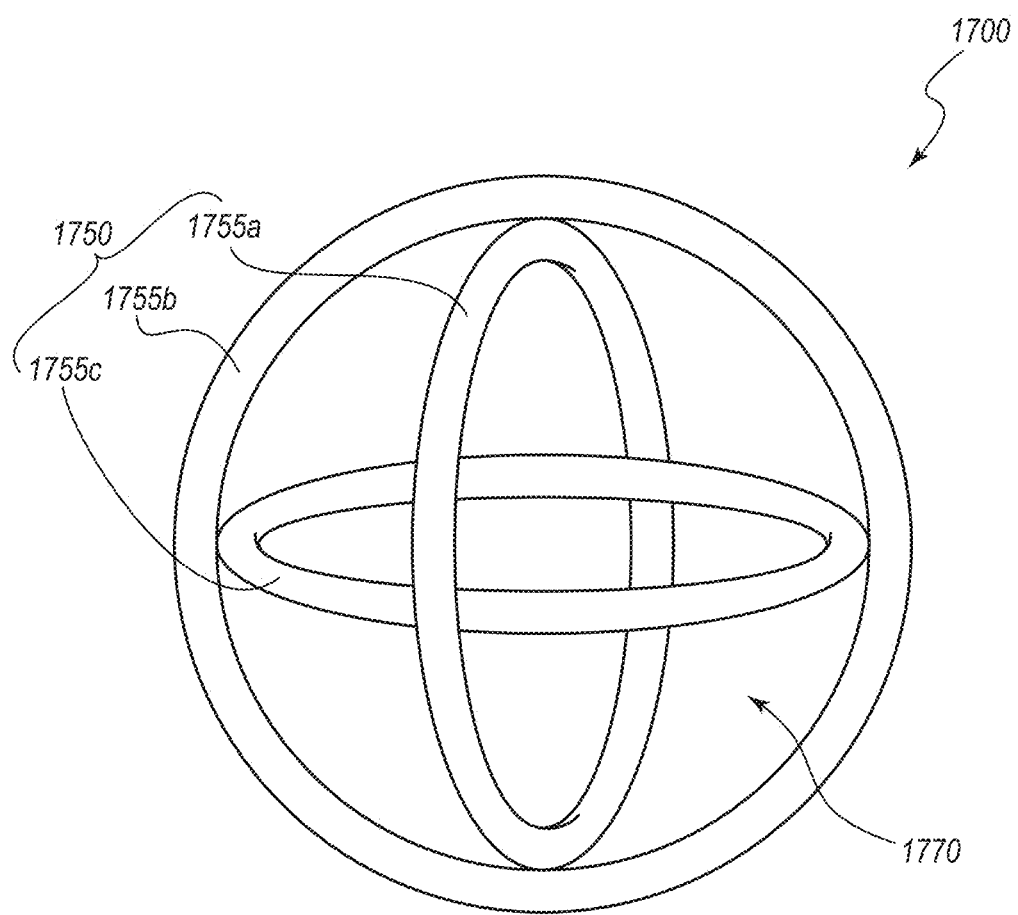
FIG. 17 is a perspective view of another embodiment of a medical device for the treatment of obesity.
Figure 18:
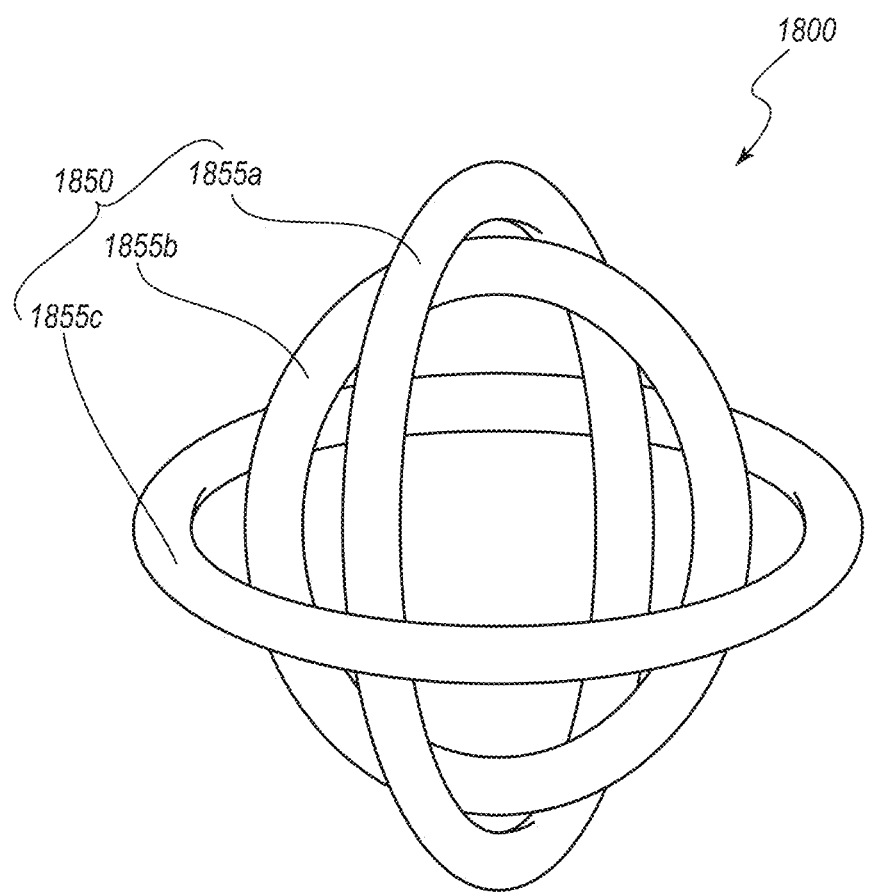
FIG. 18 is a perspective view of another embodiment of a medical device for the treatment of obesity.
Figure 19:
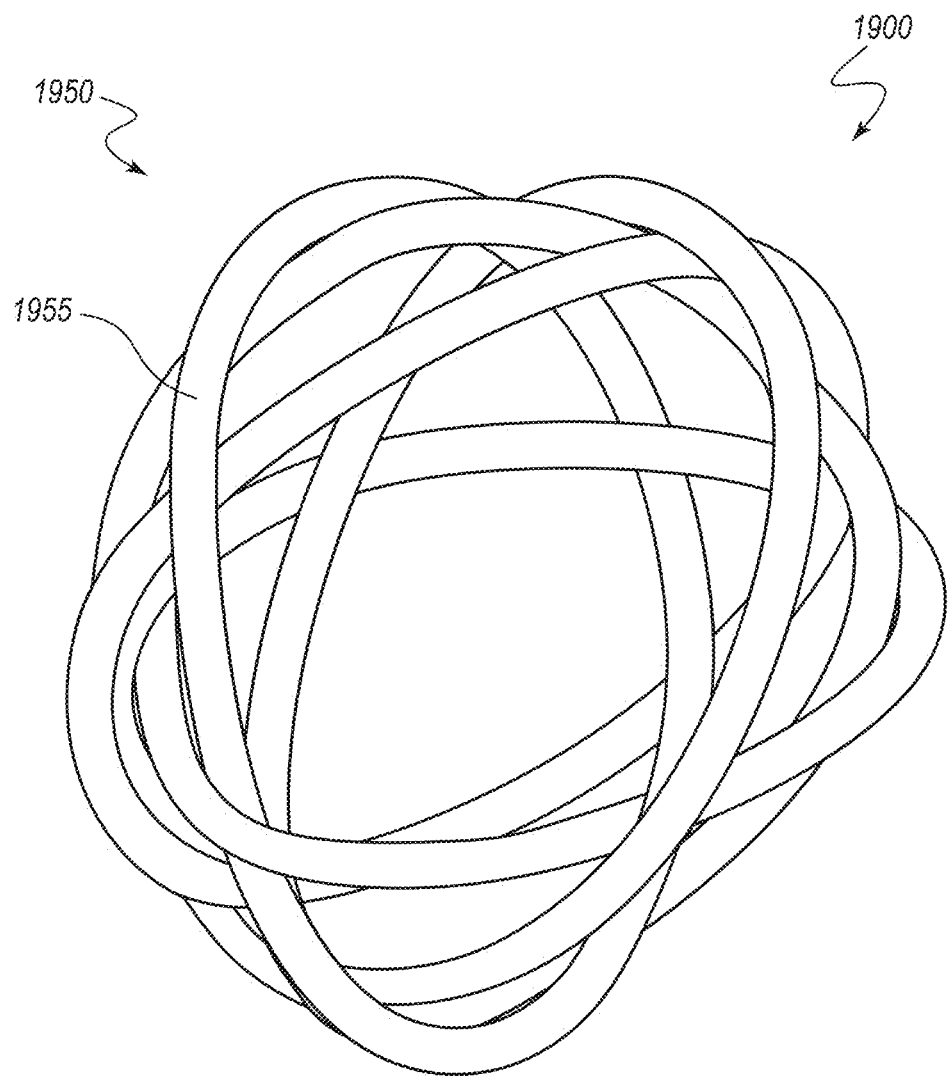
FIG. 19 is a perspective view of another embodiment of a medical device for the treatment of obesity.
Figure 20:
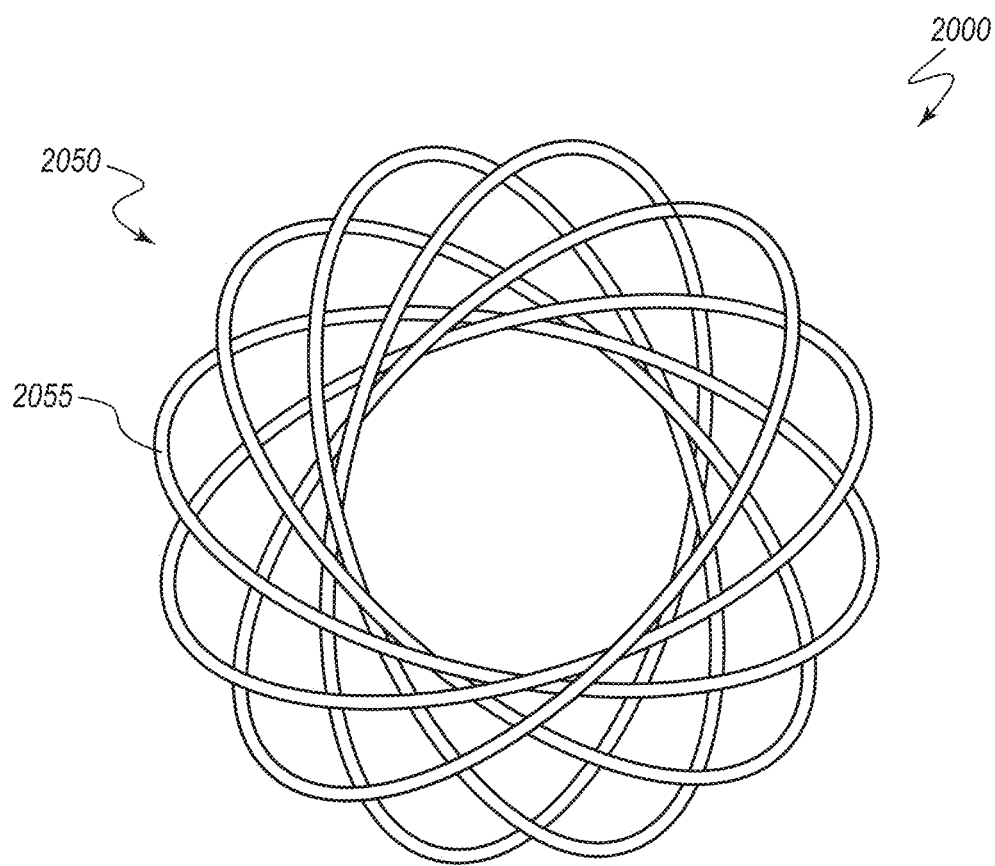
FIG. 20 is a front elevation view of another embodiment of a medical device for the treatment of obesity.

With reference to FIGS. 17-20, inflatable or expandable structures can define a wide variety of configurations that may be capable of distending the bowel while permitting passage therethrough of material so as not to obstruct the lumen of the bowel. In FIG. 17, a device 1700 includes a body 1750 formed of three structures 1755a, 1755b, 1755c that are connected to one another at mutually perpendicular orientations. In FIG. 18, a device 1800 also includes a body 1850 formed of three structures 1855a, 1855b, 1855c that are connected to one another at mutually perpendicular orientations, but in a manner different from that of the device 1700. FIG. 19 depicts a device 1900 that includes a body 1850 formed of a single structure (e.g., a single inflatable balloon, rod, etc.) that forms a netted region substantially without symmetry. FIG. 20 depicts a device 2000 that includes a body 2050 formed of multiple structures (e.g., multiple inflatable balloons, rods, etc.) that form a netted region with multiple planes of symmetry.

In the event that various embodiments are not tolerated by a patient (e.g., cause excessive anorexia, nausea, and/or vomiting), or for any other suitable reason, the device may be removed in any suitable manner. For example, various embodiments ban be partially or completely removed by scraping, dissolving, deflating, collapsing, retracting, snaring, and/or any other suitable means.

In some embodiments disclosed herein, the implanted medical device may define a space-filling or volume-defining structure that may trigger a colo-gastric brake, but may only minimally or nominally distend the bowel wall, or may not distend the wall at all. For example, the device may merely fill the space (without causing partial or complete obstruction) and, potentially, may somewhat slow the flow of material. The presence of the device and/or its slowing of material could independently trigger a colo-gastric brake.

Figure 21:
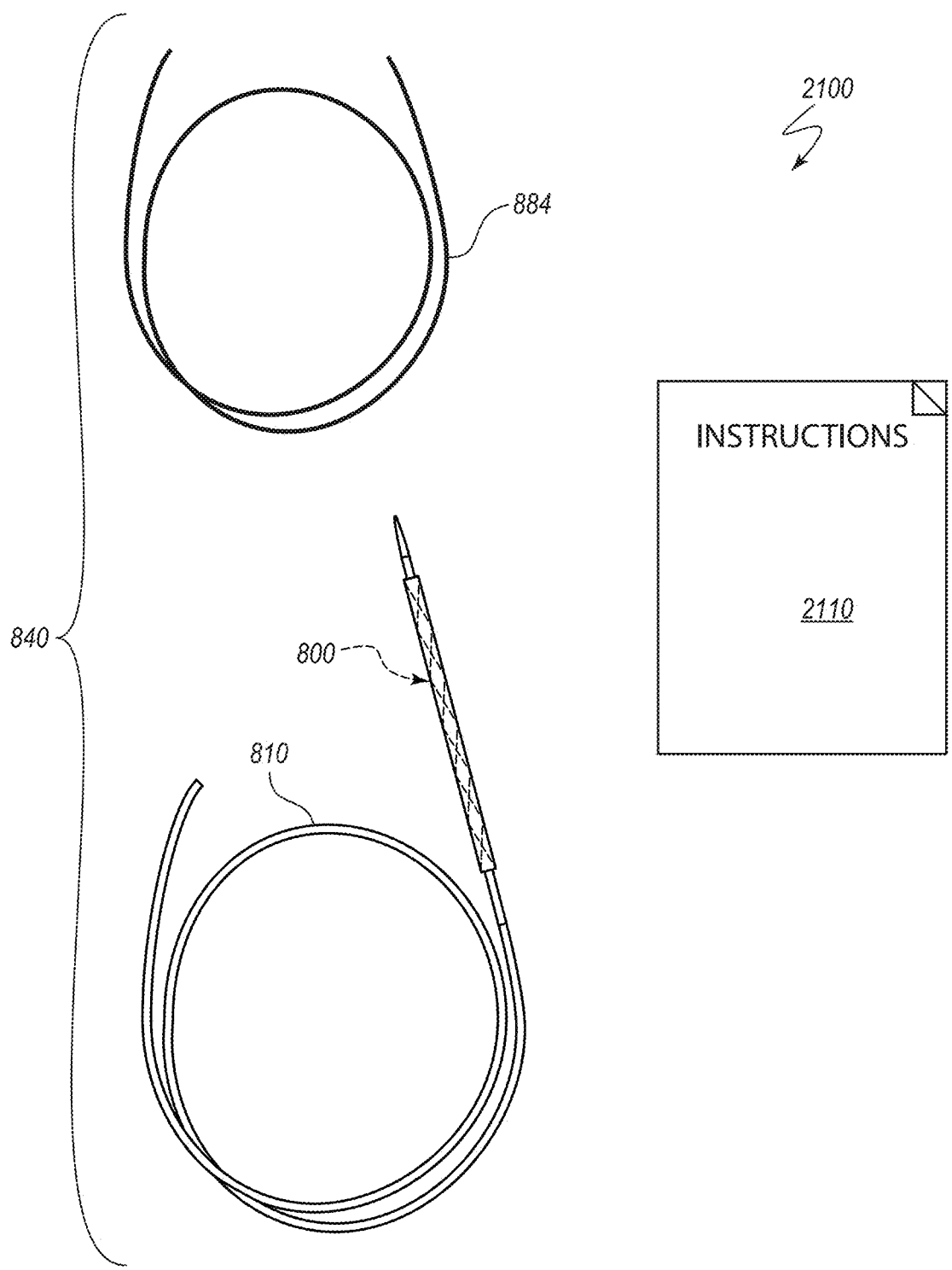
FIG. 21 is an elevation view of an embodiment of a kit for the treatment of obesity.

FIG. 21 depicts a kit 2100 that can be used in introducing a medical device into a patient. The kit 2100 can include any of the systems (e.g., implantation, deployment, delivery, and/or expansion systems) disclosed herein (i.e., those disclosed previously and/or those disclosed hereafter) and/or components thereof. For example, the kit 2100 can include any of the medical devices disclosed herein (e.g., one or more of the devices 300, 400, 500, 700, 800, 900, 1000, 1100, 1200, 1300, 1301, 1302, 1303, 1304, 1305, 1306, 1400, 1500, 1600, 1700, 1800, 1900, 2000, 2200, 2600, 2800, 2900, 3000, 3100, 3200, 3300, 3400, 3500, 3600, 3800, 3900, 4000, 4200) and/or any one or more of the systems or components thereof or associated therewith to introduce the device into the patient and/or deploy the device within the patient.

In illustrated embodiment, the kit 2100 includes the system 840 described above, which includes a guidewire 884 and the medical device 800 coupled with the catheter 810. In other embodiments, the medical device 800 may be introduced via an endoscope, or more specifically, a colonoscope (e.g., in manners previously discussed with respect to the system 840). In some embodiments, the kit 2100 may include an endoscope and/or accessories therefor, or may be specifically configured for use with a particular endoscope (e.g., a colonoscope).

The kit 2100 can include instructions for use 2110, which may provide directions with respect to any of the processes disclosed herein (i.e., any of the methods or steps thereof disclosed previously and/or hereafter). That is, the instructions for use 2110 can include directions to perform any suitable combination of method steps involving the device and/or system included in the kit 2100. For example, in the illustrated embodiment, the instructions for use 2110 can specifically recommend or direct a user to deploy the medical device within the cecum of the patient to distend the cecum for a therapeutically effective period. In various embodiments, the kit—and, in particular, the instructions for use thereof—can be approved of or authorized by a regulating body of a particular jurisdiction. For example, the kit, and the instructions for use thereof, may be approved of or authorized by the Food and Drug Administration of the United States of America and/or may comply with the regulations of other jurisdictions, such as by qualifying for CE marking in the European Union.

FIG. 22A is a side elevation view of another embodiment of an expandable medical device 2200 that is configured for placement in the cecum of a patient to treat obesity, the medical device 2200 being depicted in a contracted, low-profile, or undeployed state. The device 2200 can resemble other devices previously described, including the stent-like devices 500, 600, 700, 800, 900, etc., and can include any suitable feature described with respect thereto. For example, the device 2200 may be constructed in a variety of configurations, including self-expanding configurations, assisted-expansion configurations, etc.; the device 2200 may be constructed of any of a variety of previously disclosed materials and/or can include any of a variety of previously disclosed coatings; etc.

The device 2200 includes a highly expandable body 2250, which defines a connection hub 2251 at a proximal end thereof. In the illustrated embodiment, the body 2250 is substantially cylindrical when the device 2200 is in the contracted state. The device 2200 can define a maximum outer diameter when in the contracted state. In some embodiments, the maximum outer diameter of the device 2200 is smaller than an inner diameter of the working channel (which may also be referred to as the instrument channel, tool channel, or biopsy channel) of standard colonoscopes, which can permit delivery of the device 2200 via such a working channel. For example, in various embodiments, the maximum diameter of the device 2200 in the contracted state is no greater than 3.7, 3.8, 3.9, or 4.0 millimeters.

Figure 22B:
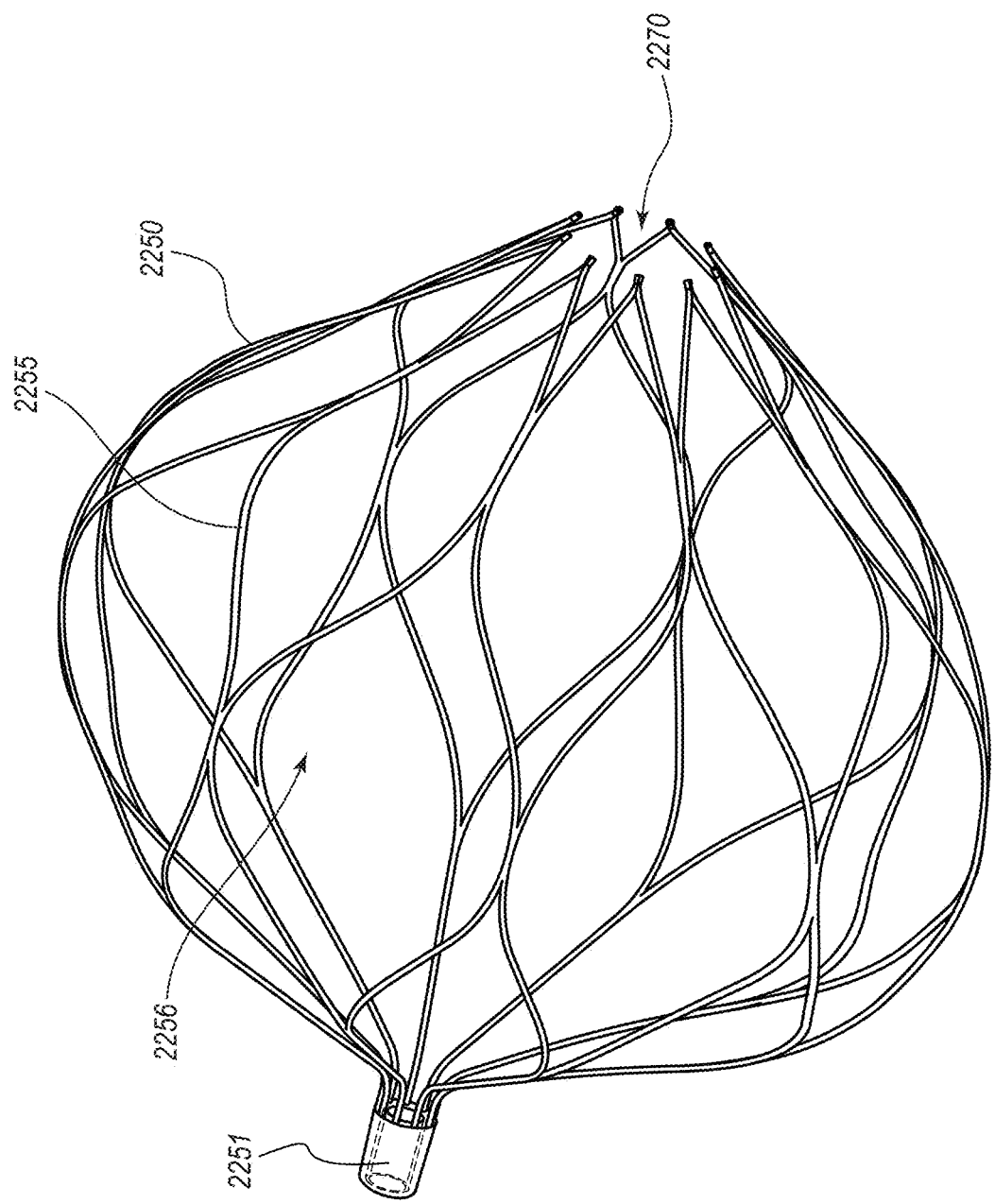
FIG. 22B is a perspective view of the medical device of FIG. 22A in an expanded or deployed state.

FIG. 22B is a perspective view of the medical device 2200 in an expanded or deployed state. The body 2250 can be formed in any suitable manner. For example, in some embodiments, the body 2250 may be formed from a laser-cut tube of any suitable material, such as, for example, Nitinol or stainless steel. In the illustrated embodiment, the body 2250 comprises a plurality of wires, struts, connectors, or support members 2255, which in the illustrated embodiment intersect at consistent angles and extend along regularly spaced paths or intervals. The widths of the support members 2255 are relatively small, such that the support members 2255 define a plurality of large openings 2256. The illustrated openings 2256 are substantially diamond-shaped, with the sides thereof being rounded and the tips thereof being pointed, and may be described as being somewhat longitudinally elongated. The openings 2256 may also be referred to as substantially vesica piscis-shaped.

In some embodiments, the struts 2255 may have relatively sharp edges, which may result from the manner in which the struts 2255 are formed. For example, in some embodiments in which the struts 2255 are formed by laser cutting, as the body 2250 is formed from a unitary tube, the struts 2255 may ultimately define substantially rectangular or substantially trapezoidal cross-sections. The corners of such cross-sectional shapes can correspond to relatively sharp edges of the struts 2255. In some embodiments, these sharp edges can press into the cecal wall as the device 2200 bears outwardly on the cecum. As further discussed below, such sharp edges may lead to acute and/or chronic inflammation of the cecal wall, may cause tissue ingrowth, and/or may cause other reactive phenomena. In other embodiments, the struts 2255 may be devoid of sharp edges. In other or further embodiments, one or more coverings may be applied to the struts 2255. In some embodiments, the one or more coverings can inhibit the struts 2255 from pressing or digging into the cecal wall (see, e.g., FIGS. 32A-33C and 35C-35E and associated text).

The body 2250 is substantially hollow, and defines a large primary channel or passageway 2270. The body 2250 may also be said to encompass, encircle, enclose, circumscribe, or delineate a large volume of space, corresponding to the region internal to the strut structure. Each of the openings 2256 defined by the support members 2255 is in fluid communication with the passageway 2270, and thus each opening 2256 defines an entrance to or exit from the primary passageway 2270.

The primary passageway 2270 may be sufficiently large to permit passage of material therethrough without substantially impeding the flow of the material. Stated otherwise, the body 2250 of the expansion device 2200 can effectively distend the wall of the cecum 110 while the passageway 2270 defined by the body 2250 can permit substantially unimpeded or unobstructed flow of the material through the body 2250. Moreover, the openings 2256 are sufficiently large and the support members 2255 sufficiently thin to permit the body 2250 to either substantially or completely leave the ileocecal valve unobstructed, depending on the specific orientation of the body 2250.

The expanded device 2200 is substantially bulbous. In the illustrated embodiment, the expanded device 2200 defines a longitudinal length that is smaller than a maximum transverse diameter of the device 2200. The maximum diameter of the expanded device 2200 can be substantially larger than the diameter of the contracted device 2200 due to the highly expansible property of the device 2200. For example, in various embodiments, the maximum diameter of the device 2200 when expanded can be no less than 15, 16, 17, 18, 19, 20, 25, 30, 35, or 40 times larger than the diameter thereof when contracted. The maximum diameter of the device 2200 when expanded, in various embodiments, can be no less than 7, 8, 9, or 10 centimeters.

Figure 23A:
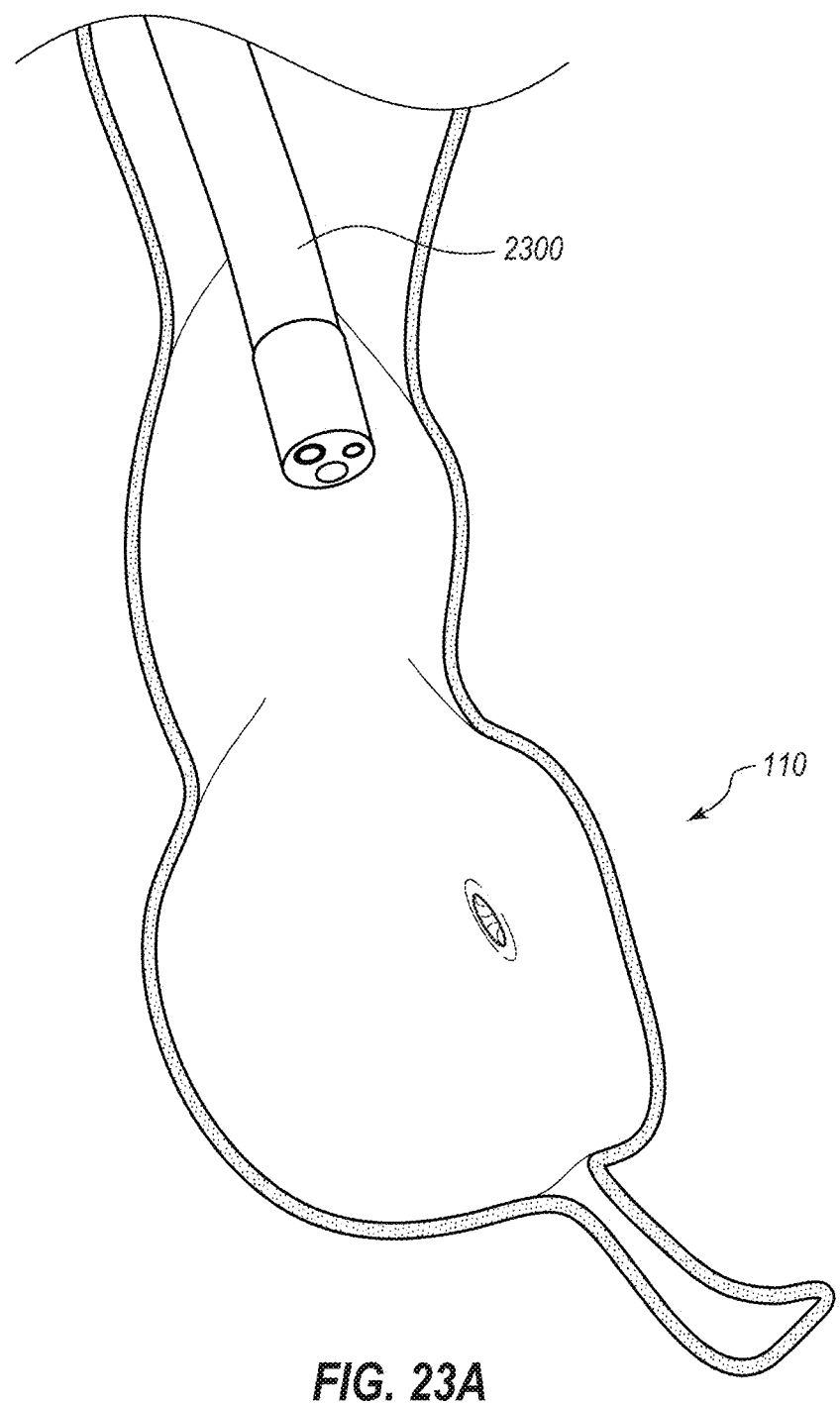
FIG. 23A is a cross-sectional view of a portion of the colon of a patient during another illustrative method in which an endoscope, shown in perspective, is being advanced toward the cecum of the patient.

FIGS. 23A-23K depict various stages of illustrative methods of deploying into, using in, and retracting from the cecum 110 certain embodiments of the device 2200. FIG. 23A is a cross-sectional view of a portion of the colon of a patient during an illustrative method in which an endoscope 2300 (e.g., a colonoscope), shown in perspective, is being advanced toward the cecum 110 of the patient for delivery of the device 2200.

Figure 23B:
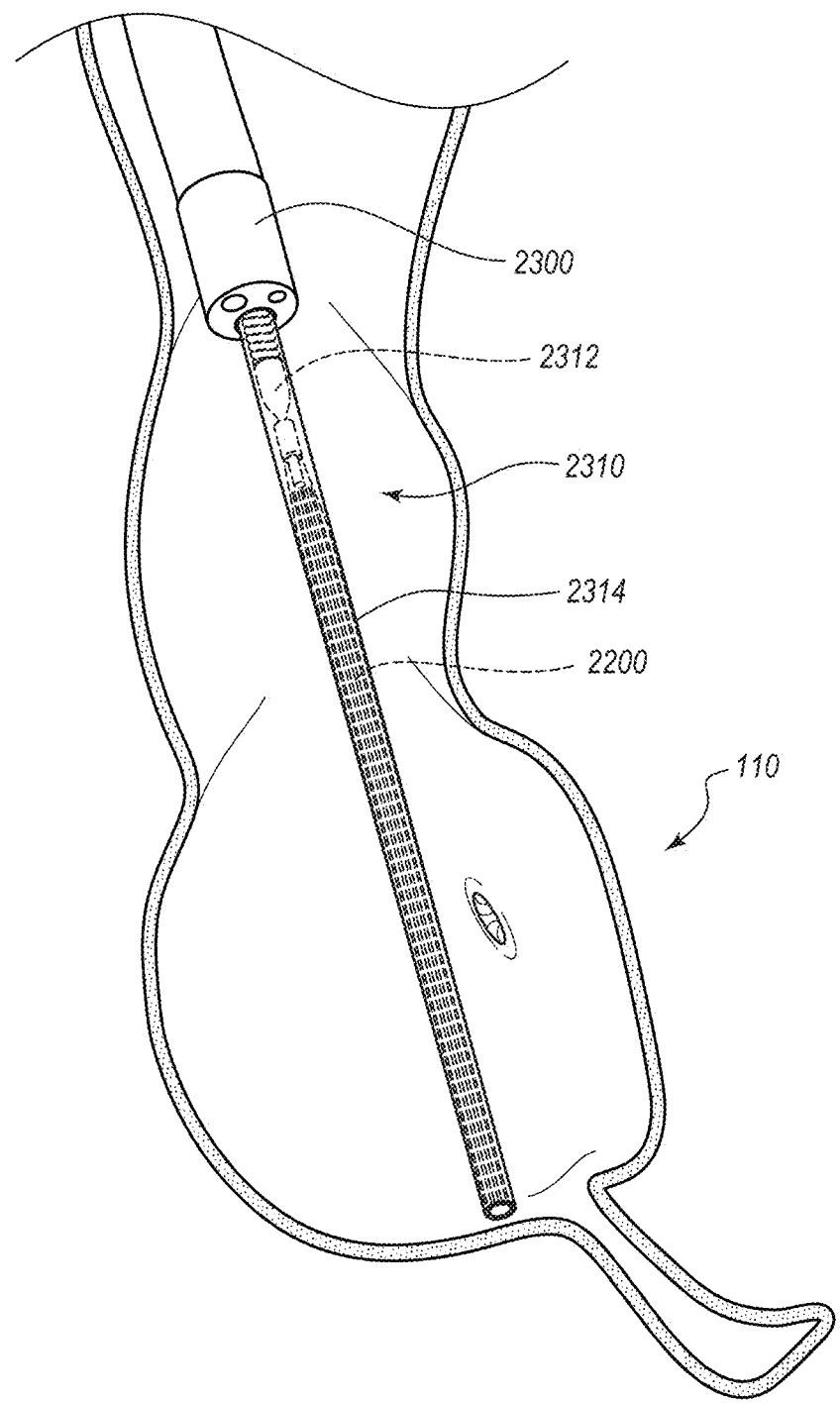
FIG. 23B depicts another stage of the method in which a deployment system is advanced out of a distal end of the endoscope into the cecum.

FIG. 23B depicts another stage of the method in which a deployment system 2310 has been advanced through the working channel of the endoscope 2300 and is advanced out of a distal end of the endoscope 2300 (from the perspective of the practitioner) into the cecum 110. The deployment system 2310 includes a push rod 2312 that is coupled to a distal end (from the perspective of the digestive tract) of the expansion device 2200 and further includes a retention sheath 2314 that maintains or assists in maintaining the expansion device 2200 in the contracted state. In other embodiments, the retention sheath 2314 may not be used. The push rod 2312 can be highly flexible and capable of bending to the contours of an endoscope positioned within the bowel of the patient, yet sufficiently rigid in a longitudinal direction to be capable of advancing the contracted device 2200 through at least a portion of the working channel of the endoscope 2300. Any suitable material is contemplated. In some embodiments, the push rod 2312 further comprises a lubricious coating to facilitate passage through the working channel.

Figure 23C:
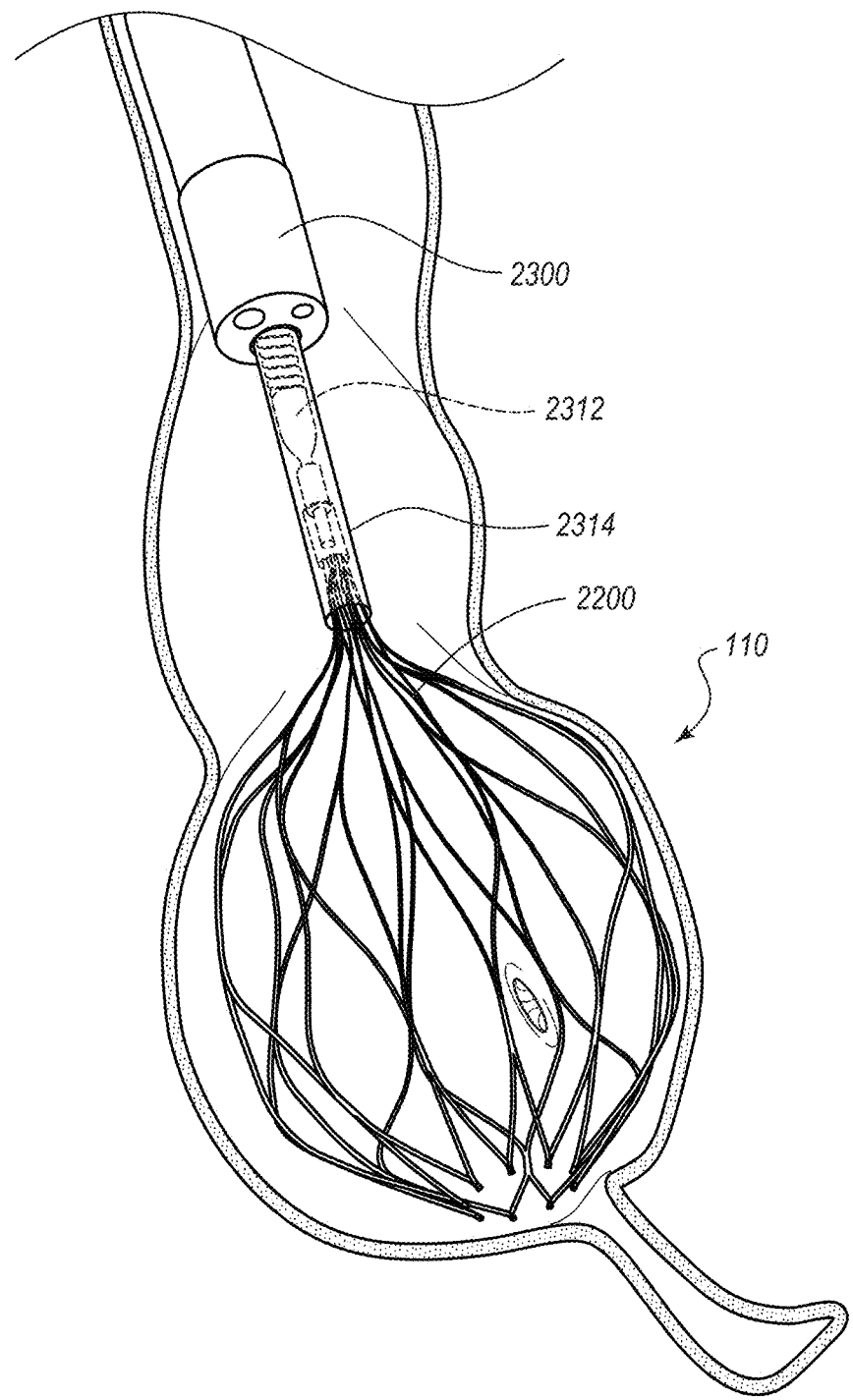
FIG. 23C depicts another stage of the method in which the expandable medical device of FIGS. 22A, 22B is being deployed within the cecum.

FIG. 23C depicts another stage of the method in which the expandable medical device 2200 is being deployed within the cecum 110. In particular, with the push rod 2312 having been advanced sufficiently to bring a proximal end (from the perspective of the digestive tract) of the expansion device 2200 into contact with or close proximity to a proximal end of the cecum 110, the retention sheath 2314 is withdrawn through the working channel of the endoscope 2300.

In the illustrated embodiment, the expansion device 2200 is self-expandable. In particular, the expansion device 2200 is formed of heat-treated nitinol. The device 2200 can be cooled (e.g., via liquid nitrogen) prior to insertion through the endoscope 2300, and can expand when heated to body temperature (and when permitted to expand by removal of the retention sheath 2314). In the illustrated embodiment, expansion of the device 2200 may be gradual as the device is heated within the body. In other embodiments, the expansion device 2200 may be formed of a resiliently flexible material that may self-expand more rapidly and/or immediately upon removal of the retention sheath 2314. Any other suitable configuration is contemplated.

Figure 23D:
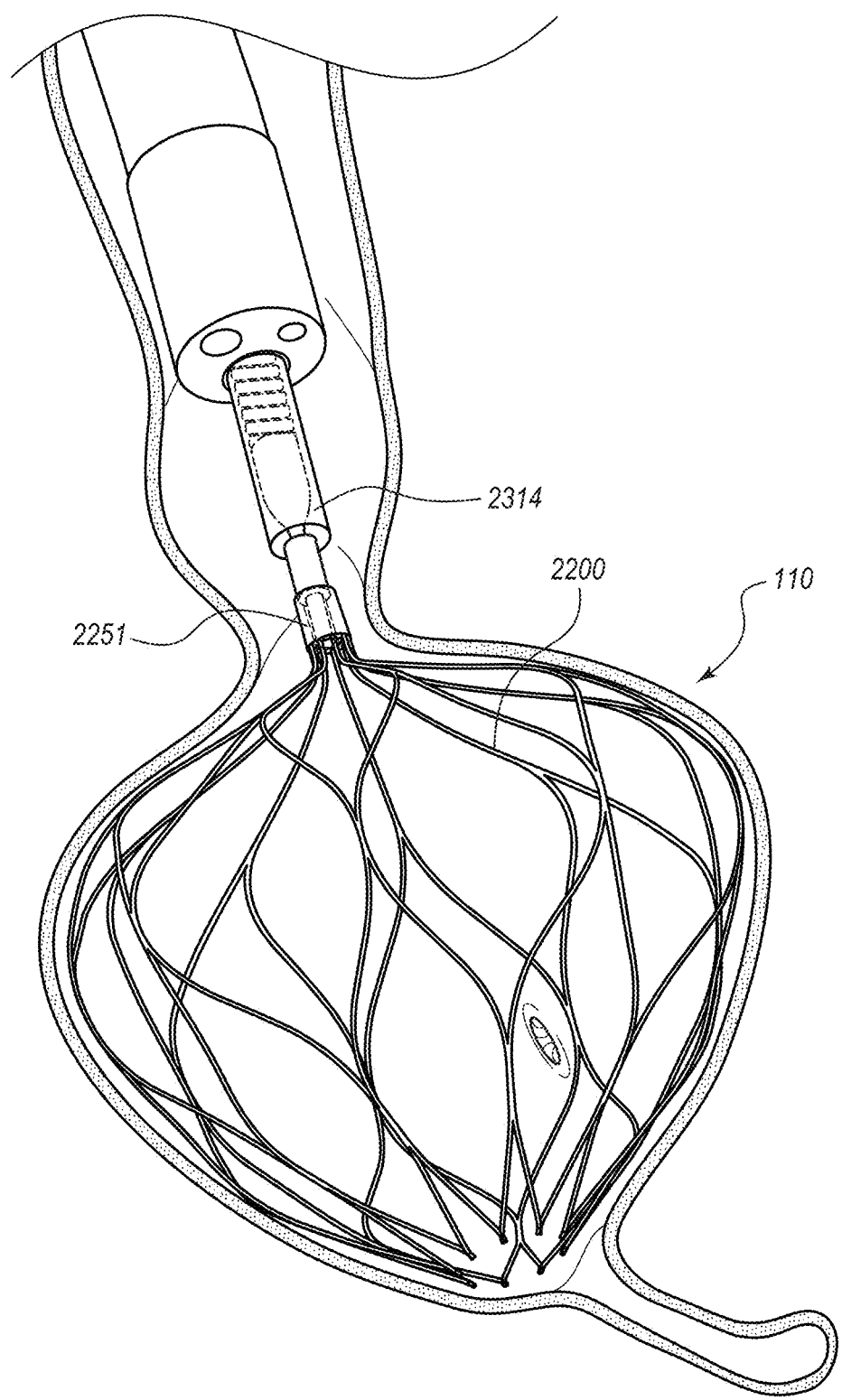
FIG. 23D depicts another stage of the method in which the expandable medical device has been deployed to expand the cecum to a pathophysiological size.

FIG. 23D depicts another stage of an illustrative method in which the expandable medical device 2200 has been fully deployed to expand the cecum 110 to a pathophysiological size. In particular, the cecum 110 can expand in conformity to an external surface defined by the device 2200. A maximum diameter and/or a volume of the cecum 110 can be significantly enlarged by the expansion device 2200. In the illustrated embodiment, both the device 2200 and the cecum 110 are substantially bulbous when the device 2200 is in the deployed configuration.

Figure 23E:
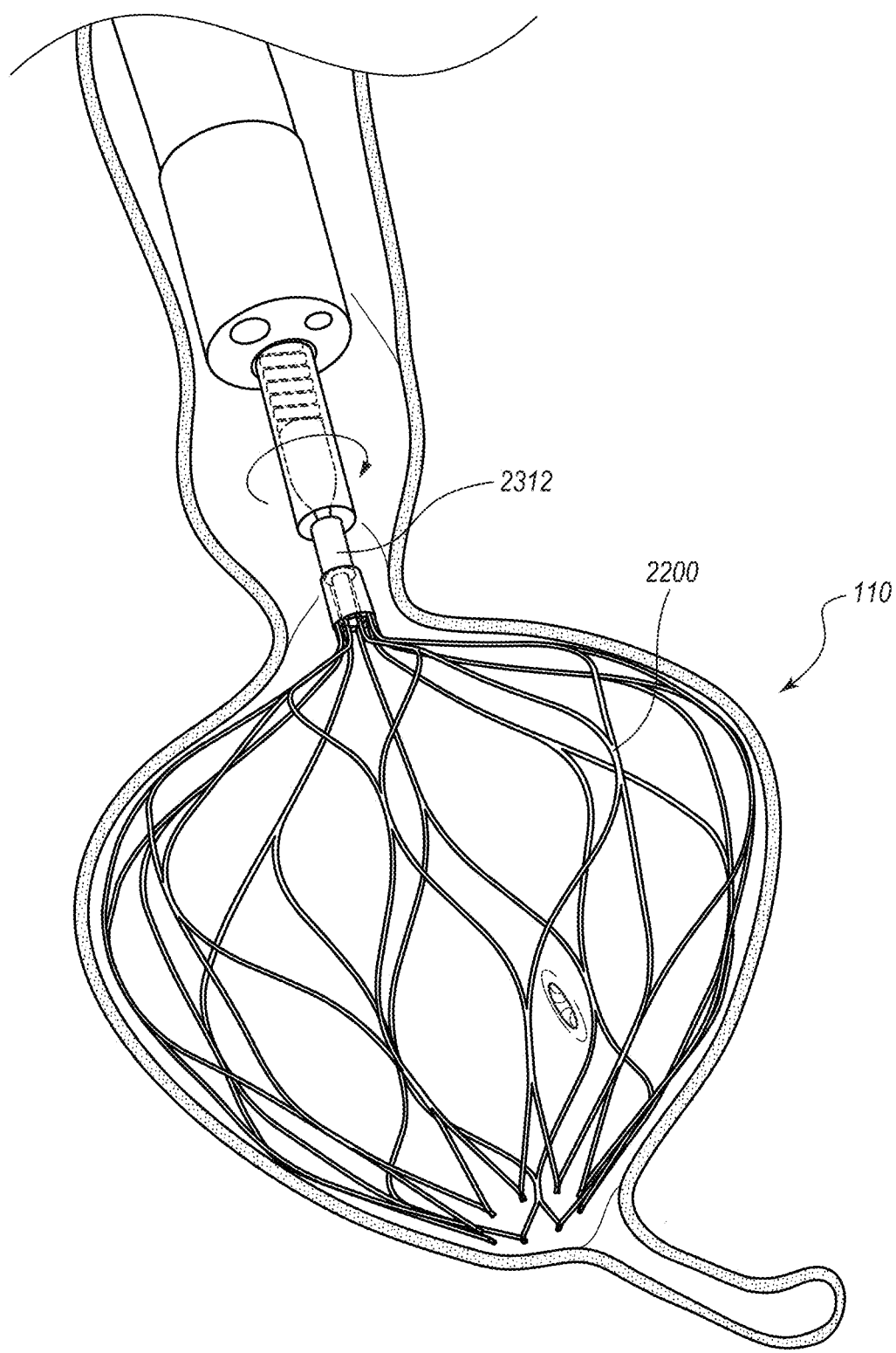
FIG. 23E depicts another stage of the method in which a push rod is being decoupled from the deployed medical device.

FIG. 23E depicts another stage of the method in which the push rod 2312 is being decoupled from the deployed medical device 2200. In particular, with the medical device 2200 coupled (e.g., in physical contact) with the sidewall of the cecum 110, the medical device 2200 can be resistant to rotation. The device 2200 thus may remain substantially stationary relative to the cecum 110 as the push rod 2312 is rotated to decouple from the medical device 2200.

Figure 23F:
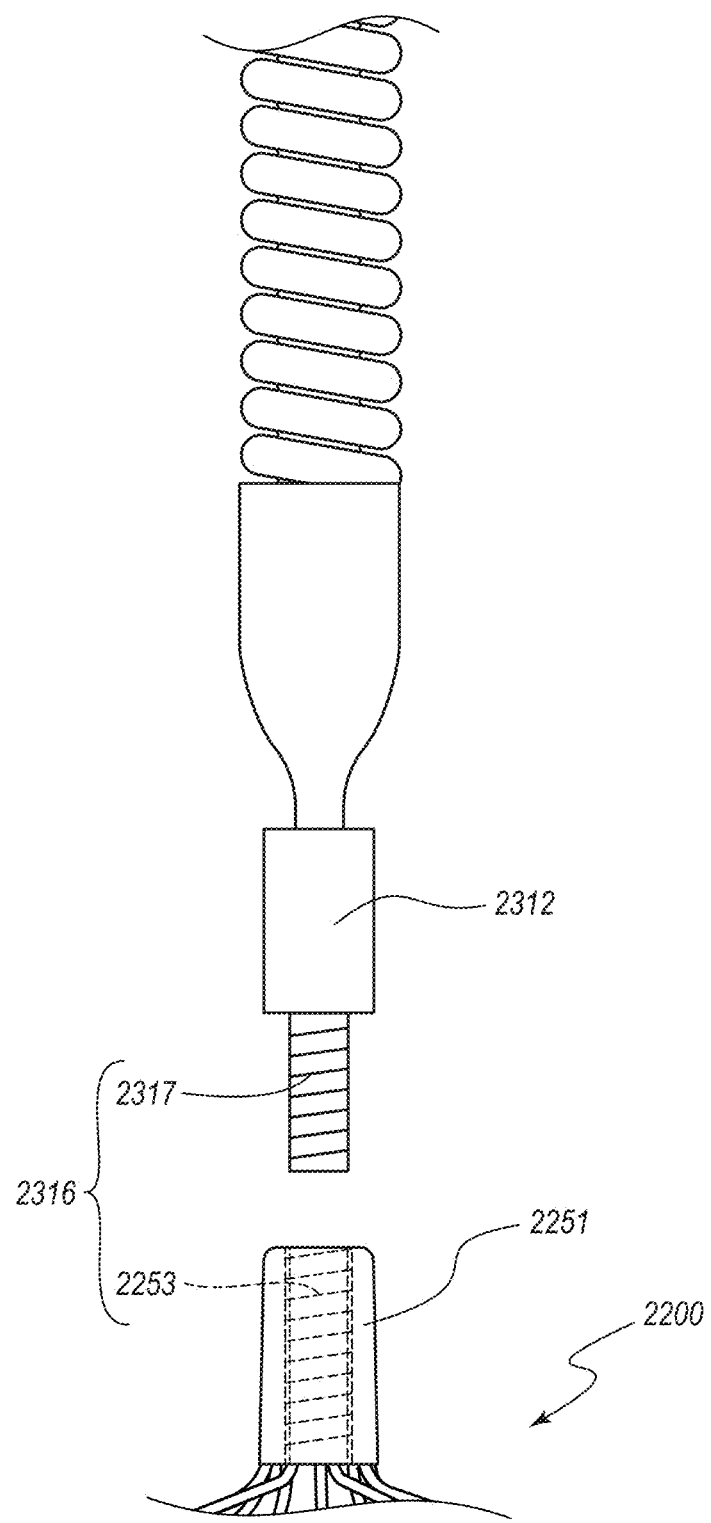
FIG. 23F depicts a further stage of the method just after the push rod has been decoupled from the medical device.

FIG. 23F depicts a further stage of the method just after the push rod 2312 has been decoupled from the medical device 2200. This image depicts the coupling interface 2316 of this particular embodiment via which the push rod 2312 and the device 2200 are selectively coupled to each other. In particular, the illustrated coupling interface 2316 comprises external threading 2317 on the push rod 2312 and complementary internal threading 2253 within the connection hub 2251 of the device 2200. Any other suitable connection interface 2316 and selectively releasable and/or selectively couplable/decouplable coupling mechanisms are contemplated.

Figure 23G:
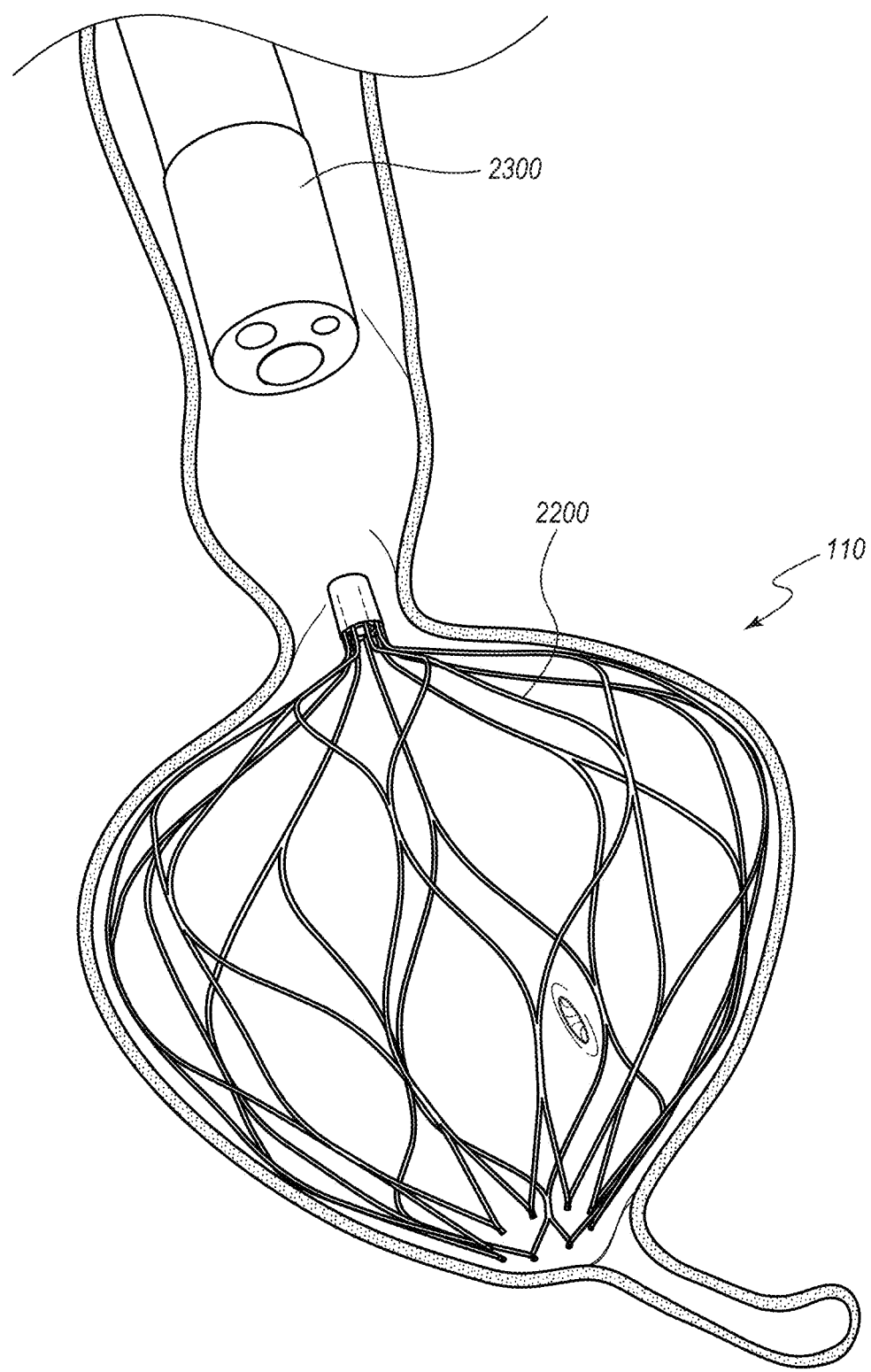
FIG. 23G depicts a further stage of the method after the push rod has been retracted relative to the endoscope.

FIG. 23G depicts a further stage of the method after the push rod 2312 has been retracted relative to the endoscope 2300. In the illustrated embodiment, no attachment mechanism beyond the intrinsic resilience of the expansion device 2200 is provided to affix the expansion device to the cecum. In some embodiments, the struts of the expansion device 2200 may push against the cecal wall so as to induce inflammatory and fibrotic responses. Eventual tissue ingrowth can further secure, attach, or embed the expansion device 2200 to or within the cecal wall.

In other methods, after the push rod 2312 has been removed from the endoscope 2300, one or more attachment mechanisms are introduced through the endoscope 2300 to secure the expansion device 2200 to the cecal wall. Any of the attachment mechanisms discussed above are contemplated. For example, in some embodiments, one or more clips, such as one or more hemoclips, may be used to secure the expansion device 2200 to the cecal wall.

The endoscope 2300 may be removed from the patient, whether separate from or simultaneously with the push rod 2312 or any systems used to further attach the expansion device 2200 to the cecal wall, such as a hemoclip delivery system of any suitable variety. The device 2200 is thus left within the cecum, e.g., for a therapeutically effective period.

Figure 23H:
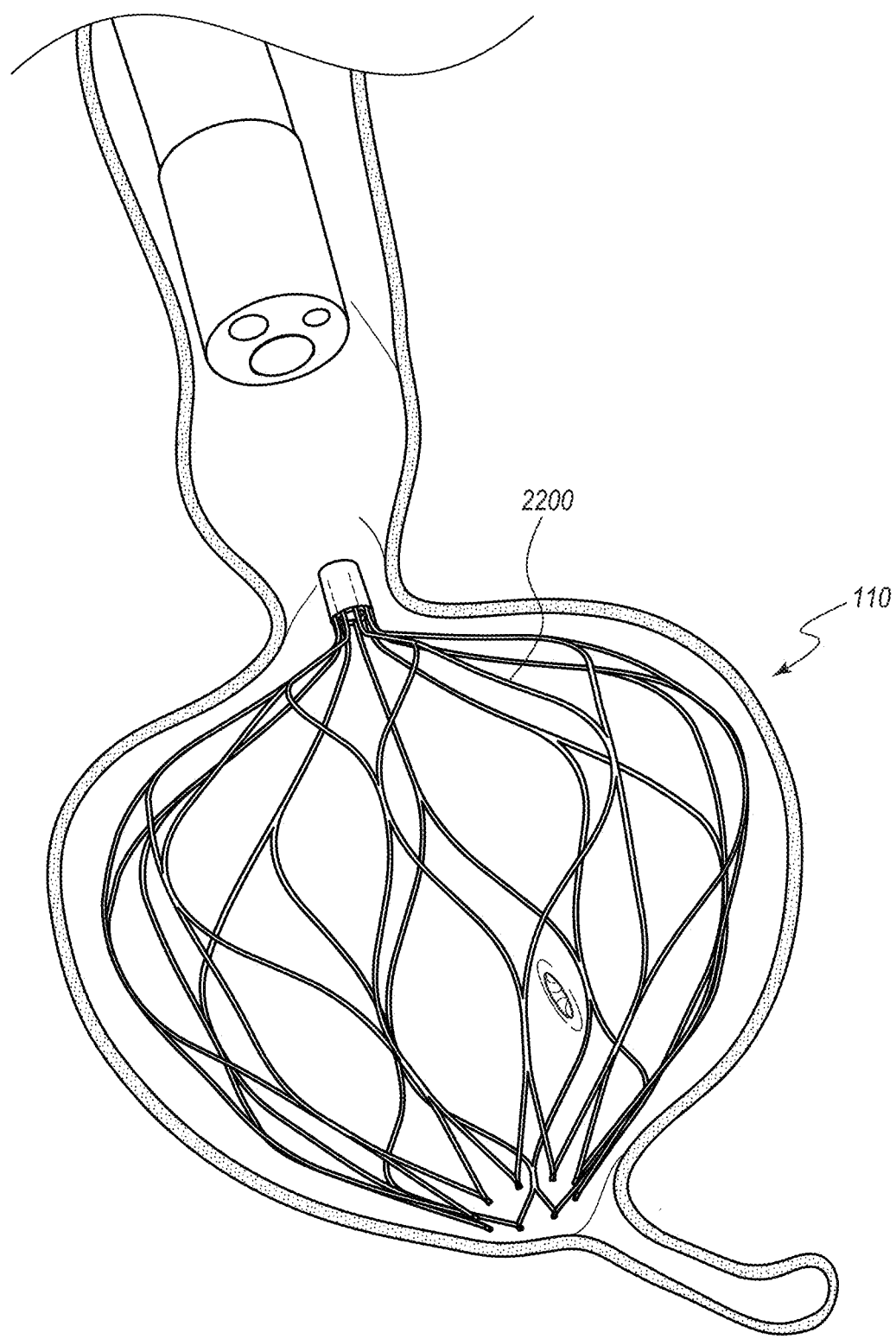
FIG. 23H depicts a further stage of the method, after the endoscope has been retracted from the patient, at which the cecum naturally expands to a size larger than the pathophysiological size.

FIG. 23H depicts a further stage of certain embodiments of the method that can occur after the expansion device 2200 has been deployed in the cecum 110, thus expanding the cecum to define an enlarged maximum diameter (shown in FIG. 23G). In the illustrated stage, the cecum 110 is permitted to naturally expand to a size (e.g., maximum diameter and/or internal volume) larger than the pathophysiological size to which the expansion device 2200 has previously expanded the cecum 110. The natural expansion can be due to natural processes, as previously described. For example, the cecum 110 may naturally expand to the increased volume, in excess of the increased minimum volume achieved via the device 2200 alone, due to passage of one or more of chyme, gas, or stool into the cecum 110. The chyme, gas, or stool may be permitted to pass through the various openings and the passageway of the medical device 2200.

In the illustrated embodiment, the expanded device 2200 does not significantly change shape or size as the cecum 110 undergoes additional expansion. In some instances, such as where the device 2200 is not otherwise connected to the cecal walls, contact between the device 2200 and the cecal wall is reduced or eliminated. The device 2200 can be free floating within the further expanded cecum, and may axially rotate, laterally rotate, longitudinally translate, and/or laterally translate within the cecum while the cecum 110 is in the state of additional enlargement.

In some instances, the natural enlargement of the cecum 110 to the size greater than the pathophysiological size achieved via the medical device 2200 alone naturally triggers a further colo-gastric brake in the patient. Stated otherwise, prior to the extra enlargement, the medical device 2200 may be solely responsible for triggering a gastric brake in the patient. During times of increased cecal size, the medical device 2200 may be only partially responsible or may not significantly contribute, or may not directly contribute, to gastric braking that can result from the enlarged size of the cecum 110 that is due, instead, either partially or entirely, to the natural enlargement of the cecum 110.

In some instances, an operational state such as depicted in FIG. 23H may arise at a time before tissue ingrowth into the medical device 2200 fixedly secures the medical device 2200 to the cecal wall. In some instances, the medical device 2200 may later be securely fixed to the cecal wall due to such tissue ingrowth. In other or further instances, the medical device 2200 may be attached to the cecal wall by any suitable attachment mechanism, such as any suitable adhesive or mechanical fastener (e.g., clips or sutures). In some embodiments where such fixed attachment occurs, the medical device 2200 may be substantially non-expandable beyond its enlarged maximum diameter, such that the medical device 2200 can resist natural expansion of the cecum to any further increased volume, in excess of the increased minimum volume achieved via the device 2200 alone, that might otherwise occur due to natural processes, such as the passage of one or more of chyme, gas, or stool into the cecum 110. In other embodiments where such fixed attachment occurs, the medical device 2200 may be capable of further expansion, such as due to an outward bias that is normally opposed by the cecum 110, such that the medical device 2200 can expand outwardly with the cecum 110 as the cecum naturally expands to a further increased volume, in excess of the increased minimum volume achieved via the device 2200 alone, due to natural processes, such as the passage of one or more of chyme, gas, or stool into the cecum 110.

Figure 23I:
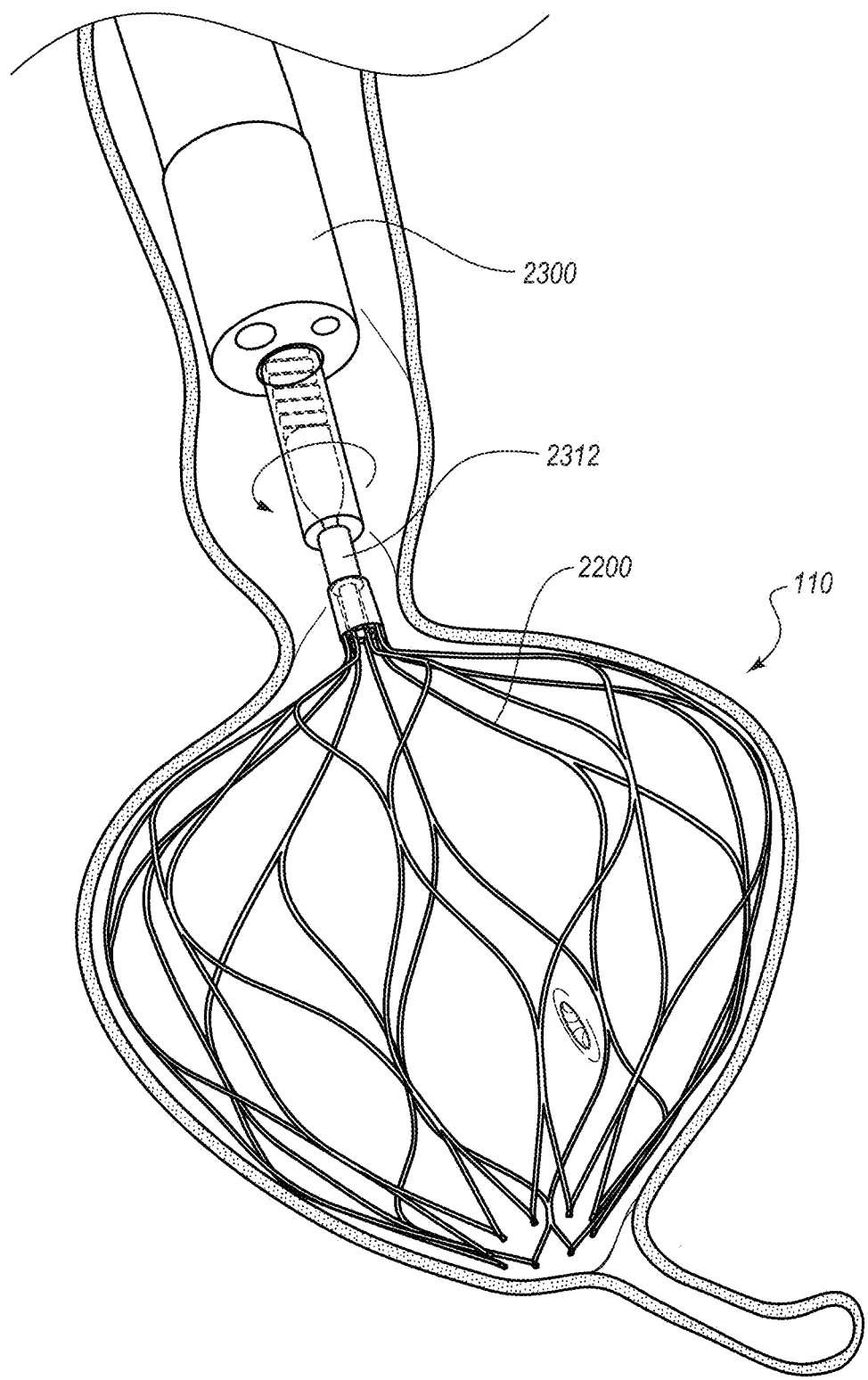
FIG. 23I depicts a further stage of the method in which an endoscope has been introduced into the bowel of the patient and the push rod (or a different push rod) is coupled to the medical device for purposes of retraction.

FIG. 23I depicts a further stage of a method in which the endoscope 2300 (or a different endoscope) has been introduced into the bowel of the patient and the push rod 2312 (or a different push rod) is coupled to the medical device 2200 for purposes of retraction. For example, the push rod 2312 can couple with the device 2200 via any suitable connection interface, such as complementary threading. As the cecal wall presses inwardly against the frame of the device 2200 in the depicted configuration, the cecum 110 can again resist rotation of the device 2200 to permit coupling of the device 2200 with the push rod 2312 in this manner. Any other suitable retraction methods are contemplated, such as those previously described.

In some embodiments, such retraction methods are best suited for situations in which there has been little or no tissue ingrowth relative to the device 2200. In other embodiments, the device 2200 may be bioresorbable and may pass naturally through the bowel in manners such as previously described, rather than being affirmatively retracted via a follow-on colonoscopy procedure.

Figure 23J:
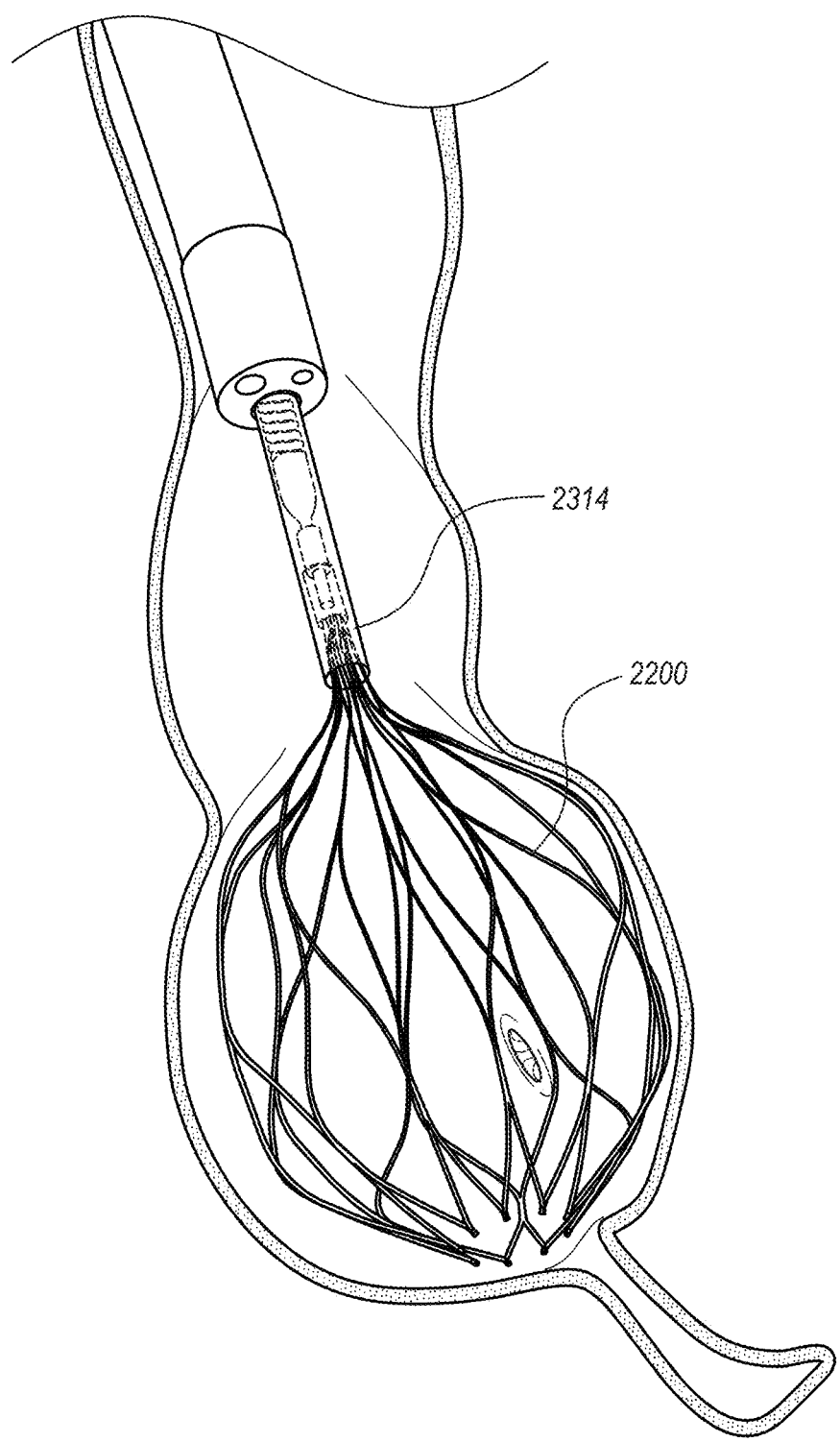
FIG. 23J depicts a further stage of the method in which a retention sleeve is advanced distally over the medical device to transition the medical device to a retracted configuration.
Figure 23K:
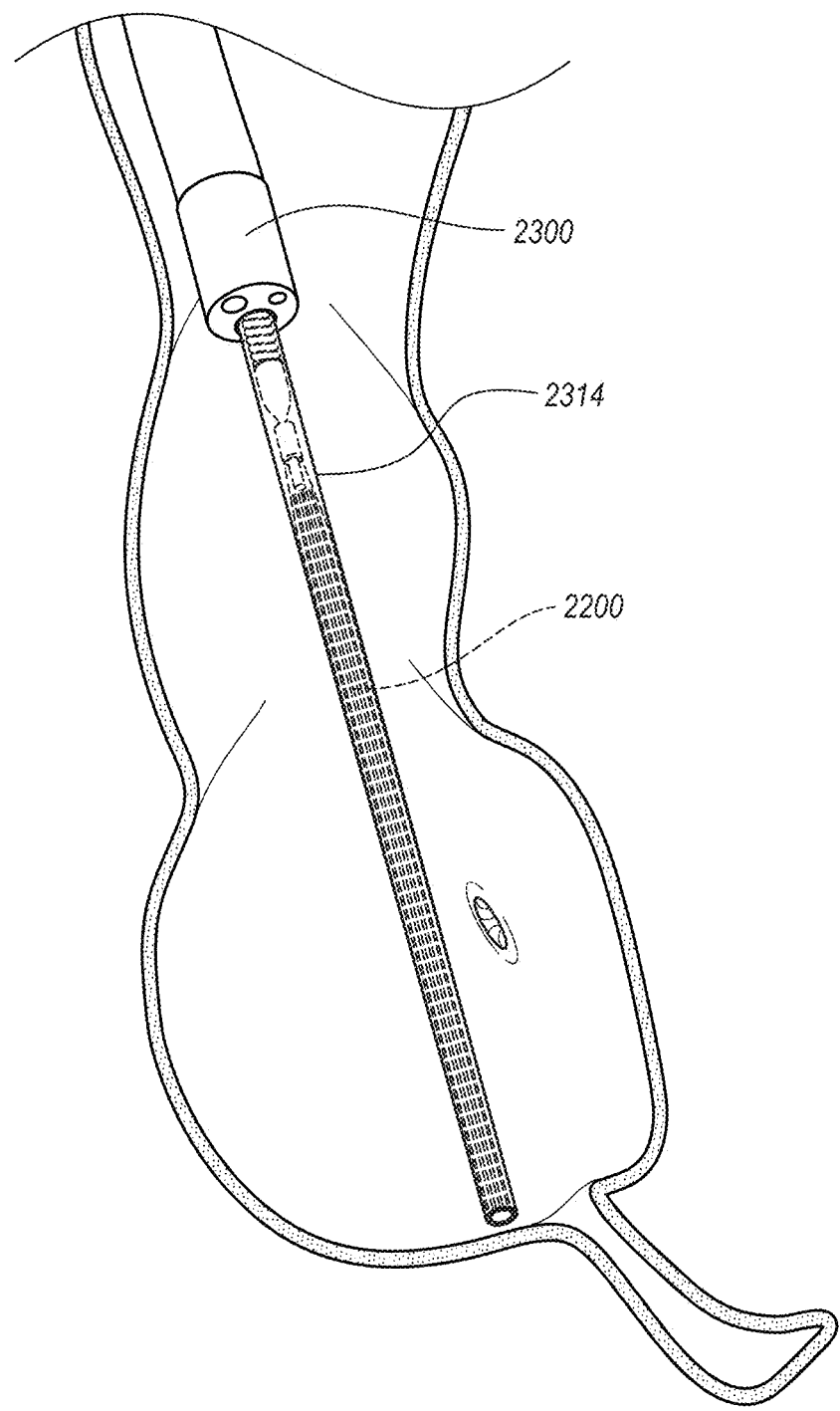
FIG. 23K depicts a further stage of the method in which the retention sleeve has been advanced over an entirety of the medical device.

FIG. 23J depicts a further stage of the method of FIG. 23I, in which the retention sleeve 2314 (or a different retention sleeve) is advanced distally over the medical device 2200 to transition the medical device to a retracted or contracted configuration. FIG. 23K depicts a further stage of the method in which the retention sleeve 2314 has been advanced over an entirety of the medical device 2200. The contracted device 2200 can then be withdrawn through and/or within the endoscope 2300, which may likewise be removed from the patient.

In further detail, in some embodiments, the push rod 2312 is advanced distally through the working channel of the endoscope 2300 and coupled with the device 2200 as shown in FIG. 23I. Thereafter, the retention sleeve 2314 is advanced distally over the push rod 2312 within the working channel of the endoscope 2300 and into contact with the distal end (from the perspective of the digestive tract) of the device 2200. Relative movement between the push rod 2312 (as attached to the device 2200) and the retention sleeve 2314 can urge the device 2200 to the collapsed or low-profile state. For example, the retention sleeve 2314 can be sufficiently rigid to substantially maintain its shape (e.g., maintain its tubular form with a maximum outer diameter that is less than the inner diameter of the working channel) as it is moved distally relative to the device 2200 and/or as the device is moved proximally relative thereto. The more malleable device 2200 thus can deform or collapse to the low-profile configuration so as to fit within the retention sleeve 2314 and subsequently be withdrawn through the endoscope 2300 while retained in the low-profile orientation within the retention sleeve 2314.

In various methods, the retention sleeve 2314 may be maintained at a fixed longitudinal position while the push rod 2312 and attached device 2200 are withdrawn proximally into the retention sleeve, the retention sleeve 2314 may be advanced distally over the device 2200 as the push rod 2312 and attached device 2200 are maintained at a fixed longitudinal position, and/or any suitable combination thereof. In other embodiments, the endoscope 2300, and in particular, the working channel of the endoscope 2300, may be used in a manner such as just described with respect to the retention sleeve 2314, and the retention sleeve 2314 can be omitted. Stated otherwise, in some embodiments, the device 2200 may be drawn directly into the working channel and/or the working channel may be advanced directly over the device 2200. The device may thereby collapse to the low-profile orientation by and be withdrawn directly through the working channel of the endoscope 2300.

Figure 24:
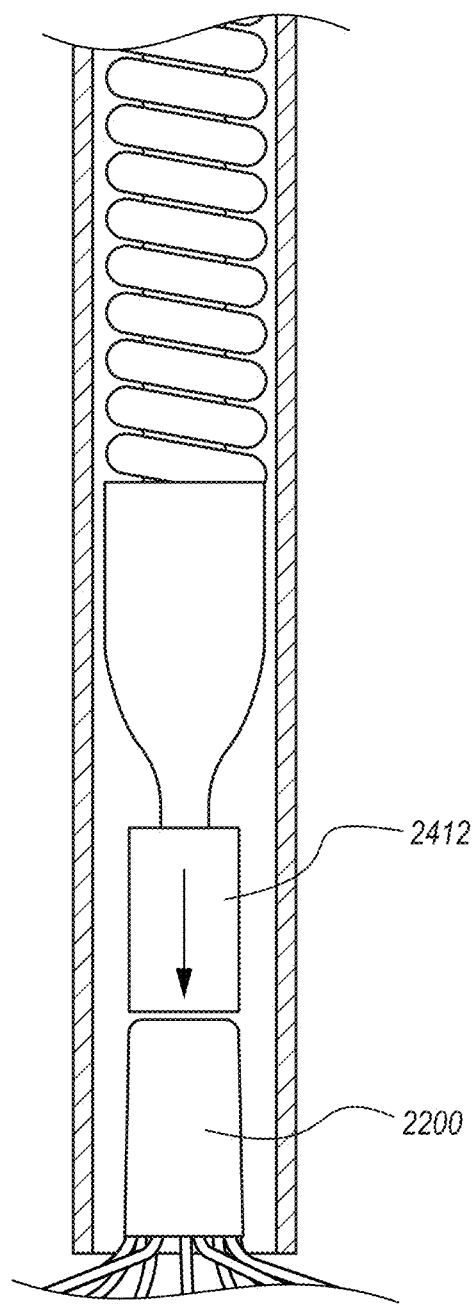
FIG. 24 depicts another embodiment of a deployment system for deploying an embodiment of a medical device within the cecum, the deployment system including a push rod and a retention sleeve.

FIG. 24 depicts another embodiment of a deployment system for deploying an embodiment of a medical device within the cecum, the deployment system including a push rod and a retention sleeve similar to those previously disclosed. The illustrated push rod 2412 may merely abut a distal end of the device 2200 for purposes of pushing the device 2200, rather than forming a more significant temporary connection or attachment therewith. In some embodiments, such a deployment system may be used with a different retrieval system, such as that discussed below with respect to FIGS. 25A-25C. In other or further embodiments, it may be desirable to leave the device 2200 within the patient without plans for a separate retrieval event. For example, in some embodiments, the device 2200 may be positioned within the cecum indefinitely without being retrieved. In some embodiments, the device 2200 may comprise a bioresorbable material, as previously disclosed, and may weaken over time so as to distend the cecum by progressively smaller amounts and/or may break down or apart, and the pieces thereof may pass through the bowel and out of the patient naturally (e.g., after passage of a therapeutically effective period). In other embodiments, the device 2200 may be formed of a more biostable material (e.g., stainless steel, Nitinol, or some other metal allow) and may remain within the cecum, in further embodiments, can continue expansion of the cecum, for an indefinite period.

Figure 25A:
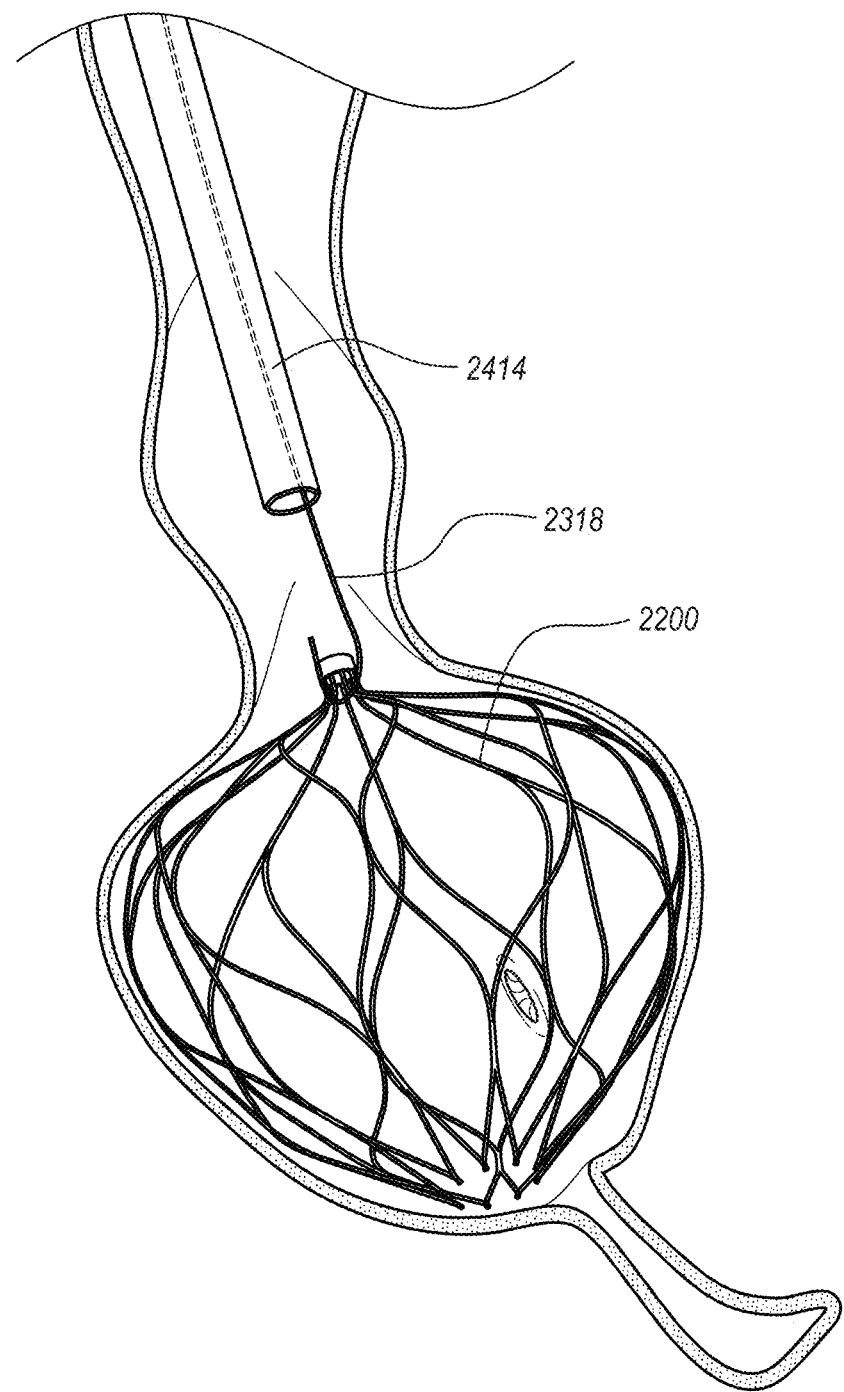
FIG. 25A depicts an embodiment of a retraction system for retracting the medical device from the cecum, the retraction system including a snare and a retention sleeve.
Figure 25B:
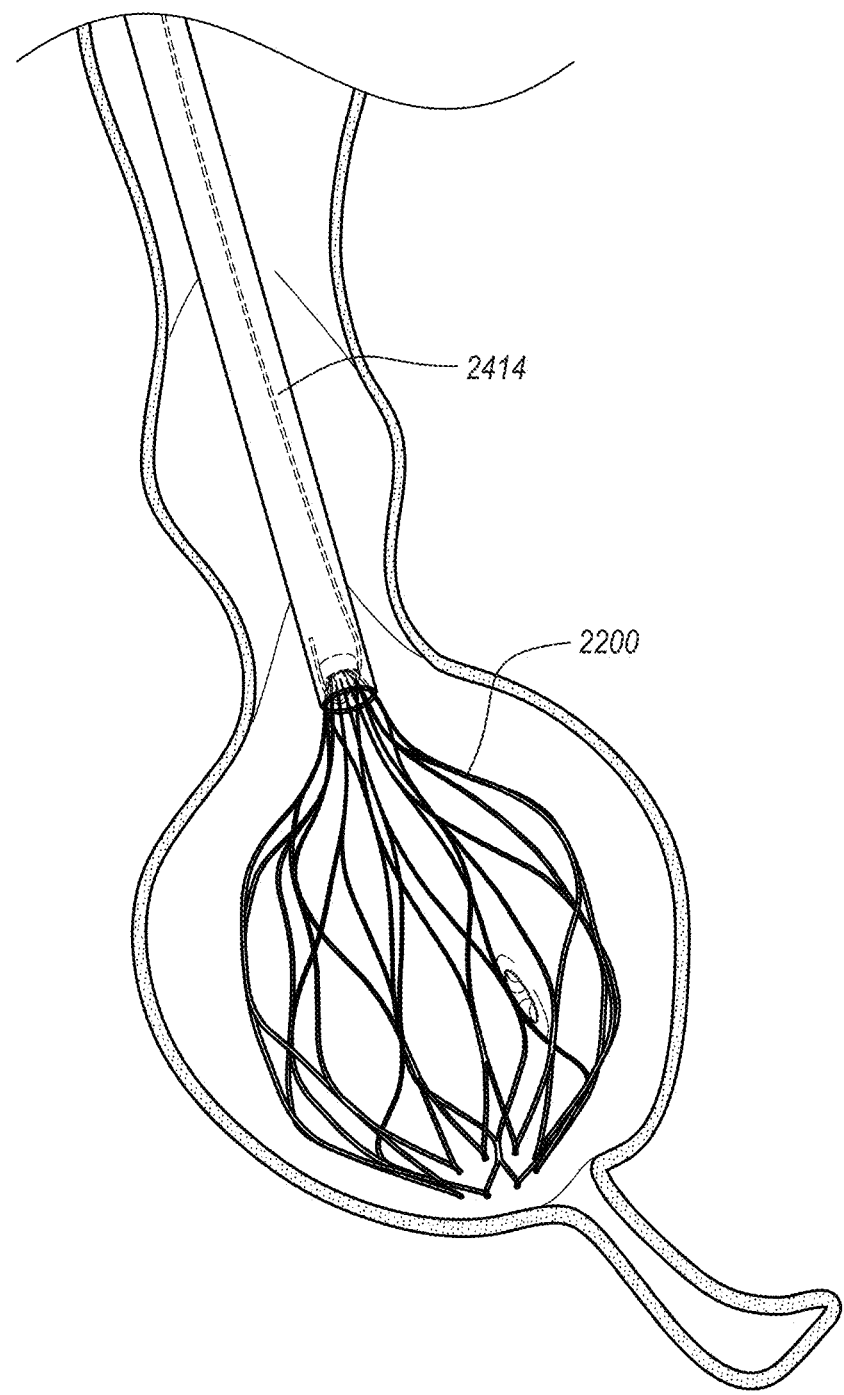
FIG. 25B depicts a further stage of retraction of the medical device from the cecum via the retraction system.
Figure 25C:
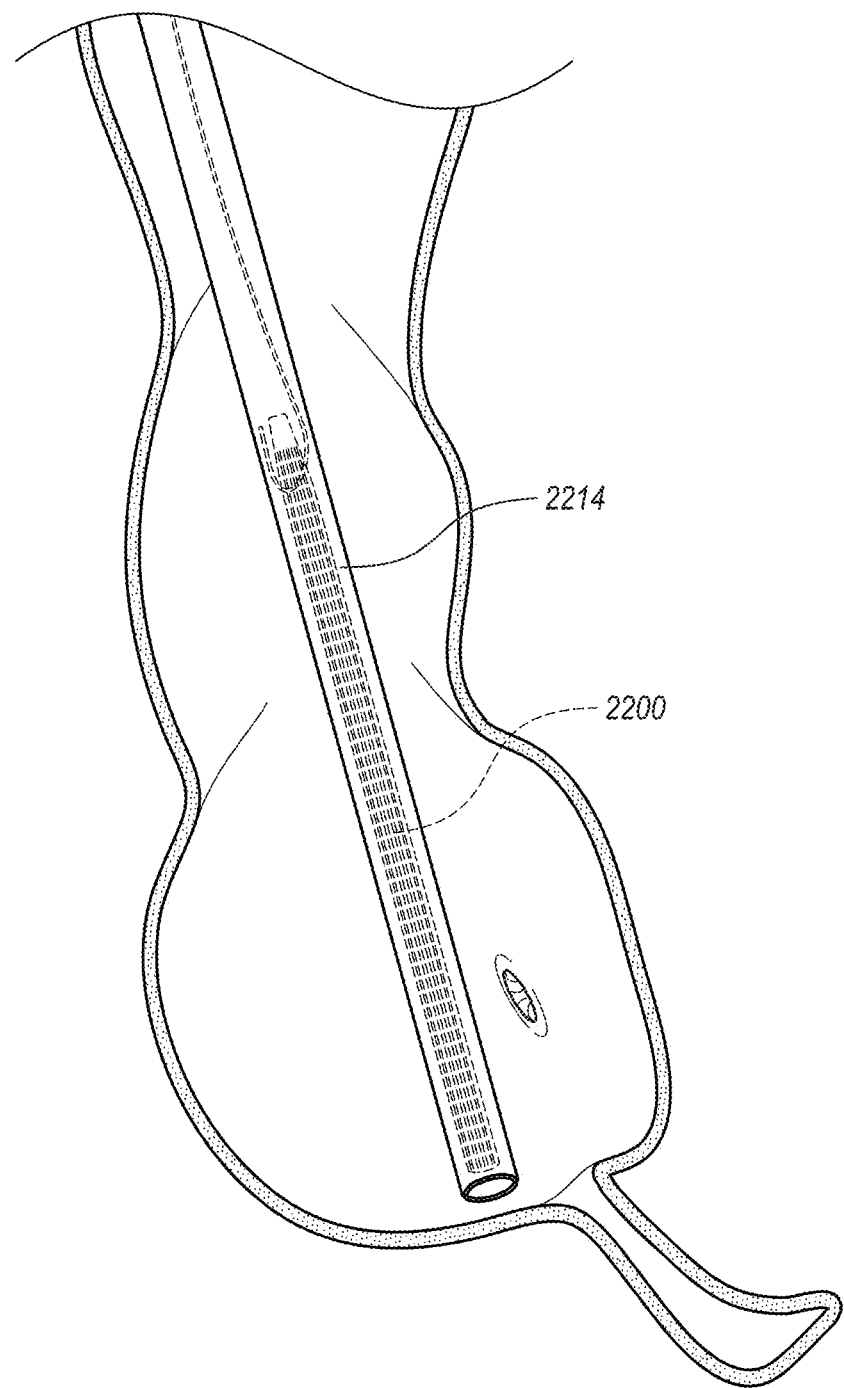
FIG. 25C depicts yet a further stage of retraction of the medical device from the cecum via the retraction system.

FIG. 25A depicts an embodiment of a retraction system for retracting the medical device 2200 from the cecum 110, the retraction system including a snare 2418 and a retention sleeve 2414. As shown in FIGS. 25A, 25B, and 25C, the snare 2418 can be used to pull the device 2200 into the retention sleeve 2414 to contract the device 2200. The retention sleeve 2414 may be advanced distally (from the perspective of the practitioner) over the device 2200 to assist in the contraction and/or the device 2200 can be drawn proximally into the sleeve 2414 in manners such as previously discussed. In other instances, the device 2200 may be retracted directly into the endoscope via the snare 2418 in manners such as previously discussed. Any other suitable retrieval method or system is contemplated.

Figure 26:
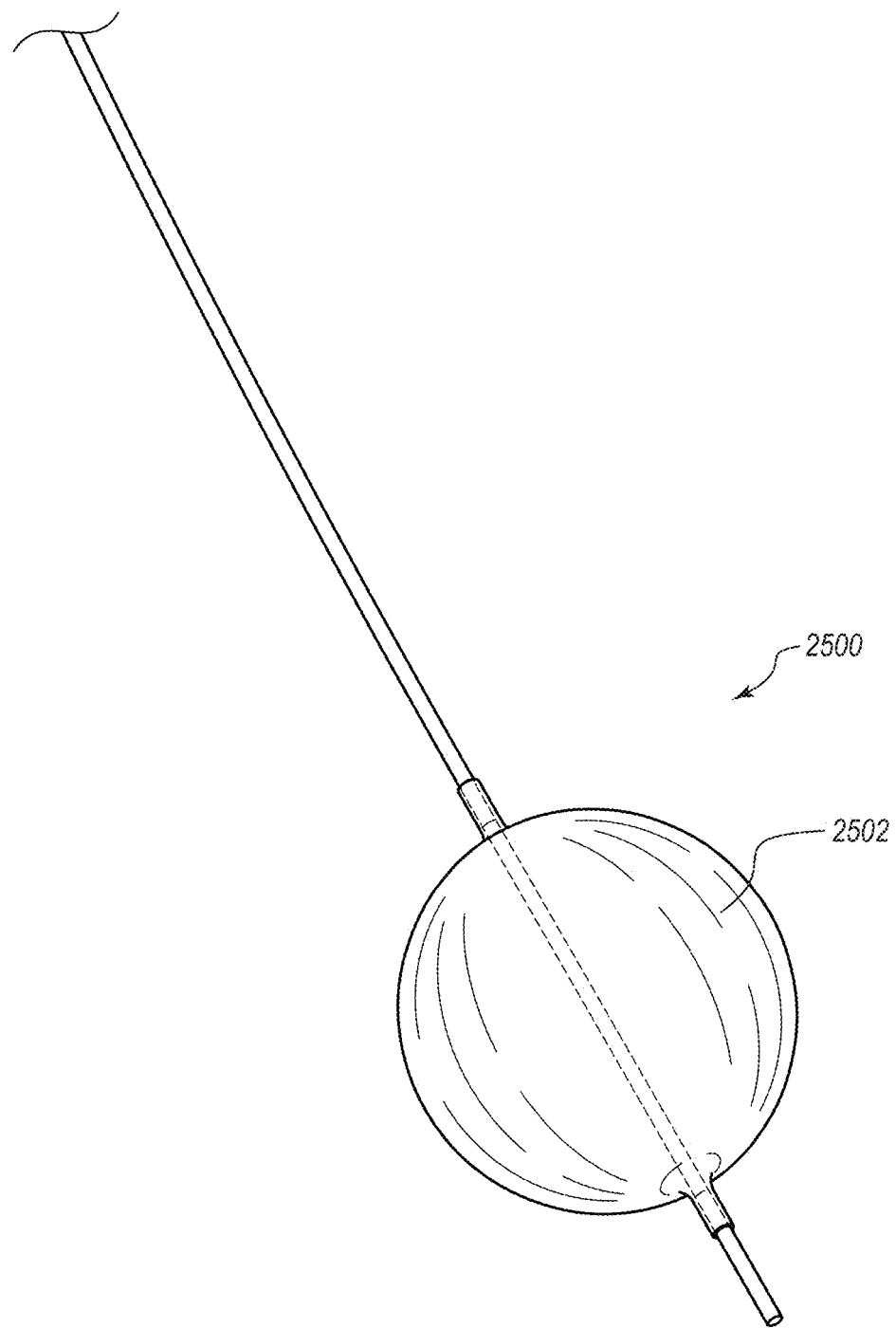
FIG. 26 depicts a balloon catheter that may be used to deploy certain embodiments of an expansion medical device within the cecum of a patient.

FIG. 26 depicts a balloon catheter 2500 that may be used to deploy certain embodiments of an expansion device within the cecum of a patient. The balloon catheter 2500 can include a balloon 2502 that can be used in manners such as previously described to deploy a non-self-expanding device. Any suitable configuration of the balloon catheter 2500 is contemplated.

Figure 27:
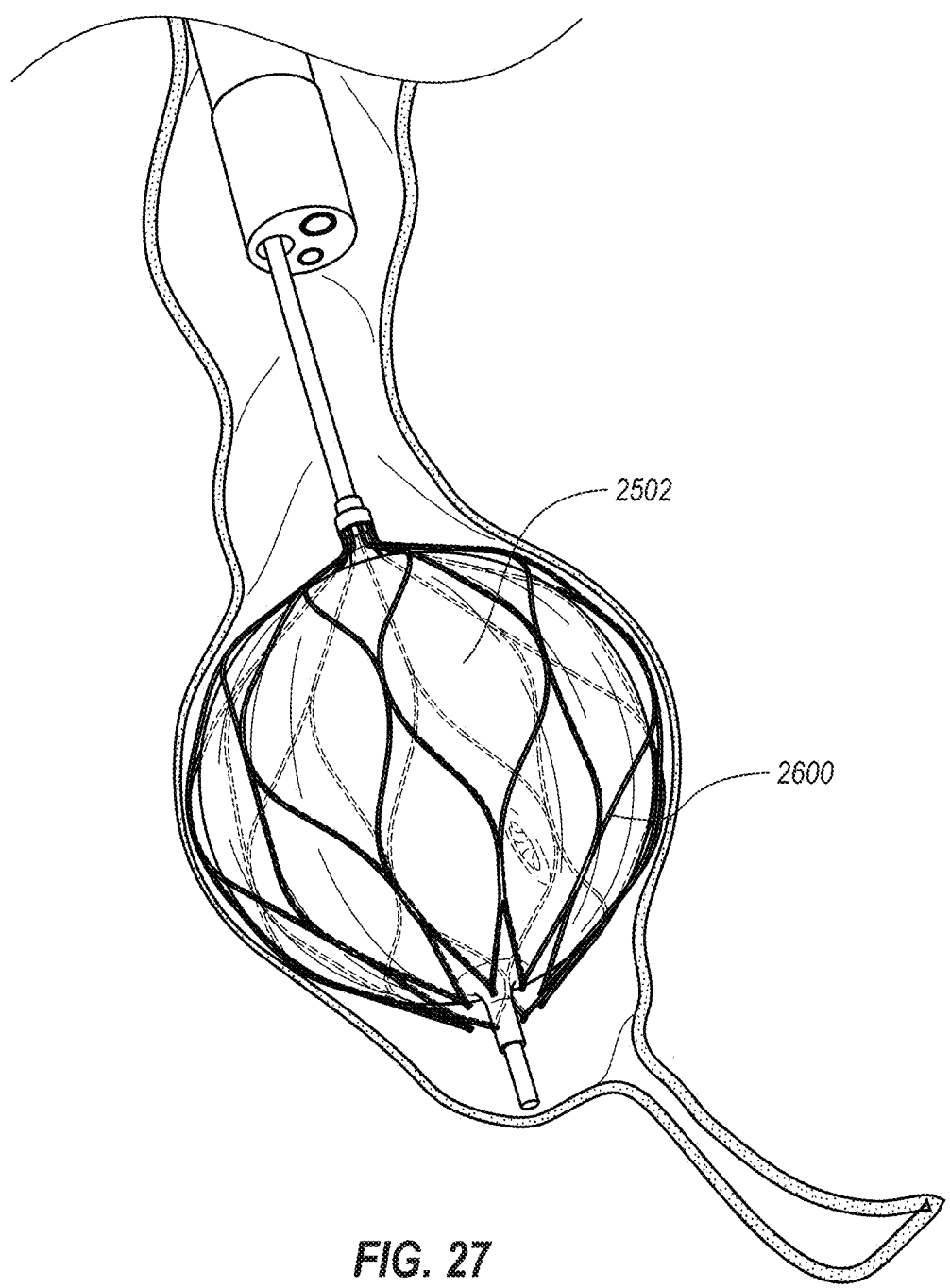
FIG. 27 depicts a stage of a method of expanding the cecum of the patient via another embodiment of an expandable medical device using the balloon catheter of FIG. 26.

FIG. 27 depicts a stage of a method of expanding the cecum of the patient via another embodiment of an expandable medical device 2600—one that is not self-expanding—using the balloon catheter 2500. As previously discussed, in some embodiments, the expansion device is preloaded over the balloon 2502, while the balloon 2502 is in a contracted state, and upon proper positioning of the low-profile expansion device within the cecum, the balloon 2502 can be inflated by a desired amount to expand the medical device into its deployed configuration.

Figure 28:
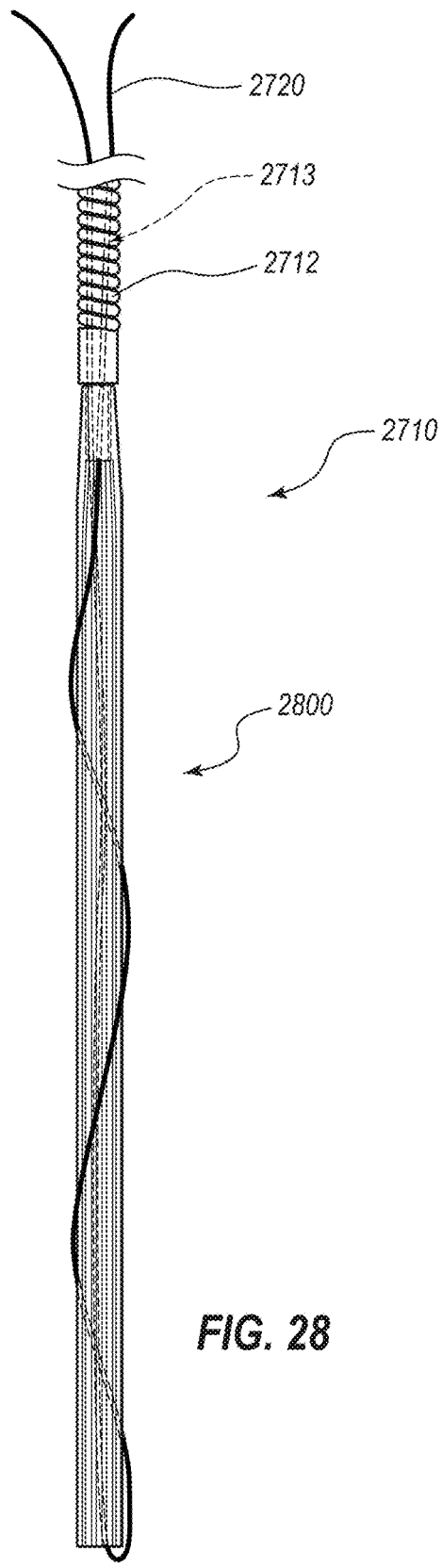
FIG. 28 depicts another embodiment of a deployment system that includes a push rod and a retention filament that selectively maintains the device in the undeployed configuration.

FIG. 28 depicts another embodiment of a deployment system 2710 that includes a push rod 2712 that defines an internal lumen 2713 and further includes a retention filament 2720 that extends through the internal lumen 2713 of the push rod 2712. The retention filament 2720 can comprise a closed loop suture that can be cut at a proximal end (from the practitioner's perspective), as shown, and withdrawn through the lumen of the push rod 2712 to permit deployment of a self-expanding device 2800. The retention filament 2720 can function similarly to the retention sleeves previously disclosed, and can selectively maintain the device 2800 in the undeployed or low-profile configuration until appropriately positioned within the cecum.

Figure 29:
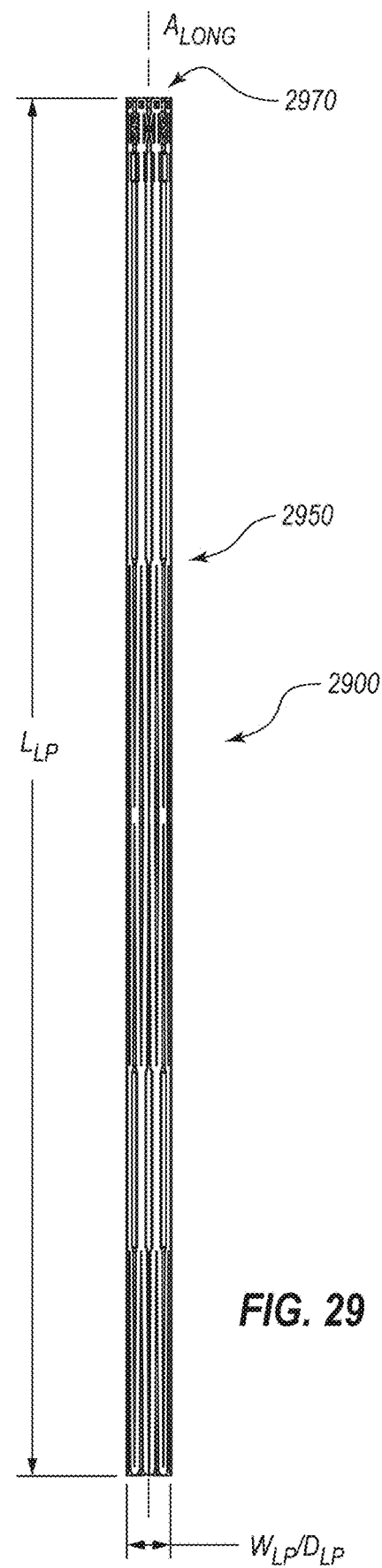
FIG. 29 is an elevation view of another embodiment of an expansion medical device configured for deployment in the cecum of a patient, the medical device being depicted in a collapsed or undeployed configuration.

FIG. 29 is an elevation view of another embodiment of an expansion device 2900 configured for deployment in the cecum of a patient, the device 2900 being depicted in a low-profile, collapsed, or undeployed orientation, state, or configuration. The device 2900 can resemble certain of the devices discussed above in many respects, such as (among others) the device 2200. Various disclosures regarding the device 2200 and other devices disclosed herein are equally applicable to the device 2900, and might not be repeated, consistent with the disclosure convention previously discussed. Similarly, disclosures hereafter regarding the device 2900 can apply to other devices as well.

As with other embodiments disclosed herein, the device 2900 can include a body 2950 that is configured to transition from the low-profile state to an enlarged or expanded state. The body 2950 can be formed of a tube (e.g., a laser-cut tube) of any suitable material, such as, for example, a metallic (e.g., stainless steel) or metal alloy (e.g., Nitinol) material. In the low-profile state, the body 2950 can define a maximum length $L_{LP}$ and a maximum width $W_{LP}$. In the illustrated embodiment, the maximum width $W_{LP}$ is substantially constant along a full length of the body 2950 and corresponds to an outer diameter $D_{LP}$ of the device 2900. In various embodiments, the maximum length $L_{LP}$ can be no less than about 6, 7, 8, 9, 10, 11, 12, 13, 14, or 15 centimeters.

The device 2900 can be tightly oriented about a longitudinal axis $A_{LONG}$ defined thereby. Stated otherwise, the device 2900 can be narrow or can define a very low profile so as to be able to be advanced through at least a portion of a working channel of an endoscope, such as a colonoscope. For example, in various embodiments, the outer diameter $D_{LP}$ can be smaller than 3.5, 3.6, 3.7, 3.8, 3.9, or 4.0 millimeters.

Stated in yet another manner, the device 2900 can have a high length-to-width aspect ratio when in the low-profile state. In various embodiments, the maximum length $L_{LP}$ can be larger than the maximum diameter $D_{LP}$ by a factor of no less than 20, 25, 30, 35, or 40.

The illustrated device 2900 is substantially cylindrical in the low-profile state. In particular, the body 2950 is shaped as a hollow cylindrical tube that defines a central passageway 2970 or lumen extending through an entirety thereof. In various embodiments, a maximum inner diameter of the tube, which corresponds to a maximum outer diameter of the passageway 2970, can be no greater than 3.0, 3.1, 3.2, 3.3, 3.4, 3.5, 3.6, 3.7, or 3.8 millimeters.

Figure 30A:
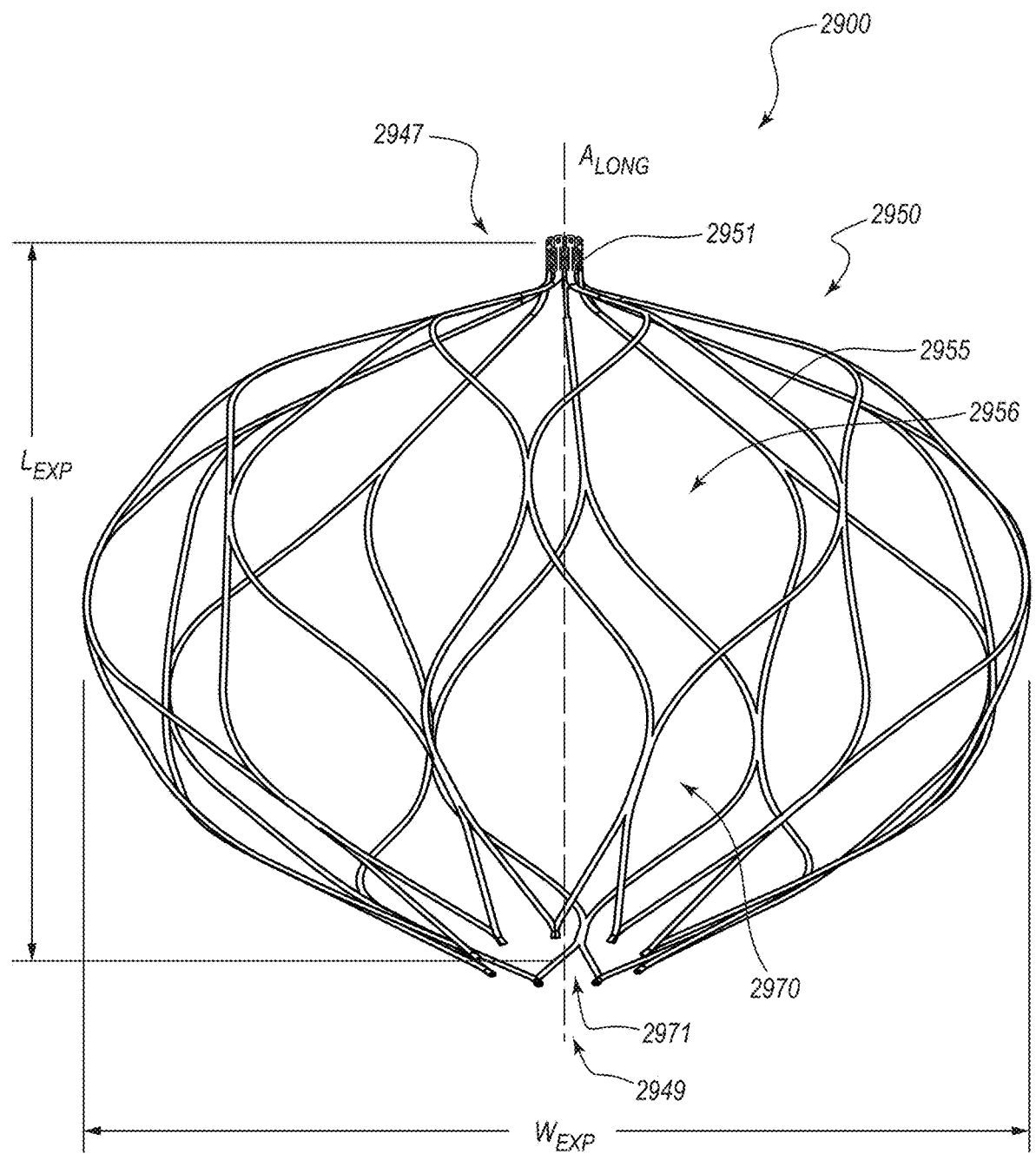
FIGS. 30A-30G are further views of the medical device of FIG. 29 depicted in an expanded or deployed configuration, with FIG. 30A being a perspective view thereof.

FIGS. 30A-30G are further views of the medical device 2900 depicted in an expanded or deployed configuration. With reference to FIG. 30A, the device 2900 is shown in a perspective view that is only slightly offset from an elevation view. In the expanded state, the body 2950 is substantially bulbous. The body 2950 includes a distal end 2947 (from the perspective of the gastrointestinal tract) and a proximal end 2949.

The distal end 2947 of the body 2950 includes a hub 2951 at which a plurality of struts 2955 gather or collect. The hub 2951 can be aligned with the longitudinal axis $A_{LONG}$ of the device 2900. The hub 2951 defines an opening 2972 at the distal end of the primary passageway 2970 of the device 2900. In certain embodiments, a size or diameter of the opening 2972 can be substantially the same as the size or diameter of the device 2900 when in the low-profile state (FIG. 29). Thus, the opening 2972 can be narrow. In some instances, the hub 2951 with a narrow opening can potentially collect material that naturally passes through the cecum of a patient over time. In other embodiments, a larger opening 2972, with or without a hub, is contemplated, and may reduce or substantially eliminate significant material collection and/or blockages that may gather thereat. For example, in some embodiments, the distal end 2947 of the device 2900 can resemble the distal ends of the devices 500, 700, 800, 900.

The proximal end 2949 of the body 2950 defines an opening 2971 at an opposite end of the primary passageway 2970. The opening 2971 is also aligned with the longitudinal axis $A_{LONG}$. In some embodiments, the opening 2971 may also be relatively small, in comparison to a maximum width $W_{EXP}$ of the device 2900 when in the expanded state. In certain embodiments, a small opening 2971 may be less prone to gather material, as compared with a proximal opening 2972 of the same size, as less material may pass thereby or therethrough due to an upstream position of the proximal opening 2972 relative to the ileocecal valve when implanted, as compared with a downstream position of the distal opening 2972.

The body 2950 includes the plurality of struts 2955, which can be formed in any suitable manner (such as those disclosed with respect to other embodiments). In the illustrated embodiment, the struts 2955 extend substantially in a longitudinal direction, but are each angled relative to a longitudinal direction. The longitudinal direction generally refers to lines that run parallel to or are collinear with the longitudinal axis $A_{LONG}$. Stated otherwise, the longitudinal direction can correspond to the proximal-to-distal orientation. The struts 2955 are curved convexly outward to define the bulbous shape depicted in FIG. 30A.

In the illustrated embodiment, adjacent struts 2955 cooperate to define a plurality of windows or openings 2956 into the primary passageway 2970. One of such openings 2956 may desirably be aligned with the ileocecal valve in manners such as previously described. In the illustrated embodiment, the openings 2956 are shaped substantially as elongated diamonds, with curved sides and pointed ends. The openings 2956 may also be described as substantially vesica piscis-shaped.

The body 2950 may be said to define a substantially oblate spheroid or bulbous shape when in the expanded state. In some instances, the body 2950 may not expand as far outwardly when in the cecum, due to resistance to expansion provided by the cecal wall. This may be seen, for example, in FIGS. 40A-40C (discussed further below), in which the implanted body 2950 defines a substantially prolate spheroid shape. In that example, as discussed further hereafter, the prolate spheroid expanded in diameter into increasingly more bulbous form over time.

The bulbous or spheroid (whether oblate or prolate) shape defined by the body 2950 in the expanded state can be significantly shorter than the elongated cylindrical shape defined by the body 2950 when in the low-profile state. Stated otherwise, the expanded-state length $L_{EXP}$ of the body 2950 can be substantially shorter than the low-profile-state length $L_{LP}$. In contrast, a maximum width $W_{EXP}$ and maximum diameter $D_{EXP}$ of the body 2950 in the expanded state can be substantially larger than the maximum width $W_{LP}$ and the maximum diameter $D_{LP}$ of the body 2950 in the low-profile state.

In various embodiments, the maximum length $L_{EXP}$ of the body 2950 in the expanded state can be no greater than about 4, 5, 6, 7, or 8 centimeters. In other or further embodiments, the maximum width $W_{EXP}$ and/or the maximum diameter $D_{EXP}$ of the body 2950 in the expanded state can be no less than about 5, 6, 7, 8, 9, 10, 11, or 12 centimeters. It may be said that the device 2900 has a low length-to-width aspect ratio when in the expanded state. In various embodiments, the maximum length $L_{EXP}$ can be larger than the maximum diameter $D_{EXP}$ by a factor of no greater than 0.75, 1.25, 1.5, 1.75, 2, 2.25, 2.5, 2.75, 3.0, or 3.5.

Figure 30B:
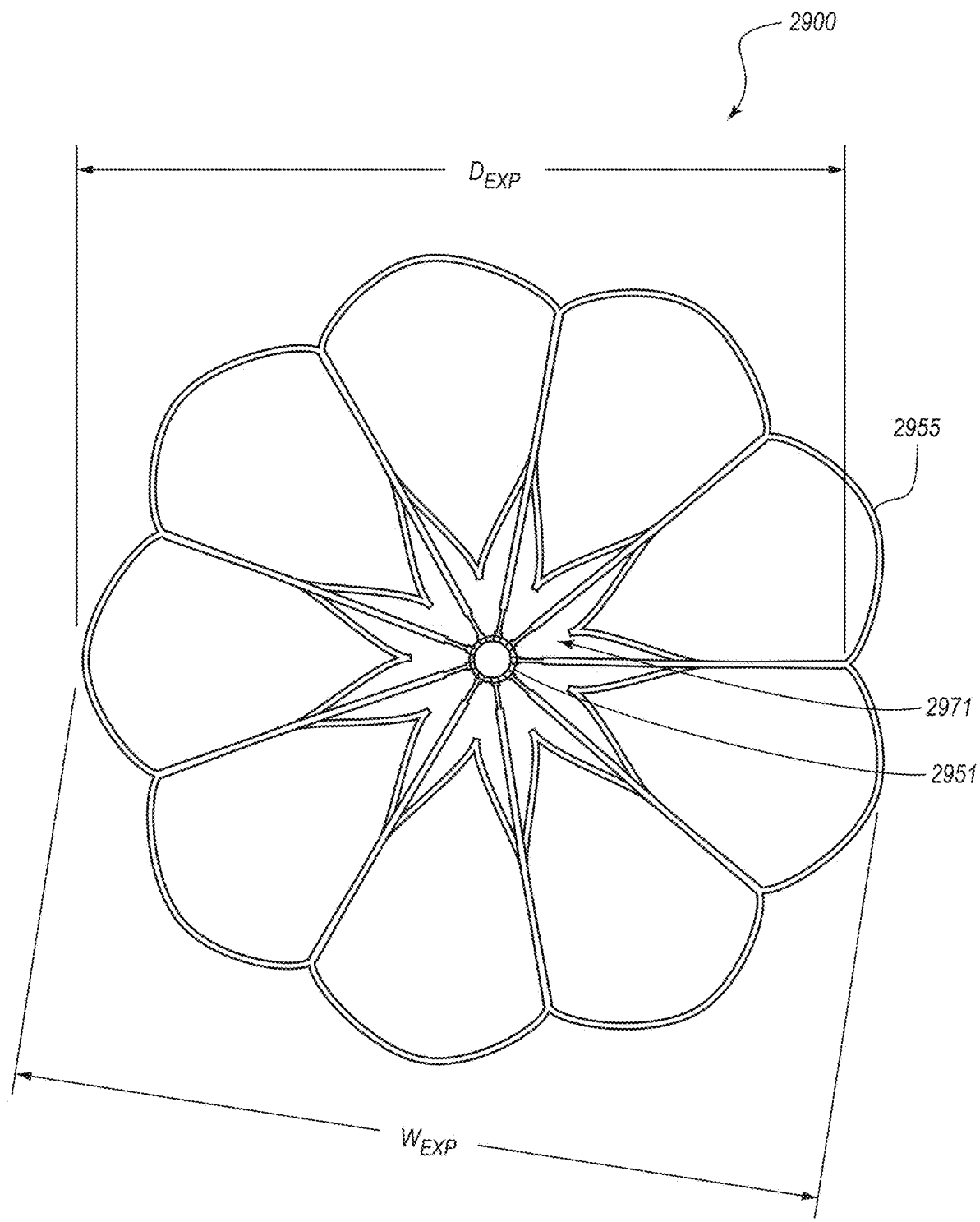

In various embodiments, the maximum length $L_{LP}$ of the body 2950, or of the three-dimensional shape defined thereby, when in the low-profile state is no less than 1.25, 1.5, 1.75, 2.0, 2.5, or 3.0 times larger than the maximum length $L_{EXP}$ of the body 2950, or of the three-dimensional shape defined thereby, when in the expanded state. In other or further embodiments, the maximum diameter $D_{EXP}$ of the three-dimensional shape or region defined or otherwise bounded by the body 2950 when the body 2950 in the expanded state is no less than 10, 15, 20, 25, or 30 times larger than the maximum diameter $D_{LP}$ of the three-dimensional shape or region defined or otherwise bounded by the body 2950 when the body 2950 is in the low-profile state FIG. 30B is a top plan view of the device 2900 in the expanded state. The illustrated device 2900 includes 9 substantially symmetrical lobes defined by the struts 2955. Due to the uneven symmetry that results, the maximum diameter $D_{EXP}$, which passes through a center of the device 2900, is slightly smaller than the maximum width $W_{EXP}$ of the device 2900.

As previously discussed, the hub 2951 at the distal end of the device 2900 can define an opening that is substantially smaller than the opening 2971 at the proximal end of the device 2900. In other embodiments, the opening at the distal end is larger than that at the proximal end. Stated otherwise, in the illustrated embodiment, the device 2900 includes what may be termed a "closed" distal end and an open proximal end (from the perspective of the digestive tract of the patient). That is, although the distal end includes large openings or windows 2956, the struts 2955 meet together in a narrow cluster near a longitudinal axis of the device 2900. In some instances, this narrow cluster or hub 2951 can block material from moving through the cecum. For example, in human patients, solid waste may pass into the primary passageway of the device 2900 through the ileocecal valve, may proceed toward the distal end of the device through the passageway of the device 2900, and may and catch on the hub. In other embodiments, the distal end can be open, such as in a manner identical or similar to the proximal end of the device 2900. In some embodiments, it may be desirable for the distal end or for both the proximal and distal ends of the device 2900 to be open.

Figure 30C:
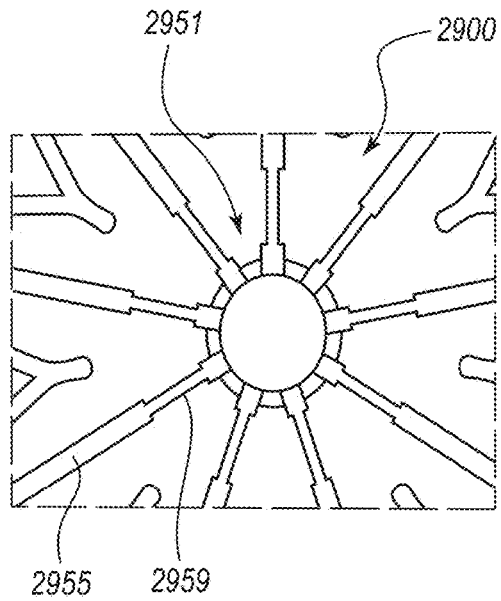
Figure 30D:
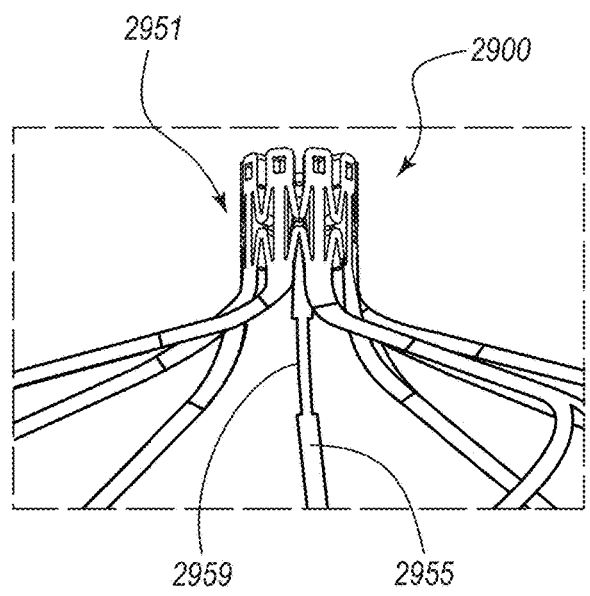
Figure 30E:
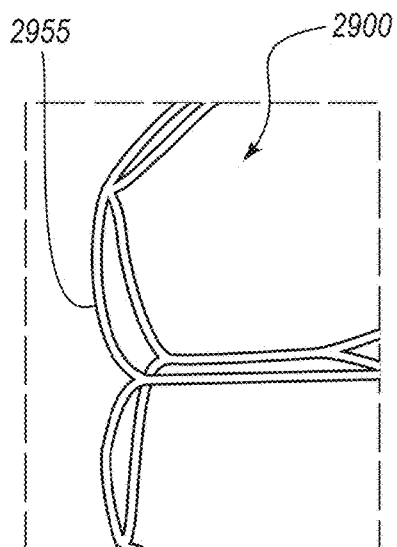

With continued reference to FIG. 30B, and with additional reference to FIG. 30E, in the illustrated embodiment, the struts 2955 can be gently sloped to assist in distributing forces at the strut/wall interface in a manner that reduces trauma to the wall. In further embodiments, the slopes at the apices may be even flatter than those shown in FIG. 30B.

As shown in FIGS. 30C and 30D, the struts 2955 can include notched, narrowed, necked, or tapered regions 2959—i.e., regions of reduced thickness—in the proximity of the hub 2951. In some instances, such regions of reduced thickness allow for greater flexure of the struts 2955 in this region. This can assist in achieving the oblate spheroid shape depicted in FIGS. 30A and 30G.

Figure 30F:
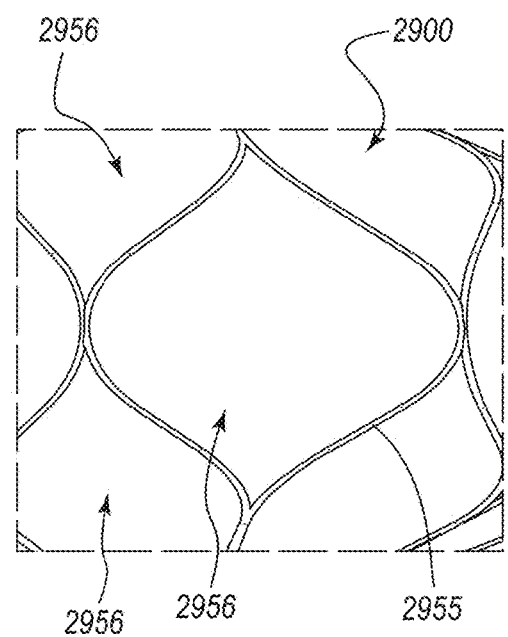
Figure 30G:
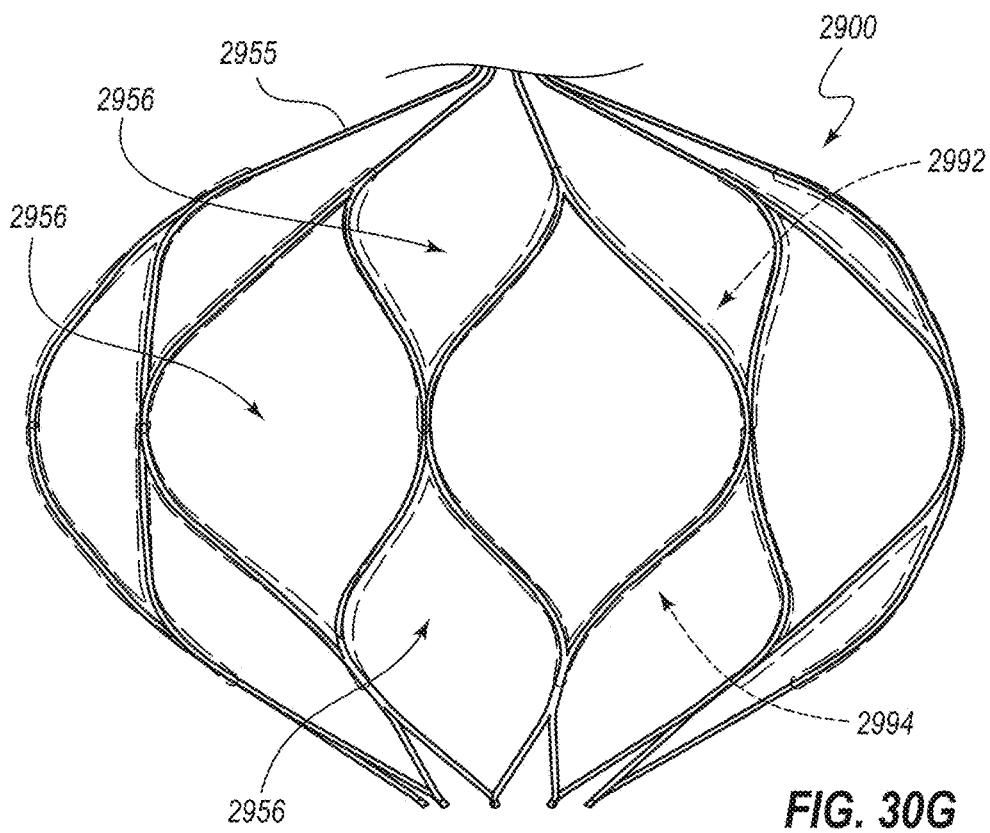

With reference to FIGS. 30F and 30G, in the illustrated embodiment, the struts 2955 define three discrete rows of interlocked or interdigitated windows 2956. Each row of windows 2956 extends about a full periphery of the device 2900.

As previously noted, in certain embodiments, the medical device 2900, as depicted in FIGS. 29-30G, may closely resemble the device 2200 discussed above, and may be deployed via a method similar to those described with respect to FIGS. 23A-23K and 24. For example, in one embodiment, the medical device 2900 is advanced through the working channel of an endoscope while in a contracted or low-profile state (FIG. 29) and delivered from the distal end (relative to the practitioner) of the endoscope into the cecum, where the medical device 2900 is permitted to self-expand. For example, in some instances, the device 2900 may be preloaded in the endoscope so as to be positioned at the distal end of the scope, the scope is then advanced into the bowel to the cecum, and then the device 2900 is delivered into the cecum. In one embodiment, the medical device 2900 is so delivered from the distal end of the endoscope via a push rod, such as discussed above with respect to FIG. 24.

As previously discussed, in some embodiments, the medical device 2900 expands the cecum to a pathophysiological size. The medical device 2900 may push on, press outwardly against, or bear against discrete or specific regions of the cecal wall, which can expand the cecum. In some instances, outward forces exerted by the strut structure of the medical device 2900 can press on a relatively small portion of the cecal wall (e.g., narrow contact bands) where the struts contact and bear against the wall. For example, in various embodiments, those regions of the medical device 2900 that bear against the narrow contact regions (e.g., narrow lines of contact) with the cecal wall, can provide pressures within a range of from about 1 to about 10; about 2 to about 6; about 3 to about 5; no less than 1, 2, 3, 4, 5, 6, 7, 8, 9, or 10; or no greater than about 1, 2, 3, 4, 5, 6, 7, 8, 9, 10 psi. In some embodiments, at least a portion of the medical device 2900, such as at some of or at least a portion of (e.g., a central portion) of the struts 2955, presses outwardly against abutting portions of the cecal wall at a pressure of about 1, 2, 3, 4, or 5 psi. In other embodiments, the medical device 2900 may press outwardly at lower pressures. For example, in some embodiments, smoother and/or wider struts may be used, which may distribute outwardly directed forces over a greater area and thereby reduce pressures applied at contact regions of the cecal wall.

In some methods, once the medical device 2900 has been deployed in the cecum of the patient, the medical device 2900 is then securely attached to the cecum. For example, in some embodiments, clips are used to secure the medical device 2900 to the cecum.

In certain embodiments, after implantation of the medical device 2900 in a manner as just described, the portions of the medical device 2900 that press against the cecal wall can induce acute and chronic inflammation of the wall. The chronic inflammation can be accompanied by fibrosis. For example, in some instances, the struts may include relatively sharp or angular edges that dig into the cecal wall. The sharp edges may result, for example, from manufacturing processes, such as laser cutting. The fibrosis may occur along the regions of the cecal wall to which force is imparted from the struts of the medical device 2900. The fibrosis can thicken the cecal wall in these contact regions. Over time, tissue ingrowth between, over, or around the struts can maintain the medical device 2900 securely fastened to the cecum and may, in some instances, inhibit explanting of the medical device 2900. More generally, outward forces provided to the cecal wall by the medical device 2900 can result in thickening of certain portions of the cecal wall.

Implantation of the medical device 2900 can further result in alteration of the microbiome of the patient, e.g., within the cecum. For example, a composition of the microbiome may change in a way that alters metabolic capabilities of the patient. That is, the microbiome may change from an "obese" microbiome (i.e., a microbiome associated with a physiological state of obesity) to or toward a "lean" microbiome (i.e., a microbiome associated with a physiological state of leanness). Obese microbiomes may, for example, be associated with phylum-level changes in the microbiota, reduced bacterial diversity, and altered representation of bacterial genes and metabolic pathways, as compared with lean microbiomes.

Without being bound by theory, one or more of a number of phenomena that may result from the enlargement of the cecum due to expansion of the medical device 2900 therein can individually cause and/or collectively contribute to subsequent weight loss for the patient. One of these phenomena, as previously discussed, is the signaling of a colo-gastric brake that can result directly from distention of the cecum due to expansion of the medical device 2900. This may be the sole phenomena responsible for weight loss due to the medical device 2900, may be one of multiple factors, or may not be present at all. Other or further of the resulting phenomena that can be induced or otherwise occur in the cecum due to expansion of the cecum, and which may be individually responsible for or may contribute to weight loss, are: acute inflammation, chronic inflammation, fibrosis, wall thickening, and alteration of the microbiome, as previously discussed. Any or all of the foregoing phenomena may contribute to anorexia and/or weight loss of a patient via hormonal-, exocrine-, neurological-, and/or microbiome-associated effects and/or other mechanisms.

One or more of the foregoing phenomena may be interrelated. For example, as a result of acute inflammation of the cecum, a number of entities are brought to the inflammation site, such as white blood cells (e.g., neutrophils). Similarly, as a result of chronic inflammation, other entities are brought to the inflammation site, such as lymphocytes and plasma cells. The presence of these entities or cells can alter the microbiome of the cecum. Further, fibrosis can be interrelated with chronic inflammation of the cecum.

Figure 31A:
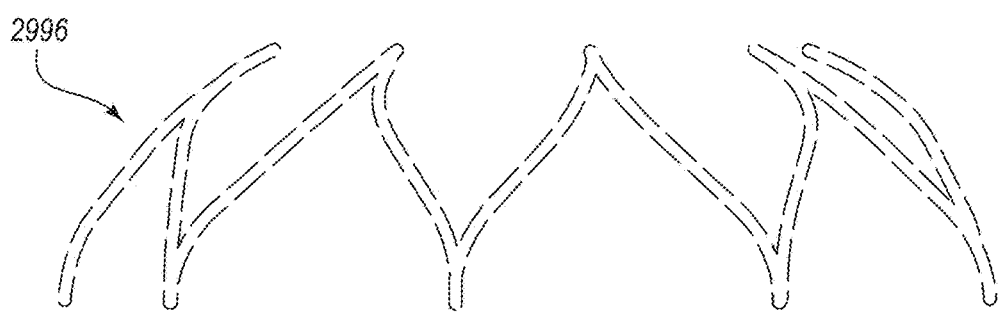
FIG. 31A is a schematic representation of a region of an illustrative cecum affected by the upper of the two force-application lines of FIG. 30G.
Figure 31B:
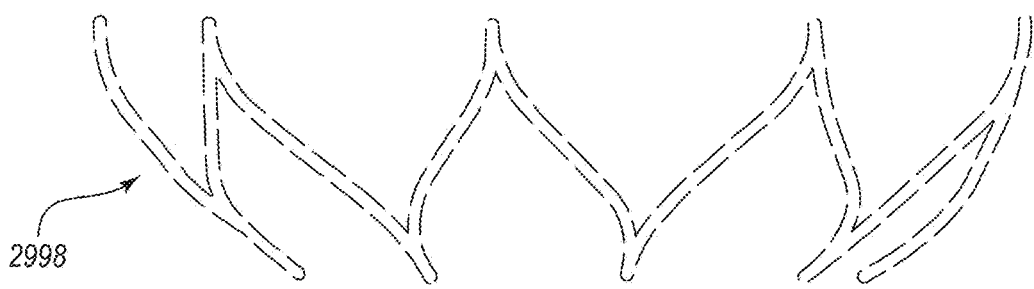
FIG. 31B is a schematic representation of a region of the illustrative cecum affected by the lower of the two force-application lines of FIG. 30G.

Without being bound by theory, fibrosis of the cecum may individually cause and/or contribute to weight loss due to interruption of pacemaker currents or signals or other effects on pacemaker activity in the cecum. For example, with reference to FIGS. 30G, 31A, and 31B, in the illustrated embodiment, the strut pattern of the device 2900 can yield a complementary pattern of fibrosis in the cecum. In the illustrated embodiment, the illustrative strut patterns 2992, 2994 outlined in FIG. 30G can result in complementary fibrosis regions, patterns, or lines 2996, 2998 of the cecum, which are schematically depicted in FIGS. 31A and 31B. These complementary patterns (strut pattern/fibrosis pattern) can extend about a full periphery or circumference of each of the device 2900 and the cecum, respectively.

Stated otherwise, a number of generally transversely directed, continuous wavy lines that follow the strut pattern, such as the illustrative substantially transversely oriented wavy lines 2992, 2994 in the medial region of the device 2900, can extend about an entirety (e.g., a full periphery) of the device 2900. These lines 2992, 2994 may also be referred to as force-application lines or regions. The resultant lines or regions of fibrosis 2996, 2998 (FIGS. 31A and 31B) likewise can extend about a full periphery of the cecum. One or more of the substantially continuous lines of fibrosis 2996, 2998 may interrupt pacemaker signals of the gut, similar to interruption of pacemaker signals that result from scarring or ablation patterns in various Cox-maze procedures for treatment of atrial fibrillation in the heart. In some instances, the lines of fibrosis 2996, 2998 need not extend about a full periphery of the cecum to adequately disrupt the pacemaker signaling to achieve weight loss. In other instances, extension of the fibrotic lines about a full periphery of the cecum yields proper disruption of pacemaker signaling to achieve weight loss.

FIGS. 32A and 32B depict another embodiment of an expandable medical device 3000 similar to other devices disclosed herein. In some embodiments, the device 3000 is self-expanding, whereas in others, the device 3000 is not self-expanding and may instead be expanded with a balloon catheter or in any other suitable manner. The medical device 3000 can include a body 3050 that includes a plurality of interconnected struts 3055. The struts 3055 may form a pattern similar to that of the device 2900, or with slight modifications, as shown.

In the illustrated embodiment, a distal end 3010 of the device 3000 may be closed in a manner to the device 2900, with the struts meeting together at a narrow hub. As shown in FIG. 32B, a proximal end 3012 is open when the device 3000 is in an expanded state. In other embodiments, the distal end 3010 is open and the proximal end 3012 is closed, and in still other embodiments, both the distal and proximal ends 3010, 3012 are open.

The medical device 3000 can further include a covering 3080 of any suitable variety. In the illustrated embodiment, the covering 3080 comprises a cover 3082 that extends about an outer periphery of the body 3050. The cover 3082 can be attached to the body 3050 in any suitable manner, including those known in the art and those yet to be devised.

For example, in various embodiments, the cover 3082 may be sutured or otherwise fastened to the body 3050. In certain polymeric embodiments, the cover 3082 may be molded over or otherwise secured to the body struts 3055.

The medical device 3000 may be referred to as a covered stent (consistent with the manner in which the term "stent" is used herein). In some embodiments, the cover 3082 may resemble coverings used in biliary stents. In various embodiments, the cover 3082 may comprise one or more of polycarbonate, polyurethane, silicone, polytetrafluoroethylene (ePTFE), fluorinated ethylene propylene (FEP), polytetrafluroethylene (PTEF), or Permalume™ Any other suitable material is contemplated.

In some embodiments, the presence of the cover 3082 can reduce inflammation and fibrosis of the cecum and can prevent or inhibit tissue ingrowth. For example, in some embodiments, the mid or central region of the device 3000 applies a greater amount of force to the cecal wall than do the proximal and distal ends of the device 3000. This can result from the geometry of the device. For example, the substantially oblate spheroid or bulbous shapes previously disclosed expand the cecum most in the central region. Similarly, the illustrated device 3000 defines a rounded substantially bicone shape, with an enlarged diameter in the mid region. The device 3000 thus may likewise press most firmly against the cecal wall in this intermediate region. Regions such as these, which may provide the greatest expansion to the cecum, may correspond to the regions of the cecum that experience the greatest inflammation, fibrosis, and ingrowth. In some embodiments, the cover 3082 can be applied to at least this middle region, such as in the illustrated embodiment, thereby significantly reducing, minimizing, or eliminating these phenomena. In certain embodiments, the cover 3082 can facilitate retrieval of the device 3000 after the device has expanded the stent for a desired amount of time. Retrieval processes such as those disclosed elsewhere herein are contemplated.

In some embodiments, other or further advantages may result from isolating the cover 3082 only to the central or middle region or band of the device 3000. For example, as previously discussed, it can be desirable in some embodiments for the distal end of the device 3000 to be substantially open to permit passage thereby of material that naturally works its way through the cecum. In the illustrated embodiment, the cover 3082 extends about a medial region of the device 3000, but does not extend over the distal ends of the struts 3050, which gather together toward a narrow hub region. This may facilitate passage of material through the distal end of the device 3000.

In other embodiments, the body 3050 may define a large open end. In certain of such embodiments, the cover 3082 may fully extend to the distal end of the body 3050.

In some embodiments, the cover 3082 may include an opening (not shown) therethrough to ensure the ileocecal valve remains unobstructed. During deployment of the device 3000, the practitioner may align the opening with the ileocecal valve, and material can pass from the ileocecal valve into an interior of the device 3000.

In the illustrated embodiment, the cover 3082 is shown substantially fully at an exterior of the body 3050 when the device 3000 is in the low-profile or collapsed state. In other embodiments, at least a portion of the cover 3082 may be positioned at an interior of the body 3050 in this collapsed state. In various embodiments, the cover 3082 may be thin and/or highly expansible to readily transition from the collapsed state to the expanded state. In other of further embodiments, the covering 3080 may additionally or alternatively include a coating applied directly to the body 3050, such as any suitable coating described elsewhere herein.

Figure 33A:
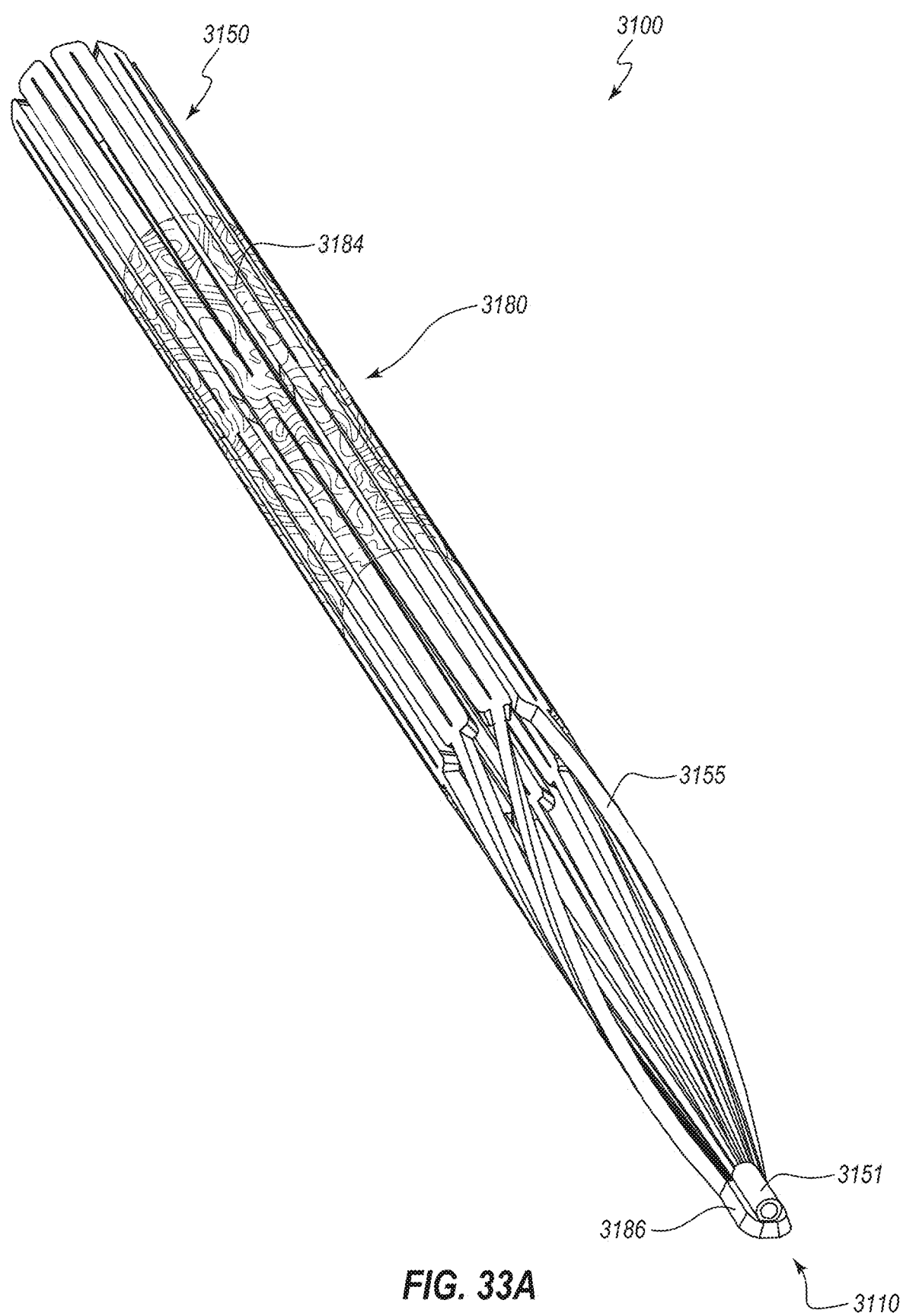
FIG. 33A is a perspective view of another embodiment of an expansion medical device that includes a distal end configured to assist in retrieval of the medical device after use and further includes a covering—specifically, a coating applied to a frame, the medical being depicted in a low-profile, collapsed, or undeployed configuration.

FIGS. 33A-33C are various views of another embodiment of an expansion medical device 3100, which can closely resemble other devices disclosed herein in many respects. The device 3100 is shown in a low-profile state in FIGS. 33A-33C, and can be configured to transition to an expanded state resembling that of other devices herein, such as, for example, any of the devices 2200, 2900, 3000.

In the illustrated embodiment, the device 3100 includes a body 3150 to which is applied a covering 3180 that can inhibit or prevent inflammation, fibrosis, and/or tissue ingrowth. In the illustrated embodiment, the covering 3180 comprises a coating 3184 applied directly to the body 3150. In some embodiments, the coating may comprise an eluting material, such as for example, a drug-eluting composition of any suitable variety, including those described elsewhere herein. The coating 3184 may be applied to the body 3150 in any suitable manner, including those known in the art and those yet to be devised.

In the illustrated embodiment, the coating 3184 is restricted to an intermediate region between the proximal and distal ends of the body 3150, similar to the region of the body 3050 covered by the covering 3080 (see FIGS. 32A and 32B). In other embodiments, the coating 3184 may cover more of the body 3150. For example, in various embodiments, the coating 3184 covers no less than 50, 60, 70, 80, 90, or 95 percent of a surface area of the body 3150.

In various embodiments, the device 3100 can be configured for retrieval, such as after passage of a therapeutically effective period. For example, by inhibiting tissue ingrowth, the covering 3180 can facilitate removal of the device 3100 from the cecum. In other or further embodiments, the device 3100 includes a distal end 3110 that facilitates or assists in collapsing of the device 3100 from an expanded state to a low-profile state, as described further hereafter.

With continued reference to FIGS. 33A-33C, the distal struts 3155 at one side of the body 3150 can slope or curve toward the other side of the body 3150, and all of the struts 3155 can gather toward a distal tip 3186 that is offset to one side of a longitudinal axis $A_{LONG}$ defined by the body 3150. With reference to FIG. 33B, each distal strut 3155 can define an angle relative to the longitudinal axis $A_{LONG}$ within a first plane (i.e., the plane of the drawing sheet) that is no greater than the acute angle α. For example, in FIG. 33B, the uppermost struts define the greatest angle, a, relative to $A_{LONG}$, the lower struts define progressively smaller angles relative to the longitudinal axis $A_{LONG}$, and the bottom strut is substantially parallel to the longitudinal axis $A_{LONG}$. Similarly, with reference to FIG. 33C, each distal strut 3155 can define an angle relative to the longitudinal axis $A_{LONG}$ within a second plane that is orthogonal to the first plane (i.e., the plane of the drawing sheet) that is no greater than the acute angle β. For example, in FIG. 33C, each of the uppermost and lowermost struts define the greatest (in magnitude) angle, ±β, relative to the longitudinal axis $A_{LONG}$, the inner or intermediate struts define progressively smaller (in magnitude) angles relative to the longitudinal axis $A_{LONG}$, and the center strut is substantially parallel to the longitudinal axis $A_{LONG}$. In various embodiments, the angles α and β may be equal, or one may be larger than the other. In any event, one or more of the distal struts may define a maximum acute angle relative to the longitudinal axis $A_{LONG}$, and each distal strut can define an angle relative to the longitudinal axis $A_{LONG}$ that is less than or equal to that maximum angle. In various embodiments, the maximum acute angle is no greater than 5, 10, 15, 20, 25, 30, or 35 degrees.

Stated in other terms, in some embodiments, each of the distal struts may be circumscribed by a cone having a vertex centered at the distal tip 3186, and an apex angle of the cone may be acute. In various embodiments, the apex angle of the cone is no greater than 10, 20, 30, 40, 45, or 50 degrees.

In the illustrated embodiment, the distal tip 3186 is offset relative to the longitudinal axis $A_{LONG}$. Likewise, each of the struts 3155 at the distal end of the body is positioned exclusively at one side of a plane that passes through the central longitudinal axis of the body when the body is in the low-profile state. In some embodiments, the distal tip 3186 includes a connection hub 3151 or connector to selectively attach to a retrieval device, such as a threaded push rod or pull rod such as previously disclosed. In the illustrated embodiment, the connection hub 3151 comprises an internally threaded tube. Other retrieval mechanisms are contemplated.

To effectuate retrieval of the device 3100, any of the techniques previously disclosed or otherwise contemplated may be employed. For example, the device 3100 may be connected to a pull rod and drawn directly into the working channel of an endoscope or may be drawn into a retention or retrieval sheath. In either case, an opening or leading edge of the working channel or retention sheath can be a substantially fixed or rigid shape, such as a circle. The angled distal end 3110 of the device 3100 can be configured to facilitate entry of the device 3100 through the opening and/or collapse of the device 3100 as it is advanced into a lumen of the working channel or retrieval sheath. For example, as the angled distal struts 3155 are pressed against the leading edge of the channel or sheath, the forces applied to the distal struts 3155 work to collapse the body 3150 to the low-profile state.

Figure 34B:
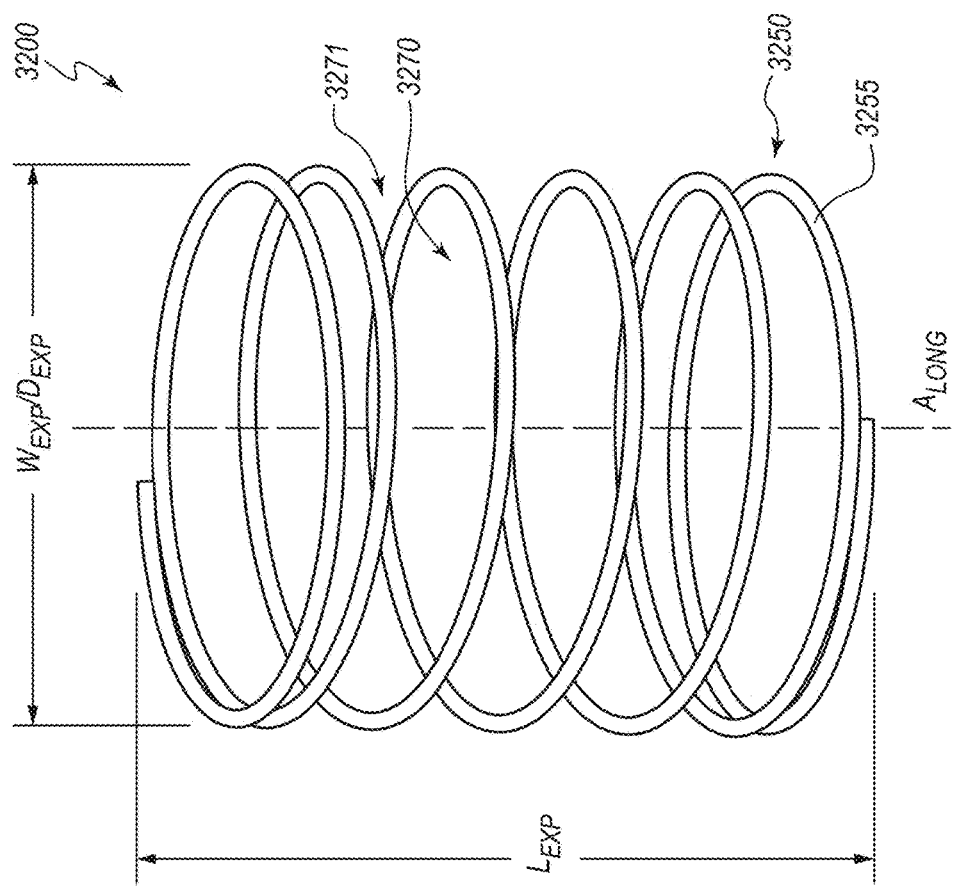
FIG. 34B is a perspective view of the medical device of FIG. 34A in an expanded or deployed configuration.
Figure 34A:
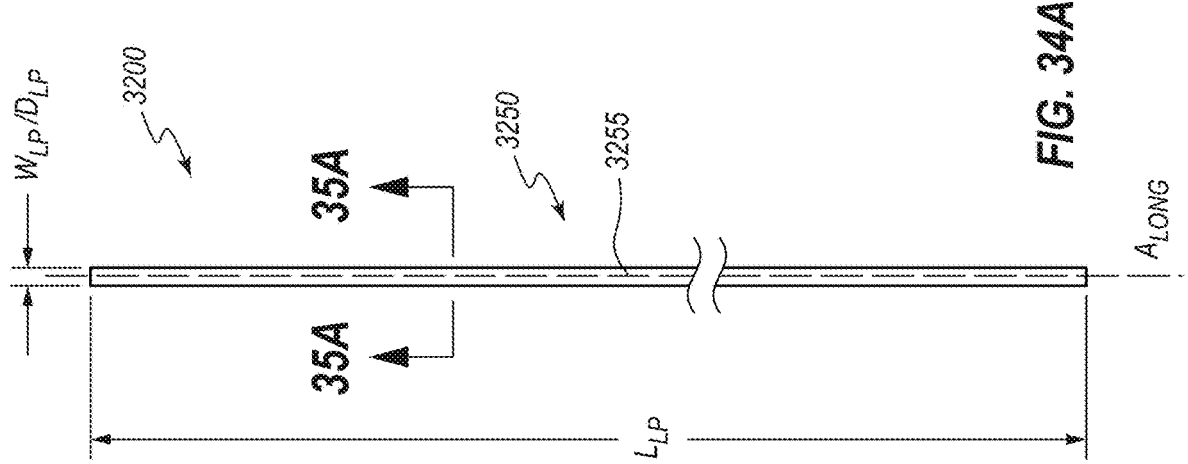
FIG. 34A is an elevation view of another embodiment of an expansion medical device shown in a low-profile or undeployed configuration.

FIGS. 34A and 34B depict another embodiment of an expansion device 3200 configured for deployment in the cecum of a patient, the device 3200 being depicted in a low-profile, collapsed, or undeployed orientation, state, or configuration in FIG. 34A and being depicted in an expanded, enlarged, or deployed configuration in FIG. 34B. The device 3200 can resemble certain of the devices discussed above in many respects, such as (among others) the device 1200. Various disclosures regarding the device 1200 and other devices disclosed herein are equally applicable to the device 3200, and might not be repeated, consistent with the disclosure convention previously discussed. Similarly, disclosures hereafter regarding the device 3200 can apply to other devices as well.

As with other embodiments disclosed herein, the device 3200 can include a body 3250 that is configured to transition from the low-profile state to the expanded state. The body 3250 can be formed of any suitable material, such as, for example, any metallic (e.g., stainless steel), shape-memory alloy (e.g., Nitinol), resilient polymer, superabsorbent polymer, or other material. Other suitable materials are contemplated, including without limitation those discussed above with respect to the device 1200. In some embodiments, the material is a resiliently flexible material that is capable of being retained in the low-profile state, such as when retained within a tubular structure (e.g., the working channel of an endoscope) or otherwise retained in a substantially linear profile, and automatically transitioning to the expanded state to define a three-dimensional profile upon and/or after having been advanced out of the tubular structure. In the illustrated embodiment, the body 3250 is formed as a single elongated element, such as a rod or wire. The illustrated wire defines a substantially circular cross-section. Other cross-sectional shapes are contemplated (oval, rectangular, diamond, etc.)

As used with respect to the body 3250, the term "linear" does not necessarily connote rectilinearity, but rather, connotes a relatively straight line and/or a configuration in which the body 3250 is constrained to follow the contour of an elongated member (such as, e.g., a guidewire, guide tube, or endoscope), and thus does not independently delineate a three-dimensional volume. In other terms, the body 3250 may be said to be substantially collinear with a working channel or retention tube within which the body 3250 is restrained, contained, or otherwise loaded, and thus may also be termed as being in a collinear or in-line configuration. The terms "linear," "in-line," and "collinear" are sufficiently broad to include deviations from rectilinearity, such as in circumstances in which the body 3250 is loaded within the working channel of an endoscope that is bent within the bowel of a patient. The body 3250 may also be said to be in a constrained or confined state when in the low-profile state, such as when loaded within a working channel or a retention tube.

In the low-profile state, the body 3250 can define a maximum length $L_{LP}$ and a maximum width $W_{LP}$. In various embodiments, the maximum length $L_{LP}$ can be no less than about 10, 15, 20, 25, 30, 35, 40, 45, 50, 55, 60, 65, 70, 75, 80, 85, 90, 95, or 100 centimeters.

In some instances, the maximum length $L_{LP}$ can be significantly longer than for embodiments such as the device 2900, as a single elongated element is reconfigured from a linear profile to form a three-dimensional shape upon transition from the low-profile to the high-profile or expanded state. The device 2900, in contrast, transitions from a three-dimensional tubular shape having a cylindrical profile, which is defined by a plurality of struts, to a three-dimensional tubular shape having a bulbous profile, as defined by the same plurality of struts (see FIGS. 29-30G).

In the illustrated embodiment, the maximum width $W_{LP}$ is substantially constant along a full length of the body 3250 and corresponds to an outer diameter $D_{LP}$ of the body 3250. The body 3250 can be tightly oriented about a longitudinal axis $A_{LONG}$ defined thereby. Stated otherwise, the device 3250 can be narrow or can define a very low profile so as to be able to be advanced through at least a portion of a working channel of an endoscope, such as a colonoscope. For example, in various embodiments, the outer diameter $D_{LP}$ can be smaller than 3.5, 3.6, 3.7, 3.8, 3.9, or 4.0 millimeters In the illustrated embodiment, the body 3250 is substantially solid. Accordingly, the outer diameter $D_{LP}$ may be said to extend exclusively through an internal region of the body 3250. This is in contrast, for example, to the device 2900 when in the low-profile state. There, the outer diameter $D_{LP}$ extends through the primary passageway 2970 defined by the tubular body 2950. Stated otherwise, the tubular body 2950 of the device 2900 defines a hollow, substantially cylindrical region (which may also be referred to as a three-dimensional region or as a tubular region), and the outer diameter $D_{LP}$ extends through both the body 2950 and through the open lumen, hollow interior, or open space defined by the body 2950.

The device 3200 can have a high length-to-width aspect ratio when in the low-profile state. In various embodiments, the maximum length $L_{LP}$ can be larger than the maximum diameter $D_{LP}$ by a factor of no less than 20, 25, 30, 35, 40, 45, 50, 60, 70, 80, 90, 100, 125, 150, 175, 200, or 225.

With reference to FIG. 34B, the body 3250 may be said to define a substantially spiraled or helical shape or profile when in the expanded state. Whereas the body 3250 defines a substantially linear profile when in the low-profile state, the body 3250 demarcates, defines, or otherwise bounds a three-dimensional shape or region. In the illustrated embodiment, the helical shape substantially corresponds to a cylinder having a maximum length $L_{EXP}$ and a maximum width $W_{EXP}$, which directly corresponds to a maximum diameter $D_{EXP}$.

The cylindrical shape defined by the body 3250 in the expanded state can be significantly shorter than the linear profile of the body 3250 when in the low-profile state. Stated otherwise, the expanded-state length $L_{EXP}$ of the body 3250 can be substantially shorter than the low-profile-state length $L_{LP}$. In contrast, a maximum width $W_{EXP}$ and maximum diameter $D_{EXP}$ of the body 3250 in the expanded state can be substantially larger than the maximum width $W_{LP}$ and the maximum diameter $D_{LP}$ of the body 3250 in the low-profile state.

In various embodiments, the maximum length $L_{EXP}$ of the body 3250 in the expanded state can be no greater than about 4, 5, 6, 7, or 8 centimeters. In other or further embodiments, the maximum width $W_{EXP}$ and/or the maximum diameter $D_{EXP}$ of the body 3250 in the expanded state can be no less than about 5, 6, 7, 8, 9, 10, 11, or 12 centimeters. It may be said that the device 3200, or a three-dimensional shape defined thereby, has a low length-to-width aspect ratio when in the expanded state. In various embodiments, the maximum length $L_{EXP}$ can be larger than the maximum diameter $D_{EXP}$ by a factor of no greater than 0.75, 1.25, 1.5, 1.75, 2, 2.25, 2.5, 2.75, 3.0, or 3.5.

In various embodiments, the maximum length $L_{LP}$ of the body 3250, or of the linear shape defined thereby, when in the low-profile state is no less than 1.25, 1.5, 1.75, 2.0, 2.5, 3.0, 3.5, 4.0, 4.5, 5, 6, 7, 8, 9, 10, 15, 20, 25, or 30 times larger than the maximum length $L_{EXP}$ of the three-dimensional shape or region defined or otherwise bounded by the body 3250 when in the expanded state. In other or further embodiments, the maximum diameter $D_{EXP}$ of the three-dimensional shape or region defined or otherwise bounded by the body 3250 when the body 3250 in the expanded state is no less than 10, 15, 20, 25, or 30 times larger than the maximum diameter $D_{LP}$ of the body 3250 when in the low-profile state.

With continued reference to FIGS. 34A and 34B, the body 3250 does not define a passageway when in the low-profile state, but does define a passageway 3270 when in the expanded state. As with the device 1200, the device 3200 further defines an extended opening 3271 or window into the passageway 3270. The opening 3271 is defined by adjacent portions of the body 3250 and spirals around the substantially cylindrical shape demarcated by the body 3250.

Any suitable variations of the device 3200 are contemplated. For example, different numbers and/or arrangements of loops or turns are contemplated. Other three-dimensional shapes or configurations than substantially cylindrical are also contemplated. For example, in other embodiments, a shape generally demarcated by the device 3200 in the expanded state, such as by spiral contours defined thereby, may be substantially bulbous (see FIG. 38).

Figure 35A:
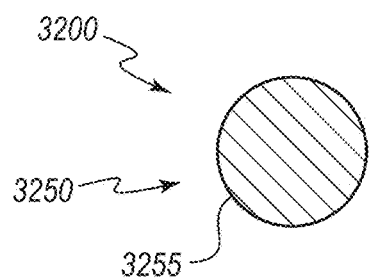
FIG. 35A is a cross-sectional view of the medical device of FIG. 34A taken along the view line 35A-35A in FIG. 34A.

With reference to FIG. 35A, as previously noted, the body 3250 of the illustrated device 3200 can comprise an elongate wire or rod 3255. When deployed, the rod 3255 may come into direct contact with the sidewall of the cecum. The rod 3255 may be placed within the cecum via an endoscope, catheter, or in any other suitable manner.

Figure 35B:
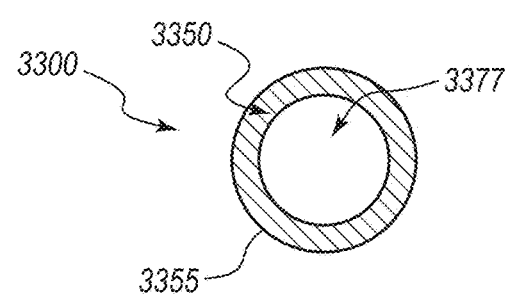
FIG. 35B is a cross-sectional view, similar to that of FIG. 35A, of another embodiment of an expansion medical device.

FIG. 35B depicts another embodiment of a device 3300 that is substantially the same as the device 3200. The device 3200 includes an elongated body 3350 such as the body 3250 shown in FIGS. 34A and 34B. However, rather than comprising a solid rod, the body 3250 is formed of an elongated tube 3355 (of any suitable material disclosed herein) that defines a channel or lumen 3377. In some embodiments, the lumen 3377 is sized to pass over a guidewire. In some embodiments, the guidewire may constrain the body 3250 to the linear profile. In various embodiments, the device 3300 may be introduced into the cecum via an endoscope and/or the guidewire. For example, in some embodiments, the device 3300 may be introduced into the cecum over a guidewire, whether in conjunction with or independently from an endoscope. Visualization other than that provided by an endoscope (e.g., fluoroscopy) may be employed in certain of such methodologies.

Figure 35C:
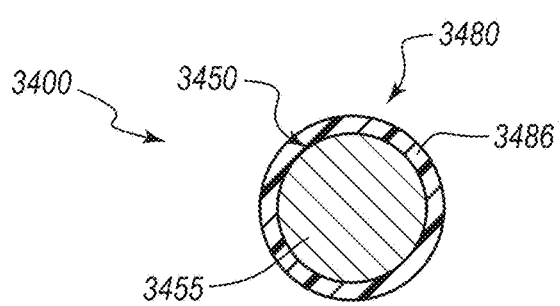
FIG. 35C is a cross-sectional view, similar to that of FIG. 35A, of another embodiment of an expansion medical device.

FIG. 35C depicts another embodiment of a device 3400 that includes a body 3450 which is substantially the same as the device 3200. The body 3450 includes a rod 3455 such as the rod 3255. The device 3400 further includes a covering 3480, such as a layer of material or coating 3486. Any suitable covering, layer, or coating is contemplated, as are any suitable method for applying the same to the rod 3455 (for example, dipping, spraying, overmolding, etc.). The covering 3480 or coating 3486 may be said to encapsulate, encompass, enclose, envelop, wrap, sheathe, or cover at least a portion of the body 3450.

Any of the coatings disclosed herein may be used. For example, in some embodiments, the covering 3480 comprises an eluting composition. In other or further embodiments, the covering 3480 comprises a polymeric material, such as, for example, silicone. The covering 3480 may, for example, inhibit inflammation, fibrosis, and/or tissue ingrowth. In various embodiments, the covering 3480 may render the device 3400 more suitable for long-term placement within the patient. For example, the cecum may better tolerate the device 3400 due to the covering 3480. This may, in some instances, permit the device 3400 to remain within the patient indefinitely and/or in other or further instances, may facilitate removal of the device 3400 if and when desired.

Figure 35D:
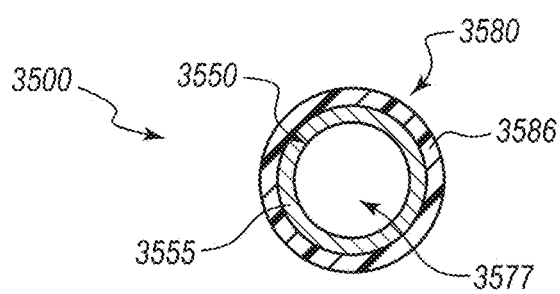
FIG. 35D is a cross-sectional view, similar to that of FIG. 35A, of another embodiment of an expansion medical device.

FIG. 35D depicts another embodiment of a device 3500, which includes a body 3550 formed as a tube 3555, similar to the body 3350 of FIG. 35B. The device 3500 further includes a covering 3580, such as a coating or layer 3586, which can resemble the covering 3480. The foregoing relevant disclosures thus apply to the device 3500. The device 3500 can further define a lumen 3577, such that the device 3500 may suitably be used with a guidewire in manners such as previously disclosed.

Figure 35E:
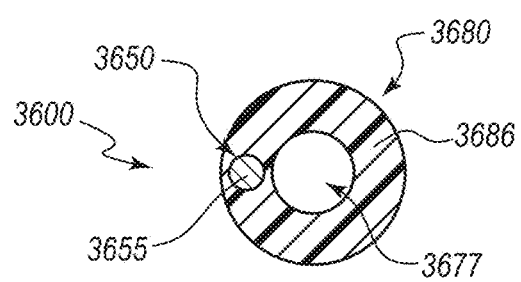
FIG. 35E is a cross-sectional view, similar to that of FIG. 35A, of another embodiment of an expansion medical device.

FIG. 35E depicts another embodiment of a device 3600, which includes a body 3650 formed as a rod 3655, similar to the body 3250 of FIG. 35A. The rod 3655 may function in manners such as the rod 3255. The device 3600 further includes a covering 3680, which is formed as tube 3686. The tube 3686 may be polymeric and/or may include, for example, any of the other materials previously described with respect to coverings. The rod 3655 is embedded within a sidewall of the tube 3686. The tube 3686 defines a lumen 3677 that may suitably be used with a guidewire in manners such as previously disclosed.

Any of the devices 3300, 3400, 3500, 3600 may generally function in manners such as described with respect to the device 3200. For example, in some embodiments, the devices 3300, 3400, 3500, 3600 are configured to transition from a low-profile configuration, such as that depicted in FIG. 34A, to an expanded configuration, such as that depicted in FIG. 34B.

Figure 36B:
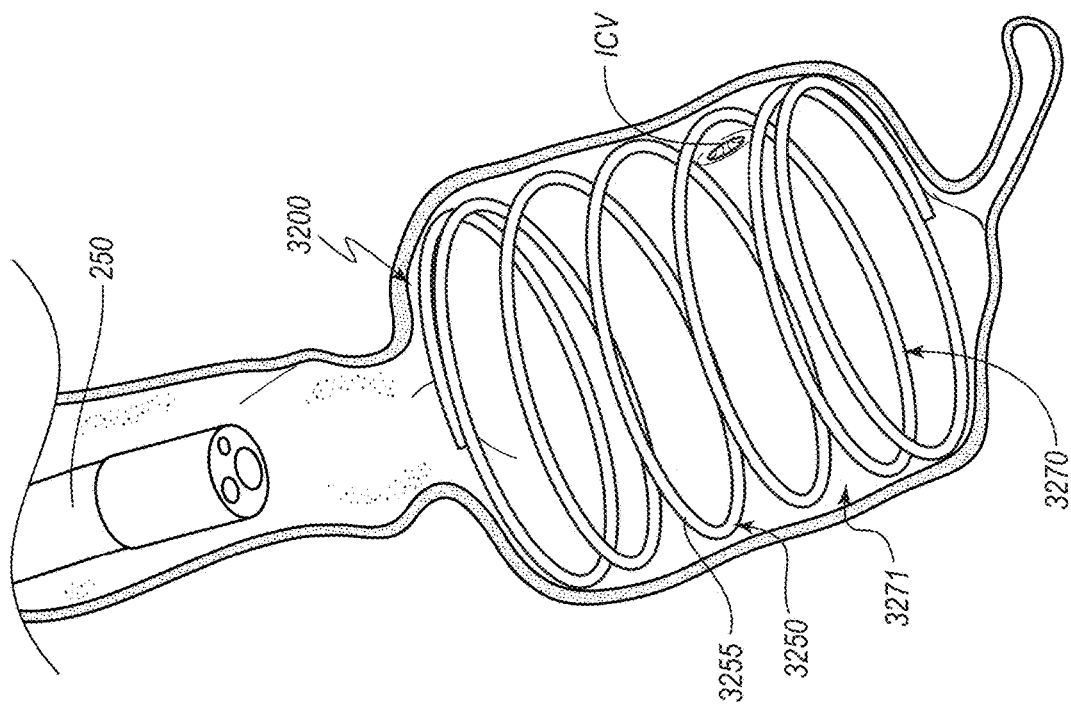
FIG. 36B depicts another stage of the illustrative method another illustrative method in which the medical device of FIGS. 34A and 34B is fully deployed within the cecum.
Figure 36A:
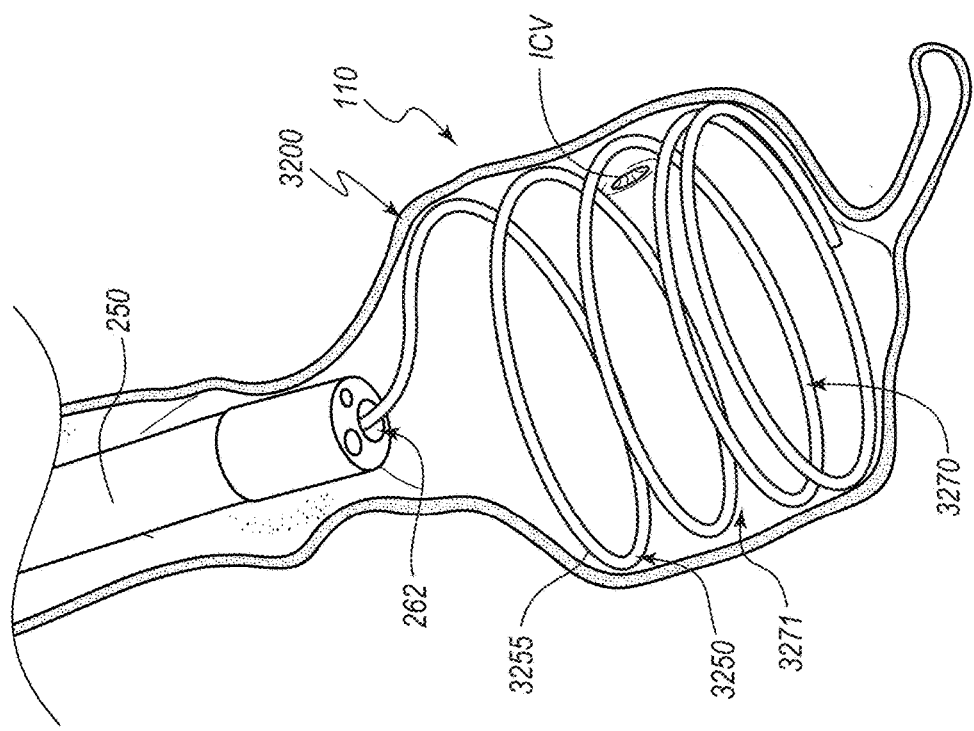
FIG. 36A is a cross-sectional view of a portion of the colon of a patient during another illustrative method in which the expandable medical device of FIGS. 34A and 34B, shown in perspective, is being delivered to the cecum of the patient directly from an instrument channel of an endoscope and naturally or automatically transitions from the low-profile stated to the expanded state within the cecum.

FIGS. 36A and 36B depict stages of an illustrative method of expanding the cecum 110 of a patient using the device 3200. In some embodiments, the device 3200 is loaded into the working channel 262 of an endoscope 250 in a low-profile state, such as by advancing the device 3200 distally through the working channel 262. The endoscope 250 is then inserted through the bowel of the patient into the cecum 110. In some methods, a practitioner may position the distal end (from the practitioner's perspective) of the endoscope 250 at the proximal end (relative to the gastrointestinal tract) of the cecum 110. The device 3200 is then advanced out of the endoscope 250 and into the cecum 110. For example, the device 3200 may be pushed through the working channel 262 via a push rod or the like.

In some embodiments, exiting the working channel 262 frees the device 3200 from being constrained to a linear profile, and the device 3200 naturally or automatically transitions to the expanded state. For example, in some embodiments, the device 3200 comprises a resilient material that naturally coils into a spiraled configuration, such as the illustrated helix, as the device 3200 is advanced out of the channel 262. In various embodiments, the coiling occurs immediately upon exiting the channel 262, whereas in others (such as in certain shape-memory embodiments), there may be a delay before coiling occurs.

In some embodiments, the practitioner may visualize the ileocecal valve ICV and positioning of the body 3250 during deployment of the device 3200 to ensure that the ileocecal valve ICV remains unobstructed. Stated otherwise, the practitioner may visualize positioning of the body 3255 against the cecal wall to ensure that the side window 3271 is aligned with the ileocecal valve/CV.

FIG. 36B depicts a stage at which the device 3200 has been fully deployed within the cecum 3200. In some embodiments, no further attachment of device 3200 to the cecum 110 is performed. The endoscope 250 may be retracted from the patient and the device 3200 left in place for a therapeutically effective period. As previously discussed, in various methods and for various different embodiments, the device 3200 may be retracted via a subsequent colonoscopy (such as, e.g., by snaring the device 3200 into the working channel 262), may be left to degrade through bioresorption and may ultimately pass naturally through the colon, or may be left in place indefinitely.

Figure 37:
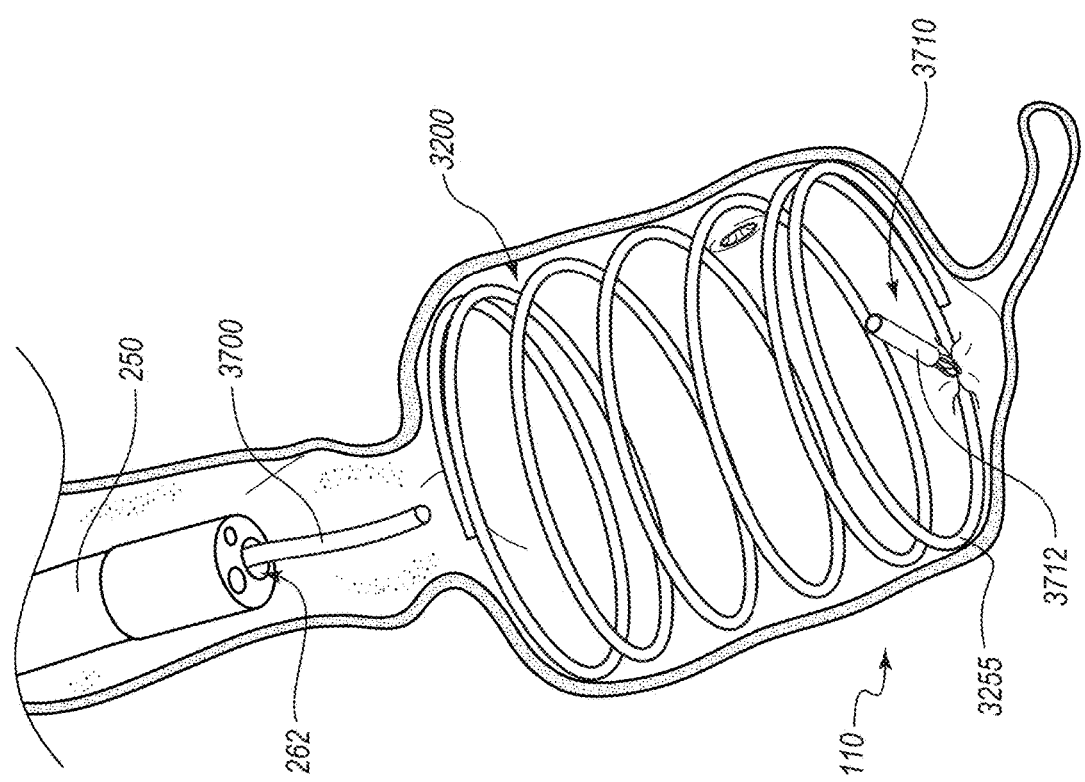
FIG. 37 depicts a stage of another illustrative method that involves deployment of the medical device of FIGS. 34A and 34B in which the medical device is attached to the wall of the cecum using one or more fasteners.

FIG. 37 depicts a stage of an additional illustrative method. The initial stages may proceed in manners such as discussed with respect to FIGS. 36A and 36B. After full deployment of the device 3200, one or more mechanical fasteners 3710 may then be used to secure the device 3200 to the cecum 110. In the stage depicted in FIG. 37, one mechanical fastener 3710, specifically a hemoclip 3712, has been used to attach the body 3255 to the cecal wall. This can be accomplished by advancing a hemoclip delivery device 3700 through the endoscope 250 in manners known in the art. Any suitable number of hemoclips and/or other fasteners may be used. In the illustrated method, more hemoclips will subsequently be used to secure the body 3255 in place.

Figure 38:
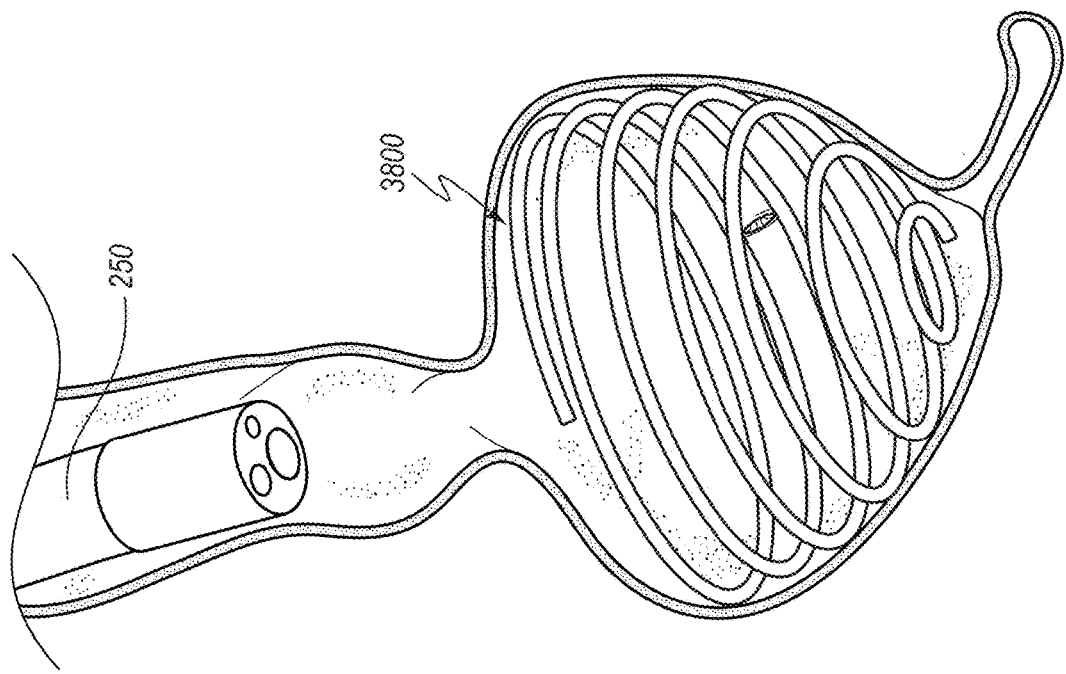
FIG. 38 depicts another illustrative method in which another embodiment of an expandable medical device has been delivered to the cecum of the patient.

FIG. 38 depicts a stage of another illustrative method, similar to that depicted in FIG. 36B, in which another embodiment of an expandable medical device 3800 has been delivered to the cecum of the patient via an endoscope 250. The medical device 3800 substantially resembles the device 3200, but forms a bulbous shape, rather than a cylindrical shape, when fully deployed. Like the device 3200, the device 3800 assumes a spiraled form when fully deployed. Other configurations are also contemplated.

Figure 39:
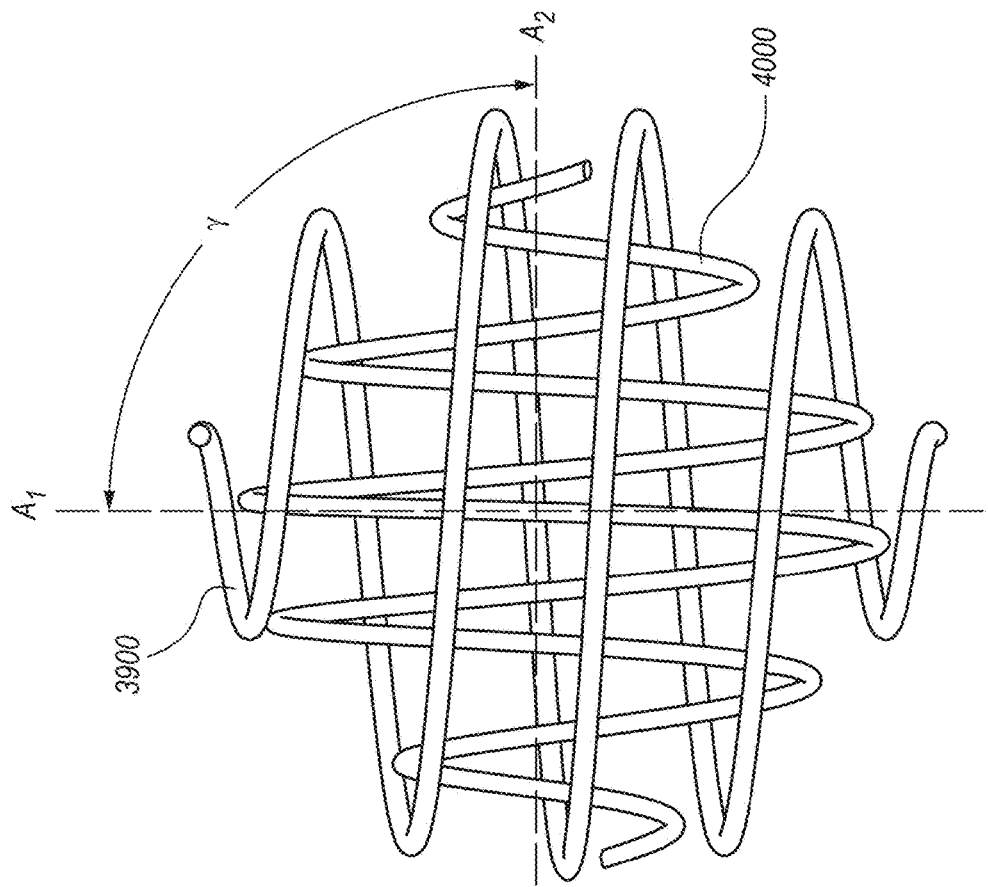
FIG. 39 depicts another illustrative method in which an embodiment of a pair of expandable medical devices has been delivered to the cecum of the patient.

FIG. 39 depicts a stage of another illustrative method in which multiple devices are deployed within the cecum. In particular, in some instances, a first spiraled device 3900 is deployed into contact with the cecum in manners such as previously disclosed. The device 3900 may define a longitudinal axis $A_1$. Subsequently, a second device 4000 is inserted into an interior of the first deployed device 3900 in manners such as previously disclosed, such as by advancing the device 4000 out of the working channel of an endoscope at a position internal to the device 3900. The second device 4000 may be permitted to self-expand and come into contact with the cecal wall and/or the first device 3900. The second device 4000 can define a second longitudinal axis $A_2$.

In some instances, it may be desirable for the axes $A_1$, $A_2$ to be an angle γ relative to each other. Such an arrangement can allow for more distributed forces to expand the cecal wall. In various embodiments, the angle α is no less than about 45, 60, 75, or 90 degrees. In the illustrated embodiment, the angle is substantially 90 degrees.

Following is a non-limiting example of a method for the treatment of obesity in which an illustrative example of a self-expanding device was used.

Example

Self-expanding stents of the variety depicted in and described above with respect to FIGS. 29-30G, and having a maximum diameter of 8.5 centimeters, were implanted in three test patients—specifically, mongrel dogs—to determine weight loss achievable thereby. Each animal had a standard bowel prep before the implant procedure. Baseline physical examination, clinical pathology sample collection, body weight, and food intake were assessed prior to implant. On the day of implant, each animal was prepped chronically and brought into the procedure room for a colonoscopy procedure. The colonoscope was advanced until reaching the cecum, and then a self-expanding stent was deployed. That is, the target implant location for all animals was the cecum, although a colonoscopy at implant and a gross necropsy analysis revealed that a portion of one of the stents was deployed in the ascending colon. Cecal implantation of the stent was successful for the remaining two animals. Hemoclips were applied endoscopically to appose each stent to the bowel.

Figure 40A:
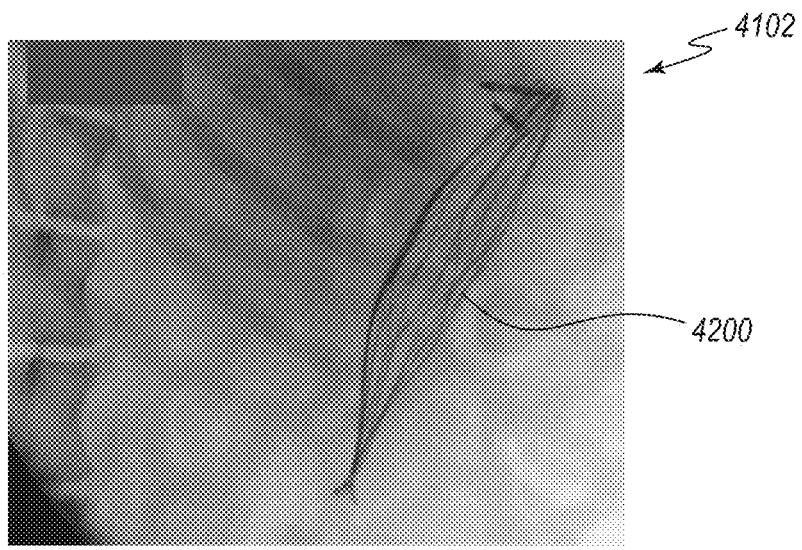
FIG. 40A is a fluoroscopy image of an embodiment of an implant after initial deployment in the cecum of a test patient (in particular, a dog)
Figure 40B:
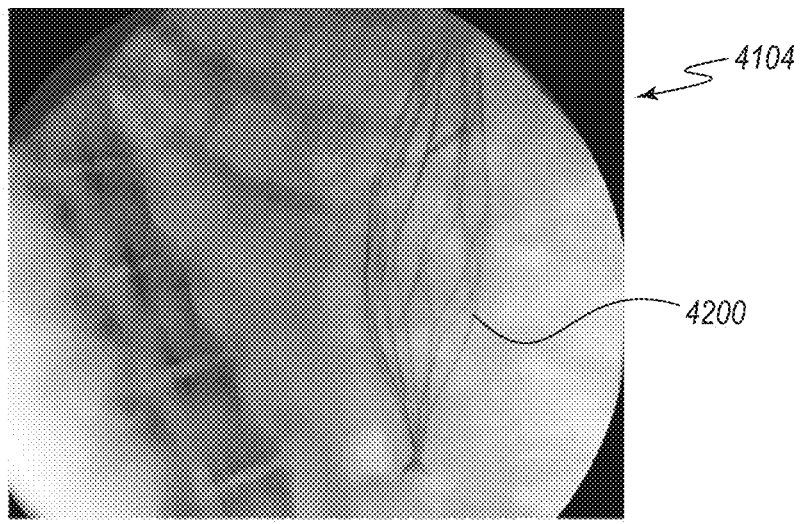
FIG. 40B is another fluoroscopy image of the implant at seven days after initial deployment.
Figure 40C:
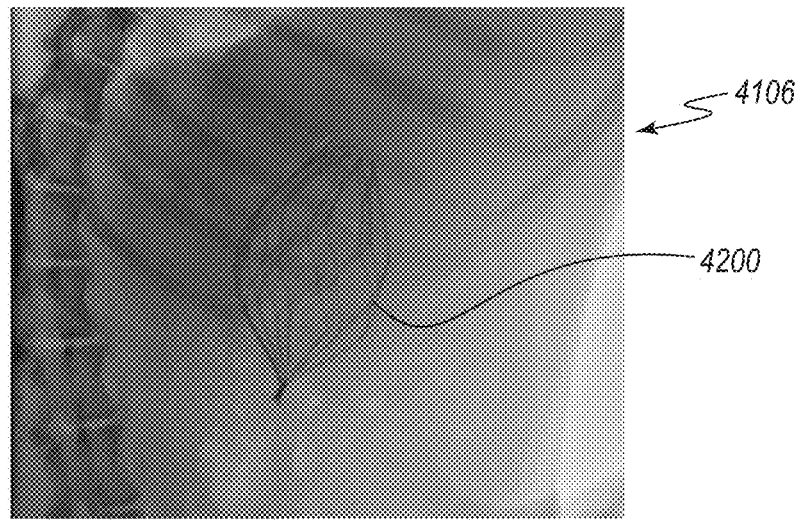
FIG. 40C is another fluoroscopy image of the implant at 28 days after initial deployment.

Stent location and expansion were imaged post-deployment by fluoroscopy. In particular, weekly fluoroscopy assessments were performed for one month following test article implant and indicated no detectable stent migration. However fractured struts were observed in two out of three implanted devices. Over time, stents expanded radially outward relative to their size on the day of implant. For example, FIGS. 40A, 40B, and 40C are fluoroscopy images 4102, 4104, 4106 of an expansible device 4200 implanted within the cecum of one of the test subjects at the day of implant, 7 days post-implant, and 28-days post-implant, respectively.

Following the procedures, the animals were recovered and survived for approximately 90 days. Daily food consumption, weekly weights, monthly physical examinations, and clinical pathology collections were also performed. Food supplements were administered in post-implant period as needed in order to support acceptable body condition and weight through the duration of the study.

After approximately 90 days, all animals had standard bowel prep prior to colonoscopy procedure and termination, followed by complete necropsy and gross examination of the implant site and organs. The implant site was harvested and fixed, and histological analysis conducted on implanted areas and device to assess tissue response.

All assessments suggested that animals remained relatively healthy throughout the duration of the study. There were no deaths or major adverse events that affected animal health or welfare. Moreover, the animals maintained normal play and kennel activity throughout the study. There was no evidence of abdominal pain, nausea, or vomiting. All labs remained normal (complete blood count, liver function test, etc.).

Feces changed in all the animals at about 7-10 days post-implant. The stools went from normal to intermittently soft-liquid stools throughout the remainder of the study. All animals displayed inappetence and weight loss. Minor excursions in clinical pathology were clinically insignificant.

Histopathological analysis of the implant device and site did not indicate penetration of fractured test article strut through the intestinal serosa. Over the implantation in-life period, the implant wires embedded into the intestinal wall and generated a mixed and generally chronic-active host cellular response.

Food Intake Results

In this example, to examine appetite, food intake was monitored after each meal for the entire duration of the study (pre and post-implant). Approximately 2.5 weeks after implant, the methods of monitoring food intake were modified such that the amount of food given and remaining for each meal was weighed and recorded, in order to more closely assess this correlate of appetite. There were some instances in which food intake could not be monitored due to complications such as animal tipping over food bowl prior to documentation. Outside of these few instances, there were no procedural complications during these assessments. Results indicate increased amounts of uneaten food post-implant. Some inter-animal variability was observed in food intake. Food intake decreased by a greater amount for those animals in which the device was implanted solely in the cecum.

High protein/calorie supplements were started on study day 26 in order to support animal health, welfare, and humane body condition due to the rapid weight loss of the animals. The supplements included hamburgers, eggs, whey, and Ensure. Despite supplementation with high protein/calorie supplements in addition to their standard dry food, the animals still showed marked weight loss from baseline, as discussed further below.

Figure 41:
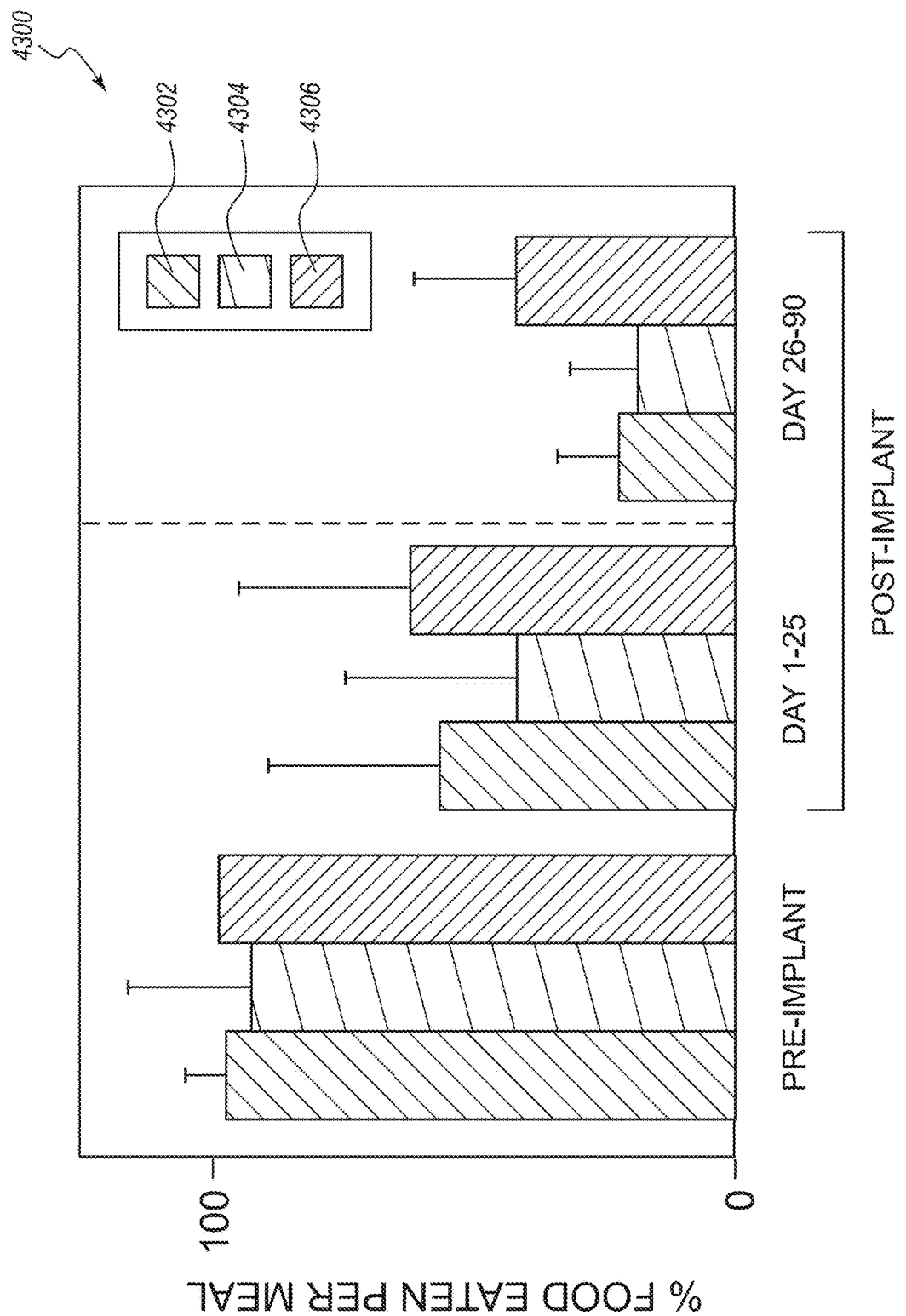
FIG. 41 is a chart depicting food consumption patterns of test patients (mongrel dogs) in which embodiments of the implant have been implanted at periods prior to implantation, one to 25 days after implantation, and 26 to 90 days after implantation (during which dietary supplements were provided)
Figure 42:
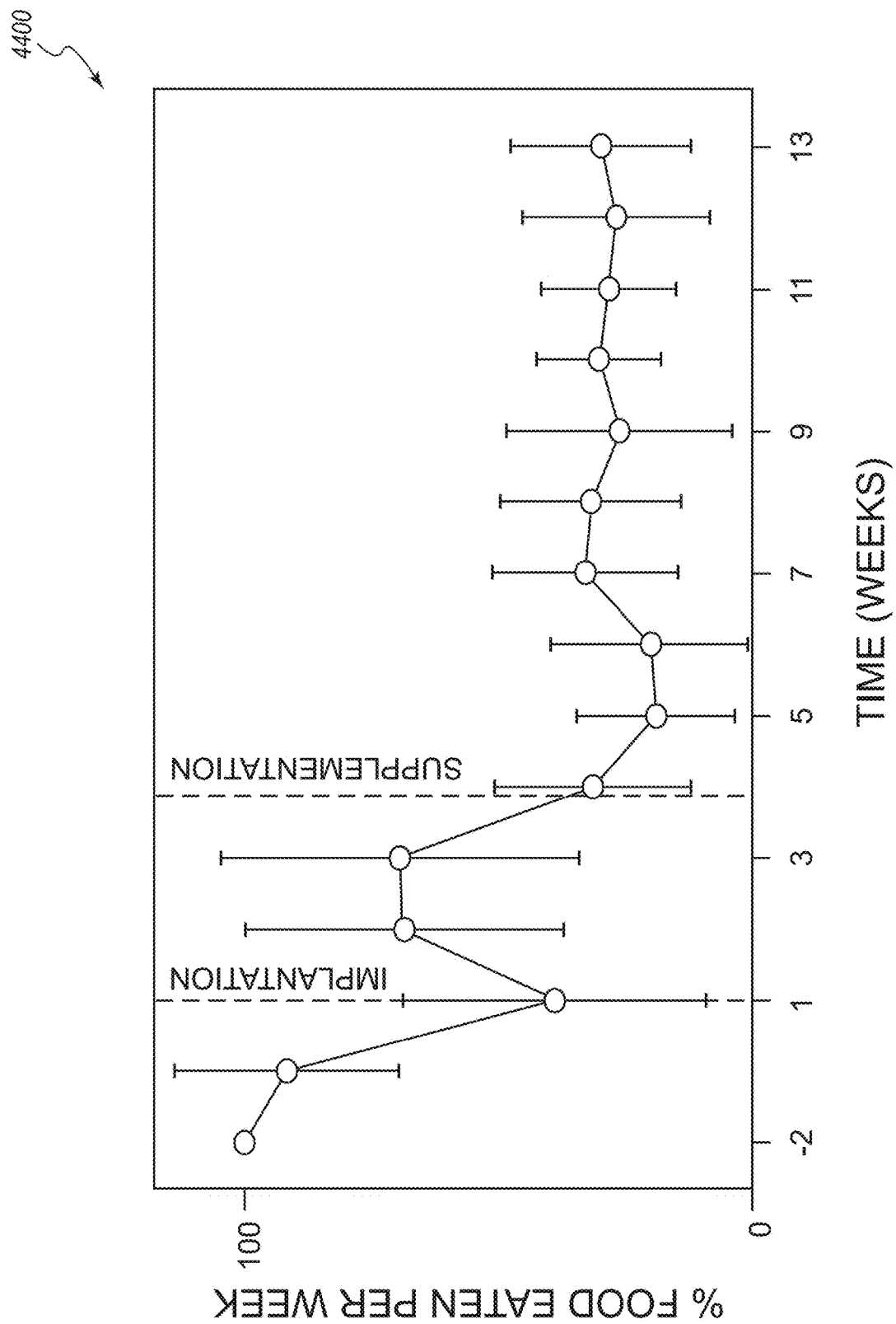
FIG. 42 is a chart depicting the average food consumption patterns of the test patients.

Results of the food intake study are provided in Table 1 below and in FIGS. 41 and 42. In particular, FIG. 41 is a bar graph 4300 comparing the food intake activity of the three test subjects during three discrete time increments: pre-implant; days 1-25 post-implant; and days 26-90 post-implant. The test subjects in which the expansible device was accurately deployed in the cecum are represented by the shading identified at 4302 and 4304. The test subject in which the expansible device was partially deployed in the ascending colon is represented by the shading identified at 4306. FIG. 42 is a plot 4400 showing the averaged food intake activity of all three test subjects.

TABLE 1

DAILY FOOD CONSUMPTION
(% of food eaten)

| Study Day (relative to implant day 0) | Animal | | |
|---|---|---|---|
| | 18C0390 (Cecum) | 18C0391 (Cecum) | 18C0395 (Cecum/Ascending Colon) |
| −14 | 100 | 100 | 100 |
| −13 | 100 | 100 | 100 |
| −12 | 100 | 100 | 100 |
| −11 | 100 | 100 | 100 |
| −10 | 100 | 100 | 100 |
| −9 | 100 | 100 | 100 |
| −8 | 100 | 100 | 100 |
| −7 | 75 | 25 | 100 |
| −6 | 100 | 100 | 100 |
| −5 | 100 | 100 | 100 |
| −4 | 100 | 100 | 100 |
| −3 | 25 | 25 | 100 |
| −2 | NA | NA | NA |
| −1 | NA | NA | NA |
| 0 | NA | NA | NA |
| 1 | 17 | 0 | 0 |
| 2 | 27 | 8 | 33 |
| 3 | 25 | 0 | 50 |
| 4 | 83 | 58 | 83 |
| 5 | 83 | 17 | 67 |
| 6 | 67 | 50 | 33 |
| 7 | 58 | 42 | 33 |
| 8 | 100 | 17 | 100 |
| 9 | 58 | 50 | 75 |
| 10 | 42 | 42 | 75 |
| 11 | 100 | 100 | 100 |
| 12 | 25 | 25 | 100 |
| 13 | 100 | 100 | 100 |
| 14 | 25 | 25 | 25 |
| 15 | 100 | 25 | 100 |
| 16 | 100 | 100 | 100 |
| 17 | 100 | 100 | 100 |
| 18 | 50 | 50 | 100 |
| 19 | 25 | 25 | 33 |
| 20 | 100 | 100 | 75 |
| 21 | 28 | 40 | 28 |
| 22 | 28 | 13 | 55 |
| 23 | 32 | 23 | 30 |
| 24 | 5 | 15 | 24 |
| 25 | 33 | 26 | 33 |
| 26 | 35 | 32 | 91 |
| 27 | 21 | 9 | 62 |
| 28 | 12 | 26 | 55 |
| 29 | 1 | 0 | 0 |
| 30 | 21 | 15 | 18 |
| 31 | 11 | 21 | 40 |
| 32 | 2 | 10 | 33 |
| 33 | 7 | 29 | 41 |
| 34 | NA | 5 | 36 |
| 35 | 20 | 0 | 40 |
| 36 | 10 | 6 | 65 |
| 37 | 21 | 6 | 67 |
| 38 | 20 | 8 | 31 |
| 39 | 15 | 7 | NA |
| 40 | 0 | 0 | 14 |
| 41 | 27 | 8 | 39 |
| 42 | 18 | 45 | 38 |
| 43 | 32 | 15 | 56 |
| 44 | 14 | 14 | 76 |
| 45 | 18 | 14 | 50 |
| 46 | 30 | 46 | 54 |
| 47 | 28 | 10 | 56 |
| 48 | 18 | 19 | 40 |
| 49 | 20 | 29 | 50 |
| 50 | 28 | 19 | 39 |
| 51 | 40 | 30 | 68 |
| 52 | 15 | 21 | 60 |
| 53 | 16 | 17 | 68 |
| 54 | 15 | 17 | 19 |
| 55 | 28 | 20 | 49 |
| 56 | 12 | 12 | 17 |
| 57 | 19 | 19 | 64 |

TABLE 1-continued

DAILY FOOD CONSUMPTION
(% of food eaten)

| | Animal | | |
|---|---|---|---|
| Study Day (relative to implant day 0) | 18C0390 (Cecum) | 18C0391 (Cecum) | 18C0395 (Cecum/Ascending Colon) |
| 58 | 32 | 19 | 26 |
| 59 | 22 | 31 | 58 |
| 60 | 5 | 4 | 52 |
| 61 | 14 | 8 | 54 |
| 62 | 0 | 8 | 78 |
| 63 | 30 | 19 | 24 |
| 64 | 23 | 27 | 22 |
| 65 | 31 | 34 | 56 |
| 66 | 55 | 25 | 27 |
| 67 | 23 | 34 | 32 |
| 68 | 25 | 31 | 57 |
| 69 | 30 | 9 | 24 |
| 70 | 18 | 13 | 17 |
| 71 | 21 | 19 | 28 |
| 72 | 34 | 37 | 40 |
| 73 | 35 | 29 | 28 |
| 74 | 23 | 13 | 68 |
| 75 | 11 | 25 | 25 |
| 76 | 36 | 46 | 30 |
| 77 | 19 | 0 | 0 |
| 78 | 15 | 43 | 41 |
| 79 | 22 | 43 | 40 |
| 80 | 30 | 40 | 39 |
| 81 | 14 | 20 | 75 |
| 82 | 30 | 10 | 42 |
| 83 | 30 | 8 | 5 |
| 84 | 40 | 15 | 26 |
| 85 | 38 | 4 | 50 |
| 86 | 55 | 12 | 28 |
| 87 | NA | NA | NA |
| 88 | NA | NA | NA |
| 89 | NA | NA | NA |
| 90 | NA | NA | NA |

NA = unavailable data due to bowl prep fasting or procedural complication

Body Weight Results

Body weights were collected approximately weekly for the entire duration of the study (pre and post-implant) in order to monitor weight loss. Results indicated marked weight loss after stent implant in all animals that varied from 8-17% of baseline weight. Due to severe weight loss and declining body condition, high calorie/protein supplements were started on day 26. Animals regained some weight after supplementation, however marked weight loss from baseline was still observed at the end of the study (day 90). Some inter-animal variability was observed in weight change, and the animals with implants positioned solely in the cecum exhibited the greatest weight change.

Veterinarian checks for body condition are performed when an animal appears too thin. Weight loss and/or appearing thin prompted veterinarian checks for all animals on study days 19, 25, and about 39. The veterinarian check at day 25 prompted commencement of supplementation on study day 26 for all animals.

As previously discussed, food intake decreased immediately after implantation. For the first two weeks following device implant, the animals on average ate approximately 75% of their feed, which was an approximately 25% decrease from baseline consumption. This decrease in food consumption was correlated with weight loss of approximately 5-10% of baseline weight. However, in the third week after implant (when animals weight loss decreased further to 10-15% of baseline weight), animals showed a marked decrease in food consumption to approximately 32%, which was subsequently correlated with an even greater weight loss of approximately 15-20% of baseline weight.

Over the full course of the study, all animals experienced weight loss following device implant that varied from 8-16% of the baseline weight, despite the commencement of high calorie/protein supplements on day 26 (out of 90).

Figure 43:
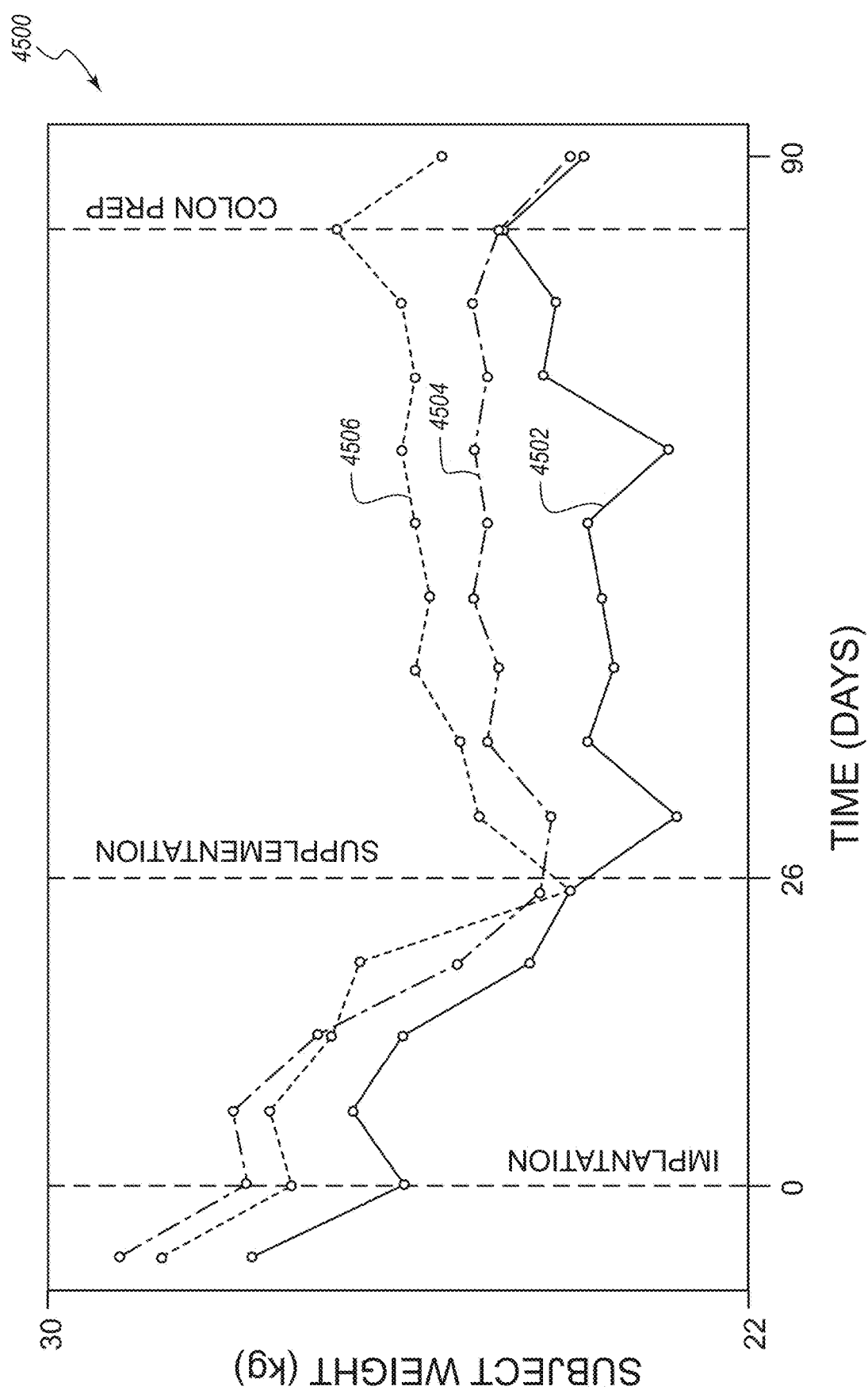
FIG. 43 is a chart depicting body weight of the test patients at various times relative to implantation of the device.

Results of the body weight study are provided in Table 2 below and in FIG. 43. FIG. 43 is a plot 4500 showing subject weight over time for each of the test subjects. The lines 4502, 4504 correspond to the test subjects in which the expansible device was accurately deployed in the cecum; the line 4506 corresponds to the test subject in which the expansible device was partially deployed in the ascending colon.

TABLE 2

Body Weights

| | Animal | | | | | |
|---|---|---|---|---|---|---|
| | 18C0390 (Cecum) | | 18C0391 (Cecum) | | 18C0395 (Cecum/Ascending Colon) | |
| Day | Wt (kg) | Wt (% change from day −3) | Wt (kg) | Wt (% change from day −3) | Wt (kg) | Wt (% change from day −3) |
| −3 (prior to bowl prep) | 29.1 | NA | 31 | NA | 30.4 | NA |
| 0 (implant) | 27 | −7.2 | 29.2 | −5.8 | 28.6 | −5.9 |
| 5 | 27.7 | −4.8 | 29.4 | −5.2 | 28.9 | −4.9 |
| 13 | 27 | −7.2 | 28.2 | −9 | 28 | −7.9 |
| 19 | 25.2 | −13.4 | 26.2 | −15.5 | 27.6 | −9.2 |
| 25 | 24.6 | −15.8 | 25 | −20.4 | 24.6 | −19.4 |
| 33 | 23.1 | −20.6 | 24.9 | −19.7 | 25.9 | −14.8 |
| 40 | 24.4 | −16.2 | 25.8 | −16.8 | 26.2 | −13.8 |
| 47 | 24 | −17.5 | 25.6 | −17.4 | 26.8 | −11.8 |
| 55 | 24.2 | −16.8 | 26 | −16.1 | 26.6 | −12.5 |
| 61 | 24.4 | −16.2 | 25.8 | −16.8 | 26.8 | −11.8 |
| 70 | 23.2 | −20.3 | 26 | −16.1 | 27 | −11.2 |

TABLE 2-continued

Body Weights

| | Animal | | | | | |
|---|---|---|---|---|---|---|
| | 18C0390 (Cecum) | | 18C0391 (Cecum) | | 18C0395 (Cecum/Ascending Colon) | |
| Day | Wt (kg) | Wt (% change from day −3) | Wt (kg) | Wt (% change from day −3) | Wt (kg) | Wt (% change from day −3) |
| 77 | 25 | −14.1 | 25.8 | −16.8 | 26.8 | −11.8 |
| 81 | 24.8 | −14.8 | 26 | −16.1 | 27 | −11.2 |
| 87 (prior to bowl prep) | 25.6 | −12 | 25.6 | −17.4 | 28 | −7.9 |
| 90 (termination) | 24.4 | −16.2 | 24.6 | −20.6 | 26.4 | −13.2 |

Gross Necropsy Results

At necropsy all organs and tissues examined were within normal limits, except for the implanted intestinal segments which had moderate serosal adhesions present at the implant site, tissue reddening, and enlargement of the intestinal segments containing the devices. Necropsy images of the implant that was in the ascending colon showed elevated linear structures visible on the serosa overlying the implant, which were interpreted to be implant wires within the intestinal wall.

Histopathology Results

Over the implantation in-life period, the implant wires embedded into the intestinal wall, with each implant having wires observed through the mucosa and outer muscular tunic to the subserosa level. Organizing to healed fibrous tracts were visible within the intervening wall layers. The muscular tunic and subserosa device wires, observed most commonly in the largest diameter implant/intestine segments, were interpreted to have embedded deeper due to the device radial forces applied to the host tissue. The histopathology sections examined did not show implant wires penetrating through the intestinal serosa.

The host cellular response to the strut wires was most pronounced at the strut/mucosa and strut/submucosa interfaces where there was associated mucosal ulceration, strut tract debris accumulation (cellular and digesta), and variable bacterial colonization. The host cellular response was mixed and generally chronic-active, composed of neutrophils, macrophages and lymphocytes. Cellular aggregates were also associated with multiple deeper strut locations (subserosa, muscular tunic) and it is speculated these cellular infiltrates represent continuing inflammation along the wire tract within the intestinal wall.

DISCUSSION

Device implant was associated with decreased food intake and weight loss in all animals, however once weight loss became greater than about 10% of initial baseline weight, more dramatic declines in feed intake were observed, which were correlated with further, exacerbated weight loss. To mitigate further loss of body condition, supplementation with high calorie/protein food commenced, and this was successful at maintaining body condition and weight in all animals for the duration of the study. Although some instances of diarrhea/soft-stool were seen throughout the post-implant period, this was not associated with any adverse clinical events or pathology. Despite the marked weight loss, recurrent soft-stool, and strut fracture in 2 out of 3 animals, all animals remained generally healthy for the duration of the study.

The test devices maintained their approximate positioning in the bowel throughout the study duration, and performed as expected in that they were observed to expand radially outward after deployment. However, fluoroscopy revealed strut fractures in two out of three devices within one week of implant, and this was confirmed upon gross examination. No bowel perforation was observed in this canine animal model.

Histopathological examination revealed that the areas of the device producing the greatest radial force on the surrounding tissue were deeply embedded, precluding removal of the device without damage. A small fraction of the strut contacting tissue was observed to have focal ulcerations, and some more deeply embedded wires showed chronic inflammation, while others did not. Device sizing and/or covering of the device, such as in manners previously disclosed, are contemplated in further embodiments. Certain of such embodiments can guard against erosion of the intestinal wall.

The claims that follow this written disclosure are expressly incorporated into the present written disclosure, with each claim standing on its own as a separate embodiment. In particular, each of the methods, kits, systems, and medical devices recited in the claims is expressly incorporated herein. Moreover, any of the methods described in this disclosure and/or the following claims may be used with any applicable medical device and/or system described in this disclosure and/or the following claims, as appropriate. Moreover, any of the kits disclosed herein and/or in the claims that follow can include instructions for carrying out any of the methods recited in this disclosure and/or in the claims that follow, as appropriate. This disclosure includes all permutations of the independent claims with their dependent claims.

Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Elements not presented in requisite means-plus-function format are not intended to be construed in accordance with 35 U.S.C. § 112(f). Embodiments of the invention in which an exclusive property or privilege is claimed are defined as follows.

The invention claimed is:

1. A method comprising:
introducing a medical device into the cecum of a patient;
distending the cecum to a pathophysiological size via the medical device to reduce an appetite of the patient; and
leaving the medical device within the cecum of the patient while the medical device at least intermittently maintains the cecum in distention.

2. The method of claim 1, wherein said leaving the medical device within the cecum of the patient comprises leaving the medical device for an amount of time sufficient for a total weight of the patient to be reduced by at least 5 percent.

3. The method of claim 1, wherein said leaving the medical device within the cecum of the patient comprises leaving the medical device for an amount of time sufficient for a total weight of the patient to be reduced by at least 10 percent.

4. The method of claim 1, wherein said leaving the medical device within the cecum of the patient comprises leaving the medical device for an amount of time sufficient for an excess weight of the patient to be reduced by at least 10 percent.

5. The method of claim 1, wherein said leaving the medical device within the cecum of the patient comprises leaving the medical device for an amount of time sufficient for an excess weight of the patient to be reduced by at least 20 percent.

6. The method of claim 1, wherein said leaving the medical device within the cecum of the patient comprises leaving the medical device for a period of no less than 2 weeks.

7. The method of claim 1, wherein said leaving the medical device within the cecum of the patient comprises leaving the medical device for a period of no less than one month.

8. The method of claim 1, wherein distending the cecum comprises expanding the medical device from a low-profile state to an expanded state.

9. The method of claim 8, wherein the medical device defines a substantially cylindrical profile when in the low-profile state and defines a bulbous profile when in the expanded state.

10. The method of claim 8, wherein the medical device defines a substantially linear profile when in the low-profile state and defines a substantially spiraled profile when in the expanded state.

11. The method of claim 8, wherein the medical device defines a first maximum diameter when in the low-profile state and defines a second maximum diameter when in the expanded state, the second maximum diameter being no less than 15 times larger than the first maximum diameter.

12. The method of claim 8, wherein the medical device defines a first maximum diameter when in the low-profile state and defines a second maximum diameter when in the expanded state, the second maximum diameter being no less than 20 times larger than the first maximum diameter.

13. The method of claim 8, wherein the medical device defines a first maximum diameter when in the low-profile state and defines a second maximum diameter when in the expanded state, the second maximum diameter being no less than 30 times larger than the first maximum diameter.

14. The method of claim 8, wherein the medical device defines a first maximum diameter when in the low-profile state and defines a second maximum diameter that is larger than the first maximum diameter when in the expanded state, wherein the first maximum diameter corresponds to an outer diameter of the medical device that extends exclusively through an internal region of the medical device itself, and wherein the second maximum diameter corresponds to an outer diameter of a three-dimensional region defined by the medical device that extends at least partially through open space encompassed by the medical device.

15. The method of claim 8, wherein the medical device defines a first maximum diameter when in the low-profile state and defines a second maximum diameter that is larger than the first maximum diameter when in the expanded state, wherein each of the first and second maximum diameters corresponds to an outer diameter of a three-dimensional region defined by the medical device that extends at least partially through open space encompassed by the medical device.

16. The method of claim 8, wherein the medical device defines a first maximum longitudinal length when in the low-profile state and defines a second maximum longitudinal length when in the expanded state, the first maximum longitudinal length being no less than 1.5 times larger than the second maximum longitudinal length.

17. The method of claim 8, wherein the medical device defines a first maximum longitudinal length when in the low-profile state and defines a second maximum longitudinal length when in the expanded state, the first maximum longitudinal length being no less than 1.75 times larger than the second maximum longitudinal length.

18. The method of claim 8, wherein the medical device defines a first maximum longitudinal length when in the low-profile state and defines a second maximum longitudinal length when in the expanded state, the first maximum longitudinal length being no less than 2 times larger than the second maximum longitudinal length.

19. The method of claim 8, wherein the medical device defines a first maximum longitudinal length when in the low-profile state and defines a second maximum longitudinal length when in the expanded state, the first maximum longitudinal length being no less than 2.5 times larger than the second maximum longitudinal length.

20. The method of claim 8, further comprising:
passing the medical device through a working channel of a colonoscope when the medical device is in the low-profile state; and
advancing the medical device past an end of the colonoscope into the cecum,
wherein said expanding the medical device from the low-profile state to the expanded state takes place after said advancing the medical device past the end of the colonoscope.

21. The method of claim 20, wherein the working channel of the colonoscope is no larger than 4 millimeters in diameter.

22. The method of claim 20, wherein said expanding the medical device from the low-profile state to the expanded state comprises expanding the medical device within the cecum to a maximum diameter of no less than 5 centimeters.

23. The method of claim 20, wherein said expanding the medical device from the low-profile state to the expanded state comprises expanding the medical device within the cecum to a maximum diameter of no less than 7 centimeters.

24. The method of claim 1, wherein the pathophysiological size of the cecum comprises a maximum diameter of the cecum of no less than 5 centimeters.

25. The method of claim 1, wherein the pathophysiological size of the cecum comprises a maximum diameter of the cecum of no less than 6 centimeters.

26. The method of claim 1, wherein the pathophysiological size of the cecum comprises a maximum diameter of the cecum of no less than 7 centimeters.

27. The method of claim 1, wherein the pathophysiological size of the cecum comprises a maximum diameter of the cecum of no less than 8 centimeters.

28. The method of claim 1, wherein the pathophysiological size of the cecum comprises an internal volume of the cecum of no less than 0.25 liters.

29. The method of claim 1, wherein the pathophysiological size of the cecum comprises an internal volume of the cecum of no less than 0.33 liters.

30. The method of claim 1, wherein the pathophysiological size of the cecum comprises an internal volume of the cecum of no less than 0.4 liters.

31. The method of claim 1, wherein said distending the cecum to the pathophysiological size comprises reorienting the cecum from a substantially tubular configuration to a substantially bulbous configuration.

32. The method of claim 1, further comprising permitting the cecum to naturally expand to an enlarged size that is larger than the pathophysiological size.

33. The method of claim 32, wherein a maximum diameter of the cecum increases when the cecum naturally expands from the pathophysiological size to the enlarged size.

34. The method of claim 32, wherein an inner volume of the cecum increases when the cecum naturally expands from the pathophysiological size to the enlarged size.

35. The method of claim 32, wherein said distending the cecum to the pathophysiological size via the medical device comprises contacting the cecum with the medical device, and wherein said permitting the cecum to naturally expand to the enlarged size reduces an amount of contact between the cecum and the medical device.

36. The method of claim 32, wherein said distending the cecum to the pathophysiological size via the medical device comprises expanding the medical device to a predetermined size within the cecum, and wherein the medical device substantially does not expand beyond the predetermined size when the cecum naturally expands to the enlarged size.

37. The method of claim 36, further comprising permitting the medical device to move relative to the cecum when the cecum has been expanded to the enlarged size.

38. The method of claim 32, further comprising permitting the medical device to move relative to the cecum when the cecum has been expanded to the enlarged size.

39. The method of claim 32, wherein the medical device freely floats within the cecum when the cecum has been expanded to the enlarged size.

40. The method of claim 32, wherein said distending the cecum to the pathophysiological size via the medical device comprises securing the medical device to the cecum, and wherein the medical device remains secured to the cecum and expands with the cecum during said permitting the cecum to naturally expand to the enlarged size.

41. The method of claim 1, further comprising orienting the medical device within the cecum such that the ileocecal valve is substantially unobstructed.

42. The method of claim 1, further comprising orienting the medical device within the cecum such that the ileocecal valve is entirely unobstructed.

43. The method of claim 1, wherein the pathophysiological size is a size that is abnormal for the cecum of the patient.

44. The method of claim 1, wherein the pathophysiological size is a size that is naturally achievable by the cecum of the patient for relatively short time intervals, but that would be indicative of a pathological event if sustained for or for at least three days.

* * * * *